(12) United States Patent
Jung et al.

(10) Patent No.: US 10,421,740 B2
(45) Date of Patent: Sep. 24, 2019

(54) PESTICIDALLY ACTIVE HETEROCYCLIC DERIVATIVES WITH SULPHUR CONTAINING SUBSTITUENTS

(71) Applicant: SYNGENTA PARTICIPATIONS AG, Basel (CH)

(72) Inventors: Pierre Joseph Marcel Jung, Stein (FR); Michel Muehlebach, Stein (CH); Andrew Edmunds, Stein (CH); Girish Rawal, Corlim Ilhas (IN); Vikas Sikervar, Corlim Ilhas (IN); Jagadish Pabba, Corlim Ilhas (IN)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 16/091,886

(22) PCT Filed: Mar. 31, 2017

(86) PCT No.: PCT/EP2017/057650
§ 371 (c)(1),
(2) Date: Oct. 5, 2018

(87) PCT Pub. No.: WO2017/174449
PCT Pub. Date: Oct. 12, 2017

(65) Prior Publication Data
US 2019/0106403 A1    Apr. 11, 2019

(30) Foreign Application Priority Data

Apr. 7, 2016 (IN) .............................. 201611012363

(51) Int. Cl.
| | | |
|---|---|---|
| *C07D 401/14* | (2006.01) | |
| *C07D 491/048* | (2006.01) | |
| *A01N 43/40* | (2006.01) | |
| *C07D 401/04* | (2006.01) | |
| *C07D 405/14* | (2006.01) | |
| *A01N 43/90* | (2006.01) | |
| *C07D 417/14* | (2006.01) | |
| *C07D 471/04* | (2006.01) | |
| *A01N 43/653* | (2006.01) | |
| *A01N 43/78* | (2006.01) | |
| *C07D 403/04* | (2006.01) | |
| *C07D 513/04* | (2006.01) | |

(52) U.S. Cl.
CPC ......... *C07D 401/04* (2013.01); *A01N 43/653* (2013.01); *A01N 43/78* (2013.01); *A01N 43/90* (2013.01); *C07D 401/14* (2013.01); *C07D 403/04* (2013.01); *C07D 405/14* (2013.01); *C07D 417/14* (2013.01); *C07D 471/04* (2013.01); *C07D 513/04* (2013.01)

(58) Field of Classification Search
CPC ................ C07D 401/14; C07D 417/14; C07D 491/048; A01N 43/40
USPC ........... 546/116, 117, 270.1, 272.4; 544/333; 514/256, 300, 302
See application file for complete search history.

(56) References Cited

FOREIGN PATENT DOCUMENTS

| | | |
|---|---|---|
| WO | 2015/144826 A1 | 10/2015 |
| WO | 2015/163478 A1 | 10/2015 |

OTHER PUBLICATIONS

International Search Report and Written Opinion for International Patent Application No. PCT/EP2017/057650 dated May 11, 2017.

*Primary Examiner* — Charanjit Aulakh
(74) *Attorney, Agent, or Firm* — Baker & Hostetler, LLP; Toni-Junell Herbert

(57) ABSTRACT

Compounds of formula (I) wherein the substituents are as defined in claim 1, and the agrochemically acceptable salts salts, stereoisomers, enantiomers, tautomers and N-oxides of those compounds, can be used as insecticides and can be prepared in a manner known per se.

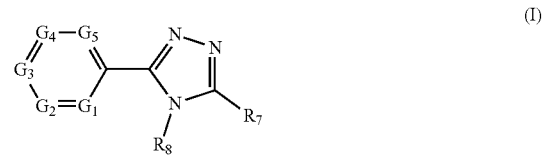

(I)

15 Claims, No Drawings

PESTICIDALLY ACTIVE HETEROCYCLIC DERIVATIVES WITH SULPHUR CONTAINING SUBSTITUENTS

CROSS-REFERENCE TO RELATED APPLICATIONS

This application is a 371 National Stage application of International Application No. PCT/EP2017/057650, filed Mar. 31, 2017, which claims priority to Indian Patent Application No. 201611012363 filed Apr. 7, 2016, the entire contents of which applications are hereby incorporated by reference.

The present invention relates to pesticidally active, in particular insecticidally active heterocyclic derivatives containing sulfur substituents, to processes for their preparation, to compositions comprising those compounds, and to their use for controlling animal pests, including arthropods and in particular insects or representatives of the order Acarina.

Heterocyclic compounds with pesticidal action are known and described, for example, in WO 2010/125985, WO 2013/018928 and WO 2015/144826. There have now been found novel pesticidally active heterocyclic triazole derivatives with sulfur containing phenyl and pyridyl substituents.

The present invention accordingly relates to compounds of formula I

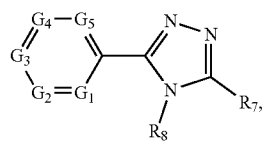

(I)

wherein $G_1$ is nitrogen or $CR_2$;

$G_2$ is nitrogen or $CR_3$;

$G_3$ is nitrogen or $CR_4$;

$G_4$ is nitrogen or $CR_5$;

$G_5$ is nitrogen or $CR_6$, with the proviso that not more than 2 nitrogens as G may follow consecutively;

$R_2$, $R_3$, $R_4$, $R_5$ and $R_6$ are, independently from each other, hydrogen, halogen, $C_1$-$C_4$haloalkyl or $C_1$-$C_4$haloalkyl substituted by one or two cyano or methoxy; or $R_2$, $R_3$, $R_4$, $R_5$ and $R_6$ are, independently from each other, $C_1$-$C_4$haloalkylsulfanyl, $C_1$-$C_4$haloalkylsulfinyl, $C_1$-$C_4$haloalkylsulfonyl, $C_1$-$C_4$haloalkoxy, $SF_5$, phenylcarbonylthio, cyano, mercapto, $C_1$-$C_4$alkoxycarbonyl, $C_1$-$C_4$ alkylcarbonyl or —C(O)$C_1$-$C_4$haloalkyl; or $R_2$, $R_3$, $R_4$, $R_5$ and $R_6$ are, independently from each other, $C_3$-$C_6$cycloalkyl which can be mono- or polysubstituted by substituents selected from the group consisting of halogen, cyano, $C_1$-$C_4$ haloalkyl and $C_1$-$C_4$alkyl;

$R_8$ is hydrogen or $C_1$-$C_4$alkyl which can be mono- or polysubstituted by substituents selected from the group consisting of halogen, $C_1$-$C_4$haloalkylsulfanyl, $C_1$-$C_4$haloalkylsulfinyl and $C_1$-$C_4$haloalkylsulfonyl;

$R_7$ is the following group:

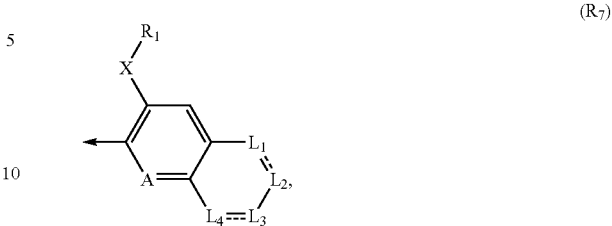

($R_7$)

wherein the arrow denotes the point of attachment to the triazole ring which contains the group $R_8$;

and wherein

X is S, S(O) or $SO_2$;

$R_1$ is $C_1$-$C_4$alkyl or is $C_3$-$C_6$cycloalkyl$C_1$-$C_4$alkyl which can be mono- or polysubstituted by substituents selected from the group consisting of halogen, cyano, $C_1$-$C_4$ haloalkyl and $C_1$-$C_4$alkyl; or $R_1$ is $C_3$-$C_6$cycloalkyl which can be mono- or polysubstituted by substituents selected from the group consisting of halogen, cyano, $C_1$-$C_4$ haloalkyl and $C_1$-$C_4$alkyl;

$L_1$, $L_2$, $L_3$ and $L_4$ form together with the two carbon atoms to which $L_1$ and $L_4$ are attached, an aromatic, partially saturated carbocyclic or heterocyclic ring system; wherein $L_1$ is nitrogen, $S(O)_n$, oxygen, N—$R_{10a}$ or $C(R_{10a})_m$;

$L_2$ is nitrogen, $S(O)_n$, oxygen, N—$R_{10b}$ or $C(R_{10b})_m$;

$L_3$ is nitrogen, $S(O)_n$, oxygen, N—$R_{10c}$, or $C(R_{10c})_m$;

$L_4$ is nitrogen, $S(O)_n$, oxygen, a direct bond, N—$R_{10d}$ or $C(R_{10d})_m$; with the provisos that no more than 2 substituents selected from $L_1$, $L_2$, $L_3$ and $L_4$ can be oxygen or sulfur; and if two L groups are oxygen, they are not adjacent to each other; and no more than three L groups can be nitrogen;

A is CH or N;

n is 0, 1 or 2;

m is 1 or 2; and $R_{10a}$, $R_{10b}$, $R_{10c}$ and $R_{10d}$ are, independently from each other, hydrogen, halogen, nitro, cyano, amino, hydroxyl, $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, $C_1$-$C_6$alkoxy, $C_1$-$C_4$alkoxy$C_1$-$C_4$alkyl, $C_1$-$C_6$haloalkoxy, $C_1$-$C_6$alkylthio, $C_1$-$C_6$ alkylsulfinyl, $C_1$-$C_6$alkylsulfonyl, $C_1$-$C_6$haloalkylthio, $C_1$-$C_6$ haloalkylsulfinyl, $C_1$-$C_6$haloalkylsulfonyl, $C_2$-$C_6$ alkylcarbonyl, $C_2$-$C_6$alkoxycarbonyl, $C_2$-$C_6$ haloalkylcarbonyl, $C_2$-$C_6$haloalkoxycarbonyl, ($C_1$-$C_6$alkyl)NH, ($C_1$-$C_6$alkyl)$_2$N, ($C_1$-$C_6$cycloalkyl)NH, ($C_1$-$C_6$cycloalkyl)$_2$N, $C_1$-$C_6$ alkylcarbonylamino, $C_1$-$C_6$cycloalkylcarbonylamino or —$SF_5$; additionally one of $R_{10a}$, $R_{10b}$, $R_{10c}$ and $R_{10d}$ can be oxo; or $R_{10a}$, $R_{10b}$, $R_{10c}$ and $R_{10d}$ are, independently from each other, $C_3$-$C_6$cycloalkyl mono- or polysubstituted by substituents selected from the group consisting of halogen, $C_1$-$C_4$ haloalkyl, $C_1$-$C_4$alkyl and cyano; and agrochemically acceptable salts, stereoisomers, enantiomers, tautomers and N-oxides of those compounds.

Compounds of formula I which have at least one basic centre can form, for example, acid addition salts, for example with strong inorganic acids such as mineral acids, for example perchloric acid, sulfuric acid, nitric acid, nitrose acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. Compounds of formula I which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine.

The alkyl groups occurring in the definitions of the substituents can be straight-chain or branched and are, for example, methyl, ethyl, n-propyl, isopropyl, n-butyl, sec-butyl, iso-butyl, tert-butyl, pentyl, hexyl, nonyl, decyl and their branched isomers. Alkylsulfanyl, alkylsulfinyl, alkylsulfonyl, alkoxy, alkenyl and alkynyl radicals are derived from the alkyl radicals mentioned. The alkenyl and alkynyl groups can be mono- or polyunsaturated.

Halogen is generally fluorine, chlorine, bromine or iodine. This also applies, correspondingly, to halogen in combination with other meanings, such as haloalkyl or halophenyl.

Haloalkyl groups preferably have a chain length of from 1 to 6 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl.

Alkoxy groups preferably have a preferred chain length of from 1 to 6 carbon atoms. Alkoxy is, for example, methoxy, ethoxy, propoxy, i-propoxy, n-butoxy, isobutoxy, sec-butoxy and tert-butoxy and also the isomeric pentyloxy and hexyloxy radicals; preferably methoxy and ethoxy.

Alkoxyalkyl groups preferably have a chain length of 1 to 6 carbon atoms.

Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

Alkylsulfanyl is for example methylsulfanyl, ethylsulfanyl, propylsulfanyl, isopropylsulfanyl, butylsulfanyl, pentylsulfanyl, and hexylsulfanyl.

Alkylsulfinyl is for example methylsulfinyl, ethylsulfinyl, propylsulfinyl, isopropylsulfinyl, a butylsulfinyl, pentylsulfinyl, and hexylsulfinyl.

Alkylsulfonyl is for example methylsulfonyl, ethylsulfonyl, propylsulfonyl, isopropylsulfonyl, butylsulfonyl, pentylsulfonyl, and hexylsulfonyl.

The cycloalkyl groups preferably have from 3 to 6 ring carbon atoms, for example cyclopropyl, cyclobutyl, cyclopentyl and cyclohexyl.

Haloalkoxy groups preferably have a chain length of from 1 to 4 carbon atoms. Haloalkoxy is, for example, difluoromethoxy, trifluoromethoxy or 2,2,2-trifluoroethoxy.

Haloalkylsulfanyl groups preferably have a chain length of from 1 to 4 carbon atoms. Haloalkylsulfanyl is, for example, difluoromethylsulfanyl, trifluoromethylsulfanyl or 2,2,2-trifluoroethylsulfanyl. Similar considerations apply to the radicals $C_1$-$C_4$haloalkylsulfinyl and $C_1$-$C_4$haloalkylsulfonyl, which may be, for example, trifluoromethylsulfinyl, trifluoromethylsulfonyl or 2,2,2-trifluoroethylsulfonyl.

In the context of this invention "mono- to polysubstituted" in the definition of the substituents, means typically, depending on the chemical structure of the substituents, monosubstituted to seven-times substituted, preferably monosubstituted to five-times substituted, more preferably mono-, double- or triple-substituted.

In the context of this invention "$L_1$, $L_2$, $L_3$ and $L_4$ form together with the two carbon atoms to which $L_1$ and $L_4$ are attached or to which $L_1$ and $L_3$ are attached when $L_4$ is a bond, an aromatic or partially saturated carbocyclic ring system", the carbocyclic ring system is preferably a group having 5 to 6 ring carbon atoms which are unsaturated or partially saturated, for example, but are not limited to phenyl and cyclohexenyl.

In the context of this invention "$L_1$, $L_2$, $L_3$ and $L_4$ form together with the two carbon atoms to which $L_1$ and $L_4$ are attached or to which $L_1$ and $L_3$ are attached when $L_4$ is a bond, an aromatic or partially saturated heterocyclic ring system", the heterocyclic ring system is preferably a group comprising 1 to 3 heteroatoms in the ring, which are unsaturated or partially saturated, for example, but are not limited to pyrrolyl; pyrazolyl; isoxazolyl; furanyl; thienyl; imidazolyl; oxazolyl; thiazolyl; isothiazolyl; triazolyl; oxadiazolyl; thiadiazolyl; tetrazolyl; furyl; pyridyl; pyrimidyl; pyrazinyl; pyridazinyl; triazinyl; pyranyl; pyrrolidinyl, piperidinyl; pyrrolidinyl-2-one; piperidinyl-2-one.

m is 1 or 2, depending on the hybridization of the carbon atom.

If m is 2 in the definition $C(R_{10a})_m$, $R_{10a}$ can be the same or different; for example one $R_{10a}$ can be hydrogen and the other methyl. This is also valid for the definitions of $C(R_{10b})_m$, $C(R_{10c})_m$ and $C(R_{10d})_m$.

The compounds of formula I according to the invention also include hydrates which may be formed during the salt formation.

Free radicals represents methyl groups.

In preferred compounds of formula I, $R_7$ is selected from the group consisting of $J_1$ to $J_{16}$ (where the arrow represents the point of attachment of the group J to the triazole ring which contains the group $R_8$), and wherein A, X and $R_1$ are as defined above,

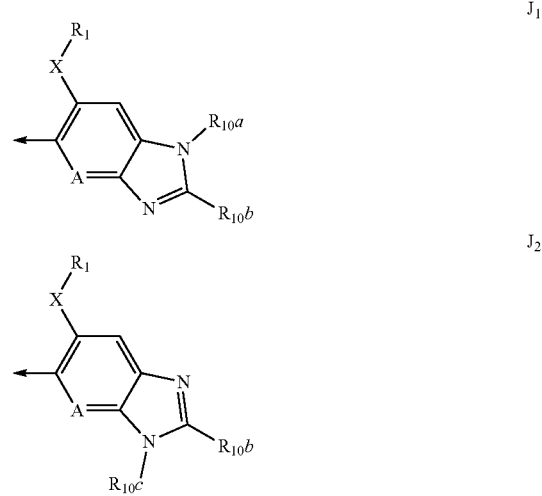

-continued
J₃
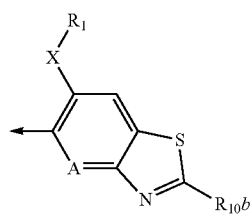
J₄
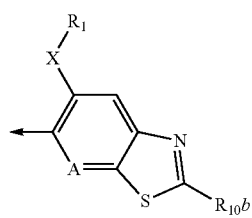
J₅
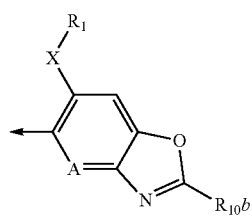
J₆
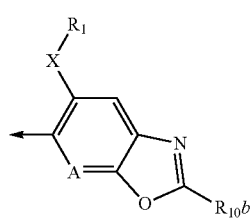
J₇
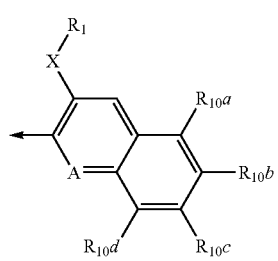
J₈
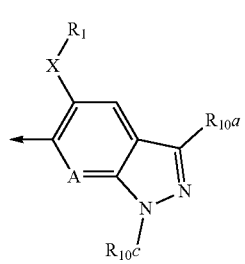
J₉
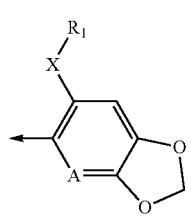
-continued
J₁₀
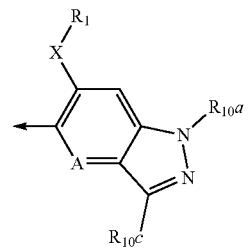
J₁₁
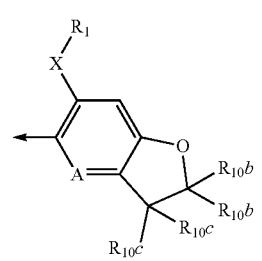
J₁₂
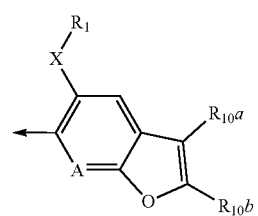
J₁₃
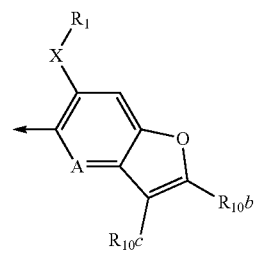
J₁₄
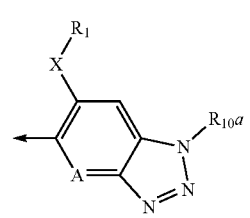
J₁₅
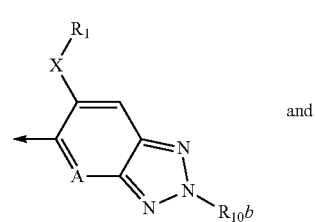
and -continued

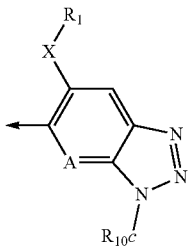
J$_{16}$ in particular selected from J$_1$ to J$_4$ and J$_7$ or J$_{11}$;

wherein each group J$_1$ to J$_{16}$ preferably is mono or disubstituted with R$_{10a}$, R$_{10b}$, R$_{10c}$ and R$_{10d}$, wherein R$_{10a}$, R$_{10b}$, R$_{10c}$ and R$_{10d}$ are independently selected from hydrogen, halogen, cyano, amino, C$_3$-C$_6$cycloalkyl, C$_1$-C$_6$ haloalkyl, C$_1$-C$_6$alkoxy, C$_1$-C$_4$alkoxyC$_1$-C$_4$alkyl, C$_1$-C$_6$ haloalkoxy, C$_1$-C$_6$alkylthio, C$_1$-C$_6$alkylsulfinyl, C$_1$-C$_6$ alkylsulfonyl, C$_1$-C$_6$haloalkylthio, C$_1$-C$_6$haloalkylsulfinyl or C$_1$-C$_6$haloalkylsulfonyl.

A preferred group of compounds of formula I is represented by the compounds of formula I-1a

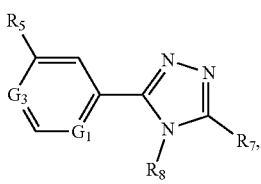
(I-1a)

wherein R$_7$ is

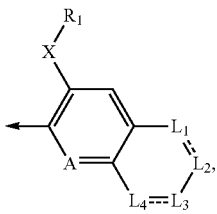
(R$_7$)

and X, A, R$_1$, R$_5$, R$_8$, G$_1$, G$_3$, L$_1$, L$_2$, L$_3$ and L$_4$ are as defined under formula I above, and wherein the arrow denotes the point of attachment to the triazole ring which contains the group R$_8$.

EMBODIMENT (A1)

Preferred are compounds of formula I-1a, wherein
A is C—H or N;
G$_1$ is nitrogen or CR$_2$;
G$_3$ is nitrogen or CR$_4$;
X is S, S(O) or SO$_2$;
R$_1$ is C$_1$-C$_4$alkyl, C$_3$-C$_6$cycloalkyl-C$_1$-C$_4$alkyl or C$_3$-C$_6$cycloalkyl;
R$_8$ is C$_1$-C$_4$alkyl which can be mono- or polysubstituted by substituents selected from halogen, C$_1$-C$_4$ haloalkylsulfanyl, C$_1$-C$_4$haloalkylsulfinyl and C$_1$-C$_4$haloalkylsulfonyl;

R$_2$, R$_4$ and R$_5$ are, independently from each other, hydrogen, halogen, C$_1$-C$_4$haloalkyl, C$_1$-C$_4$haloalkyl substituted by one or two cyano or methoxy; or R$_2$, R$_4$ and R$_5$ are, independently from each other, C$_1$-C$_4$haloalkylsulfanyl, C$_1$-C$_4$haloalkylsulfinyl, C$_1$-C$_4$ haloalkylsulfonyl, C$_1$-C$_4$haloalkoxy, SF$_5$, phenylcarbonylthio, cyano, mercapto, C$_1$-C$_4$alkoxycarbonyl, C$_1$-C$_4$ alkylcarbonyl or —C(O)C$_1$-C$_4$haloalkyl; or R$_2$, R$_4$ and R$_5$ are, independently from each other, C$_3$-C$_6$cycloalkyl which can be mono- or polysubstituted by substituents selected from the group consisting of halogen, cyano, C$_1$-C$_4$ haloalkyl and C$_1$-C$_4$alkyl;

L$_1$, L$_2$, L$_3$ and L$_4$ are as defined under formula I above; and

R$_{10a}$, R$_{10b}$, R$_{10c}$ and R$_{10d}$, independently from each other, are hydrogen, halogen, nitro, cyano, hydroxyl, C$_1$-C$_6$alkyl, C$_2$-C$_6$alkenyl, C$_2$-C$_6$alkynyl, C$_3$-C$_6$cycloalkyl, C$_3$-C$_6$ cycloalkyl-C$_1$-C$_4$ cycloalkyl, C$_1$-C$_6$haloalkyl, C$_2$-C$_6$ haloalkenyl, C$_2$-C$_6$haloalkynyl, C$_3$-C$_6$halocycloalkyl, C$_3$-C$_6$ cyclohaloalkyl-C$_1$-C$_4$ cycloalkyl, C$_1$-C$_6$alkoxy, C$_1$-C$_4$ alkoxyC$_1$-C$_4$alkyl, C$_1$-C$_6$haloalkoxy, C$_1$-C$_4$alkylthio, C$_1$-C$_4$ alkylsulfinyl, C$_1$-C$_4$alkylsulfonyl, C$_1$-C$_4$haloalkylthio, C$_1$-C$_4$haloalkylsulfinyl, C$_1$-C$_4$haloalkylsulfonyl, C$_2$-C$_4$ alkylcarbonyl, C$_2$-C$_6$alkoxycarbonyl or —SF$_5$; additionally one of R$_{10a}$, R$_{10b}$, R$_{10c}$ and R$_{10d}$ can be oxo.

EMBODIMENT (A2)

Further preferred are compounds of formula I-1a

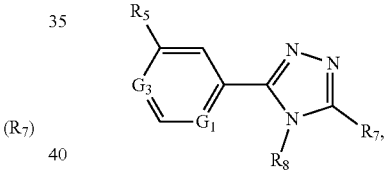
(I-1a)

wherein R$_7$ is selected from the group consisting of J$_1$ to J$_{16}$ (where the arrow represents the point of attachment of the group J to the triazole ring which contains the group R$_8$),

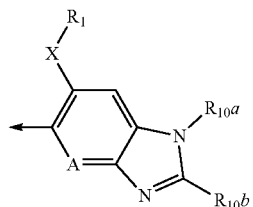
J$_1$

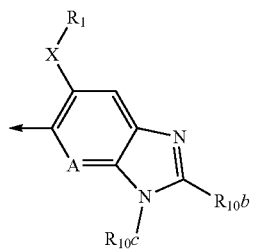
J$_2$

J₃
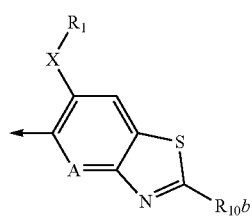
J₄
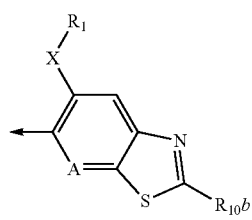
J₅
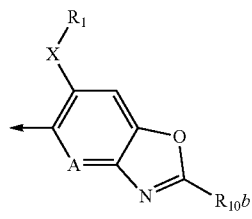
J₆
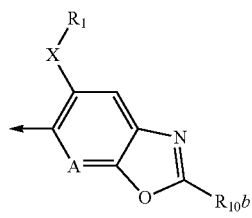
J₇
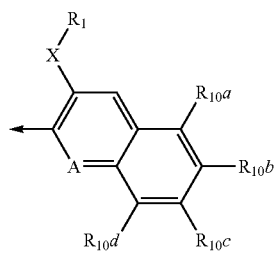
J₈
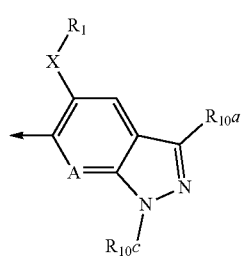
J₉
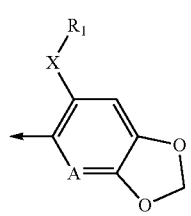
J₁₀
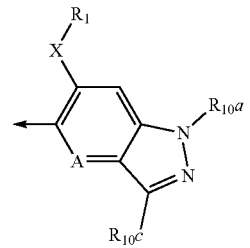
J₁₁
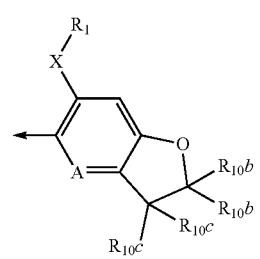
J₁₂
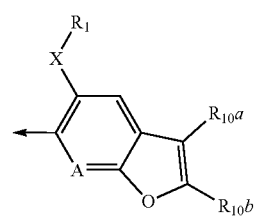
J₁₃
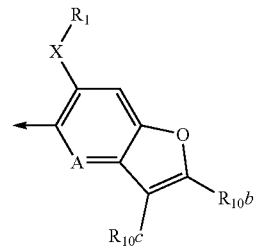
J₁₄
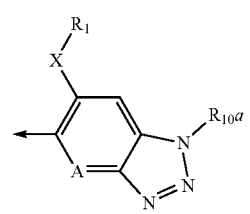
J₁₅
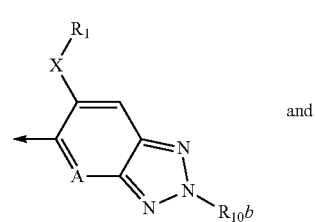
and -continued

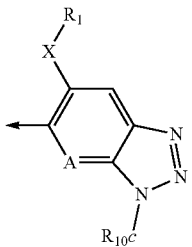

and A, X, $G_1$, $G_3$, $R_1$, $R_5$, $R_8$, $R_{10a}$, $R_{10b}$, $R_{10c}$ and $R_{10d}$ are as defined under Embodiment (A1).

EMBODIMENT (A3)

Further preferred are compounds of formula I-1a

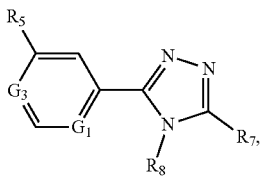

(I-1a)

wherein $R_7$ is as defined under Embodiment (A2) above and

A is C—H or N;
$G_1$ is nitrogen or $CR_2$;
$G_3$ is nitrogen or $CR_4$;
X is S, S(O) or $SO_2$;
$R_1$ is $C_1$-$C_4$alkyl;
$R_8$ is $C_1$-$C_4$alkyl;
$R_2$, $R_4$ and $R_5$ are, independently from each other, hydrogen, halogen or $C_1$-$C_4$haloalkyl; or
$R_2$, $R_4$ and $R_5$ are, independently from each other, $C_1$-$C_4$haloalkylsulfanyl, $C_1$-$C_4$haloalkylsulfinyl, $C_1$-$C_4$haloalkylsulfonyl, $C_1$-$C_4$haloalkoxy or cyano; and
$R_{10a}$, $R_{10b}$, $R_{10c}$ and $R_{10d}$, independently from each other, are hydrogen, halogen, nitro, cyano, hydroxyl, $C_1$-$C_6$alkyl, $C_2$-$C_6$alkenyl, $C_2$-$C_6$alkynyl, $C_3$-$C_6$cycloalkyl, $C_3$-$C_6$cycloalkyl-$C_1$-$C_4$ cycloalkyl, $C_1$-$C_6$haloalkyl, $C_2$-$C_6$haloalkenyl, $C_2$-$C_6$haloalkynyl, $C_3$-$C_6$halocycloalkyl, $C_3$-$C_6$cyclohaloalkyl-$C_1$-$C_4$ cycloalkyl, $C_1$-$C_6$alkoxy, $C_1$-$C_4$alkoxy$C_1$-$C_4$alkyl, $C_1$-$C_6$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl, $C_1$-$C_4$haloalkylsulfonyl, $C_2$-$C_4$alkylcarbonyl or $C_2$-$C_6$alkoxycarbonyl.

EMBODIMENT (A4)

Further preferred are compounds of formula I-1a

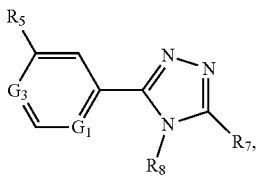

(I-1a)

wherein $R_7$ is as defined under Embodiment (A2) above and

A is C—H or N;
$G_1$ is nitrogen or $CR_2$;
$G_3$ is nitrogen or $CR_4$;
X is S, S(O) or $SO_2$;
$R_1$ is $C_1$-$C_4$alkyl;
$R_8$ is $C_1$-$C_4$alkyl;
$R_2$, $R_4$ and $R_5$ are, independently from each other, hydrogen, $C_1$-$C_4$haloalkyl, $C_1$-$C_4$haloalkylsulfanyl, $C_1$-$C_4$haloalkylsulfinyl, $C_1$-$C_4$haloalkylsulfonyl, $C_1$-$C_4$haloalkoxy or cyano; and
$R_{10a}$, $R_{10b}$, $R_{10c}$ and $R_{10d}$, independently from each other, are hydrogen, halogen, nitro, cyano, hydroxyl, $C_1$-$C_6$alkyl, $C_2$-$C_6$alkenyl, $C_2$-$C_6$alkynyl, $C_3$-$C_6$cycloalkyl, $C_3$-$C_6$cycloalkyl-$C_1$-$C_4$ cycloalkyl, $C_1$-$C_6$haloalkyl, $C_2$-$C_6$haloalkenyl, $C_2$-$C_6$haloalkynyl, $C_3$-$C_6$halocycloalkyl, $C_3$-$C_6$cyclohaloalkyl-$C_1$-$C_4$ cycloalkyl, $C_1$-$C_6$alkoxy, $C_1$-$C_4$alkoxy$C_1$-$C_4$alkyl, $C_1$-$C_6$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl, $C_1$-$C_4$haloalkylsulfonyl, $C_2$-$C_4$alkylcarbonyl or $C_2$-$C_6$alkoxycarbonyl.

EMBODIMENT (A5)

Further preferred are compounds of formula I-1a

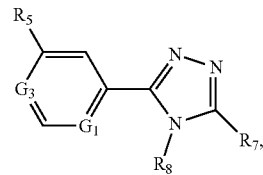

(I-1a)

wherein $R_7$ is as defined under Embodiment (A2) above and

A is C—H or N;
$G_1$ is nitrogen or $CR_2$;
$G_3$ is nitrogen or $CR_4$;
X is S, S(O) or $SO_2$;
$R_1$ is $C_1$-$C_4$alkyl;
$R_8$ is $C_1$-$C_4$alkyl;
$R_2$, $R_4$ and $R_5$ are, independently from each other, hydrogen or $C_1$-$C_4$haloalkyl; and
$R_{10a}$, $R_{10b}$, $R_{10c}$ and $R_{10d}$, independently from each other, are hydrogen, halogen, cyano, $C_1$-$C_6$alkyl, $C_3$-$C_6$cycloalkyl, $C_3$-$C_6$cycloalkyl-$C_1$-$C_4$ cycloalkyl, $C_1$-$C_6$haloalkyl, $C_3$-$C_6$halocycloalkyl, $C_3$-$C_6$cyclohaloalkyl-$C_1$-$C_4$ cycloalkyl, $C_1$-$C_6$alkoxy, $C_1$-$C_4$alkoxy$C_1$-$C_4$alkyl, $C_1$-$C_6$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl or $C_1$-$C_4$haloalkylsulfonyl.

EMBODIMENT (A6)

Further preferred are compounds of formula I-1a

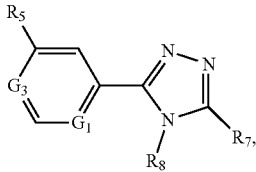
(I-1a)

wherein R$_7$ is as defined under Embodiment (A2) above and

A is C—H or N;
G$_1$ is nitrogen and G$_3$ is CR$_4$; or
G$_1$ and G$_3$ are nitrogen; or
G$_3$ is nitrogen and G$_1$ is CR$_2$;
X is S, S(O) or SO$_2$;
R$_1$ is C$_1$-C$_4$alkyl;
R$_8$ is C$_1$-C$_4$alkyl;
R$_2$ and R$_4$ are, independently from each other, hydrogen or C$_1$-C$_4$haloalkyl;
R$_5$ is C$_1$-C$_4$haloalkyl; and
R$_{10a}$, R$_{10b}$, R$_{10c}$, and R$_{10d}$, independently from each other, are hydrogen, halogen, cyano, C$_1$-C$_6$alkyl, C$_3$-C$_6$cycloalkyl, C$_3$-C$_6$cycloalkyl-C$_1$-C$_4$ cycloalkyl, C$_1$-C$_6$haloalkyl, C$_3$-C$_6$halocycloalkyl, C$_3$-C$_6$cyclohaloalkyl-C$_1$-C$_4$ cycloalkyl, C$_1$-C$_6$alkoxy, C$_1$-C$_4$alkoxyC$_1$-C$_4$alkyl, C$_1$-C$_6$haloalkoxy, C$_1$-C$_4$alkylthio, C$_1$-C$_4$alkylsulfinyl, C$_1$-C$_4$alkylsulfonyl, C$_1$-C$_4$haloalkylthio, C$_1$-C$_4$haloalkylsulfinyl or C$_1$-C$_4$haloalkylsulfonyl.

EMBODIMENT (A7)

Further preferred are compounds of formula I-1a

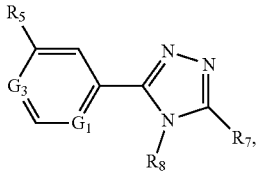
(I-1a)

wherein R$_7$ is as defined under Embodiment (A2) above and

A is C—H or N;
G$_1$ is nitrogen and G$_3$ is CR$_4$; or
G$_1$ and G$_3$ are nitrogen; or
G$_3$ is nitrogen and G$_1$ is CR$_2$;
X is S, S(O) or SO$_2$;
R$_1$ is ethyl;
R$_8$ is methyl;
R$_2$ and R$_4$ are hydrogen;
R$_5$ is trifluoromethyl; and
R$_{10a}$, R$_{10b}$, R$_{10c}$, and R$_{10d}$, independently from each other, are hydrogen, halogen, cyano, C$_1$-C$_6$alkyl, C$_3$-C$_6$cycloalkyl, C$_3$-C$_6$cycloalkyl-C$_1$-C$_4$ cycloalkyl, C$_1$-C$_6$haloalkyl, C$_3$-C$_6$halocycloalkyl, C$_3$-C$_6$cyclohaloalkyl-C$_1$-C$_4$ cycloalkyl, C$_1$-C$_6$alkoxy, C$_1$-C$_4$alkoxyC$_1$-C$_4$alkyl, C$_1$-C$_6$haloalkoxy, C$_1$-C$_4$alkylthio, C$_1$-C$_4$alkylsulfinyl, C$_1$-C$_4$alkylsulfonyl, C$_1$-C$_4$haloalkylthio, C$_1$-C$_4$haloalkylsulfinyl or C$_1$-C$_4$haloalkylsulfonyl.

EMBODIMENT (A8)

Further preferred are compounds of formula I-1a

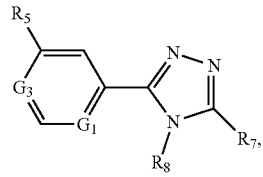
(I-1a)

wherein R$_7$ is selected from the group consisting of J$_1$ to J$_4$, J$_7$, J$_{11}$ and J$_{14}$ to J$_{16}$;

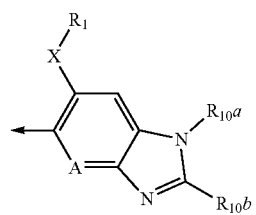
J$_1$

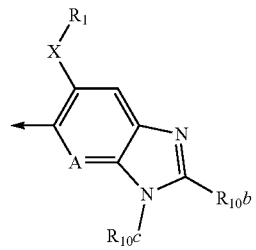
J$_2$

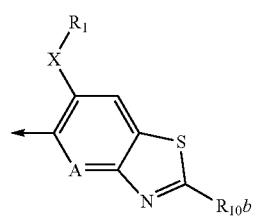
J$_3$

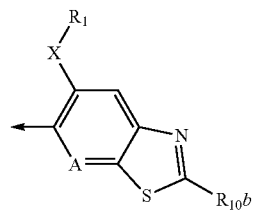
J$_4$

-continued

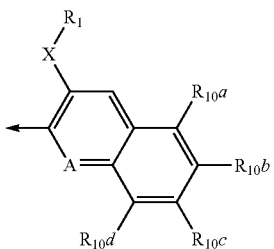

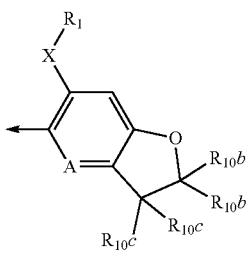

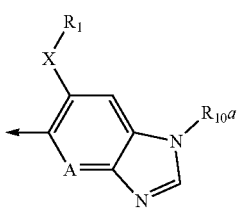

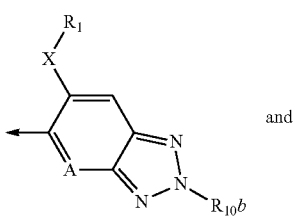

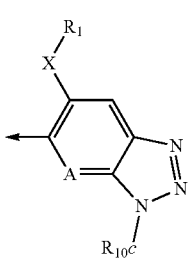

in particular selected from the group consisting of $J_1$ to $J_4$, $J_7$ and $J_{11}$; and
wherein
A is C—H or N;
$G_1$ is nitrogen and $G_3$ is $CR_4$; or
$G_1$ and $G_3$ are nitrogen; or
$G_3$ is nitrogen and $G_1$ is $CR_2$;
X is S, S(O) or $SO_2$;
$R_1$ is ethyl;
$R_8$ is methyl;
$R_2$ and $R_4$ are hydrogen;
$R_5$ is trifluoromethyl; and
$R_{10a}$, $R_{10b}$, $R_{10c}$ and $R_{10d}$, independently from each other, are hydrogen, halogen, cyano, $C_1$-$C_6$alkyl, $C_3$-$C_6$cycloalkyl, $C_3$-$C_6$cycloalkyl-$C_1$-$C_4$ cycloalkyl, $C_1$-$C_6$haloalkyl, $C_3$-$C_6$halocycloalkyl, $C_3$-$C_6$cyclohaloalkyl-$C_1$-$C_4$ cycloalkyl, $C_1$-$C_6$alkoxy, $C_1$-$C_4$alkoxy$C_1$-$C_4$alkyl, $C_1$-$C_6$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl or $C_1$-$C_4$haloalkylsulfonyl.

EMBODIMENT (A9)

Further preferred are compounds of formula I-1a

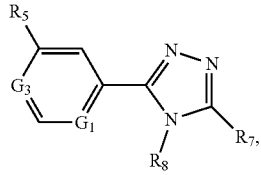

(I-1a)

wherein $R_7$ is selected from the group consisting of $J_1$, $J_3$, $J_4$, $J_7$, $J_{11}$ and $J_{14}$ to $J_{16}$;

$J_1$

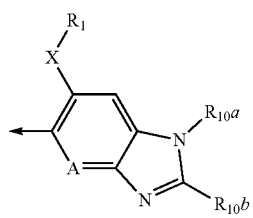

$J_3$

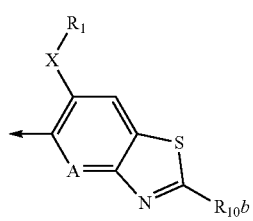

$J_4$

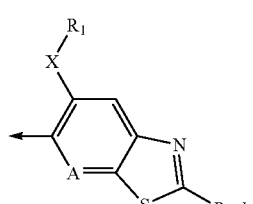

$J_7$

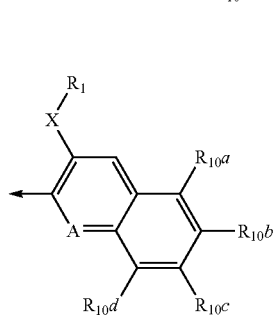

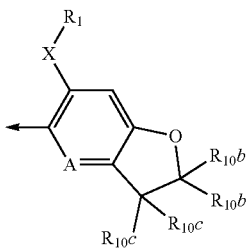

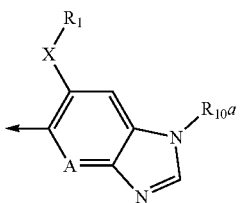

and

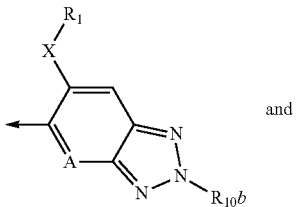

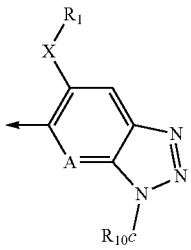

wherein
A is C—H or N;
$G_1$ is nitrogen and $G_3$ is $CR_4$; or
$G_1$ and $G_3$ are nitrogen;
X is S or $SO_2$;
$R_1$ is ethyl;
$R_8$ is methyl;
$R_4$ is hydrogen;
$R_5$ is trifluoromethyl; and
$R_{10a}$, $R_{10b}$, $R_{10c}$ and $R_{10d}$, independently from each other, are hydrogen, $C_1$-$C_6$alkyl, $C_1$-$C_6$haloalkyl or $C_1$-$C_4$alkoxy$C_1$-$C_4$alkyl.

Another preferred group of compounds of formula I is represented by the compounds of formula I-1c

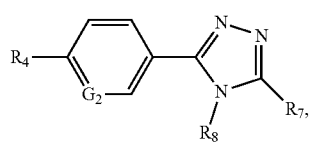
(I-1c)

wherein $R_7$ is

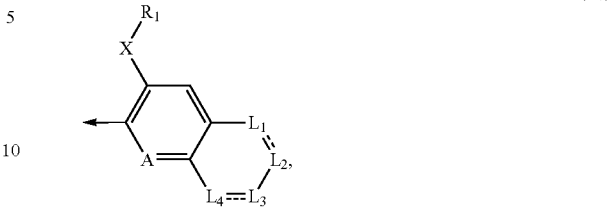
(R7)

and X, A, $R_1$, $R_4$, $R_8$, $G_2$, $L_1$, $L_2$, $L_3$ and $L_4$ are as defined under formula I above, and wherein the arrow denotes the point of attachment to the triazole ring which contains the group $R_8$.

EMBODIMENT (B1)

Preferred are compounds of formula I-1c, wherein
A is C—H or N;
$G_2$ is nitrogen or $CR_3$;
X is S, S(O) or $SO_2$;
$R_1$ is $C_1$-$C_4$alkyl, $C_3$-$C_6$cycloalkyl-$C_1$-$C_4$alkyl or $C_3$-$C_6$cycloalkyl;
$R_8$ is $C_1$-$C_4$alkyl which can be mono- or polysubstituted by substituents selected from halogen, $C_1$-$C_4$ haloalkylsulfanyl, $C_1$-$C_4$haloalkylsulfinyl and $C_1$-$C_4$haloalkylsulfonyl;
$R_3$ and $R_4$ are, independently from each other, hydrogen, halogen, $C_1$-$C_4$haloalkyl, $C_1$-$C_4$haloalkyl substituted by one or two cyano or methoxy; or
$R_3$ and $R_4$ are, independently from each other, $C_1$-$C_4$haloalkylsulfanyl, $C_1$-$C_4$haloalkylsulfinyl, $C_1$-$C_4$ haloalkylsulfonyl, $C_1$-$C_4$haloalkoxy, $SF_5$, phenylcarbonylthio, cyano, mercapto, $C_1$-$C_4$alkoxycarbonyl, $C_1$-$C_4$ alkylcarbonyl or —C(O)$C_1$-$C_4$haloalkyl; or
$R_3$ and $R_4$ are, independently from each other, $C_3$-$C_6$cycloalkyl which can be mono- or polysubstituted by substituents selected from the group consisting of halogen, cyano, $C_1$-$C_4$ haloalkyl and $C_1$-$C_4$alkyl; $L_1$, $L_2$, $L_3$ and $L_4$ are as defined under formula I above; and
$R_{10a}$, $R_{10b}$, $R_{10c}$ and $R_{10d}$, independently from each other, are hydrogen, halogen, nitro, cyano, hydroxyl, $C_1$-$C_6$alkyl, $C_2$-$C_6$alkenyl, $C_2$-$C_6$alkynyl, $C_3$-$C_6$cycloalkyl, $C_3$-$C_6$ cycloalkyl-$C_1$-$C_4$ cycloalkyl, $C_1$-$C_6$haloalkyl, $C_2$-$C_6$ haloalkenyl, $C_2$-$C_6$haloalkynyl, $C_3$-$C_6$halocycloalkyl, $C_3$-$C_6$ cyclohaloalkyl-$C_1$-$C_4$ cycloalkyl, $C_1$-$C_6$alkoxy, $C_1$-$C_4$ alkoxy$C_1$-$C_4$alkyl, $C_1$-$C_6$haloalkoxy, $C_1$-$C_4$alkylthio, $C_1$-$C_4$ alkylsulfinyl, $C_1$-$C_4$alkylsulfonyl, $C_1$-$C_4$haloalkylthio, $C_1$-$C_4$haloalkylsulfinyl, $C_1$-$C_4$haloalkylsulfonyl, $C_2$-$C_4$ alkylcarbonyl, $C_2$-$C_6$alkoxycarbonyl or —$SF_5$; additionally one of $R_{10a}$, $R_{10b}$, $R_{10c}$ and $R_{10d}$ can be oxo.

EMBODIMENT (B2)

Further preferred are compounds of formula I-1c

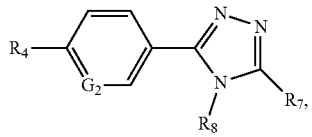
(I-1c)

wherein R$_7$ is selected from the group consisting of J$_1$ to J$_{16}$ (where the arrow represents the point of attachment of the group J to the triazole ring which contains the group R$_8$),
J$_1$
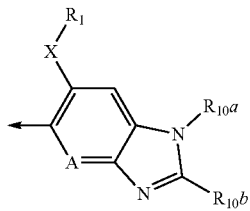
J$_2$
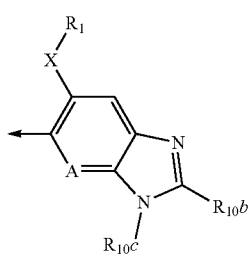
J$_3$
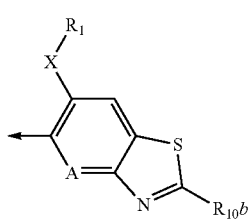
J$_4$
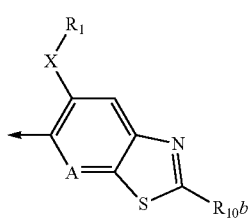
J$_5$
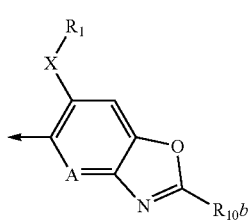
J$_6$
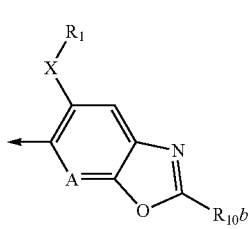
J$_7$
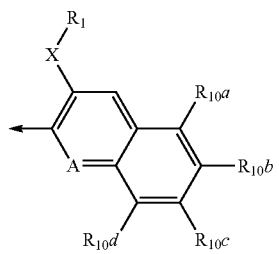
J$_8$
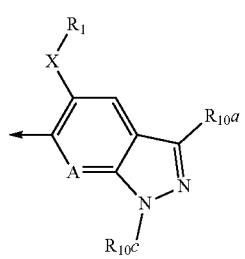
J$_9$
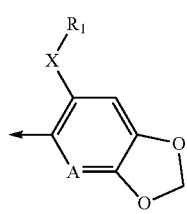
J$_{10}$
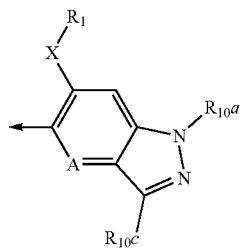
J$_{11}$
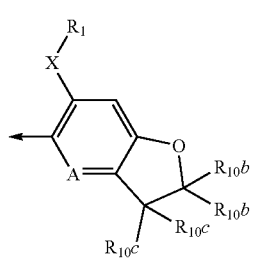
J$_{12}$
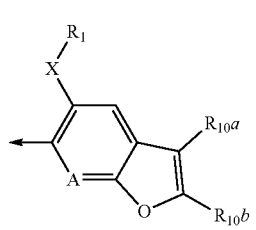

-continued

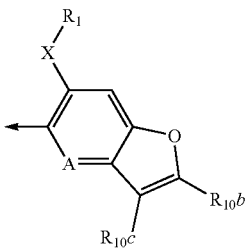
J13

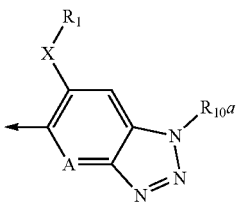
J14

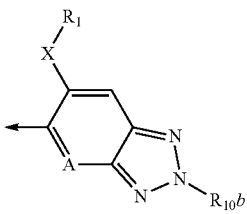
and
J15

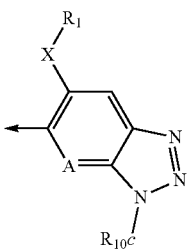
J16 and A, X, G₂, R₁, R₄, R₈, R$_{10a}$, R$_{10b}$, R$_{10c}$ and R$_{10d}$ are as defined under Embodiment (B1).

EMBODIMENT (B3)

Further preferred are compounds of formula I-1c

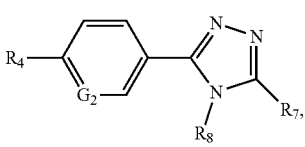
(I-1c)

wherein $R_7$ is as defined under Embodiment (B2) above and
A is C—H or N;
G₂ is nitrogen or CR₃;
X is S, S(O) or SO₂;
R₁ is C₁-C₄alkyl;
R₈ is C₁-C₄alkyl;
R₃ and R₄ are, independently from each other, hydrogen, halogen or C₁-C₄haloalkyl; or
R₃ and R₄ are, independently from each other, C₁-C₄haloalkylsulfanyl, C₁-C₄haloalkylsulfinyl, C₁-C₄haloalkylsulfonyl, C₁-C₄haloalkoxy or cyano; and R$_{10a}$, R$_{10b}$, R$_{10c}$ and R$_{10d}$, independently from each other, are hydrogen, halogen, nitro, cyano, hydroxyl, C₁-C₆alkyl, C₂-C₆alkenyl, C₂-C₆alkynyl, C₃-C₆cycloalkyl, C₃-C₆cycloalkyl-C₁-C₄ cycloalkyl, C₁-C₆haloalkyl, C₂-C₆haloalkenyl, C₂-C₆haloalkynyl, C₃-C₆halocycloalkyl, C₃-C₆cyclohaloalkyl-C₁-C₄ cycloalkyl, C₁-C₆alkoxy, C₁-C₄alkoxyC₁-C₄alkyl, C₁-C₆haloalkoxy, C₁-C₄alkylthio, C₁-C₄alkylsulfinyl, C₁-C₄alkylsulfonyl, C₁-C₄halo- alkylthio, C₁-C₄haloalkylsulfinyl, C₁-C₄haloalkylsulfonyl, C₂-C₄alkylcarbonyl or C₂-C₆alkoxycarbonyl.

EMBODIMENT (B4)

Further preferred are compounds of formula I-1c

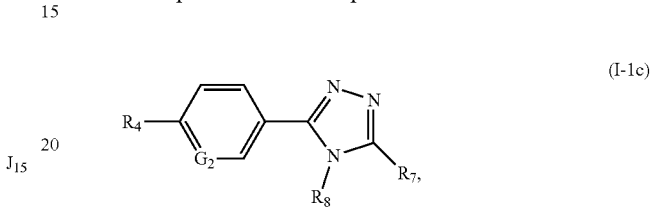
(I-1c)

wherein $R_7$ is as defined under Embodiment (B2) above and
A is C—H or N;
G₂ is nitrogen or CR₃;
X is S, S(O) or SO₂;
R₁ is C₁-C₄alkyl;
R₈ is C₁-C₄alkyl;
R₃ and R₄ are, independently from each other, hydrogen, C₁-C₄haloalkyl, C₁-C₄haloalkylsulfanyl, C₁-C₄haloalkylsulfinyl, C₁-C₄haloalkylsulfonyl, C₁-C₄haloalkoxy or cyano; and
R$_{10a}$, R$_{10b}$, R$_{10c}$ and R$_{10d}$, independently from each other, are hydrogen, halogen, nitro, cyano, hydroxyl, C₁-C₆alkyl, C₂-C₆alkenyl, C₂-C₆alkynyl, C₃-C₆cycloalkyl, C₃-C₆cycloalkyl-C₁-C₄ cycloalkyl, C₁-C₆haloalkyl, C₂-C₆haloalkenyl, C₂-C₆haloalkynyl, C₃-C₆halocycloalkyl, C₃-C₆cyclohaloalkyl-C₁-C₄ cycloalkyl, C₁-C₆alkoxy, C₁-C₄alkoxyC₁-C₄alkyl, C₁-C₆haloalkoxy, C₁-C₄alkylthio, C₁-C₄alkylsulfinyl, C₁-C₄alkylsulfonyl, C₁-C₄haloalkylthio, C₁-C₄haloalkylsulfinyl, C₁-C₄haloalkylsulfonyl, C₂-C₄alkyl- carbonyl or C₂-C₆alkoxycarbonyl.

EMBODIMENT (B5)

Further preferred are compounds of formula I-1c

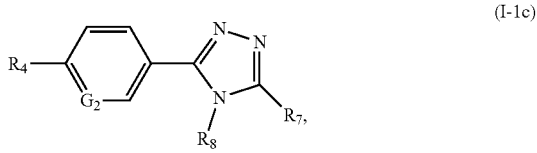
(I-1c)

wherein $R_7$ is as defined under Embodiment (B2) above and
A is C—H or N;
G₂ is nitrogen or CR₃;
X is S, S(O) or SO₂;
R₁ is C₁-C₄alkyl;
R₈ is C₁-C₄alkyl;

$R_3$ and $R_4$ are, independently from each other, hydrogen or $C_1$-$C_4$haloalkyl; and $R_{10a}$, $R_{10b}$, $R_{10c}$ and $R_{10d}$, independently from each other, are hydrogen, halogen, cyano, $C_1$-$C_6$alkyl, $C_3$-$C_6$cycloalkyl, $C_3$-$C_6$cycloalkyl-$C_1$-$C_4$ cycloalkyl, $C_1$-$C_6$haloalkyl, $C_3$-$C_6$halocycloalkyl, $C_3$-$C_6$cyclohaloalkyl-$C_1$-$C_4$ cycloalkyl, $C_1$-$C_6$alkoxy, $C_1$-$C_4$alkoxyC_1$-$C_4$alkyl, $C_1$-$C_6$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl or $C_1$-$C_4$haloalkylsulfonyl.

EMBODIMENT (B6)

Further preferred are compounds of formula I-1c

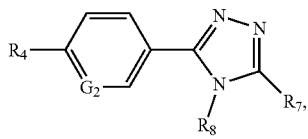

(I-1c)

wherein $R_7$ is as defined under Embodiment (B2) above and

A is C—H or N;
$G_2$ is nitrogen or $CR_3$;
X is S, S(O) or $SO_2$;
$R_1$ is ethyl;
$R_8$ is methyl;
$R_3$ is hydrogen;
$R_4$ is trifluoromethyl; and
$R_{10a}$, $R_{10b}$, $R_{10c}$, and $R_{10d}$, independently from each other, are hydrogen, halogen, cyano, $C_1$-$C_6$alkyl, $C_3$-$C_6$cycloalkyl, $C_3$-$C_6$cycloalkyl-$C_1$-$C_4$ cycloalkyl, $C_1$-$C_6$haloalkyl, $C_3$-$C_6$halocycloalkyl, $C_3$-$C_6$cyclohaloalkyl-$C_1$-$C_4$ cycloalkyl, $C_1$-$C_6$alkoxy, $C_1$-$C_4$alkoxyC_1$-$C_4$alkyl, $C_1$-$C_6$ haloalkoxy, $C_1$-$C_4$alkylthio, $C_1$-$C_4$alkylsulfinyl, $C_1$-$C_4$ alkylsulfonyl, $C_1$-$C_4$haloalkylthio, $C_1$-$C_4$haloalkylsulfinyl or $C_1$-$C_4$haloalkylsulfonyl.

EMBODIMENT (B7)

Further preferred are compounds of formula I-1c

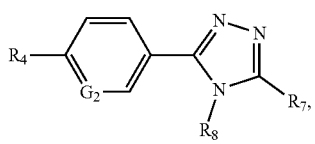

(I-1c)

wherein $R_7$ is selected from the group consisting of $J_1$ to $J_4$, $J_7$, $J_{11}$ and $J_{14}$ to $J_{16}$;

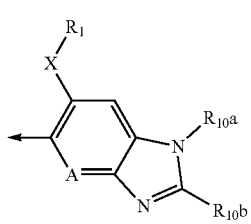

$J_1$

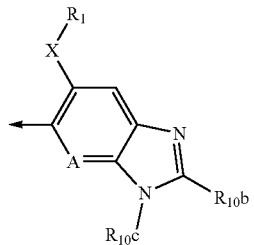

$J_2$

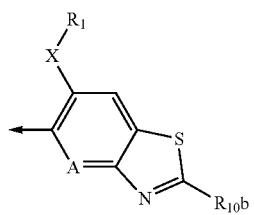

$J_3$

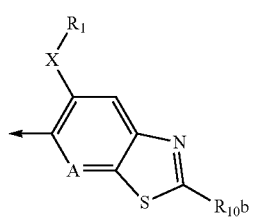

$J_4$

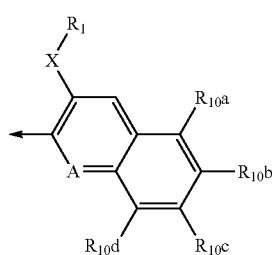

$J_7$

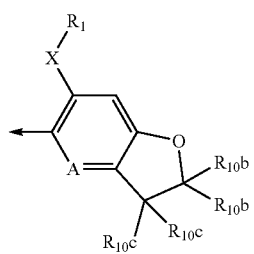

$J_{11}$

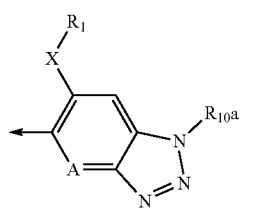

$J_{14}$

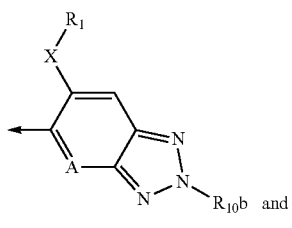

J_{15}

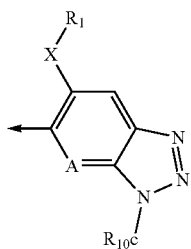

J_{16} and wherein

A is C—H or N;
$G_2$ is nitrogen or $CR_3$;
X is S, S(O) or $SO_2$;
$R_1$ is ethyl;
$R_8$ is methyl;
$R_3$ is hydrogen;
$R_4$ is trifluoromethyl; and
$R_{10a}$, $R_{10b}$, $R_{10c}$ and $R_{10d}$, independently from each other, are hydrogen, halogen, cyano, $C_1$-$C_6$alkyl, $C_3$-$C_6$cycloalkyl, $C_3$-$C_6$cycloalkyl-$C_1$-$C_4$ cycloalkyl, $C_1$-$C_6$haloalkyl, $C_3$-$C_6$halocycloalkyl, $C_3$-$C_6$cyclohaloalkyl-$C_1$-$C_4$ cycloalkyl, $C_1$-$C_6$alkoxy, $C_1$-$C_4$alkoxy$C_1$-$C_4$alkyl, $C_1$-$C_6$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl or $C_1$-$C_4$haloalkylsulfonyl.

EMBODIMENT (B8)

Further preferred are compounds of formula I-1c

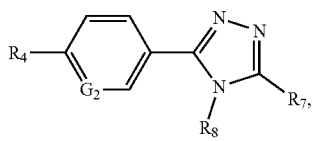

(I-1c)

wherein $R_7$ is selected from the group consisting of $J_1$, $J_3$, $J_4$, $J_7$, $J_{11}$ and $J_{14}$ to $J_{16}$;

$J_1$

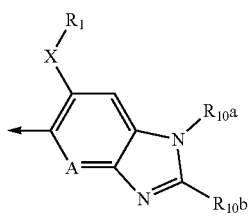

$J_3$

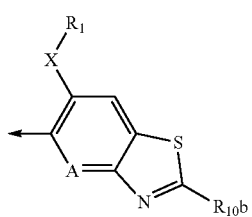

$J_4$

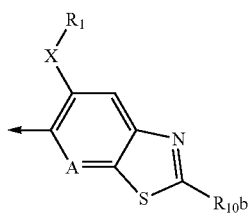

$J_7$

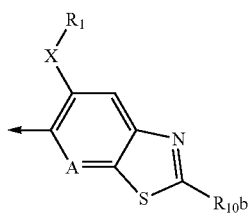

$J_{11}$

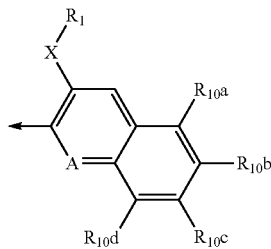

$J_{14}$

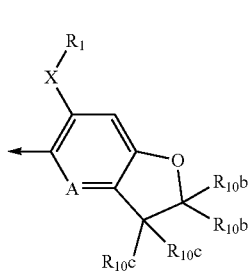

$J_{15}$

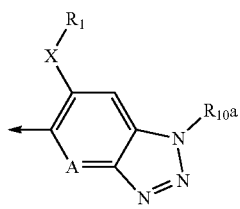

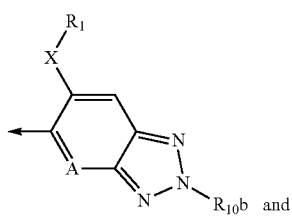

and

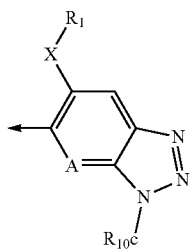

J₁₆

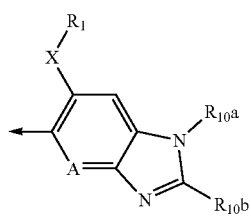

J₁

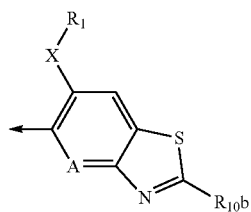

J₃ and wherein
A is C—H or N;
G₂ is nitrogen or CR₃;
X is S or SO₂;
R₁ is ethyl;
R₈ is methyl;
R₃ is hydrogen;
R₄ is trifluoromethyl; and
R₁₀ₐ, R₁₀ᵦ, R₁₀ᵧ and R₁₀d, independently from each other, are hydrogen, $C_1$-$C_6$alkyl, $C_1$-$C_6$haloalkyl or $C_1$-$C_4$alkoxy$C_1$-$C_4$alkyl.

EMBODIMENT (B9)

Further preferred are compounds of formula I-1c

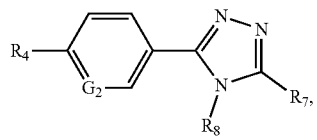

(I-1c)

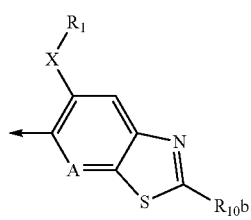

J₄ wherein R₇ is the group J₁;

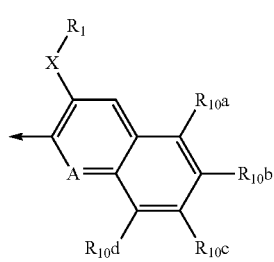

J₇

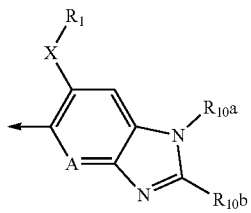

J₁

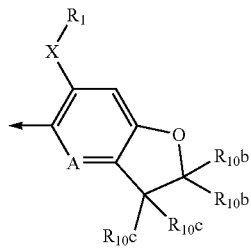

J₁₁ wherein
A is C—H or N;
G₂ is nitrogen;
X is S or SO₂;
R₁ is ethyl;
R₈ is methyl;
R₄ is trifluoromethyl; and
R₁₀ₐ and R₁₀ᵦ, independently from each other, are hydrogen or $C_1$-$C_6$haloalkyl.

In an outstanding group of compounds of formula I, the ring, which is formed by the groups G₁ to G₅, represents pyridyl or pyrimidyl, which both can be substituted by $C_1$-$C_4$haloalkyl;
R₈ is methyl; and
R₇ is selected from the group consisting of J₁, J₃, J₄, J₇, J₁₁ and J₁₄ to J₁₆ (where the arrow represents the point of attachment of the group J to the triazole ring which contains the group R₈)

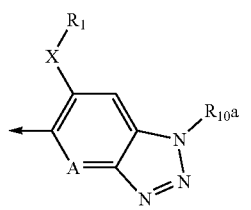

J₁₄

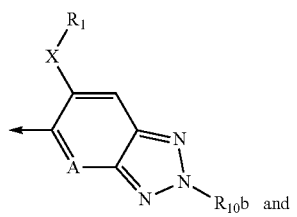

J₁₅ and

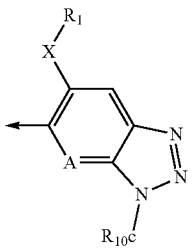

wherein
each radical X—$R_1$ is ethylsulfanyl or ethylsulfonyl; and $R_{10a}$, $R_{10b}$, $R_{10c}$ and $R_{10d}$, independently from each other, are hydrogen, $C_1$-$C_6$alkyl, $C_1$-$C_6$haloalkyl or $C_1$-$C_4$alkoxy$C_1$-$C_4$alkyl.

The process according to the invention for preparing compounds of formula I is carried out by methods known to those skilled in the art. More specifically, the subgroup of compounds of formula I, wherein X is SO (sulfoxide) and/or $SO_2$ (sulfone), may be obtained by means of an oxidation reaction of the corresponding sulfide compounds of formula I, wherein X is S, involving reagents such as, for example, m-chloroperoxybenzoic acid (mCPBA), hydrogen peroxide, oxone, sodium periodate, sodium hypochlorite or tert-butyl hypochlorite amongst other oxidants. The oxidation reaction is generally conducted in the presence of a solvent. Examples of the solvent to be used in the reaction include aliphatic halogenated hydrocarbons such as dichloromethane and chloroform; alcohols such as methanol and ethanol; acetic acid; water; and mixtures thereof. The amount of the oxidant to be used in the reaction is generally 1 to 3 moles, preferably 1 to 1.2 moles, relative to 1 mole of the sulfide compounds I to produce the sulfoxide compounds I, and preferably 2 to 2.2 moles of oxidant, relative to 1 mole of of the sulfide compounds I to produce the sulfone compounds I. Such oxidation reactions are disclosed, for example, in WO 2013/018928.

The subgroup of compounds of formula I, wherein X is S (sulfide) and wherein $R_7$, $R_8$, $G_1$, $G_2$, $G_3$, $G_4$, and $G_5$ are as defined above,

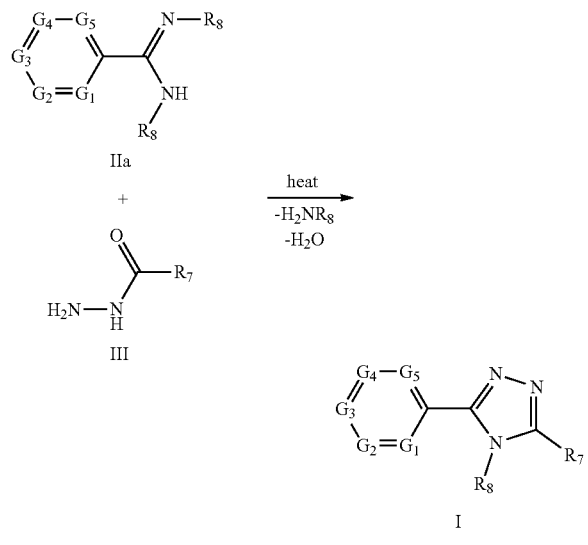

may be prepared (scheme 1) by reacting an amidine compound of formula IIa, or a salt thereof (such as a hydrohalide salt, preferably a hydrochloride or a hydrobromide salt, or any other equivalent salt), wherein $R_8$, $G_1$, $G_2$, $G_3$, $G_4$, and $G_5$ are as defined above, with a hydrazide compound of formula III, or a salt thereof, wherein $R_7$ is as defined above and wherein X is S (sulfide), optionally in presence of a base such as alkali metal carbonates, for example sodium carbonate or potassium carbonate, in a solvent such as methanol, ethanol, isopropanol, acetonitrile, pyridine, acetic acid, N,N-dimethyl-formamide or N,N-dimethylacetamide, at temperatures between 0 and 200° C., preferably between 50 and 150° C., optionally under microwave irradiation. Such a process may be carried out in analogy to, for example, G. Bonanomi et al., ChemMedChem 2010, 5, 705-715. The compounds of formula IIa may be reacted with any configuration (E or Z, or any mixture thereof) on the carbon-nitrogen double bond.

Alternatively, the subgroup of compounds of formula I, wherein X is S (sulfide) and wherein $R_7$, $R_8$, $G_1$, $G_2$, $G_3$, $G_4$, and $G_5$ are as defined above,

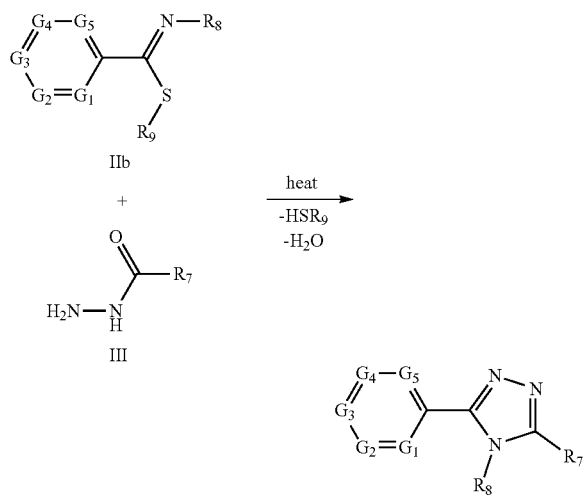

may be prepared (scheme 2) by reacting an alkyl carboximidothioate compound of formula IIb, or a salt thereof (such as a hydrohalide salt, preferably a hydrochloride or a hydrobromide salt, or any other equivalent salt), wherein $R_8$, $G_1$, $G_2$, $G_3$, $G_4$, and $G_5$ are as defined above, and in which $R_9$ is $C_{1-6}$alkyl, with a hydrazide compound of formula III, or a salt thereof (such as a hydrohalide salt, preferably a hydrochloride or a hydrobromide salt, or any other equivalent salt), wherein $R_7$ is as defined above and wherein X is S (sulfide), optionally in presence of a base such as alkali metal carbonates, for example sodium carbonate or potassium carbonate, in a solvent such as methanol, ethanol, isopropanol, acetonitrile, pyridine, acetic acid, N,N-dimethylformamide or N,N-dimethylacetamide, at temperatures between 0 and 200° C., preferably between ambient temperature and 180° C., optionally under microwave irradiation. Such a process may be carried out in analogy to, for example, M. H. Klingele et al, Eur. J. Org. Chem. 2004, 3422-3434. The compounds of formula IIb may be reacted with any configuration (E or Z, or any mixture thereof) on the carbon-nitrogen double bond.

Compounds of formula IIa, or a salt thereof (such as a hydrohalide salt, preferably a hydrochloride or a hydrobromide salt, or any other equivalent salt), wherein $R_8$, $G_1$, $G_2$, $G_3$, $G_4$, and $G_5$ are as defined above,

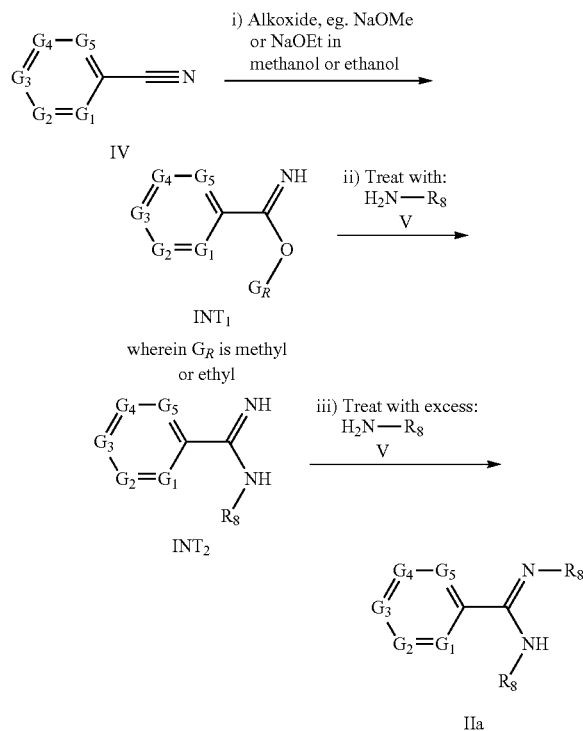

may be prepared (scheme 3) by reacting a nitrile compound of formula IV, wherein $G_1$, $G_2$, $G_3$, $G_4$, and $G_5$ are as defined above, sequentially with i) a catalytic amount (preferably 0.01 to 0.5 equivalent) or an equimolar amount of an alkoxide, preferably sodium methoxide NaOMe or sodium ethoxide NaOEt, in an alcoholic solvent, such as methanol or ethanol, at temperatures between 0 and 100° C., to generate an imidate intermediate of the formula $INT_1$ (or a salt and/or a tautomer thereof); followed by ii) treatment with an amine reagent of formula V $$R_8\text{—}NH_2 \quad (V),$$

or a salt thereof (such as a hydrohalide salt, preferably a hydrochloride or a hydrobromide salt, or any other equivalent salt), wherein $R_8$ is as defined above, optionally in the presence of an acid (such as a hydrohalide acid, preferably hydrochloric acid or hydrobromic acid, or any other equivalent acid), at temperatures between 0-180° C., to generate an amidine intermediate of the formula $INT_2$ (or a salt and/or a tautomer thereof); followed by iii) treatment with an excess of the amine reagent of formula V, or a salt thereof (such as a hydrohalide salt, preferably a hydrochloride or a hydrobromide salt, or any other equivalent salt), wherein $R_8$ is as defined above, preferably in the presence of an acid (such as a hydrohalide acid, preferably hydrochloric acid or hydrobromic acid, or any other equivalent acid), at temperatures between 0-180° C., to form the compound of the formula IIa, or a salt and/or a tautomer thereof. The compounds of formula IIa may be isolated with any configuration (E or Z, or any mixture thereof) on the carbon-nitrogen double bond. Steps ii) and iii) may be combined, for example to allow a direct formation of a compound of formula IIa from a compound of formula $INT_1$. Steps ii) and/or iii) may also be performed under microwave irradiation, each optionally also in a pressurized vessel. Compounds of the formula $INT_1$ may alternatively be prepared under conditions and variants of the Pinner reaction known to a person skilled in the art, typically by treating a compound of the formula IV with a hydrohalide acid, preferably hydrochloric acid, in presence of alcoholic reagents such as methanol or ethanol, preferably in an inert solvent such as diethyl ether, tetrahydrofuran or dioxane, at temperatures between −40 and 50° C., preferably between −20 and 20° C. The described process to prepare compounds of the formula IIa from compounds of the formula IV may include isolation and purification of the intermediates $INT_1$ and/or $INT_2$ (which may be isolated as free bases or as salts (e.g. a hydrohalide salt, more specifically a hydrochloride or hydrobromide salt, or any other equivalent salt)), however this process is advantageously conducted as a one-pot preparation. In the particular situation where $R_8$ is methyl or ethyl, the amine reagent of formula V may be engaged in the above reaction as a gas, as a salt (such as a hydrohalide salt, preferably a hydrochloride or a hydrobromide salt, or any other equivalent salt), or as a solution in solvents such as methanol, ethanol, tetrahydrofuran or water.

Compounds of formula IIb, or a salt thereof (such as a hydrohalide salt, preferably a hydrochloride or a hydrobromide salt, or any other equivalent salt), wherein $R_8$, $G_1$, $G_2$, $G_3$, $G_4$, and $G_5$ are as defined above, and in which $R_9$ is $C_{1-6}$alkyl,

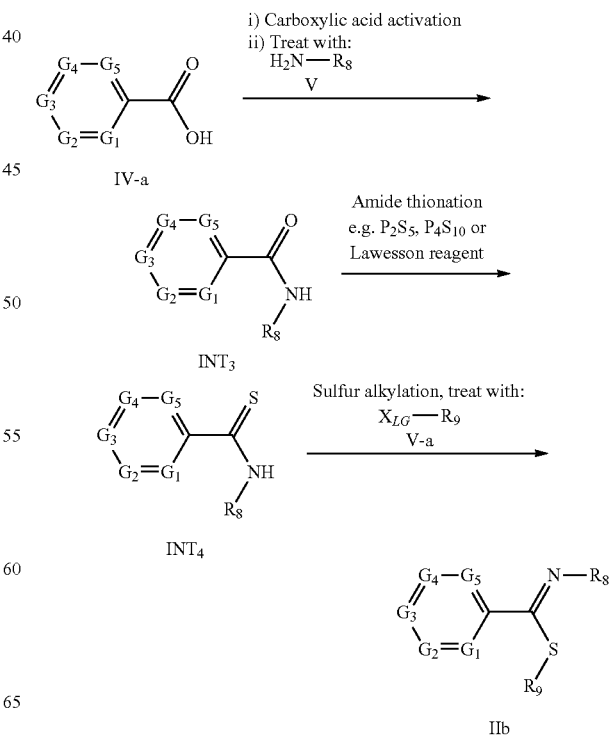

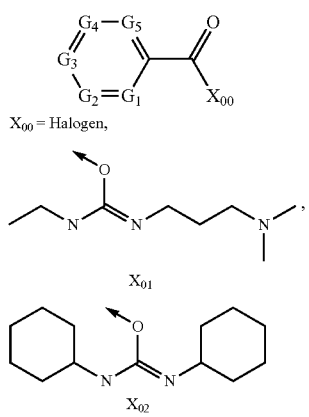

$X_{00}$ = Halogen, may be prepared (scheme 4) by reacting a compound of formula $INT_4$, wherein $R_8$, $G_1$, $G_2$, $G_3$, $G_4$, and $G_5$ are as defined above, with an alkylation reagent of formula V-a, wherein $R_9$ is $C_{1-6}$alkyl, and in which $X_{LG}$ is a leaving group, such as a halogen (especially bromine or iodine), or a leaving group $OSO_2R_{38}$, wherein $R_{38}$ is $C_1$-$C_6$alkyl, $C_1$-$C_6$haloalkyl, or phenyl optionally substituted by nitro or $C_1$-$C_3$alkyl (especially a sulfonate such as mesylate, triflate or tosylate) or a sulfate (forming for example the alkylating agent V-a dimethylsulfate, in the particular situation where $R_9$ is methyl), preferably in the presence of a suitable base, such as sodium hydride or sodium, potassium or cesium carbonate, in an inert solvent such as tetrahydrofuran, dioxane, acetonitrile, N,N-dimethylformamide, N,N-dimethylacetamide, N-methyl-2-pyrrolidone or dimethyl sulfoxide. Another advantageous base/solvent combination for this transformation is also, for example, an alkoxide, preferably sodium methoxide NaOMe or sodium ethoxide NaOEt, in an alcoholic solvent, such as methanol or ethanol, at temperatures between 0-100° C., preferably around room temperature. The compounds of formula IIb may be isolated with any configuration (E or Z, or any mixture thereof) on the carbon-nitrogen double bond. Such a process may be carried out in analogy to, for example, M. H. Klingele et al, Eur. J. Org. Chem. 2004, 3422-3434.

Compounds of formula $INT_4$, wherein $R_8$, $G_1$, $G_2$, $G_3$, $G_4$, and $G_5$ are as defined above, may be prepared by reacting a compound of formula $INT_3$, wherein $R_8$, $G_1$, $G_2$, $G_3$, $G_4$, and $G_5$ are as defined above, with a thionation agent, such as phosphorus decasulfide $P_4S_{10}$ (also called phosphorus pentasulfide $P_2S_5$), or the Lawesson reagent (2,4-bis(4-methoxyphenyl)-1,3,2,4-dithiadiphosphetane-2,4-dithione), in inert solvents such as toluene, xylene, tetrahydrofuran, dioxane or pyridine, at temperatures between 0-200° C., preferably between 50 and 150° C., optionally under microwave irradiation. Such a process may be carried out in analogy to, for example, T. Ozturk et al., Chem. Rev. 2010, 110, 3419-3478.

Compounds of formula $INT_3$, wherein $R_8$, $G_1$, $G_2$, $G_3$, $G_4$, and $G_5$ are as defined above, may be prepared by i) activation of a compound of formula IV-a, wherein $G_1$, $G_2$, $G_3$, $G_4$, and $G_5$ are as defined above, by methods known to those skilled in the art and described in, for example, Tetrahedron, 2005, 61 (46), 10827-10852, to form an activated species IV-aa, wherein $G_1$, $G_2$, $G_3$, $G_4$, and $G_5$ are as defined above and wherein $X_{00}$ is halogen, preferably chlorine. For example, compounds IV-aa where $X_{00}$ is halogen, preferably chlorine, are formed by treatment of IV-a with, for example, oxallyl chloride $(COCl)_2$ or thionyl chloride $SOCl_2$ in the presence of catalytic quantities of N,N-dimethylformamide DMF in inert solvents such as methylene chloride $CH_2Cl_2$ or tetrahydrofuran THF at temperatures between 20 to 100° C., preferably 25° C. Alternatively, treatment of compounds of formula IV-a with, for example, 1-ethyl-3-(3-dimethylaminopropyl)carbodiimide EDC or dicyclohexyl carbodiimide DCC will generate an activated species IV-aa, wherein $X_{00}$ is $X_{01}$ or $X_{02}$ respectively, in an inert solvent, such as pyridine or tetrahydrofuran THF, optionally in the presence of a base, such as triethylamine, at temperatures between 50-180° C.; followed by ii) treatment of the activated species IV-aa with an amine reagent of formula V $$R_8-NH_2 \quad (V),$$

or a salt thereof (such as a hydrohalide salt, preferably a hydrochloride or a hydrobromide salt, or any other equivalent salt), wherein $R_8$ is as defined above, optionally in the presence of a base, such as triethylamine or pyridine, in an inert solvents such as dichloromethane, tetrahydrofuran, dioxane or toluene, at temperatures between 0 and 50° C., to form the compounds of formula $INT_3$. Certain bases, such as pyridine and triethylamine, may be employed successfully as both base and solvent.

Compounds of formula IV and compounds of formula IV-a, wherein $G_1$, $G_2$, $G_3$, $G_4$, and $G_5$ are as defined above, may be known compounds or may be prepared by known methods, described in the literature.

Compounds of the formula III, or a salt thereof (such as a hydrohalide salt, preferably a hydrochloride or a hydrobromide salt, or any other equivalent salt), wherein $R_7$ is as defined above, Scheme 5:

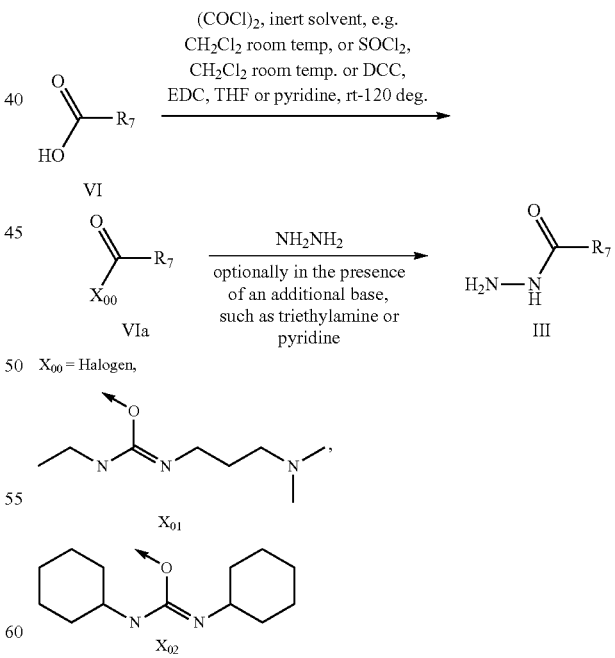

$X_{00}$ = Halogen, may be prepared (scheme 5) by i) activation of compound of formula VI, wherein $R_7$ is as defined above, by methods known to those skilled in the art and described in, for example, Tetrahedron, 2005, 61 (46), 10827-10852, to form an activated species VIa, wherein $R_7$ is as defined above and wherein $X_{00}$ is halogen, preferably chlorine. For example, compounds VIa where $X_{00}$ is halogen, preferably chlorine, are formed by treatment of VI with, for example, oxallyl chloride $(COCl)_2$ or thionyl chloride $SOCl_2$ in the presence of catalytic quantities of N,N-dimethylformamide DMF in inert solvents such as methylene chloride $CH_2Cl_2$ or tetrahydrofuran THF at temperatures between 20 to 100° C., preferably 25° C. Alternatively, treatment of compounds of formula VI with, for example, 1-ethyl-3-(3-dimethylaminopropyl)carbodiimide EDC or dicyclohexyl carbodiimide DCC will generate an activated species VIa, wherein $X_{00}$ is $X_{01}$ or $X_{02}$ respectively, in an inert solvent, such as pyridine or tetrahydrofuran THF, optionally in the presence of a base, such as triethylamine, at temperatures between 50-180° C.; followed by ii) Treatment of the activated species VIa with hydrazine $NH_2NH_2$ (or a salt thereof), possibly in form of a hydrate, preferably hydrazine monohydrate, optionally in the presence of a base, such as triethylamine or pyridine, in an inert solvents such as dichloromethane, tetrahydrofuran, dioxane or toluene, at temperatures between 0 and 50° C., to form the compounds of formula III.

Alternatively, compounds of the formula III, or a salt thereof (such as a hydrohalide salt, preferably a hydrochloride or a hydrobromide salt, or a trifluoroacetic acid salt, or any other equivalent salt), wherein $R_7$ is as defined above, Scheme 6:

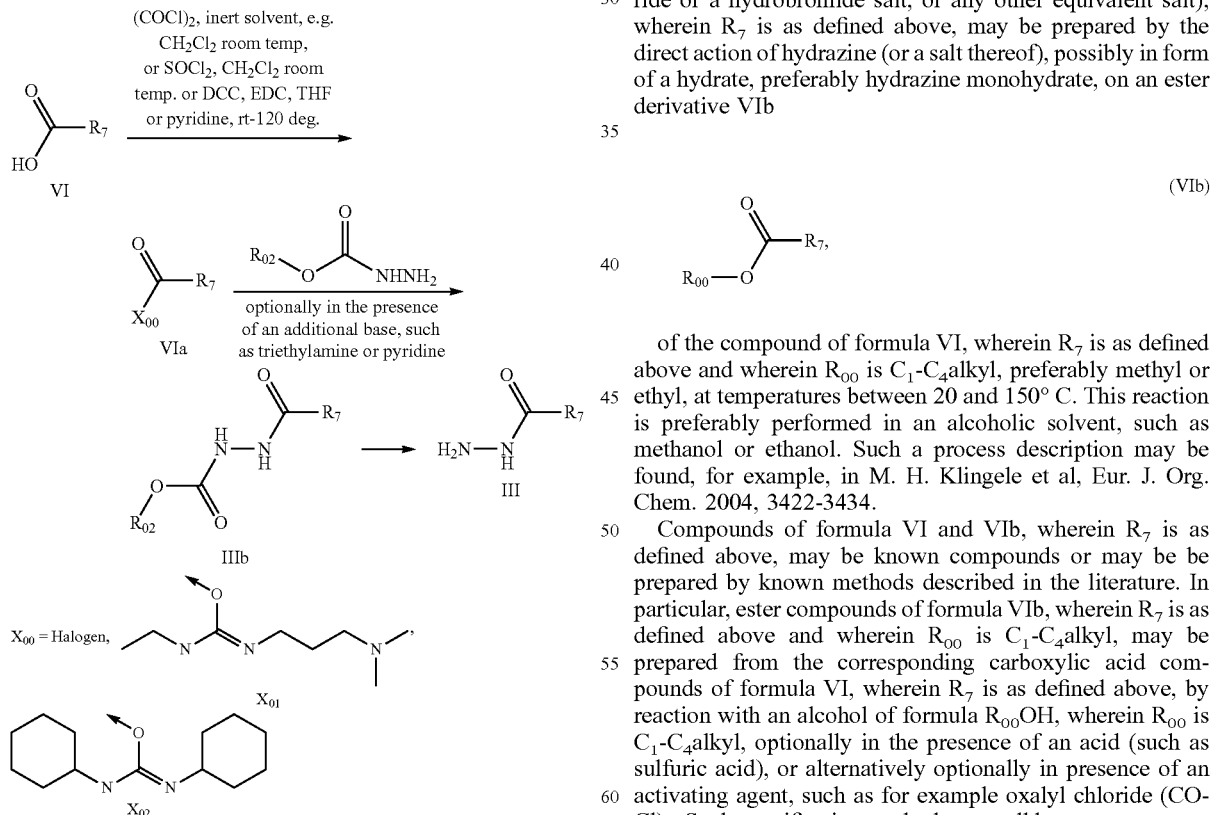

can be prepared (scheme 6) by treating compounds of the formula IIIb, wherein $R_7$ is as defined above, and in which $R_{02}$ is $C_1$-$C_6$alkyl (for example tert-butyl), benzyl or benzyl substituted by one or two methoxy, with an acid, such as for example a hydrohalide acid, preferably hydrochloride or hydrobromide acid, or trifluoroacetic acid, optionally in presence of a solvent, such as tetrahydrofuran, dioxane or dichloromethane, at temperatures between 0 and 150° C.

Compounds of the formula IIIb, wherein $R_7$ is as defined above, and in which $R_{02}$ is $C_1$-$C_6$alkyl (for example tert-butyl), benzyl or benzyl substituted by one or two methoxy, can be prepared by treating previously described compounds of the formula VIa, wherein $R_{00}$ and $R_7$ are as described above, with hydrazine compounds of formula $NH_2NH$—C(O)$OR_{02}$ (or a salt thereof), wherein $R_{02}$ is $C_1$-$C_6$alkyl (for example tert-butyl), benzyl or benzyl substituted by one or two methoxy, optionally in the presence of a base, such as triethylamine or pyridine, in an inert solvents such as dichloromethane, tetrahydrofuran, dioxane or toluene, at temperatures between 0 and 50° C. The activation of compounds of formula VI to form an activated species VIa was described above. Reagents of the formula $NH_2NH$—C(O)$OR_{02}$ (or a salt thereof), wherein $R_{02}$ is as defined above, may be either known, commercially available or may be prepared by methods known to a person skilled in the art.

The described process (scheme 6) to prepare compounds of the formula III from compounds of the formula VI may include isolation and purification of the intermediates VIa and IIIb, however this process is also advantageously conducted by engaging crude VIa and IIIb into their respective next steps.

Alternatively, compounds of the formula III, or a salt thereof (such as a hydrohalide salt, preferably a hydrochloride or a hydrobromide salt, or any other equivalent salt), wherein $R_7$ is as defined above, may be prepared by the direct action of hydrazine (or a salt thereof), possibly in form of a hydrate, preferably hydrazine monohydrate, on an ester derivative VIb

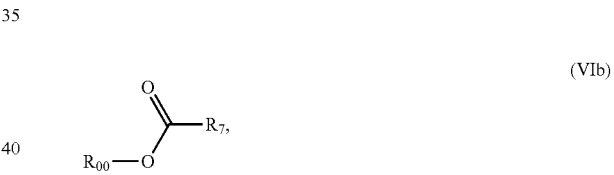

of the compound of formula VI, wherein $R_7$ is as defined above and wherein $R_{00}$ is $C_1$-$C_4$alkyl, preferably methyl or ethyl, at temperatures between 20 and 150° C. This reaction is preferably performed in an alcoholic solvent, such as methanol or ethanol. Such a process description may be found, for example, in M. H. Klingele et al, Eur. J. Org. Chem. 2004, 3422-3434.

Compounds of formula VI and VIb, wherein $R_7$ is as defined above, may be known compounds or may be be prepared by known methods described in the literature. In particular, ester compounds of formula VIb, wherein $R_7$ is as defined above and wherein $R_{00}$ is $C_1$-$C_4$alkyl, may be prepared from the corresponding carboxylic acid compounds of formula VI, wherein $R_7$ is as defined above, by reaction with an alcohol of formula $R_{00}$OH, wherein $R_{00}$ is $C_1$-$C_4$alkyl, optionally in the presence of an acid (such as sulfuric acid), or alternatively optionally in presence of an activating agent, such as for example oxalyl chloride (CO-Cl)$_2$. Such esterification methods are well known to a person skilled in the art.

Compounds of formula VI-I2-1 and VI-I2-1a define the particular subgroup of compounds of formula VI, wherein $R_7$ is as defined in formula I, and wherein $L_1$, $L_2$, $L_3$ and $L_4$ form together with the two carbon atoms to which $L_1$ and $L_4$ are attached an aromatic heterocyclic ring system, in which $L_1$ is $N-R_{10a}$, $L_2$ is $C(R_{10b})_m$, m is 1, $L_3$ is nitrogen and $L_4$ is a direct bond, and wherein $R_{10a}$, $R_{10b}$, A, X and $R_1$ are as defined in formula I.

Compounds of formula VI-I2-1, wherein X is S (sulfide),

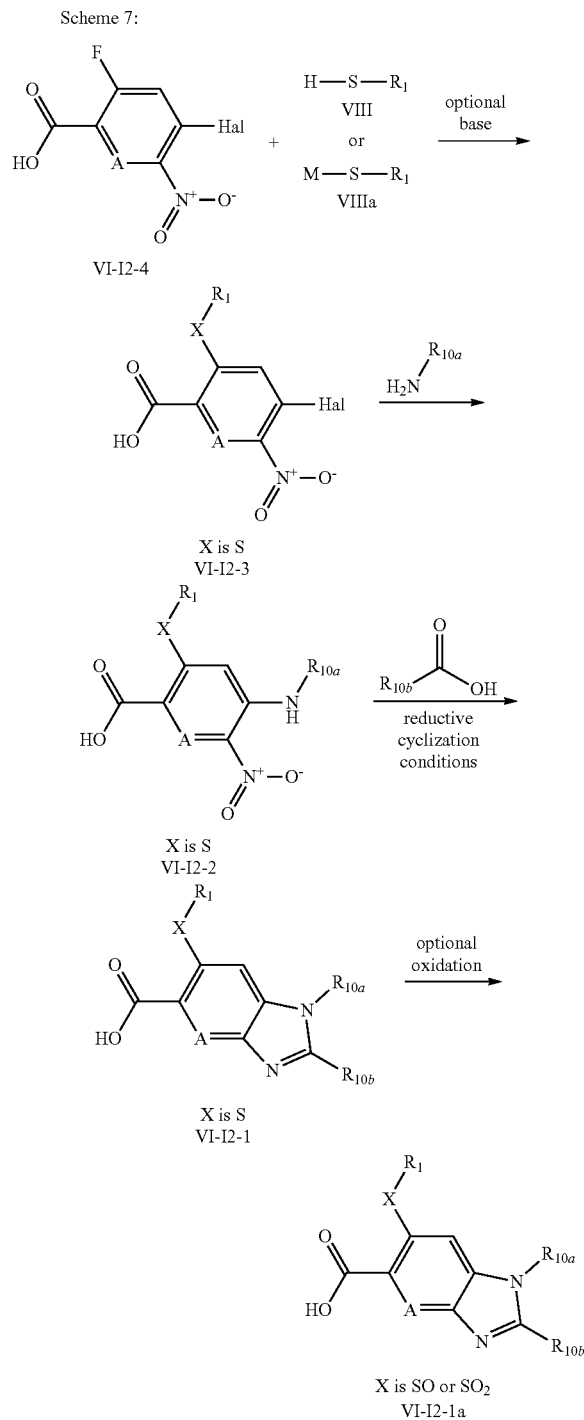

can be prepared (scheme 7) by reacting compounds of formula VI-I2-2, wherein X is S (sulfide), and wherein $R_{10a}$, A and $R_1$ are as defined above, with a compound of the formula $R_{10b}COOH$, wherein $R_{10b}$ is as defined above, under reductive cyclization conditions. Such reductive cyclization conditions can be achieved, for example, using zinc dust and compound $R_{10b}COOH$ (whereby $R_{10b}COOH$ can act both as reagent and solvent or diluent), at temperatures between 0° C. and 120° C., preferably between 0° C. and reflux temperature.

Compounds of formula VI-I2-2, wherein X is S (sulfide), and wherein $R_{10a}$, A and $R_1$ are as defined above, can be prepared by reacting compounds of formula VI-I2-3, wherein X is S (sulfide), and wherein A and $R_1$ are as defined above, and in which Hal is a halogen such as, for example, fluorine, chlorine or bromine (preferably fluorine or chlorine), with a reagent of the formula $R_{10a}NH_2$, or a salt thereof (such as a hydrohalide salt, preferably a hydrochloride or a hydrobromide salt, or any other equivalent salt), wherein $R_{10a}$ is as defined above, optionally in presence of an additional base. This transformation is preferably performed in suitable solvents (or diluents) such as alcohols, amides, esters, ethers, nitriles and water, particularly preferred are methanol, ethanol, 2,2,2-trifluoroethanol, propanol, iso-propanol, N,N-dimethylformamide, N,N-dimethylacetamide, dioxane, tetrahydrofuran, dimethoxyethane, acetonitrile, ethyl acetate, water or mixtures thereof, at temperatures between 0-150° C., preferably at temperatures ranging from room temperature to the boiling point of the reaction mixture, optionally under microwave irradiation or pressurized conditions using an autoclave.

Compounds of formula VI-I2-3, wherein X is S (sulfide), and wherein A and $R_1$ are as defined above, and in which Hal is a halogen such as, for example, fluorine, chlorine or bromine (preferably fluorine or chlorine), can be prepared by reacting compounds of formula VI-I2-4, wherein A is as defined above, and in which Hal is a halogen such as, for example, fluorine, chlorine or bromine (preferably fluorine or chlorine), with a reagent of the formula VIII $$R_1-SH \qquad (VIII),$$

or a salt thereof, wherein $R_1$ is as defined in formula I, optionally in the presence of a suitable base, such as alkali metal carbonates, for example sodium carbonate and potassium carbonate, or alkali metal hydrides such as sodium hydride, or alkali metal hydroxides such as sodium hydroxide and potassium hydroxide, or sodium or potassium tert-butoxide, in an inert solvent at temperatures preferably between 25-120° C. Examples of solvent to be used include ethers such as THF, ethylene glycol dimethyl ether, tert-butylmethyl ether, and 1,4-dioxane, aromatic hydrocarbons such as toluene and xylene, nitriles such as acetonitrile or polar aprotic solvents such as N,N-dimethylformamide, N,N-dimethylacetamide, N-methyl-2-pyrrolidone NMP or dimethyl sulfoxide. Examples of salts of the compound of formula VIII include compounds of the formula VIIIa $$R_1-S-M \qquad (VIIIa),$$

wherein $R_1$ is as defined above and wherein M is, for example, sodium or potassium.

Oxidation of compounds of formula VI-I2-1, wherein the substituents are as defined above, and in which X is S (sulfide), with a suitable oxidizing agent (scheme 7), into compounds of formula VI-I2-1a, wherein X is SO (sulfoxide) or $SO_2$ (sulfone) may be achieved under conditions already described above.

Compounds of formula VI-I2-4, wherein A is as defined above, and in which Hal is a halogen such as, for example, fluorine, chlorine or bromine (preferably fluorine or chlorine), may be either known, commercially available or may be prepared by methods known to a person skilled in the art.

Reagents of the formula $R_{10a}NH_2$, or a salt thereof, wherein $R_{10a}$ is as defined above, and of the formula $R_{10b}$COOH, wherein $R_{10b}$ is as defined above, may be either known, commercially available or may be prepared by methods known to a person skilled in the art.

Compounds of formula VIb-I7 define the particular subgroup of compounds of formula VIb, wherein $R_7$ is as defined in formula I, and in which $R_{00}$ is $C_1$-$C_4$alkyl, and wherein $L_1$, $L_2$, $L_3$ and $L_4$ form together with the two carbon atoms to which $L_1$ and $L_4$ are attached a partially saturated heterocyclic ring system, in which $L_1$ is oxygen, $L_2$ is $C(R_{10b})_m$ wherein m is 2, $L_3$ is $C(R_{10c})_m$ wherein m is 2 and $L_4$ is a direct bond, and wherein $R_{10b}$, $R_{10c}$, A, X and $R_1$ are as defined in formula I.

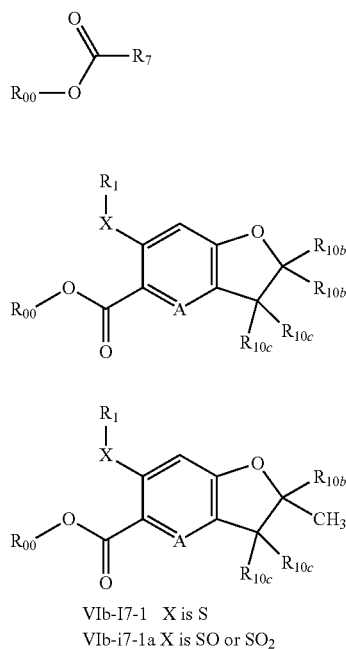

VIb-I7-1  X is S
VIb-i7-1a X is SO or $SO_2$

Compounds of formula VIb-I7-1 and VIb-I7-1a further define the particular subgroup of compounds of formula VIb-I7, wherein one group $R_{10b}$ is methyl.

Compounds of formula VIb-I7-1, wherein X is S (sulfide),

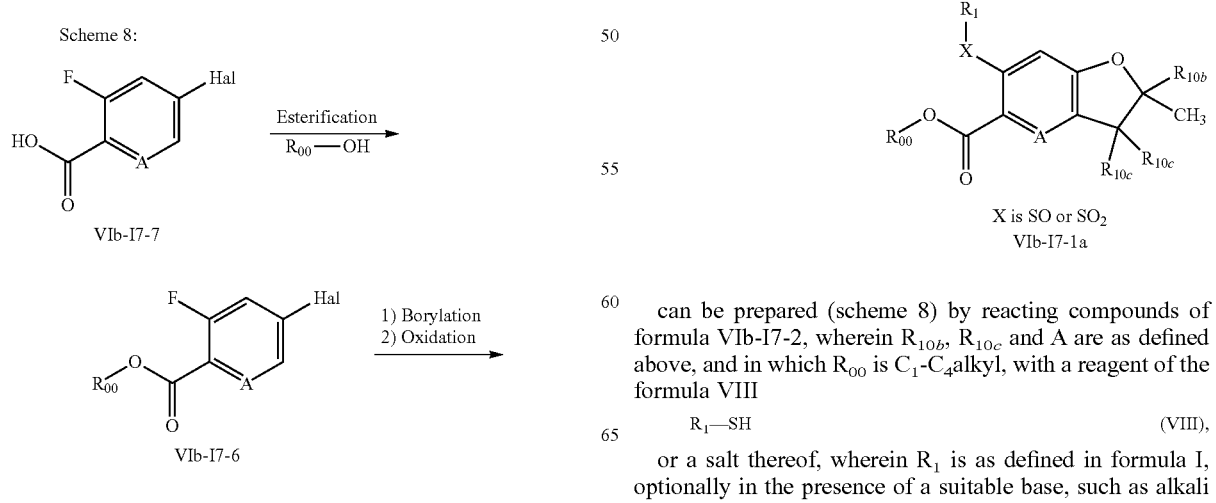

can be prepared (scheme 8) by reacting compounds of formula VIb-I7-2, wherein $R_{10b}$, $R_{10c}$ and A are as defined above, and in which $R_{00}$ is $C_1$-$C_4$alkyl, with a reagent of the formula VIII $R_1$—SH  (VIII), or a salt thereof, wherein $R_1$ is as defined in formula I, optionally in the presence of a suitable base, such as alkali metal carbonates, for example sodium carbonate and potassium carbonate, or alkali metal hydrides such as sodium hydride, or alkali metal hydroxides such as sodium hydroxide and potassium hydroxide, or sodium or potassium tert-butoxide, in an inert solvent at temperatures preferably between 0-120° C. Examples of solvent to be used include ethers such as THF, ethylene glycol dimethyl ether, tert-butylmethyl ether, and 1,4-dioxane, aromatic hydrocarbons such as toluene and xylene, nitriles such as acetonitrile or polar aprotic solvents such as N,N-dimethylformamide, N,N-dimethylacetamide, N-methyl-2-pyrrolidone or dimethyl sulfoxide. Examples of salts of the compound of formula VIII include compounds of the formula VIIIa $$R_1—S-M \qquad (VIIIa),$$

wherein $R_1$ is as defined above and wherein M is, for example, sodium or potassium.

Oxidation of compounds of formula VIb-I7-1, wherein the substituents are as defined above, and in which X is S (sulfide), with a suitable oxidizing agent, into compounds of formula VIb-I7-1a, wherein X is SO (sulfoxide) or $SO_2$ (sulfone) can be achieved under conditions already described above.

Compounds of formula VIb-I7-2, wherein $R_{10b}$, $R_{10c}$ and A are as defined above, and in which $R_{00}$ is $C_1$-$C_4$alkyl, can be prepared from compounds of formula VIb-I7-3, wherein $R_{10b}$, $R_{10c}$ and A are as defined above, and in which $R_{00}$ is $C_1$-$C_4$alkyl, by running sequentially 1) a rearrangement reaction under thermal conditions, known as Claisen rearrangement, whereby typically the compound of formula VIb-I7-3 is heated at temperatures between 20 and 350° C., preferably between 80 and 280° C., in an inert solvent, such as N,N-dimethylformamide, N,N-dimethylacetamide or N-methyl-2-pyrrolidone NMP. Such reactions and reaction conditions are well known to person skilled in the art, see for example Strategic Applications of Named Reactions in Organic Synthesis by Kurti, Laszlo; Czako, Barbara; Editors; 2005, page 88. The intermediate product of this thermal rearrangement VIb-I7-Int is then further subjected to 2) a ring closing step, whereby typically said intermediate product VIb-I7-Int is heated at temperatures between 20 and 250° C., preferably between 80 and 200° C., in presence of a Brønsted or Lewis acid, in an inert solvent. Advantageously the solvent (or diluent) may simultaneously act as acid and such ring closing step may be performed in, for example, formic acid or acetic acid, under refluxing conditions. The described process to prepare compounds of the formula VIb-I7-2 from compounds of the formula VIb-I7-3 may include isolation and purification of the intermediate VIb-I7-Int, however this process is also advantageously conducted by engaging crude VIb-I7-Int into the cyclisation step 2.

Compounds of formula VIb-I7-3, wherein $R_{10b}$, $R_{10c}$ and A are as defined above, and in which $R_{00}$ is $C_1$-$C_4$alkyl, can be prepared by reacting compounds of formula VIb-I7-5, wherein A is as defined above, and in which $R_{00}$ is $C_1$-$C_4$alkyl, with halo-allyl reagents of formula VIb-I7-4, wherein $X_a$ is a halogen leaving group, preferably chlorine or bromine, and in which $R_{10b}$ and $R_{10c}$ are as defined above, in presence of a base such as sodium hydride or sodium, potassium or cesium carbonate, optionally in presence of an additive, such as sodium or potassium iodide, preferably in catalytic amount, in an inert solvent such as acetone, tetrahydrofuran, dioxane, acetonitrile, N,N-dimethyl-formamide, N,N-dimethylacetamide, N-methyl-2-pyrrolidone or dimethyl sulfoxide (or mixtures thereof), at temperatures between 0 and 180° C., preferably between 20 and 150° C., optionally under microwave irradiation. Such an alkylation reaction to form ethers of the formula VIb-I7-3 is well known by a person skilled in the art and could be done according to conditions described, for example in Organic Letters, 17(12), 3118-3121; 2015; Tetrahedron, 2004, 60, 7973-7981 or Protective groups in organic synthesis (third edition, Theodora W. Greene, Peter G. M. Wuts 1999) p 262.

Compounds of formula VIb-I7-5, wherein A is as defined above, and in which $R_{00}$ is $C_1$-$C_4$alkyl, can be prepared from compounds of formula VIb-I7-6, wherein A is as defined above, and in which $R_{00}$ is $C_1$-$C_4$alkyl, and wherein Hal is a halogen such as, for example, chlorine, bromine or iodine (preferably bromine or iodine), by running sequentially 1) a borylation reaction, whereby typically the compound of formula VIb-I7-5 is reacted with bispinacol diborane $(Bpin)_2$ under palladium catalysis. Such an introduction of a pinacolborate functional group can be performed in an aprotic solvent, such as dioxane, in presence of a base, preferably a weak base, such as potassium acetate KOAc. [1,1'-Bis(diphenylphosphino)ferrocene]dichloropalladium (II), also known as palladium dppf dichloride or Pd(dppf) $Cl_2$, is a common catalyst for this type of reaction. Other palladium source/ligand combination involve, for example, tris(dibenzylideneacetone) dipalladium and tricyclohexylphosphine. The temperature of the reaction is preferably performed between 0° C. and the boiling point of the reaction mixture, or the reaction may be performed under microwave irradiation. The intermediate product of this borylation reaction is then further subjected to 2) an oxidation step, whereby typically said intermediate product is treated with hydrogen peroxide $H_2O_2$, for example a 30% $H_2O_2$ solution in water, in an inert solvent such as tetrahydrofuran or dioxane, at temperatures between 0 and 100° C., preferably around room temperature. The described process to prepare compounds of the formula VIb-I7-5 from compounds of the formula VIb-I7-6 may include isolation and purification of the borylated intermediate, however this process is also advantageously conducted by engaging said crude intermediate into the oxidation step 2.

Compounds of formula VIb-I7-6, wherein A is as defined above, and in which $R_{00}$ is $C_1$-$C_4$alkyl, and wherein Hal is a halogen such as, for example, chlorine, bromine or iodine (preferably bromine or iodine) can be prepared from compounds of formula VIb-I7-7, wherein A is as defined above, and wherein Hal is a halogen such as, for example, chlorine, bromine or iodine (preferably bromine or iodine) by an esterification step involving an alcohol of formula $R_{00}$—OH, wherein $R_{00}$ is $C_1$-$C_4$alkyl, under conditions already described above.

Halo-allyl reagents of formula VIb-I7-4, wherein $X_a$ is a halogen leaving group, preferably chlorine or bromine, and in which $R_{10b}$ and $R_{10c}$ are as defined above, may be either known, commercially available or may be prepared by methods known to a person skilled in the art.

Compounds of formula VIb-I7-7, wherein A is as defined above, and wherein Hal is a halogen such as, for example, chlorine, bromine or iodine (preferably bromine or iodine), Scheme 9:

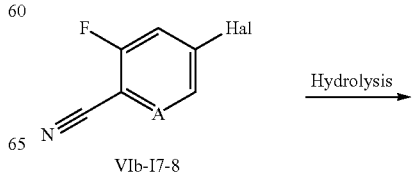

VIb-I7-8

-continued

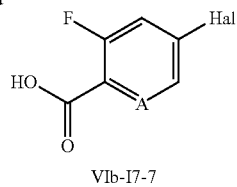

VIb-I7-7 can be prepared (scheme 9) from compounds of formula VIb-I7-8, wherein A is as defined above, and wherein Hal is a halogen such as, for example, chlorine, bromine or iodine (preferably bromine or iodine) by hydrolysis, for example through heating in concentrated acid, such as concentrated hydrochloric acid HCl conc., optionally in the presence of an inert solvent, such as ethers (for example tetrahydrofuran, ethylene glycol dimethyl ether, or 1,4-dioxane). Such hydrolysis conditions, and variants thereof, are known to a person skilled in the art.

Compounds of formula VIb-I7-8 and compounds of formula VIb-I7-7, wherein A is as defined above, and wherein Hal is a halogen such as, for example, chlorine, bromine or iodine (preferably bromine or iodine), may be either known, commercially available or may be prepared by methods known to a person skilled in the art.

Compounds of formula VIb-I7-1b, in which X is S (sulfide), and compounds of formula VIb-I7-1c, in which X is SO (sulfoxide) or $SO_2$ (sulfone), and for both wherein $R_1$, $R_{10b}$, $R_{10c}$ and A are as defined above, Scheme 10:

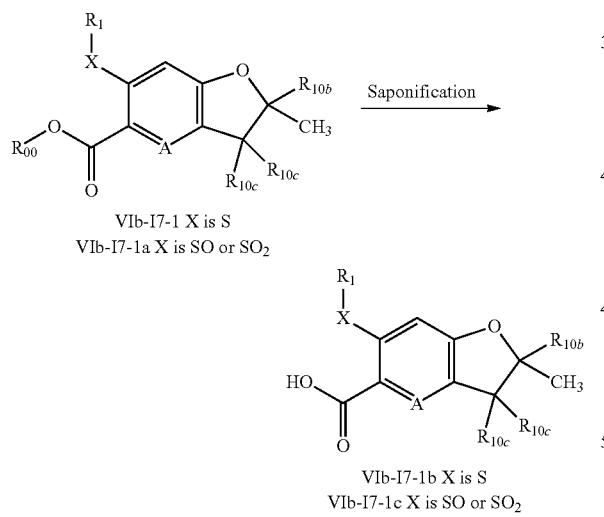

can be prepared (scheme 10) from compounds of formula VIb-I7-1, in which X is S (sulfide), and respectively compounds of formula VIb-I7-1a, in which X is SO (sulfoxide) or $SO_2$ (sulfone), and for both wherein $R_1$, $R_{10b}$, $R_{10c}$ and A are as defined above, and in which $R_{00}$ is $C_1$-$C_4$alkyl, by a saponification reaction. Conditions for such a reaction, typically hydrolysis by water in presence of a base, are known to a person skilled in the art (using for example: aqueous sodium, potassium or lithium hydroxide in methanol, ethanol, tetrahydrofuran or dioxane at room temperature or up to refluxing conditions).

Compounds of formula VIb-I7-1d define the particular subgroup of compounds of formula VIb-I7-1, VIb-I7-1a, VIb-I7-1b and VIb-I7-1c, wherein X, $R_1$ and A are as defined above, and in which $R_{100}$ is hydrogen or $C_1$-$C_4$alkyl, and wherein $R_{10b}$ is specifically methyl and $R_{10c}$ is specifically hydrogen. Such compounds of formula VIb-I7-1d

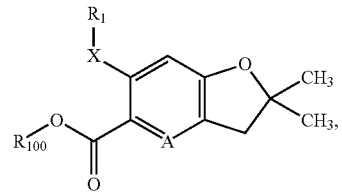

wherein X, $R_1$ and A are as defined under formula I above, and in which $R_{100}$ is hydrogen or $C_1$-$C_4$alkyl, preferably methyl or ethyl, are novel and especially developed for the preparation of the compounds of formula I of this invention. The compounds of formula VIb-I7-1d therefore constitute a further object of the invention. The preferred substituent definitions for the compounds of formula I are also valid for the compounds of formula VIb-I7-1d.

Compounds of formula I-A6-1 define the particular subgroup of compounds of formula I, wherein $R_7$ is as defined in formula I, and wherein $L_1$, $L_2$, $L_3$ and $L_4$ form together with the two carbon atoms to which $L_1$ and $L_4$ are attached an aromatic heterocyclic ring system, in which $L_1$ is nitrogen, $L_2$ is $C(R_{10b})_m$, m is 1, $L_3$ is $S(O)_n$, n is 0 and $L_4$ is a direct bond, and wherein $R_8$, $G_1$ to $G_5$, $R_{10b}$, A, X and $R_1$ are as defined in formula I.

Compounds of formula I-A6-1,

Scheme 11:

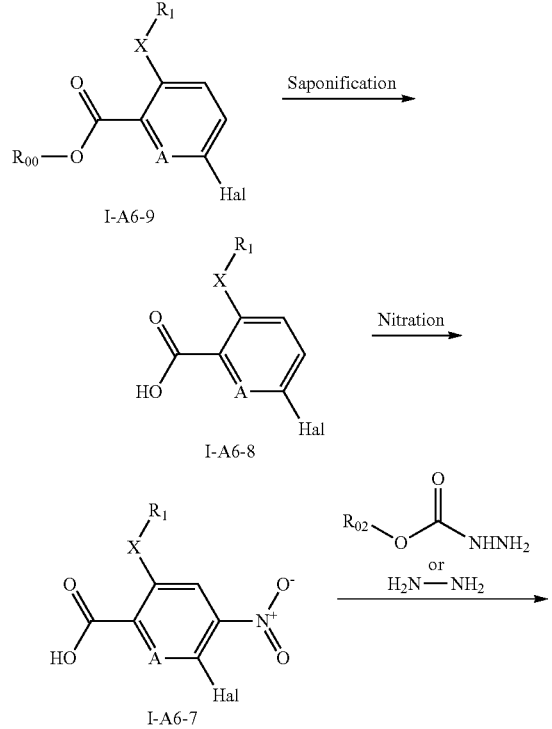

-continued

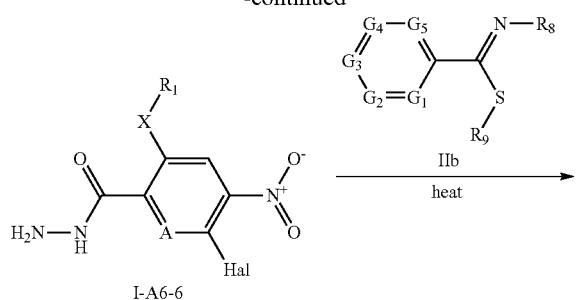

I-A6-6

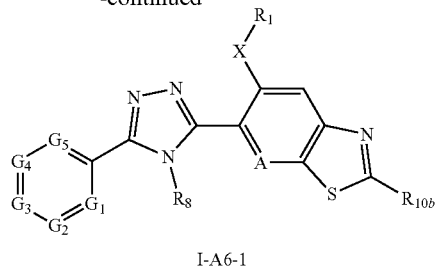

I-A6-1

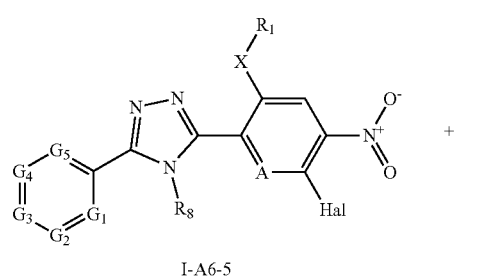

I-A6-5

+

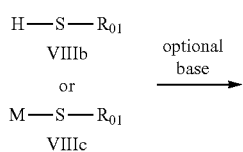

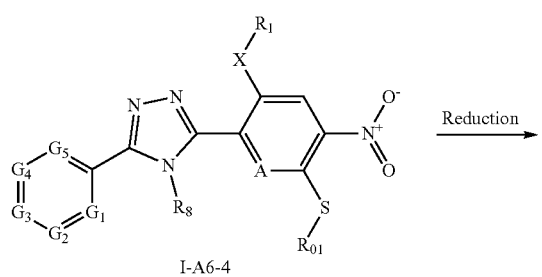

I-A6-4

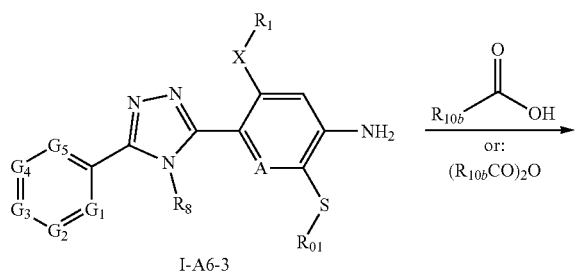

I-A6-3

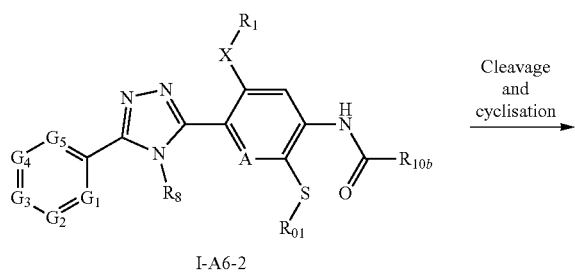

I-A6-2 can be prepared (scheme 11) by treating compounds of formula I-A6-2, wherein $R_{01}$ is $C_1$-$C_6$alkyl, preferably tert-butyl, and wherein $R_8$, $G_1$ to $G_5$, $R_{10b}$, A, X and $R_1$ are as defined above, with for example trifluoroacetic acid or trifluoroacetic anhydride to achieve cleavage of the $R_{01}$ group and concomitant ring closure, whereby trifluoroacetic acid or trifluoroacetic anhydride can act both as reagent and solvent or diluent. Such cyclization conditions may be performed, optionally in presence of an inert solvent, such as dichloromethane, 1,2-dichloroethane, toluene or xylene, at temperatures between 0 and 180° C., preferably between 20 and 150° C., optionally under microwave irradiation.

Compounds of formula I-A6-2, wherein $R_{01}$ is $C_1$-$C_6$alkyl, preferably tert-butyl, and wherein $R_8$, $G_1$ to $G_5$, $R_{10b}$, A, X and $R_1$ are as defined above, can be prepared by reacting compounds of formula I-A6-3, or a salt thereof (such as a hydrohalide salt, preferably a hydrochloride or a hydrobromide salt, or a trifluoroacetic acid salt, or any other equivalent salt), wherein $R_{01}$ is $C_1$-$C_6$alkyl, preferably tert-butyl, and wherein $R_8$, $G_1$ to $G_5$, A, X and $R_1$ are as defined above, with compounds of formula $R_{10b}C(O)OH$ or compounds of formula $(R_{10b}CO)_2O$, wherein $R_{10b}$ is as defined above, optionally in presence of a base, whereby the compounds of formula $R_{10b}C(O)OH$ or of formula $(R_{10b}CO)_2O$, can act both as reagent and solvent or diluent. The reaction may be performed, optionally in presence of an inert solvent, such as dichloromethane, tetrahydrofuran, dioxane, acetonitrile, N,N-dimethylformamide, N,N-dimethylacetamide, N-methyl-2-pyrrolidone or dimethyl sulfoxide (or mixtures thereof), at temperatures between 0 and 180° C., preferably between 20 and 150° C., optionally under microwave irradiation. Compounds of formula $R_{10b}C(O)OH$ may need an activation step in presence of an activating agent, such as for example oxalyl chloride $(COCl)_2$, to form activated species of the formula $R_{10b}C(O)X_{00}$, wherein $X_{00}$ is as defined in scheme 5 (in analogy to the transformation of compounds of the formula VI into compounds of the formula VIa described previously).

Compounds of formula I-A6-3, or a salt thereof (such as a hydrohalide salt, preferably a hydrochloride or a hydrobromide salt, or a trifluoroacetic acid salt, or any other equivalent salt), wherein $R_{01}$ is $C_1$-$C_6$alkyl, preferably tert-butyl, and wherein $R_8$, $G_1$ to $G_5$, A, X and $R_1$ are as defined above, can be prepared by reduction of compounds of formula I-A6-4, wherein $R_{01}$ is $C_1$-$C_6$alkyl, preferably tert-butyl, and wherein $R_8$, $G_1$ to $G_5$, A, X and $R_1$ are as defined above, under conditions known to a person skilled in the art, such as for example using zinc dust and acetic acid or trifluoroacetic acid, or mixtures thereof, or using molecular hydrogen $(H_2)$, optionally under pressure, usually in the presence of a catalyst such as nickel, palladium or platinum, in alcoholic solvents (such as for example methanol or ethanol), at temperatures between 0° C. and 120° C., preferably between 30° C. and reflux temperature.

Compounds of formula I-A6-4, wherein $R_{01}$ is $C_1$-$C_6$alkyl, preferably tert-butyl, and wherein $R_8$, $G_1$ to $G_5$, A, X and $R_1$ are as defined above, can be prepared by reacting compounds of formula I-A6-5, wherein $R_8$, $G_1$ to $G_5$, A, X and $R_1$ are as defined above, and in which Hal is a halogen such as, for example, fluorine, chlorine or bromine (preferably fluorine or chlorine), with a reagent of the formula VIIIb $R_{01}$—SH  (VIIIb), or a salt thereof, wherein $R_{01}$ is $C_1$-$C_6$alkyl, preferably tert-butyl, optionally in the presence of a suitable base, such as alkali metal carbonates, for example sodium carbonate and potassium carbonate, or alkali metal hydrides such as sodium hydride, or alkali metal hydroxides such as sodium hydroxide and potassium hydroxide, or sodium or potassium tert-butoxide, in an inert solvent at temperatures preferably between 0-120° C. Examples of solvent to be used include ethers such as THF, ethylene glycol dimethyl ether, tert-butylmethyl ether, and 1,4-dioxane, aromatic hydrocarbons such as toluene and xylene, nitriles such as acetonitrile or polar aprotic solvents such as N,N-dimethylformamide, N,N-dimethylacetamide, N-methyl-2-pyrrolidone or dimethyl sulfoxide. Examples of salts of the compound of formula VIIIb include compounds of the formula VIIIc $R_{01}$—S-M  (VIIIc), wherein $R_{01}$ is $C_1$-$C_6$alkyl, preferably tert-butyl, and wherein M is, for example, sodium or potassium.

Compounds of formula I-A6-5, wherein $R_8$, $G_1$ to $G_5$, A, X and $R_1$ are as defined above, and in which Hal is a halogen such as, for example, fluorine, chlorine or bromine (preferably fluorine or chlorine), can be prepared by reacting hydrazide compounds of formula I-A6-6, or a salt thereof (such as a hydrohalide salt, preferably a hydrochloride or a hydrobromide salt, or a trifluoroacetic acid salt, or any other equivalent salt), wherein A, X and $R_1$ are as defined above, and in which Hal is a halogen such as, for example, fluorine, chlorine or bromine (preferably fluorine or chlorine), with compounds of formula IIb, or a salt thereof (such as a hydrohalide salt, preferably a hydrochloride or a hydrobromide salt, or any other equivalent salt), wherein $R_8$ and $G_1$ to $G_5$ are as defined above, and in which $R_9$ is $C_{1-6}$alkyl, under conditions analogous to those reported above for the transformation [(III)+(IIb)→(I), scheme 2].

Compounds of formula I-A6-6, or a salt thereof (such as a hydrohalide salt, preferably a hydrochloride or a hydrobromide salt, or a trifluoroacetic acid salt, or any other equivalent salt), wherein A, X and $R_1$ are as defined above, and in which Hal is a halogen such as, for example, fluorine, chlorine or bromine (preferably fluorine or chlorine), can be prepared by reacting compounds of formula I-A6-7, wherein A, X and $R_1$ are as defined above, and in which Hal is a halogen such as, for example, fluorine, chlorine or bromine (preferably fluorine or chlorine), with hydrazine $NH_2NH_2$ (or a salt thereof), possibly in form of a hydrate, preferably hydrazine monohydrate, or with hydrazine compounds of formula $NH_2NH$—$C(O)OR_{02}$ (or a salt thereof), wherein $R_{02}$ is $C_1$-$C_6$alkyl (for example tert-butyl), benzyl or benzyl substituted by one or two methoxy, under conditions analogous to those reported above for the transformation [(VI)→(VIa)→(III), scheme 5] or the transformation [(VI)→(VIa)→(IIIb)→(III), scheme 6]. Reacting compounds of formula I-A6-7, wherein A, X and $R_1$ are as defined above, and in which Hal is a halogen such as, for example, fluorine, chlorine or bromine (preferably fluorine or chlorine), with hydrazine compounds of formula $NH_2NH$—$C(O)OR_{02}$ (or a salt thereof), wherein $R_{02}$ is $C_1$-$C_6$alkyl (for example tert-butyl), benzyl or benzyl substituted by one or two methoxy, Scheme 11a:

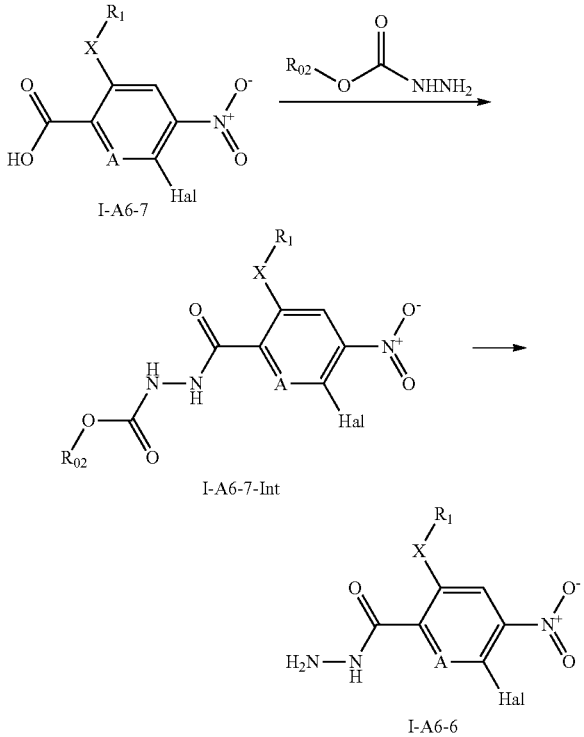

can also be achieved (scheme 11a) in presence of amide coupling reagents, such as DIC, EDC, HATU, HBTU, HCTU or PyBOP known to a person skilled in the art, optionally in presence of a base, such as triethylamine, ethyl diisopropylamine or pyridine, in solvents, such as dichloromethane, tetrahydrofuran, tert-butylmethyl ether or 1,4-dioxane, aromatic hydrocarbons such as toluene and xylene, nitriles such as acetonitrile or polar aprotic solvents such as N,N-dimethylformamide, N,N-dimethylacetamide, N-methyl-2-pyrrolidone or dimethyl sulfoxide, at temperatures between 0° C. and 120° C., preferably between 0 and 80° C., to form compounds of formula I-A6-7-Int, wherein A, X and $R_1$ are as defined above, and in which Hal is a halogen such as, for example, fluorine, chlorine or bromine (preferably fluorine or chlorine), and wherein $R_{02}$ is $C_1$-$C_6$alkyl (for example tert-butyl), benzyl or benzyl substituted by one or two methoxy.

Treating compounds of formula I-A6-7-Int, wherein A, X and $R_1$ are as defined above, and in which Hal is a halogen such as, for example, fluorine, chlorine or bromine (preferably fluorine or chlorine), and wherein $R_{02}$ is $C_1$-$C_6$alkyl (for example tert-butyl), benzyl or benzyl substituted by one or two methoxy, with an acid, such as for example a hydrohalide acid, preferably hydrochloride or hydrobromide acid, or trifluoroacetic acid, optionally in presence of a solvent, such as tetrahydrofuran, dioxane or dichloromethane, at temperatures between 0 and 150° C. will deliver the compounds of formula I-A6-6, or a salt thereof (such as a hydrohalide salt, preferably a hydrochloride or a hydrobromide salt, or a trifluoroacetic acid salt, or any other equivalent salt), wherein A, X and $R_1$ are as defined above, and in which Hal is a halogen such as, for example, fluorine, chlorine or bromine (preferably fluorine or chlorine) (see scheme 6).

Compounds of formula I-A6-7, wherein A, X and $R_1$ are as defined above, and in which Hal is a halogen such as, for example, fluorine, chlorine or bromine (preferably fluorine or chlorine), can be prepared by a nitration reaction on compounds of formula I-A6-8, wherein A, X and $R_1$ are as defined above, and in which Hal is a halogen such as, for example, fluorine, chlorine or bromine (preferably fluorine or chlorine), under conditions known to a person skilled in the art, such as for example using fuming nitric acid, in presence of concentrated sulfuric acid, at temperatures between 0° C. and 120° C., preferably between 50° C. and reflux temperature.

Compounds of formula I-A6-8, wherein A, X and $R_1$ are as defined above, and in which Hal is a halogen such as, for example, fluorine, chlorine or bromine (preferably fluorine or chlorine), can be prepared by a saponification reaction on compounds of formula I-A6-9, wherein A, X and $R_1$ are as defined above, and in which Hal is a halogen such as, for example, fluorine, chlorine or bromine (preferably fluorine or chlorine), and wherein $R_{00}$ is $C_1$-$C_4$alkyl. Conditions for such a reaction, typically hydrolysis by water in presence of a base, are known to a person skilled in the art (using for example: aqueous sodium, potassium or lithium hydroxide in methanol, ethanol, tetrahydrofuran or dioxane at room temperature or up to refluxing conditions).

Compounds of formula I-A6-9, wherein A, X and $R_1$ are as defined above, and in which Hal is a halogen such as, for example, fluorine, chlorine or bromine (preferably fluorine or chlorine), and wherein $R_{00}$ is $C_1$-$C_4$alkyl, may be either known, commercially available or may be prepared by methods known to a person skilled in the art (see in particular experimental part, EXAMPLE I5, step I5.1). Reagents of the formula $R_{10b}C(O)OH$ or of formula $(R_{10b}CO)_2O$, wherein $R_{10b}$ is as defined above, may be either known, commercially available or may be prepared by methods known to a person skilled in the art.

Oxidation of any compounds of formula I-A6-1 to I-A6-9 (scheme 11 and 11a), wherein the substituents are as defined above, and in which X is S (sulfide), with a suitable oxidizing agent, into corresponding compounds wherein X is SO (sulfoxide) or $SO_2$ (sulfone) may be achieved under conditions already described above.

Compounds of formula I-A8-1 define the particular subgroup of compounds of formula I, wherein $R_7$ is as defined in formula I, and wherein $L_1$, $L_2$, $L_3$ and $L_4$ form together with the two carbon atoms to which $L_1$ and $L_4$ are attached an aromatic heterocyclic ring system, in which $L_1$ is $S(O)_n$, n is 0, $L_2$ is $C(R_{10b})_m$, m is 1, $L_3$ is nitrogen and $L_4$ is a direct bond, and wherein $R_8$, $G_1$ to $G_5$, $R_{10b}$, A, X and $R_1$ are as defined in formula I.

Compounds of formula I-A8-1,

Scheme 12:

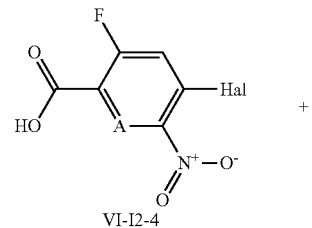

VI-I2-4

+

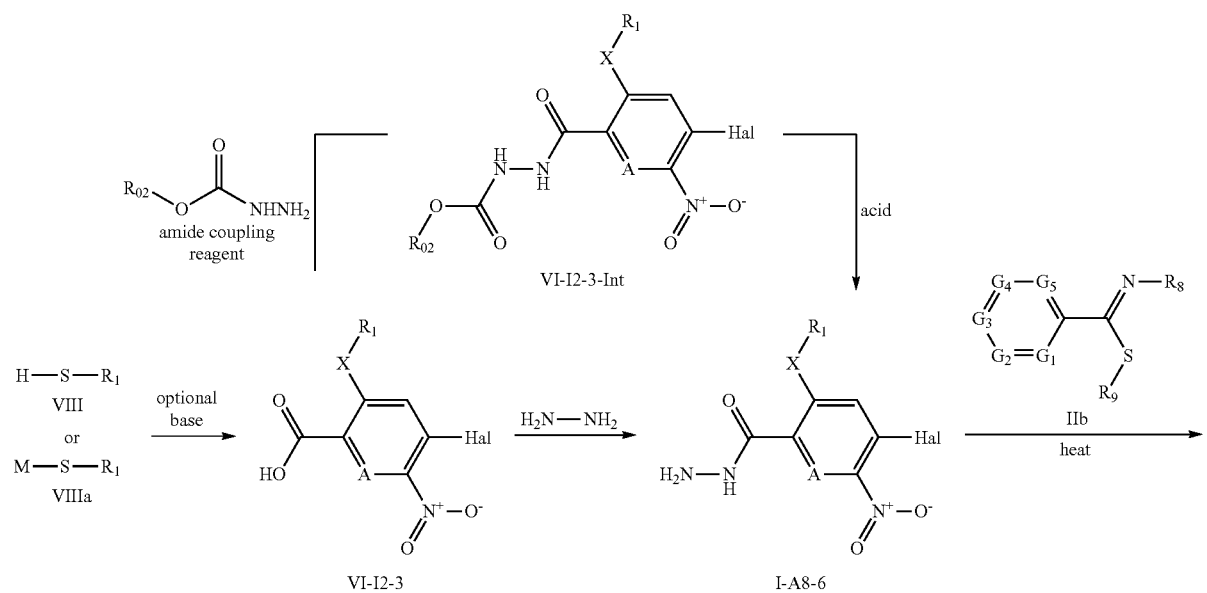

-continued

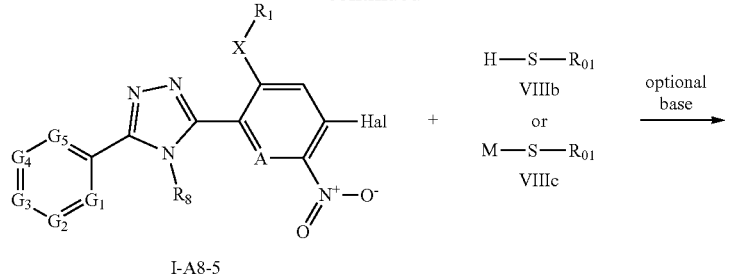

I-A8-5

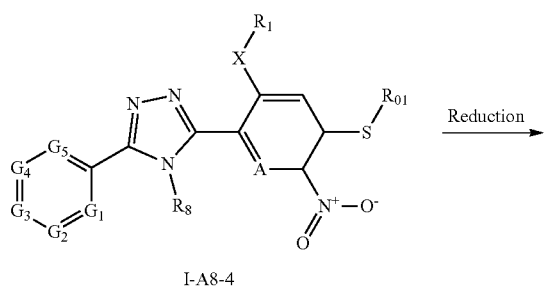

I-A8-4

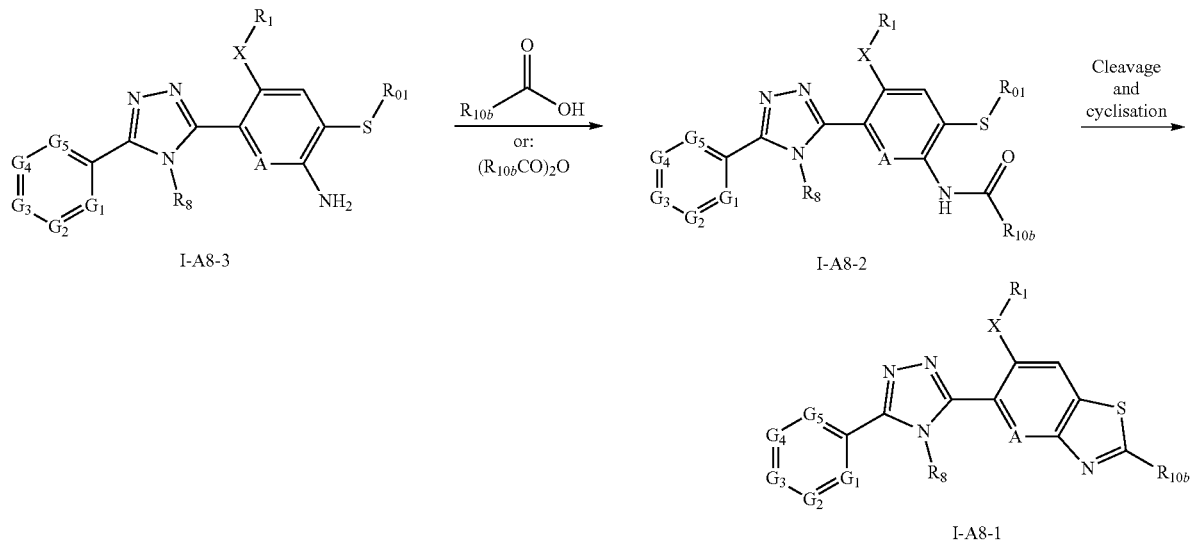

can be prepared from compounds of formula VI-I2-4, wherein A is as defined above, and in which Hal is a halogen such as, for example, fluorine, chlorine or bromine (preferably fluorine or chlorine), by performing the steps shown in the sequence of scheme 12. The transformation of compounds of formula VI-I2-4 into compounds of formula VI-I2-3 was described previously in scheme 7. The transformation of compounds of formula VI-I2-3 into compounds of formula I-A8-1 can be achieved in analogy to steps described in schemes 11 and 11a (see text, descriptions and preparation methods associated to the conversion of I-A6-7 to I-A6-1), possibly by changing the order of certain steps in the sequence and by slightly adapting reaction conditions in a manner known to a person skilled in the art, wherein all substituent definitions mentioned previously are also valid for the compounds shown herein.

Oxidation of any compounds of formula I-A8-1 to I-A8-6 (scheme 12) and VI-I2-3, wherein the substituents are as defined above, and in which X is S (sulfide), with a suitable oxidizing agent, into corresponding compounds wherein X is SO (sulfoxide) or $SO_2$ (sulfone) may be achieved under conditions already described above.

Compounds of formula I-A13-1 define the particular subgroup of compounds of formula I, wherein $R_7$ is as defined in formula I, and wherein $L_1$, $L_2$, $L_3$ and $L_4$ form together with the two carbon atoms to which $L_1$ and $L_4$ are attached an aromatic heterocyclic ring system, in which $L_1$ is $C(R_{10a})_m$, m is 1, $L_2$ is nitrogen, $L_3$ is nitrogen and $L_4$ is a direct bond, and wherein $R_8$, $G_1$ to $G_5$, $R_{10a}$, A, X and $R_1$ are as defined in formula I.

Compounds of formula I-A13-1,

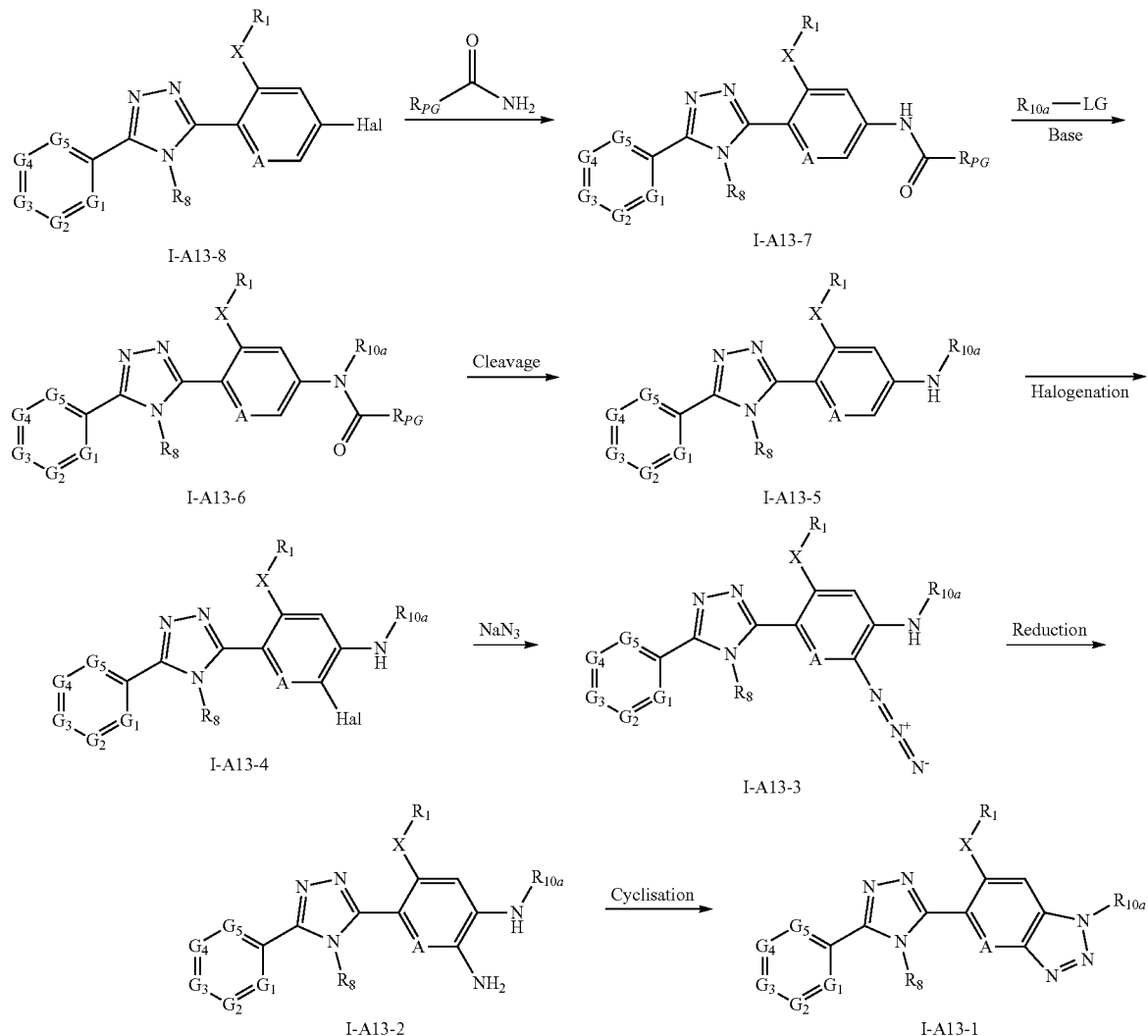

Scheme 13:

can be prepared (scheme 13) by treating compounds of formula I-A13-2, wherein $R_8$, $G_1$ to $G_5$, $R_{10a}$, A, X and $R_1$ are as defined above, with for example sodium nitrite, in presence of water and a mineral acid, or an organic acid, such as acetic acid, optionally in presence of an inert solvent, at temperatures between −10 and 80° C., preferably between 0 and 50° C. to achieve cyclisation.

Compounds of formula I-A13-2, wherein $R_8$, $G_1$ to $G_5$, $R_{10a}$, A, X and $R_1$ are as defined above, can be prepared by reacting compounds of formula I-A13-3, wherein $R_8$, $G_1$ to $G_5$, $R_{10a}$, A, X and $R_1$ are as defined above, with trivalent phosphorous compounds, for example trialkyl- or triarylphosphines, preferably triphenylphosphine, and hydrolyzing in situ the generated iminophosphorane (or aza-ylide, Staudinger reaction) with water, optionally in presence of acid, such as hydrochloric or hydrobromic acid. Overall, azide compounds of formula I-A13-3 undergo a formal reduction to form primary amine compounds of formula I-A13-2 in this transformation. This reaction may be performed in an inert solvent such as tetrahydrofuran or dioxane, at temperatures between 0 and 180° C., preferably between 20 and 150° C., optionally under microwave irradiation. Alternatively, azido compounds of formula I-A13-3 may be reduced to amino compounds of formula I-A13-2 using molecular hydrogen ($H_2$), optionally under pressure, usually in the presence of a catalyst such as nickel, palladium or platinum, in inert solvents (such as for example ethyl acetate, methanol or ethanol), at temperatures between 0° C. and 120° C., preferably between 30° C. and reflux temperature.

Compounds of formula I-A13-3, wherein $R_8$, $G_1$ to $G_5$, $R_{10a}$, A, X and $R_1$ are as defined above, can be prepared by reacting compounds of formula I-A13-4, wherein $R_8$, $G_1$ to $G_5$, $R_{10a}$, A, X and $R_1$ are as defined above, and in which Hal is a halogen such as, for example, chlorine, bromine or iodine (preferably chlorine or bromine), with for example sodium azide $NaN_3$, in an inert solvent such as tetrahydrofuran, dioxane, acetonitrile, N,N-dimethylformamide, N,N-dimethylacetamide, N-methyl-2-pyrrolidone or dimethyl sulfoxide (or mixtures thereof), at temperatures between 0 and 180° C., preferably between 20 and 150° C., optionally under microwave irradiation.

Compounds of formula I-A13-4, wherein $R_8$, $G_1$ to $G_5$, $R_{10a}$, A, X and $R_1$ are as defined above, and in which Hal is a halogen such as, for example, chlorine, bromine or iodine (preferably chlorine or bromine), can be prepared by a halogenation reaction, which involves for example, reacting compounds of formula I-A13-5, wherein $R_8$, $G_1$ to $G_5$, $R_{10a}$, A, X and $R_1$ are as defined above, with halogenating reagents such as N-chlorosuccinimide (NCS), N-bromosuccinimide (NBS) or N-iodo-succinimide (NIS), or alternatively chlorine, bromine or iodine. Such halogenation reactions are carried out in an inert solvent, such as chloroform, carbon tetrachloride, 1,2-dichloroethane, acetic acid, ethers, acetonitrile or N,N-dimethylformamide, at temperatures between 20-200° C., preferably room temperature to 100° C.

Compounds of formula I-A13-5, wherein $R_8$, $G_1$ to $G_5$, $R_{10a}$, A, X and $R_1$ are as defined above, can be prepared by treating compounds of formula I-A13-6, wherein $R_8$, $G_1$ to $G_5$, $R_{10a}$, A, X and $R_1$ are as defined above, and in which $R_{PG}$ is $C_1$-$C_6$alkyl, $C_1$-$C_6$alkoxy (for example tert-butyloxy), benzyloxy or benzyloxy substituted by one or two methoxy, preferably $R_{PG}$ is tert-butyloxy, with an acid, such as for example a hydrohalide acid, preferably hydrochloride or hydrobromide acid, or trifluoroacetic acid, optionally in presence of water, optionally in presence of a solvent, such as tetrahydrofuran, dioxane or dichloromethane, at temperatures between 0 and 150° C.

Compounds of formula I-A13-6, wherein $R_8$, $G_1$ to $G_5$, $R_{10a}$, A, X and $R_1$ are as defined above, and in which $R_{PG}$ is $C_1$-$C_6$alkyl, $C_1$-$C_6$alkoxy (for example tert-butyloxy), benzyloxy or benzyloxy substituted by one or two methoxy, preferably $R_{PG}$ is tert-butyloxy, can be prepared by reacting compounds of formula I-A13-7, wherein $R_8$, $G_1$ to $G_5$, A, X and $R_1$ are as defined above, and in which $R_{PG}$ is $C_1$-$C_6$alkyl, $C_1$-$C_6$alkoxy (for example tert-butyloxy), benzyloxy or benzyloxy substituted by one or two methoxy, preferably $R_{PG}$ is tert-butyloxy, with a reagent of formula $R_{10a}$-LG, wherein $R_{10a}$ is as defined above and in which LG is a leaving group such as halogen, preferably iodine, bromine or chlorine, in presence of a base, such as sodium carbonate, potassium carbonate or cesium carbonate, or sodium hydride, in a appropriate solvent such as for example tetrahydrofuran, dioxane, N,N-dimethyl-formamide, N,N-dimethylacetamide or acetonitrile, at temperatures between 0 and 150° C.

Compounds of formula I-A13-7, wherein $R_8$, $G_1$ to $G_5$, A, X and $R_1$ are as defined above, and in which $R_{PG}$ is $C_1$-$C_6$alkyl, $C_1$-$C_6$alkoxy (for example tert-butyloxy), benzyloxy or benzyloxy substituted by one or two methoxy, preferably $R_{PG}$ is tert-butyloxy, can be prepared by reacting compounds of formula I-A13-8, wherein $R_8$, $G_1$ to $G_5$, A, X and $R_1$ are as defined above, and in which Hal is a halogen such as, for example, chlorine, bromine or iodine (preferably bromine or iodine), with a reagent of formula $R_{PG}C(O)NH_2$, wherein $R_{PG}$ is $C_1$-$C_6$alkyl, $C_1$-$C_6$alkoxy (for example tert-butyloxy), benzyloxy or benzyloxy substituted by one or two methoxy, preferably $R_{PG}$ is tert-butyloxy, in presence of a palladium based catalyst, for example tetrakis(triphenylphosphine)palladium(0), or palladium(II)acetate or tris(dibenzylidene-acetone)dipalladium(0) in presence of a phosphine ligand, such as 2-dicyclohexylphosphino-2',4',6'-triisopropylbiphenyl tricyclohexylphosphane XPhos, (1,1'bis(diphenyl-phosphino)ferrocene)dichloropalladium-dichloromethane (1:1 complex) or chloro(2-dicyclohexyl-phosphino-2',4',6'-triisopropyl-1,1'-biphenyl)[2-(2'-amino-1,1'-biphenyl)]palladium(II) (XPhos palladacycle), in presence of a base, like sodium, potassium or cesium carbonate, tripotassium phosphate or cesium fluoride, in a solvent or a solvent mixture, like, for example dioxane, acetonitrile or N,N-dimethylformamide, preferably under inert atmosphere. The reaction temperature can preferentially range from room temperature to the boiling point of the reaction mixture, or the reaction may be performed under microwave irradiation.

Reagents of the formula $R_{10a}$-LG, wherein $R_{10a}$ and LG are as defined above, and of the formula $R_{PG}C(O)NH_2$, wherein $R_{PG}$ is as defined above, may be either known, commercially available or may be prepared by methods known to a person skilled in the art. Compounds of formula I-A13-8, wherein $R_8$, $G_1$ to $G_5$, A, X and $R_1$ are as defined above, and in which Hal is a halogen such as, for example, chlorine, bromine or iodine (preferably bromine or iodine), are known compounds and may be prepared by methods described, for example, in WO 2017/016910.

Oxidation of any compounds of formula I-A13-1 to I-A13-8 (scheme 13), wherein the substituents are as defined above, and in which X is S (sulfide), with a suitable oxidizing agent, into corresponding compounds wherein X is SO (sulfoxide) or $SO_2$ (sulfone) may be achieved under conditions already described above.

Compounds of formula I-A9-1 define the particular subgroup of compounds of formula I, wherein $R_7$ is as defined in formula I, and wherein $L_1$, $L_2$, $L_3$ and $L_4$ form together with the two carbon atoms to which $L_1$ and $L_4$ are attached an aromatic heterocyclic ring system, in which $L_1$ is $C(R_{10a})_m$, m is 1, $L_2$ is nitrogen, $L_3$ is nitrogen and $L_4$ is a direct bond, and wherein $R_8$, $G_1$ to $G_5$, $R_{10a}$, A, X and $R_1$ are as defined in formula I.

Compounds of formula I-A18-1 define the particular subgroup of compounds of formula I, wherein $R_7$ is as defined in formula I, and wherein $L_1$, $L_2$, $L_3$ and $L_4$ form together with the two carbon atoms to which $L_1$ and $L_4$ are attached an aromatic heterocyclic ring system, in which $L_1$ is nitrogen, $L_2$ is $C(R_{10b})_m$, m is 1, $L_3$ is nitrogen and $L_4$ is a direct bond, and wherein $R_8$, $G_1$ to $G_5$, $R_{10b}$, A, X and $R_1$ are as defined in formula I.

Compounds of formula I-A10-1 define the particular subgroup of compounds of formula I, wherein $R_7$ is as defined in formula I, and wherein $L_1$, $L_2$, $L_3$ and $L_4$ form together with the two carbon atoms to which $L_1$ and $L_4$ are attached an aromatic heterocyclic ring system, in which $L_1$ is nitrogen, $L_2$ is nitrogen, $L_3$ is $C(R_{10c})_m$, m is 1 and $L_4$ is a direct bond, and wherein $R_8$, $G_1$ to $G_5$, $R_{10c}$, A, X and $R_1$ are as defined in formula I.

Compounds of formula I-A9-1, I-A18-1 and I-A10-1,

Scheme 14:

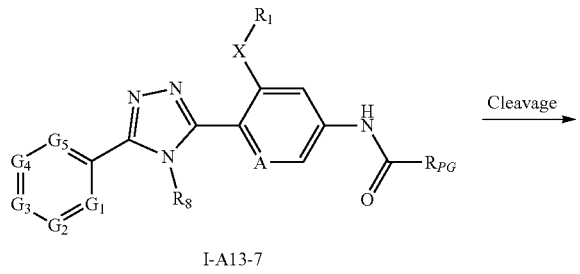

I-A13-7

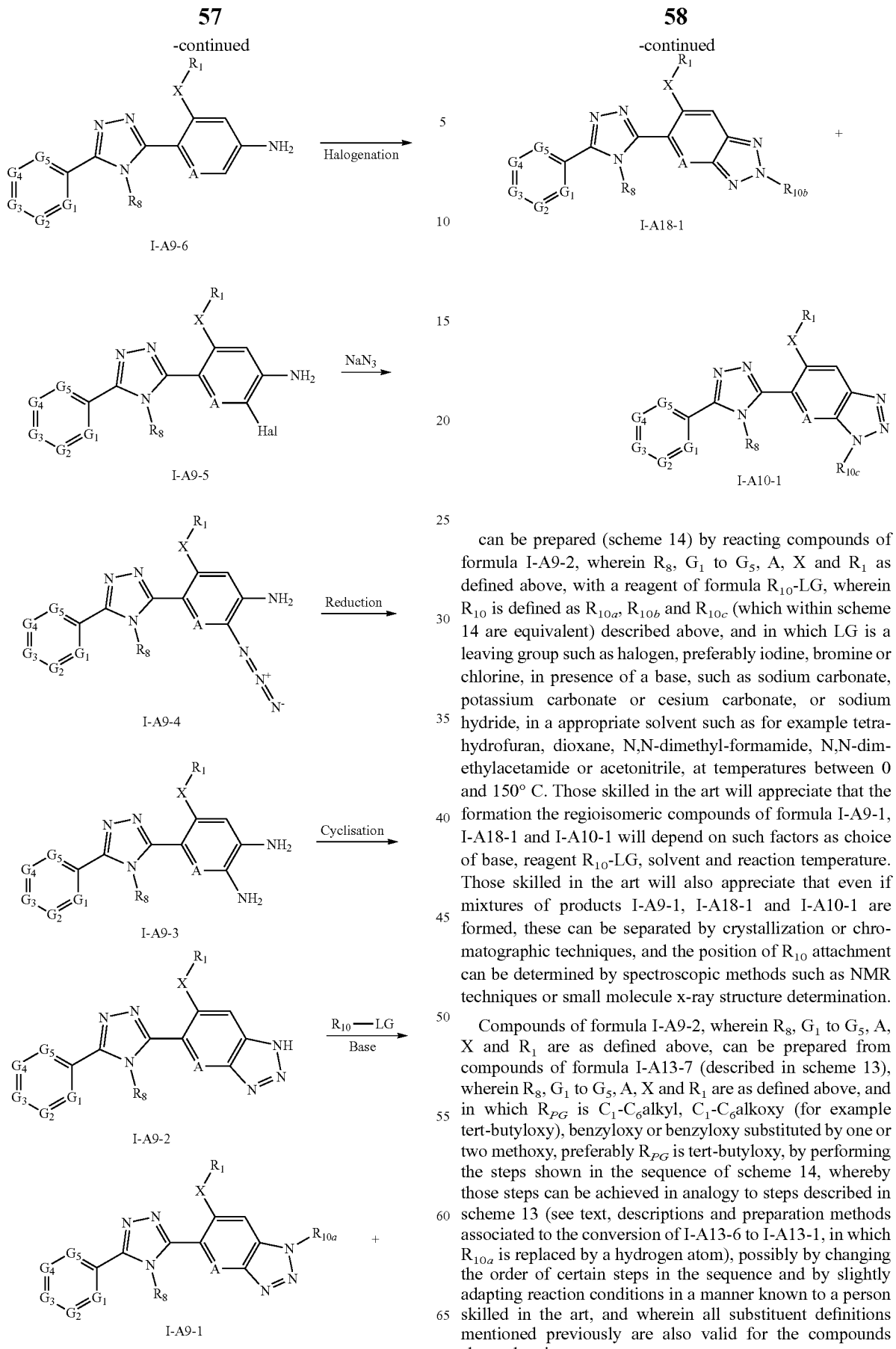

can be prepared (scheme 14) by reacting compounds of formula I-A9-2, wherein $R_8$, $G_1$ to $G_5$, A, X and $R_1$ as defined above, with a reagent of formula $R_{10}$-LG, wherein $R_{10}$ is defined as $R_{10a}$, $R_{10b}$ and $R_{10c}$ (which within scheme 14 are equivalent) described above, and in which LG is a leaving group such as halogen, preferably iodine, bromine or chlorine, in presence of a base, such as sodium carbonate, potassium carbonate or cesium carbonate, or sodium hydride, in a appropriate solvent such as for example tetrahydrofuran, dioxane, N,N-dimethyl-formamide, N,N-dimethylacetamide or acetonitrile, at temperatures between 0 and 150° C. Those skilled in the art will appreciate that the formation the regioisomeric compounds of formula I-A9-1, I-A18-1 and I-A10-1 will depend on such factors as choice of base, reagent $R_{10}$-LG, solvent and reaction temperature. Those skilled in the art will also appreciate that even if mixtures of products I-A9-1, I-A18-1 and I-A10-1 are formed, these can be separated by crystallization or chromatographic techniques, and the position of $R_{10}$ attachment can be determined by spectroscopic methods such as NMR techniques or small molecule x-ray structure determination.

Compounds of formula I-A9-2, wherein $R_8$, $G_1$ to $G_5$, A, X and $R_1$ are as defined above, can be prepared from compounds of formula I-A13-7 (described in scheme 13), wherein $R_8$, $G_1$ to $G_5$, A, X and $R_1$ are as defined above, and in which $R_{PG}$ is $C_1$-$C_6$alkyl, $C_1$-$C_6$alkoxy (for example tert-butyloxy), benzyloxy or benzyloxy substituted by one or two methoxy, preferably $R_{PG}$ is tert-butyloxy, by performing the steps shown in the sequence of scheme 14, whereby those steps can be achieved in analogy to steps described in scheme 13 (see text, descriptions and preparation methods associated to the conversion of I-A13-6 to I-A13-1, in which $R_{10a}$ is replaced by a hydrogen atom), possibly by changing the order of certain steps in the sequence and by slightly adapting reaction conditions in a manner known to a person skilled in the art, and wherein all substituent definitions mentioned previously are also valid for the compounds shown herein.

Oxidation of any compounds of formula I-A9-1 to I-A9-6 (scheme 14), I-A18-1 and I-A10-1, wherein the substituents are as defined above, and in which X is S (sulfide), with a suitable oxidizing agent, into corresponding compounds wherein X is SO (sulfoxide) or $SO_2$ (sulfone) may be achieved under conditions already described above.

Compounds of formula I, wherein $R_7$, $R_8$, $G_1$, $G_2$, $G_3$, $G_4$, and $G_5$ are as defined in formula I and wherein X is S (sulfide),

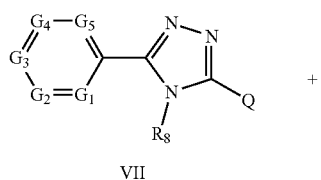
VII

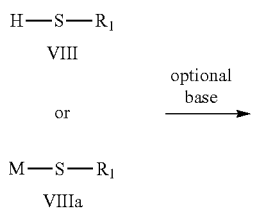

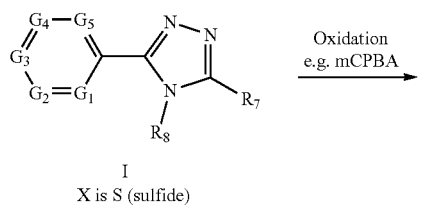

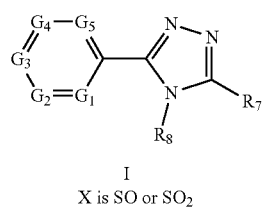

can also be prepared by reacting a compound of formula VII, wherein $R_8$, $G_1$, $G_2$, $G_3$, $G_4$, and $G_5$ are as described in formula I and wherein Q is:

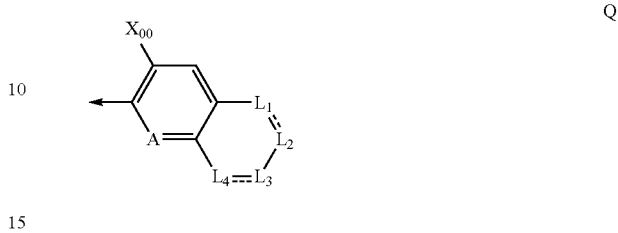

wherein A is as defined in formula I, and wherein $X_{00}$ is a halogen (preferably fluorine, chlorine or bromine), with a compound of formula VIII

or a salt thereof, wherein $R_1$ is as defined in formula I, optionally in the presence of a suitable base, such as alkali metal carbonates, for example sodium carbonate and potassium carbonate, or alkali metal hydrides such as sodium hydride, or alkali metal hydroxides such as sodium hydroxide and potassium hydroxide, in an inert solvent at temperatures preferably between 25-120° C. Examples of solvent to be used include ethers such as THF, ethylene glycol dimethyl ether, tert-butylmethyl ether, and 1,4-dioxane, aromatic hydrocarbons such as toluene and xylene, nitriles such as acetonitrile or polar aprotic solvents such as N,N-dimethylformamide, N,N-dimethylacetamide, N-methyl-2-pyrrolidone or dimethyl sulfoxide. Examples of salts of the compound of formula VIII include compounds of the formula VIIIa

wherein $R_1$ is as defined above and wherein M is, for example, sodium or potassium.

Compounds of formula VII, wherein $R_8$, $G_1$, $G_2$, $G_3$, $G_4$, and $G_5$ are as defined above, and wherein Q is as described above,

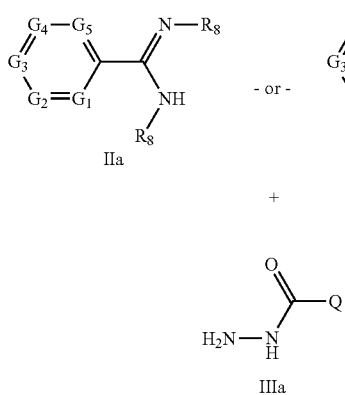

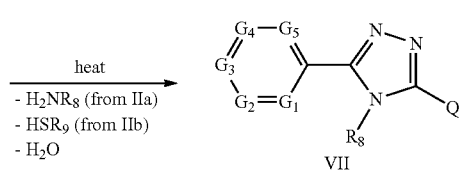

may be prepared by reacting an amidine compound of formula IIa, or a salt thereof (such as a hydrohalide salt, preferably a hydrochloride or a hydrobromide salt, or any other equivalent salt), wherein $R_8$, $G_1$, $G_2$, $G_3$, $G_4$, and $G_5$ are as defined above;

or alternatively, by reacting an alkyl carboximidothioate compound of formula IIb, or a salt thereof (such as a hydrohalide salt, preferably a hydrochloride or a hydrobromide salt, or any other equivalent salt), wherein $R_8$, $G_1$, $G_2$, $G_3$, $G_4$, and $G_5$ are as defined above, and in which $R_9$ is $C_{1-6}$alkyl;

with a hydrazide compound of formula IIIa, or a salt thereof (such as a hydrohalide salt, preferably a hydrochloride or a hydrobromide salt, or any other equivalent salt), wherein Q is described above, optionally in presence of a base such as alkali metal carbonates, for example sodium carbonate or potassium carbonate, in a solvent such as methanol, ethanol, isopropanol, acetonitrile, pyridine, acetic acid, N,N-dimethylformamide or N,N-dimethylacetamide, at temperatures between 0 and 200° C., preferably between 50 and 180° C., optionally under microwave irradiation. The compounds of formula IIa or IIb may be reacted with any configuration (E or Z, or any mixture thereof) on the carbon-nitrogen double bond.

Compounds of formula IIIa, or a salt thereof (such as a hydrohalide salt, preferably a hydrochloride or a hydrobromide salt, or any other equivalent salt), wherein Q is as defined above, may be prepared in analogy to processes described above in the context of the preparation of compounds of the formula III as described in scheme 15.

Scheme 15:

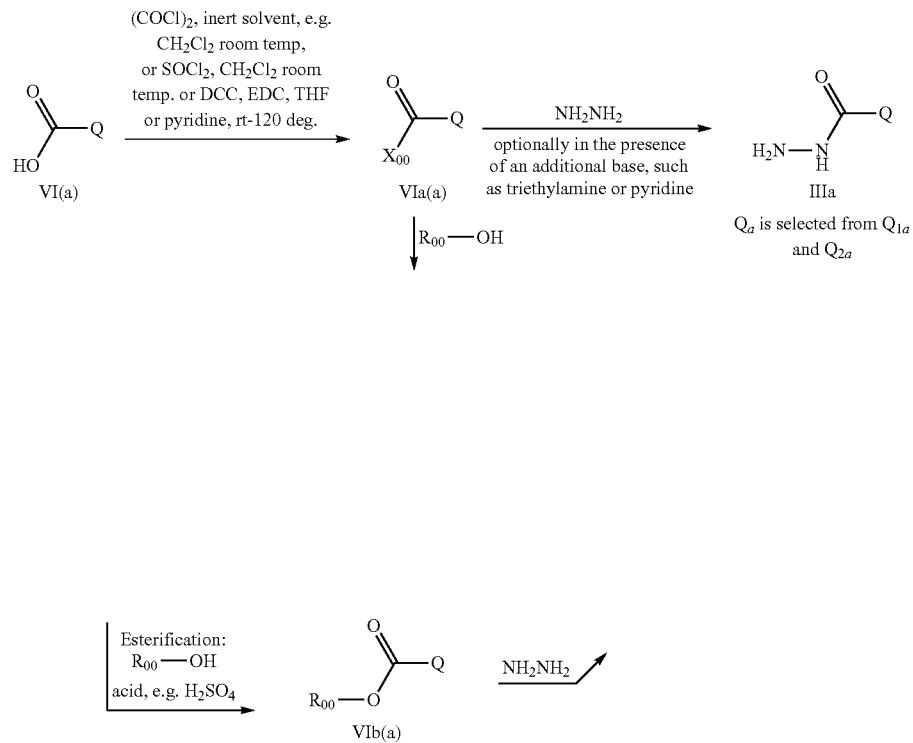

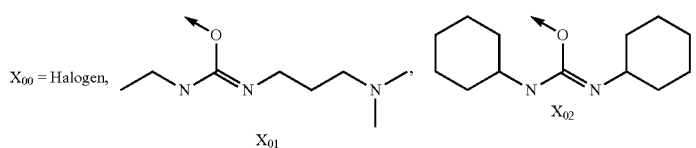

Compounds of formula VI(a) and VIb(a), wherein Q and $R_{00}$ are as defined above, are known compounds or can be prepared by known methods, described in the literature.

Compounds of formula Ia, wherein X is SO or $SO_2$ and A, X, $R_1$, $R_8$, $L_1$, $L_2$, $L_3$, $L_4$, $G_1$, $G_2$, $G_3$, $G_4$, and $G_5$ are as defined above and wherein Z represented $R_{10a}$, $R_{10b}$, $R_{10c}$ and $R_{10d}$ which are as defined above in formula I, Scheme 16:

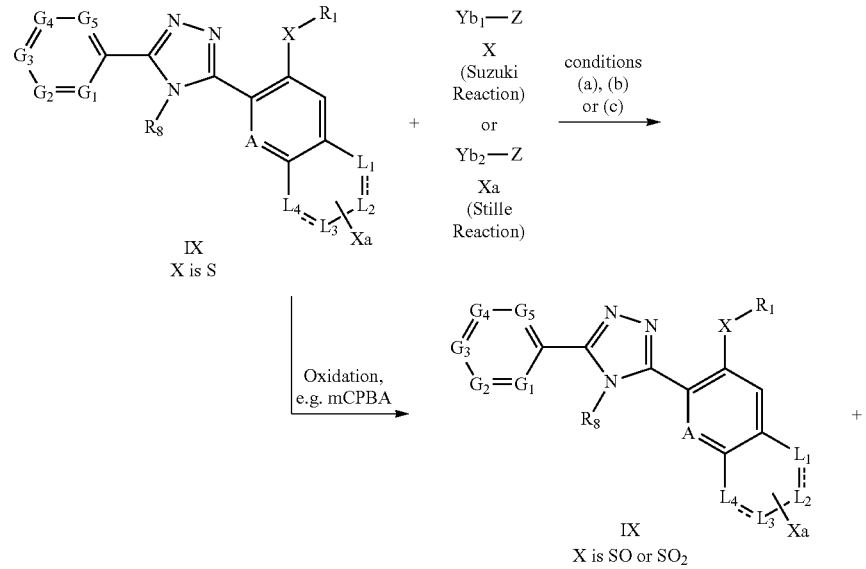

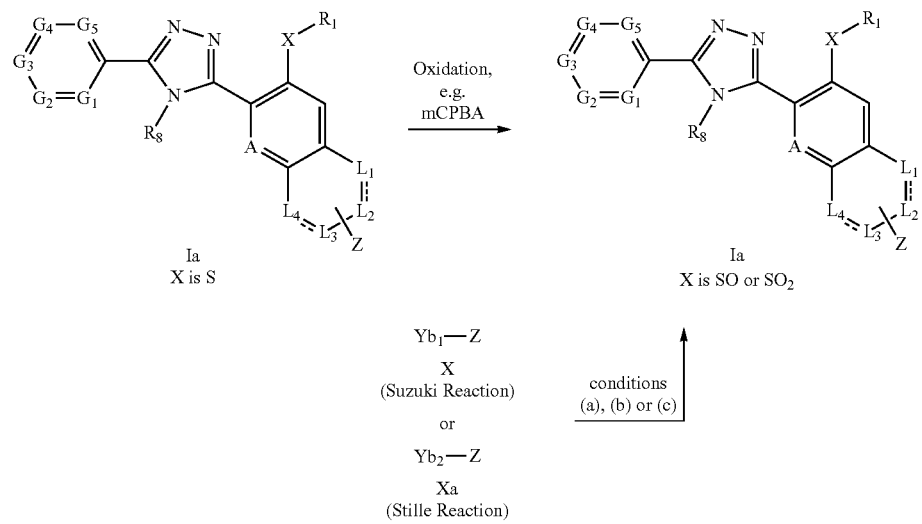

(a) Suzuki reaction: Pd cat. (e.g. $Pd(PPh_3)_4$ or $Pd(dppf)Cl_2$), base (e.g. $Na_2CO_3$), solvent (e.g. 1,2-dimethoxyethane/water), 25-180° C.
(b) Stille reaction: Pd cat. (e.g. $Pd(PPh_3)_4$ or $Pd(PPh_3)Cl_2$), solvent (e.g. toluene), 25-180° C.

may be prepared by a Suzuki reaction (scheme 16), which involves for example, reacting compounds of formula IX, wherein A, X, $R_1$, $R_8$, $L_1$, $L_2$, $L_3$, $L_4$, $G_1$, $G_2$, $G_3$, $G_4$, and $G_5$ are as defined above, and in which X is SO or $SO_2$, and wherein Xa is a leaving group like, for example, chlorine, bromine or iodine (preferably bromine), or an aryl- or alkylsulfonate such as trifluoromethanesulfonate, with compounds of formula X, wherein Z represented $R_{10a}$, $R_{10b}$, $R_{10c}$ and $R_{10d}$ which are as defined above in formula I, such as cyclopropyl, and wherein $Y_{b1}$ can be a boron-derived functional group, such as for example $B(OH)_2$ or $B(OR_{b1})_2$ wherein $R_{b1}$ can be a $C_1$-$C_4$alkyl group or the two groups $OR_{b1}$ can form together with the boron atom a five membered ring, as for example a pinacol boronic ester. The reaction may be catalyzed by a palladium based catalyst, for example tetrakis(triphenylphosphine)-palladium(0), (1,1'bis(diphenylphosphino)ferrocene)dichloro-palladium-dichloromethane (1:1 complex) or chloro(2-dicyclohexylphosphino-2',4',6'-triisopropyl-1,1'-biphenyl)[2-(2'-amino-1,1'-biphenyl)]palladium(II) (XPhos palladacycle), in presence of a base, like sodium carbonate, tripotassium phosphate or cesium fluoride, in a solvent or a solvent mixture, like, for example dioxane, acetonitrile, N,N-dimethyl-formamide, a mixture of 1,2-dimethoxyethane and water or of dioxane/water, or of toluene/water, preferably under inert atmosphere. The reaction temperature can preferentially range from room temperature to the boiling point of the reaction mixture, or the reaction may be performed under microwave irradiation. Such Suzuki reactions are well known to those skilled in the art and have been reviewed, for example, in *J. Orgmet. Chem.* 576, 1999, 147-168. Xa is or could be including in the definition of $R_{10a}$, $R_{10b}$, $R_{10c}$ and $R_{10d}$ and Z represented $R_{10a}$, $R_{10b}$, $R_{10c}$ and $R_{10d}$.

Alternatively compounds of formula Ia, wherein X is SO or $SO_2$, may be prepared by a Stille reaction between compounds of formula Xa, wherein Z represented $R_{10a}$, $R_{10b}$, $R_{10c}$ and $R_{10d}$ which are as defined above in formula I, and wherein $Y_{b2}$ is a trialkyl tin derivative, preferably tri-n-butyl tin or tri-methyl-tin, and compounds of formula IX, wherein A, X, $R_1$, $R_8$, $L_1$, $L_2$, $L_3$, $L_4$, $G_1$, $G_2$, $G_3$, $G_4$, and $G_5$ are as defined above, and in which X is SO or $SO_2$, and wherein Xa is a leaving group like, for example, chlorine, bromine or iodine (preferably bromine), or an aryl- or alkylsulfonate such as trifluoromethanesulfonate. Such Stille reactions are usually carried out in the presence of a palladium catalyst, for example tetrakis(triphenylphosphine) palladium(0), or bis(triphenylphosphine) palladium(II) dichloride, in an inert solvent such as N,N-dimethylformamide, acetonitrile, toluene or dioxane, optionally in the presence of an additive, such as cesium fluoride, or lithium chloride, and optionally in the presence of a further catalyst, for example copper(I)iodide. Such Stille couplings are also well known to those skilled in the art, and have been described in for example *J. Org. Chem.*, 2005, 70, 8601-8604, *J. Org. Chem.*, 2009, 74, 5599-5602, and *Angew. Chem. Int. Ed.*, 2004, 43, 1132-1136. Xa is or could be including in the definition of $R_{10a}$, $R_{10b}$, $R_{10c}$ and $R_{10d}$ and Z represented $R_{10a}$, $R_{10b}$, $R_{10c}$ and $R_{10d}$.

Compounds of formula IX, wherein A, X, $R_1$, $R_8$, $L_1$, $L_2$, $L_3$, $L_4$, $G_1$, $G_2$, $G_3$, $G_4$, and $G_5$ are as defined above, and in which X is S (sulfide), and wherein Xa is a leaving group like, for example, chlorine, bromine or iodine (preferably bromine), or an aryl- or alkylsulfonate such as trifluoromethanesulfonate,

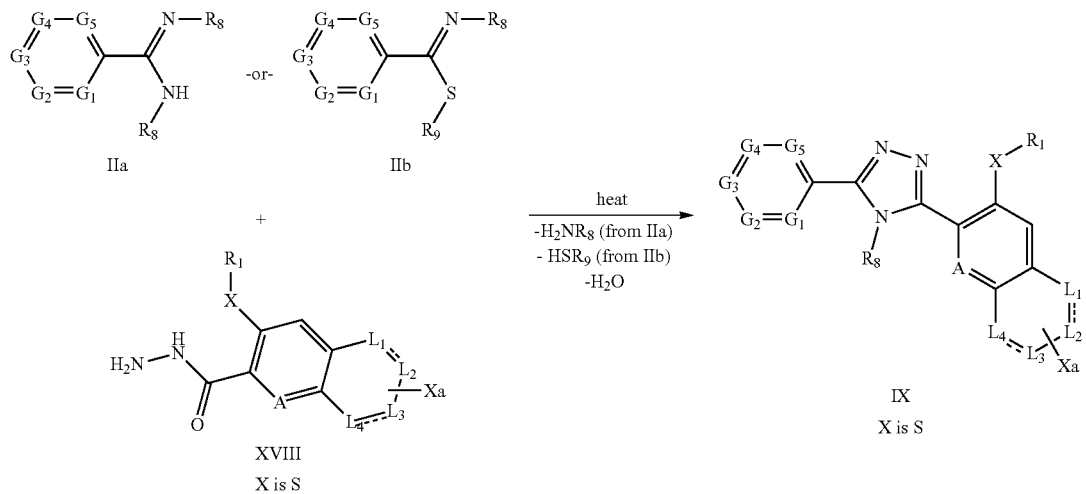

Scheme 17:

may be prepared (scheme 17) by reacting an amidine compound of formula IIa, or a salt thereof (such as a hydrohalide salt, preferably a hydrochloride or a hydrobromide salt, or any other equivalent salt), wherein $R_8$, $G_1$, $G_2$, $G_3$, $G_4$, and $G_5$ are as defined above;

or alternatively, by reacting an alkyl carboximidothioate compound of formula IIb, or a salt thereof (such as a hydrohalide salt, preferably a hydrochloride or a hydrobromide salt, or any other equivalent salt), wherein $R_8$, $G_1$, $G_2$, $G_3$, $G_4$, and $G_5$ are as defined above, and in which $R_9$ is $C_{1-6}$alkyl;

with a hydrazide compound of formula XVIII, or a salt thereof (such as a hydrohalide salt, preferably a hydrochloride or a hydrobromide salt, or any other equivalent salt), wherein A and $R_1$ are as defined above, and in which X is S (sulfide), and wherein Xa is a leaving group like, for example, chlorine, bromine or iodine (preferably bromine), or an aryl- or alkylsulfonate such as trifluoromethanesulfonate, optionally in presence of a base such as alkali metal carbonates, for example sodium carbonate or potassium carbonate, in a solvent such as methanol, ethanol, isopropanol, acetonitrile, pyridine, acetic acid, N,N-dimethylformamide or N,N-dimethylacetamide, at temperatures between 0 and 200° C., preferably between 50 and 180° C., optionally under microwave irradiation. The compounds of formula IIa or IIb may be reacted with any configuration (E or Z, or any mixture thereof) on the carbon-nitrogen double bond. Xa is or could be including in the definition of $R_{10a}$, $R_{10b}$, $R_{10c}$ and $R_{10d}$.

Compounds of formula XVIII, or a salt thereof, wherein A and $R_1$ are as defined above, and in which X is S (sulfide), and wherein Xa is a leaving group like, for example, chlorine, bromine or iodine (preferably bromine), or an aryl- or alkylsulfonate such as trifluoromethanesulfonate,

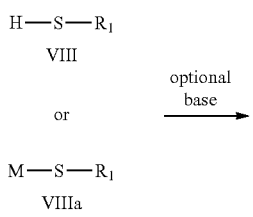

Scheme 18:

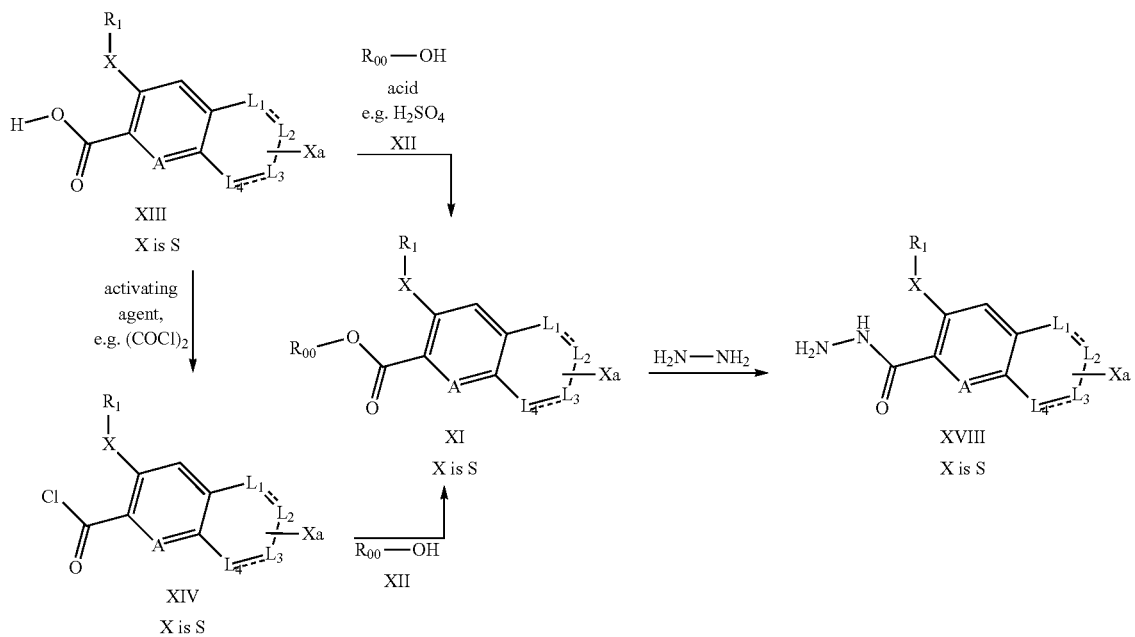

may be prepared (scheme 18) in analogy to processes described above (see for example preparation of compounds of the formula III, or scheme 15) from compounds of the formula XIII, via compounds of the formula XI, wherein A and $R_1$ are as defined above, and in which X is S (sulfide), and wherein Xa is a leaving group like, for example, chlorine, bromine or iodine (preferably bromine), or an aryl- or alkylsulfonate such as trifluoromethanesulfonate, and wherein $R_{00}$ is $C_1$-$C_4$alkyl, preferably methyl or ethyl.

Compounds of formula XIII, wherein A and $R_1$ are as defined above, and in which X is S (sulfide), and wherein Xa is a leaving group like, for example, chlorine, bromine or iodine (preferably bromine), or an aryl- or alkylsulfonate such as trifluoromethanesulfonate, Scheme 19:

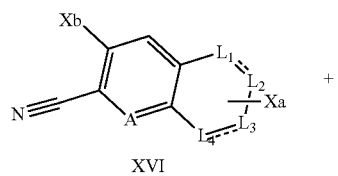

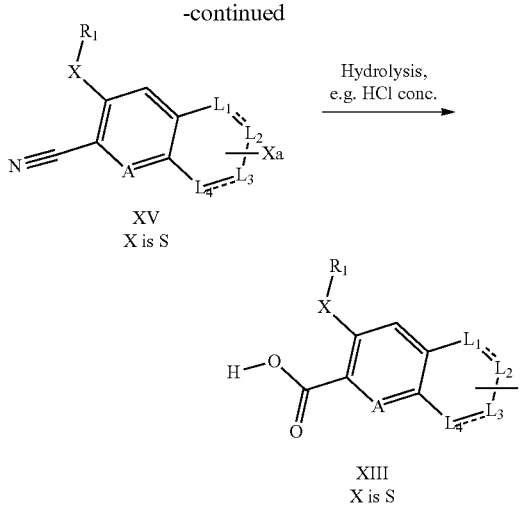

may be prepared (scheme 19) by hydrolysing compounds of formula XV, wherein X is S, and wherein A, $R_1$ and Xa are as defined above, for example through heating in concentrated acid, such as concentrated hydrochloric acid HCl conc., optionally in the presence of an inert solvent, such as ethers (for example tetrahydrofuran, ethylene glycol dimethyl ether, or 1,4-dioxane). Such hydrolysis conditions, and variants thereof, are known to a person skilled in the art.

Compounds of formula XV, wherein X is S, and wherein A, $R_1$ and Xa are as defined above, may be prepared by reacting compounds of formula XVI, wherein A and Xa are as defined above, and in which Xb is a leaving group such as, for example, a halogen (preferably fluorine, chlorine or bromine) or nitro, with a compound of formula VIII, or a salt thereof. VIIIa, wherein $R_1$ is as defined in formula I, optionally in the presence of a suitable base, such as alkali metal carbonates, for example sodium carbonate and potassium carbonate, or alkali metal hydrides such as sodium hydride, or alkali metal hydroxides such as sodium hydroxide and potassium hydroxide, optionally in the presence of a catalytic amount of an additive, such as an ammonium salt (for example tetrabutylammonium bromide TBAB), in an inert solvent at temperatures preferably between 25-120° C. Examples of solvent to be used include ethers such as THF, ethylene glycol dimethyl ether, tert-butylmethyl ether, and 1,4-dioxane, aromatic hydrocarbons such as toluene and xylene, nitriles such as acetonitrile, polar aprotic solvents such as N,N-dimethylformamide, N,N-dimethylacetamide, N-methyl-2-pyrrolidone or dimethyl sulfoxide, or water. Examples of salts of the compound of formula VIII include compounds of the formula VIIIa

(VIIIa), wherein $R_1$ is as defined above and wherein M is, for example, sodium or potassium.

Compounds of formula I wherein Z is $C_1$-$C_6$haloalkylsulfanyl (e.g. compounds Iae and/or Iaf), $C_1$-$C_6$haloalkylsulfinyl and $C_1$-$C_6$haloalkylsulfonyl can be prepared by the methods shown in scheme 20.

Scheme 20:

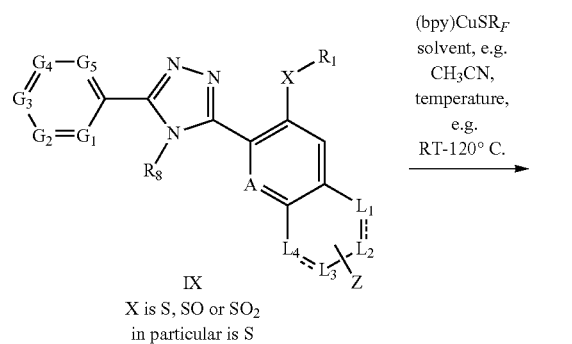

IX
X is S, SO or $SO_2$
in particular is S

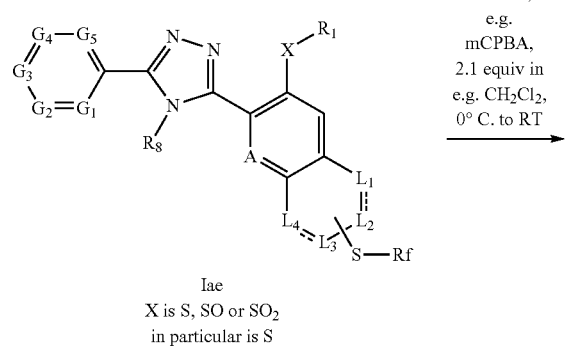

Iae
X is S, SO or $SO_2$
in particular is S

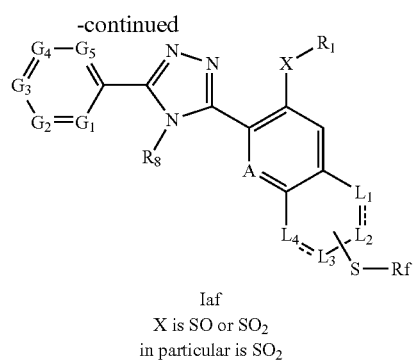

Iaf
X is SO or $SO_2$
in particular is $SO_2$

As shown in scheme 20, treatment of compounds of formula IX, wherein X is S, SO or $SO_2$ (in particular S), and in which A, $R_1$, $R_8$, $G_1$, $G_2$, $G_3$, $G_4$, and $G_5$ are as defined above and wherein Xa is preferably halogen (even more preferably chlorine, bromine or iodine), with a bipyridine copper reagent (bpy)$CuSR_F$, wherein $R_F$ is $C_1$-$C_6$haloalkyl, and in which bpy is bipyridyl, in an inert solvent such as acetonitrile, at temperatures between room temperature and 120° C., optionally under microwave heating, leads to compounds of formula Iae, wherein X is S, SO or $SO_2$ (in particular S), and in which A, $R_1$, $R_8$, $G_1$, $G_2$, $G_3$, $G_4$, and $G_5$ are as defined above and wherein $R_F$ is $C_1$-$C_6$haloalkyl. Such chemistry is known and has been described in the literature, for example, in Angew. Chem. Int. Ed. 2013, 52, 1548-1552. A preferred reagent for this transformation is (bpy)$CuSCF_3$ (CAS 1413732-47-4) for the particular preparation of compounds of formula Iae and Iaf, wherein $R_F$ is trifluoromethyl.

Compounds of formula Iae, wherein X is S or SO, can be further oxidized to, for example, compounds of formula Iaf, wherein X is SO or $SO_2$ (in particular $SO_2$), and in which A, $R_1$, $R_8$, $G_1$, $G_2$, $G_3$, $G_4$, and $G_5$ are as defined above and wherein $R_F$ is $C_1$-$C_6$haloalkyl, by methods known to those skilled in the art and described herein above.

Compounds of formula IVc (VIc including VI and VIa),

Scheme 21:

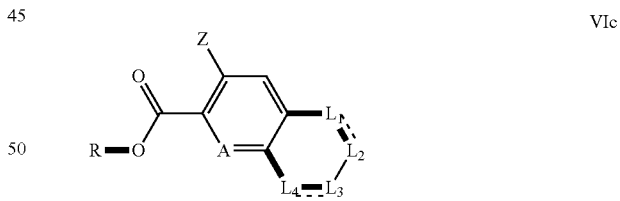

wherein Z is X—$R_1$ or a leaving group or a group that could be transformed in leaving group such as, for example halogen, amine or nitro, and wherein X, A, $R_1$, $L_1$, $L_2$, $L_3$, $L_4$ and A are as described under formula I above and wherein R is C1-C6 alkyl group or hydrogen, may be either known, commercially available or may be made by methods known to a person skilled in the art.

Compounds of formula VIc, wherein $R_1$, A, $L_1$, $L_2$, $L_3$, $L_4$ and A are as described under formula I above, and wherein Z is a leaving group, for example halogen, preferably fluorine, chlorine, and wherein R is alkyl or hydrogen can be reacted with compounds of formula VIII $R_1$—SH (VIII), or a salt thereof, wherein $R_1$ is as defined in formula I, optionally in the presence of a suitable base, such as alkali metal carbonates, for example sodium carbonate and potassium carbonate, or alkali metal hydrides such as sodium hydride, or alkali metal hydroxides such as sodium hydroxide and potassium hydroxide, in an inert solvent at temperatures preferably between 25-120° C., to generate compounds of formula VIc, wherein R is alkyl or hydrogen, $R_1$ is as described under formula I above, and in which A, X, $L_1$, $L_2$, $L_3$ and $L_4$ are as described under formula I above. Examples of solvent to be used include ethers such as THF, ethylene glycol dimethyl ether, tert-butylmethyl ether, and 1,4-dioxane, aromatic hydrocarbons such as toluene and xylene, nitriles such as acetonitrile or polar aprotic solvents such as N,N-dimethylformamide, N,N-dimethylacetamide, N-methyl-2-pyrrolidone or dimethyl sulfoxide. Examples of salts of the compound of formula V include compounds of the formula Va $R_1$—S-M    (VIIIa), wherein $R_1$ is as defined above and wherein M is, for example, sodium or potassium. This is illustrated for compounds of formula IId in scheme 22.

Scheme 22:

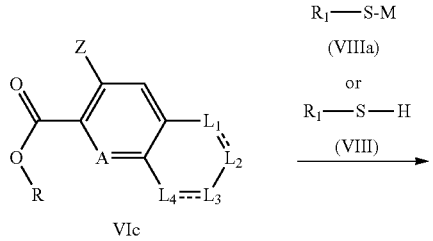

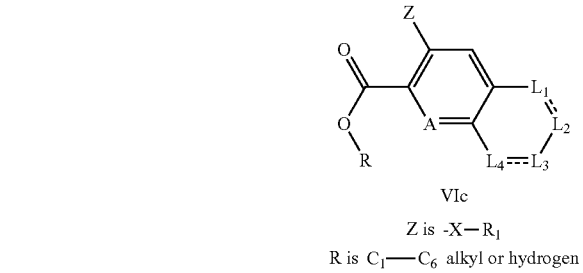

VIc
Z is -X—$R_1$
R is $C_1$—$C_6$ alkyl or hydrogen

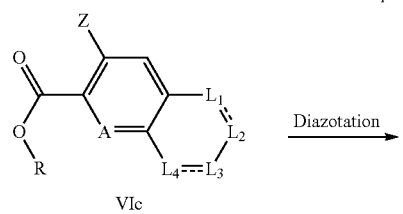

VIc
Z is a leaving group such as amine
R is $C_1$—$C_6$ alkyl or hydrogen

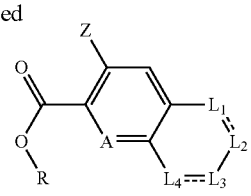

VIc
Z is -X—$R_1$
R is $C_1$—$C_6$ alkyl or hydrogen

Alternatively, compounds of formula VIc, wherein Z is a amine and wherein A, $L_1$, $L_2$, $L_3$ and $L_4$ are as described under formula I above, and wherein R is alkyl or hydrogen can be transformed to compounds of formula VIc via diazotation and reaction with dialkyldisulfide. This transformation is well known and could be made by methods known to a person skilled in the art (see for example: Synthetic Communications, 31(12), 1857-1861; 2001 or Organic & Biomolecular Chemistry, 6(4), 745-761; 2008).

Compounds of formula VIc, wherein Z is a amine and wherein A, $L_1$, $L_2$, $L_3$ and $L_4$ are as described under formula I above, and wherein R is alkyl or hydrogen can be transformed to compounds of formula VIe via diazotation and reaction with sodium sulphide, followed by reduction. This transformation is well known and could be made by methods known to a person skilled in the art (see for example: US 20040116734 or Chemische Berichte, 120(7), 1151-73; 1987). Alkylation of compound VIe with $R_1$—$X_{LG}$, wherein $R_1$ is as described under formula I above and wherein $X_{LG}$ is a leaving group, such as halogen, preferably iodine, bromine or chlorine, in presence of a base, such as sodium carbonate, potassium carbonate or cesium carbonate, or sodium hydride, in a appropriate solvent such as for example N,N-dimethylformamide, N,N-dimethylacetamide or acetonitrile, to generate a compound of formula VIc, wherein $R_1$ is as described under formula I above. See scheme 23.

Scheme 23:

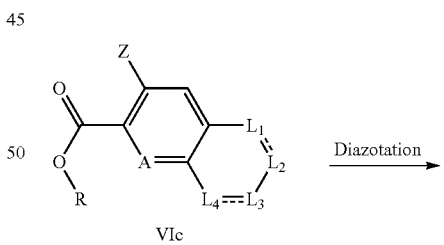

VIc
Z is a leaving group such as amine
R is $C_1$—$C_6$ alkyl or hydrogen

Diazotation →

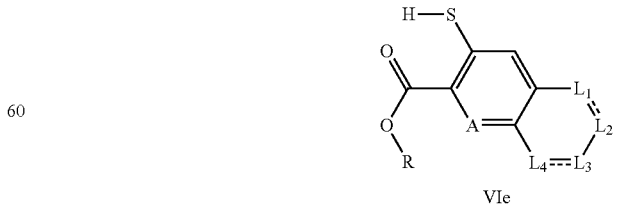

VIe

↓ $R_1$—$X_{LG}$

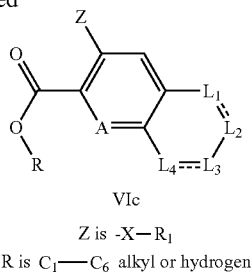

Vlc

Z is —X—R$_1$
R is C$_1$—C$_6$ alkyl or hydrogen

Compound of formula (VIc), wherein R is hydrogen and A, L$_1$, L$_2$, L$_3$ and L$_4$ are as described under formula I above, may be prepared by reaction of a compound of formula (VIc), wherein R is alkyl via hydrolysis. For instance, in the case where R is methyl or ethyl, the hydrolysis can be done with water and a base, such as potassium hydroxide or lithium hydroxide, in the absence or in the presence of a solvent, such as, for instance, tetrahydrofuran or methanol. In the case where R is, for example, tert-butyl, the hydrolysis is done in the presence of acid, such as trifluoroacetic acid or hydrochloric acid. The reaction is carried out at a temperature of from −120° C. to +130° C., preferably from −100° C. to 100° C. See scheme 24.

Scheme 24:

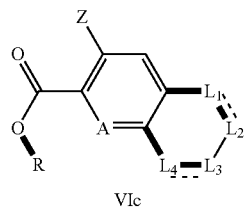

Vlc

Z is —X—R$_1$
R is C$_1$—C$_6$ alkyl

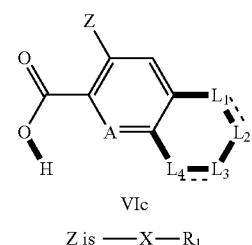

Vlc

Z is —X—R$_1$
R is hydrogen

Alternatively, compound of formula VIc wherein R is hydrogen and A, L$_1$, L$_2$, L$_3$ and L$_4$ are as described under formula I above, may be prepared by reaction of a compound of formula (XIX) wherein Z is a leaving group as nitro or halogen such as fluorine and wherein A, L$_1$, L$_2$, L$_3$ and L$_4$ are as described under formula I above by reaction of a compound of formula VIII or VIIIa

R$_1$—SH (VIII),

R$_1$—S-M (VIIIa), to give compounds of formula XIXa or a salt thereof, wherein R$_1$ is as defined in formula I, optionally in the presence of a suitable base, such as alkali metal carbonates, for example sodium carbonate and potassium carbonate, or alkali metal hydrides such as sodium hydride, or alkali metal hydroxides such as sodium hydroxide and potassium hydroxide, in an inert solvent at temperatures preferably between 25-120° C. Examples of solvent to be used include ethers such as THF, ethylene glycol dimethyl ether, tert-butylmethyl ether, and 1,4-dioxane, aromatic hydrocarbons such as toluene and xylene, nitriles such as acetonitrile or polar aprotic solvents such as N,N-dimethylformamide, N,N-dimethylacetamide, N-methyl-2-pyrrolidone or dimethyl sulfoxide. Examples of salts of the compound of formula VIII include compounds of the formula VIIIa R$_1$—S-M (VIIIa), wherein R$_1$ is as defined above and wherein M is, for example, sodium or potassium. Compounds of formula VIc may be prepared by hydrolysis of the cyano of compound of formula XIXa in acidic or basic conditions. This transformation is well known and could be made by methods known to a person skilled in the art (see for example: Comprehensive Organic Transformations: A Guide to Functional Group Preparations. Edited by Richard C. Larock 1989 p 993, VCH publishers).

This is illustrated for compounds of formula II in scheme 25.

Scheme 25:

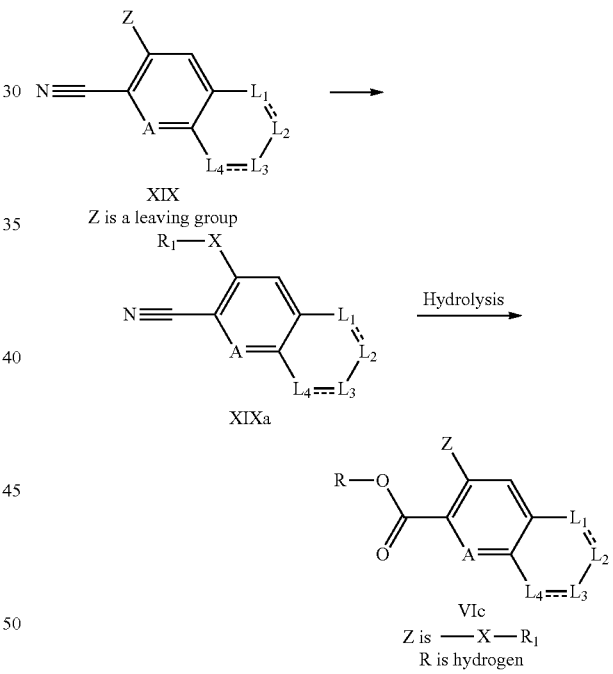

Compounds of formula XIX are either known, commercially available or may be made by methods known to a person skilled in the art.

Alternatively, compound of formula VIc, where in R is Hydrogen, may be prepared by reaction of a compound of formula (XX) where in Z is a leaving group as nitro or halogen such as fluorine and wherein A, L$_1$, L$_2$, L$_3$ and L$_4$ are as described under formula I above by oxidation in presence of a oxidant such as oxygen, hydrogen peroxide or an metal oxide such as chromium trioxide with or without acid such as sulfuric acid with or without metal catalyst. This transformation is well known and could be made by methods known to a person skilled in the art (see for example: Comprehensive Organic Transformations: A Guide to Functional Group Preparations. Edited by Richard C. Larock 1989 p 823, VCH publishers). This is illustrated for compounds of formula II in scheme 26.

Scheme 26:

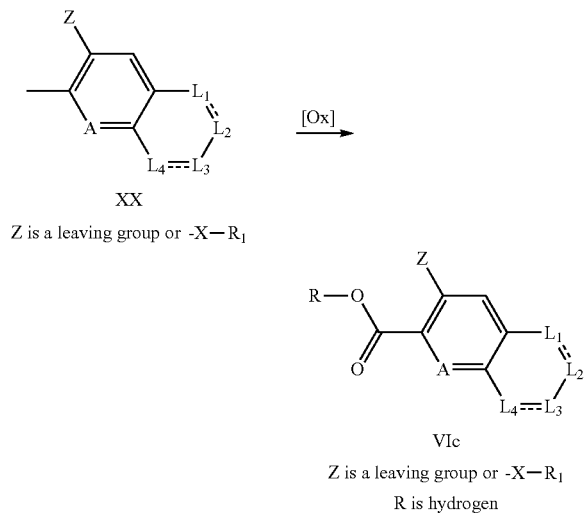

Compounds of formula XX are either known, commercially available or may be made by methods known to a person skilled in the art.

Compound of formula VIc, wherein R is $C_1$-$C_6$ alkyl and A, $L_1$, $L_2$, $L_3$ and $L_4$ are as described under formula I above and Z is $NH_2$, may be prepared by reaction of a compound of formula (XXI) with a compound of formula XXII wherein, for example $X_{00}$ is an halogen such as, for example, bromide and R is $C_1$-$C_6$ alkyl such as, for example, ethyl. these reactions are known to a person skilled in the art and are, for example described in Tetrahedron 60 (2004) 2937-2942. This is illustrated for compounds of formula VIc in scheme 27.

Scheme 27:

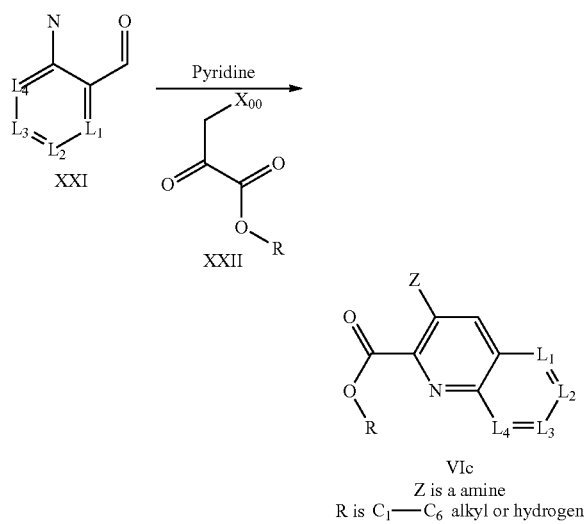

The reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo[5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reaction is advantageously carried out in a temperature range from approximately −80° C. to approximately +140° C., preferably from approximately −30° C. to approximately +100° C., in many cases in the range between ambient temperature and approximately +80° C.

A compound of formula I can be converted in a manner known per se into another compound of formula I by replacing one or more substituents of the starting compound of formula I in the customary manner by (an)other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds of formula I can be prepared in a manner known per se. Thus, for example, acid addition salts of compounds of formula I are obtained by treatment with a suitable acid or a suitable ion exchanger reagent and salts with bases are obtained by treatment with a suitable base or with a suitable ion exchanger reagent.

Salts of compounds of formula I can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds of formula I can be converted in a manner known per se into other salts of compounds of formula I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula I, which have salt-forming properties can be obtained in free form or in the form of salts.

The compounds of formula I and, where appropriate, the tautomers thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds of formula I, in free form or in salt form, which can be obtained depending on which starting materials and procedures have been chosen can be separated in a known manner into the pure diasteromers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl cellulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

N-oxides can be prepared by reacting a compound of the formula I with a suitable oxidizing agent, for example the $H_2O_2$/urea adduct in the presence of an acid anhydride, e.g. trifluoroacetic anhydride. Such oxidations are known from the literature, for example from J. Med. Chem., 32 (12), 2561-73, 1989 or WO 00/15615.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds of formula I and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds according to the following Table 1 below can be prepared according to the methods described above. The examples which follow are intended to illustrate the invention and show preferred compounds of formula I.

Table 1:

This table discloses the 108 compounds 1.001 to 1.108 of the formula I-1b:

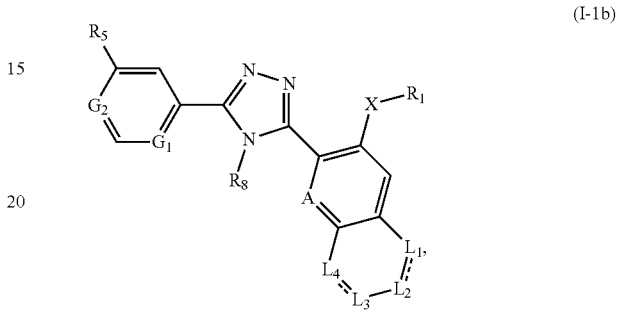

(I-1b)

wherein $R_1$ is ethyl, $R_8$ is methyl and X, A, $R_5$, $G_1$, $G_2$, $L_1$, $L_2$, $L_3$ and $L_4$ are as defined below:

TABLE 1

| Comp. No | X | $G_1$ | $G_2$ | $R_5$ | A | $L_1$ | $L_2$ | $L_3$ | $L_4$ |
|---|---|---|---|---|---|---|---|---|---|
| 1.001 | S | N | CH | $CF_3$ | CH | CH | CH | CH | CH |
| 1.002 | SO | N | CH | $CF_3$ | CH | CH | CH | CH | CH |
| 1.003 | $SO_2$ | N | CH | $CF_3$ | CH | CH | CH | CH | CH |
| 1.004 | S | N | CH | $CF_3$ | N | CH | CH | CH | CH |
| 1.005 | SO | N | CH | $CF_3$ | N | CH | CH | CH | CH |
| 1.006 | $SO_2$ | N | CH | $CF_3$ | N | CH | CH | CH | CH |
| 1.007 | S | N | N | $CF_3$ | CH | CH | CH | CH | CH |
| 1.008 | SO | N | N | $CF_3$ | CH | CH | CH | CH | CH |
| 1.009 | $SO_2$ | N | N | $CF_3$ | CH | CH | CH | CH | CH |
| 1.010 | S | N | N | $CF_3$ | N | CH | CH | CH | CH |
| 1.011 | SO | N | N | $CF_3$ | N | CH | CH | CH | CH |
| 1.012 | $SO_2$ | N | N | $CF_3$ | N | CH | CH | CH | CH |
| 1.013 | S | CH | N | $CF_3$ | CH | CH | CH | CH | CH |
| 1.014 | SO | CH | N | $CF_3$ | CH | CH | CH | CH | CH |
| 1.015 | $SO_2$ | CH | N | $CF_3$ | CH | CH | CH | CH | CH |
| 1.016 | S | CH | N | $CF_3$ | N | CH | CH | CH | CH |
| 1.017 | SO | CH | N | $CF_3$ | N | CH | CH | CH | CH |
| 1.018 | $SO_2$ | CH | N | $CF_3$ | N | CH | CH | CH | CH |
| 1.019 | S | N | CH | $CF_3$ | CH | N | $C(CF_3)$ | $N(CH_3)$ | Bond |
| 1.020 | SO | N | CH | $CF_3$ | CH | N | $C(CF_3)$ | $N(CH_3)$ | Bond |
| 1.021 | $SO_2$ | N | CH | $CF_3$ | CH | N | $C(CF_3)$ | $N(CH_3)$ | Bond |
| 1.022 | S | N | CH | $CF_3$ | N | N | $C(CF_3)$ | $N(CH_3)$ | Bond |
| 1.023 | SO | N | CH | $CF_3$ | N | N | $C(CF_3)$ | $N(CH_3)$ | Bond |
| 1.024 | $SO_2$ | N | CH | $CF_3$ | N | N | $C(CF_3)$ | $N(CH_3)$ | Bond |
| 1.025 | S | N | N | $CF_3$ | CH | N | $C(CF_3)$ | $N(CH_3)$ | Bond |
| 1.026 | SO | N | N | $CF_3$ | CH | N | $C(CF_3)$ | $N(CH_3)$ | Bond |
| 1.027 | $SO_2$ | N | N | $CF_3$ | CH | N | $C(CF_3)$ | $N(CH_3)$ | Bond |
| 1.028 | S | N | N | $CF_3$ | N | N | $C(CF_3)$ | $N(CH_3)$ | Bond |
| 1.029 | SO | N | N | $CF_3$ | N | N | $C(CF_3)$ | $N(CH_3)$ | Bond |
| 1.030 | $SO_2$ | N | N | $CF_3$ | N | N | $C(CF_3)$ | $N(CH_3)$ | Bond |
| 1.031 | S | CH | N | $CF_3$ | CH | N | $C(CF_3)$ | $N(CH_3)$ | Bond |
| 1.032 | SO | CH | N | $CF_3$ | CH | N | $C(CF_3)$ | $N(CH_3)$ | Bond |
| 1.033 | $SO_2$ | CH | N | $CF_3$ | CH | N | $C(CF_3)$ | $N(CH_3)$ | Bond |
| 1.034 | S | CH | N | $CF_3$ | N | N | $C(CF_3)$ | $N(CH_3)$ | Bond |
| 1.035 | SO | CH | N | $CF_3$ | N | N | $C(CF_3)$ | $N(CH_3)$ | Bond |
| 1.036 | $SO_2$ | CH | N | $CF_3$ | N | N | $C(CF_3)$ | $N(CH_3)$ | Bond |
| 1.037 | S | N | CH | $CF_3$ | CH | $N(CH_3)$ | $C(CF_3)$ | N | Bond |
| 1.038 | SO | N | CH | $CF_3$ | CH | $N(CH_3)$ | $C(CF_3)$ | N | Bond |
| 1.039 | $SO_2$ | N | CH | $CF_3$ | CH | $N(CH_3)$ | $C(CF_3)$ | N | Bond |
| 1.040 | S | N | CH | $CF_3$ | N | $N(CH_3)$ | $C(CF_3)$ | N | Bond |
| 1.041 | SO | N | CH | $CF_3$ | N | $N(CH_3)$ | $C(CF_3)$ | N | Bond |
| 1.042 | $SO_2$ | N | CH | $CF_3$ | N | $N(CH_3)$ | $C(CF_3)$ | N | Bond |

TABLE 1-continued

| Comp. No | X | $G_1$ | $G_2$ | $R_5$ | A | $L_1$ | $L_2$ | $L_3$ | $L_4$ |
|---|---|---|---|---|---|---|---|---|---|
| 1.043 | S | N | N | $CF_3$ | CH | $N(CH_3)$ | $C(CF_3)$ | N | Bond |
| 1.044 | SO | N | N | $CF_3$ | CH | $N(CH_3)$ | $C(CF_3)$ | N | Bond |
| 1.045 | $SO_2$ | N | N | $CF_3$ | CH | $N(CH_3)$ | $C(CF_3)$ | N | Bond |
| 1.046 | S | N | N | $CF_3$ | N | $N(CH_3)$ | $C(CF_3)$ | N | Bond |
| 1.047 | SO | N | N | $CF_3$ | N | $N(CH_3)$ | $C(CF_3)$ | N | Bond |
| 1.048 | $SO_2$ | N | N | $CF_3$ | N | $N(CH_3)$ | $C(CF_3)$ | N | Bond |
| 1.049 | S | CH | N | $CF_3$ | CH | $N(CH_3)$ | $C(CF_3)$ | N | Bond |
| 1.050 | SO | CH | N | $CF_3$ | CH | $N(CH_3)$ | $C(CF_3)$ | N | Bond |
| 1.051 | $SO_2$ | CH | N | $CF_3$ | CH | $N(CH_3)$ | $C(CF_3)$ | N | Bond |
| 1.052 | S | CH | N | $CF_3$ | N | $N(CH_3)$ | $C(CF_3)$ | N | Bond |
| 1.053 | SO | CH | N | $CF_3$ | N | $N(CH_3)$ | $C(CF_3)$ | N | Bond |
| 1.054 | $SO_2$ | CH | N | $CF_3$ | N | $N(CH_3)$ | $C(CF_3)$ | N | Bond |
| 1.055 | S | N | CH | $CF_3$ | CH | S | $C(CF_3)$ | N | Bond |
| 1.056 | SO | N | CH | $CF_3$ | CH | S | $C(CF_3)$ | N | Bond |
| 1.057 | $SO_2$ | N | CH | $CF_3$ | CH | S | $C(CF_3)$ | N | Bond |
| 1.058 | S | N | CH | $CF_3$ | N | S | $C(CF_3)$ | N | Bond |
| 1.059 | SO | N | CH | $CF_3$ | N | S | $C(CF_3)$ | N | Bond |
| 1.060 | $SO_2$ | N | CH | $CF_3$ | N | S | $C(CF_3)$ | N | Bond |
| 1.061 | S | N | N | $CF_3$ | CH | S | $C(CF_3)$ | N | Bond |
| 1.062 | SO | N | N | $CF_3$ | CH | S | $C(CF_3)$ | N | Bond |
| 1.063 | $SO_2$ | N | N | $CF_3$ | CH | S | $C(CF_3)$ | N | Bond |
| 1.064 | S | N | N | $CF_3$ | N | S | $C(CF_3)$ | N | Bond |
| 1.065 | SO | N | N | $CF_3$ | N | S | $C(CF_3)$ | N | Bond |
| 1.066 | $SO_2$ | N | N | $CF_3$ | N | S | $C(CF_3)$ | N | Bond |
| 1.067 | S | CH | N | $CF_3$ | CH | S | $C(CF_3)$ | N | Bond |
| 1.068 | SO | CH | N | $CF_3$ | CH | S | $C(CF_3)$ | N | Bond |
| 1.069 | $SO_2$ | CH | N | $CF_3$ | CH | S | $C(CF_3)$ | N | Bond |
| 1.07 | S | CH | N | $CF_3$ | N | S | $C(CF_3)$ | N | Bond |
| 1.071 | SO | CH | N | $CF_3$ | N | S | $C(CF_3)$ | N | Bond |
| 1.072 | $SO_2$ | CH | N | $CF_3$ | N | S | $C(CF_3)$ | N | Bond |
| 1.073 | S | N | CH | $CF_3$ | CH | N | $C(CF_3)$ | S | Bond |
| 1.074 | SO | N | CH | $CF_3$ | CH | N | $C(CF_3)$ | S | Bond |
| 1.075 | $SO_2$ | N | CH | $CF_3$ | CH | N | $C(CF_3)$ | S | Bond |
| 1.076 | S | N | CH | $CF_3$ | N | N | $C(CF_3)$ | S | Bond |
| 1.077 | SO | N | CH | $CF_3$ | N | N | $C(CF_3)$ | S | Bond |
| 1.078 | $SO_2$ | N | CH | $CF_3$ | N | N | $C(CF_3)$ | S | Bond |
| 1.079 | S | N | N | $CF_3$ | CH | N | $C(CF_3)$ | S | Bond |
| 1.08 | SO | N | N | $CF_3$ | CH | N | $C(CF_3)$ | S | Bond |
| 1.081 | $SO_2$ | N | N | $CF_3$ | CH | N | $C(CF_3)$ | S | Bond |
| 1.082 | S | N | N | $CF_3$ | N | N | $C(CF_3)$ | S | Bond |
| 1.083 | SO | N | N | $CF_3$ | N | N | $C(CF_3)$ | S | Bond |
| 1.084 | $SO_2$ | N | N | $CF_3$ | N | N | $C(CF_3)$ | S | Bond |
| 1.085 | S | CH | N | $CF_3$ | CH | N | $C(CF_3)$ | S | Bond |
| 1.086 | SO | CH | N | $CF_3$ | CH | N | $C(CF_3)$ | S | Bond |
| 1.087 | $SO_2$ | CH | N | $CF_3$ | CH | N | $C(CF_3)$ | S | Bond |
| 1.088 | S | CH | N | $CF_3$ | N | N | $C(CF_3)$ | S | Bond |
| 1.089 | SO | CH | N | $CF_3$ | N | N | $C(CF_3)$ | S | Bond |
| 1.090 | $SO_2$ | CH | N | $CF_3$ | N | N | $C(CF_3)$ | S | Bond |
| 1.091 | S | N | CH | $CF_3$ | CH | O | $C(CH_3)_2$ | $CH_2$ | Bond |
| 1.092 | SO | N | CH | $CF_3$ | CH | O | $C(CH_3)_2$ | $CH_2$ | Bond |
| 1.093 | $SO_2$ | N | CH | $CF_3$ | CH | O | $C(CH_3)_2$ | $CH_2$ | Bond |
| 1.094 | S | N | CH | $CF_3$ | N | O | $C(CH_3)_2$ | $CH_2$ | Bond |
| 1.095 | SO | N | CH | $CF_3$ | N | O | $C(CH_3)_2$ | $CH_2$ | Bond |
| 1.096 | $SO_2$ | N | CH | $CF_3$ | N | O | $C(CH_3)_2$ | $CH_2$ | Bond |
| 1.097 | S | N | N | $CF_3$ | CH | O | $C(CH_3)_2$ | $CH_2$ | Bond |
| 1.098 | SO | N | N | $CF_3$ | CH | O | $C(CH_3)_2$ | $CH_2$ | Bond |
| 1.099 | $SO_2$ | N | N | $CF_3$ | CH | O | $C(CH_3)_2$ | $CH_2$ | Bond |
| 1.100 | S | N | N | $CF_3$ | N | O | $C(CH_3)_2$ | $CH_2$ | Bond |
| 1.101 | SO | N | N | $CF_3$ | N | O | $C(CH_3)_2$ | $CH_2$ | Bond |
| 1.102 | $SO_2$ | N | N | $CF_3$ | N | O | $C(CH_3)_2$ | $CH_2$ | Bond |
| 1.103 | S | CH | N | $CF_3$ | CH | O | $C(CH_3)_2$ | $CH_2$ | Bond |
| 1.104 | SO | CH | N | $CF_3$ | CH | O | $C(CH_3)_2$ | $CH_2$ | Bond |
| 1.105 | $SO_2$ | CH | N | $CF_3$ | CH | O | $C(CH_3)_2$ | $CH_2$ | Bond |
| 1.106 | S | CH | N | $CF_3$ | N | O | $C(CH_3)_2$ | $CH_2$ | Bond |
| 1.107 | SO | CH | N | $CF_3$ | N | O | $C(CH_3)_2$ | $CH_2$ | Bond |
| 1.108 | $SO_2$ | CH | N | $CF_3$ | N | O | $C(CH_3)_2$ | $CH_2$ | Bond | and the N-oxides of the compounds of Table 1.

The compounds of formula I according to the invention are preventively and/or curatively valuable active ingredients in the field of pest control, even at low rates of application, which have a very favorable biocidal spectrum and are well tolerated by warm-blooded species, fish and plants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i. e. in destruction of the pests, which takes place either immediately or only after some time has elapsed, for example during ecdysis, or indirectly, for example in a reduced oviposition and/or hatching rate, a good activity corresponding to a destruction rate (mortality) of at least 50 to 60%.

Examples of the abovementioned animal pests are:

from the order Acarina, for example,

*Acalitus* spp., *Aculus* spp., *Acaricalus* spp., *Aceria* spp., *Acarus siro*, *Amblyomma* spp., *Argas* spp., *Boophilus* spp., *Brevipalpus* spp., *Bryobia* spp., *Calipitrimerus* spp., *Chorioptes* spp., *Dermanyssus gallinae*, *Dermatophagoides* spp., *Eotetranychus* spp., *Eriophyes* spp., *Hemitarsonemus* spp., *Hyalomma* spp., *Ixodes* spp., *Olygonychus* spp., *Ornithodoros* spp., *Polyphagotarsone latus*, *Panonychus* spp., *Phyllocoptruta oleivora*, *Phytonemus* spp., *Polyphagotarsonemus* spp., *Psoroptes* spp., *Rhipicephalus* spp., *Rhizoglyphus* spp., *Sarcoptes* spp., *Steneotarsonemus* spp., *Tarsonemus* spp. and *Tetranychus* spp.;

from the order Anoplura, for example,

*Haematopinus* spp., *Linognathus* spp., *Pediculus* spp., *Pemphigus* spp. and *Phylloxera* spp.;

from the order Coleoptera, for example,

*Agriotes* spp., *Amphimallon majale*, *Anomala orientalis*, *Anthonomus* spp., *Aphodius* spp., *Astylus atromaculatus*, *Ataenius* spp., *Atomaria linearis*, *Chaetocnema tibialis*, *Cerotoma* spp., *Conoderus* spp., *Cosmopolites* spp., *Cotinis nitida*, *Curculio* spp., *Cyclocephala* spp., *Dermestes* spp., *Diabrotica* spp., *Diloboderus abderus*, *Epilachna* spp., *Eremnus* spp., *Heteronychus arator*, *Hypothenemus hampei*, *Lagria vilosa*, *Leptinotarsa decemLineata*, *Lissorhoptrus* spp., *Liogenys* spp., *Maecolaspis* spp., *Maladera castanea*, *Megascelis* spp., *Melighetes aeneus*, *Melolontha* spp., *Myochrous armatus*, *Orycaephilus* spp., *Otiorhynchus* spp., *Phyllophaga* spp., *Phlyctinus* spp., *Popillia* spp., *Psylliodes* spp., *Rhyssomatus aubtilis*, *Rhizopertha* spp., *Scarabeidae*, *Sitophilus* spp., *Sitotroga* spp., *Somaticus* spp., *Sphenophorus* spp., *Sternechus subsignatus*, *Tenebrio* spp., *Tribolium* spp. and *Trogoderma* spp.;

from the order Diptera, for example,

*Aedes* spp., *Anopheles* spp., *Antherigona soccata*, *Bactrocea oleae*, *Bibio hortulanus*, *Bradysia* spp., *Calliphora erythrocephala*, *Ceratitis* spp., *Chrysomyia* spp., *Culex* spp., *Cuterebra* spp., *Dacus* spp., *Delia* spp., *Drosophila melanogaster*, *Fannia* spp., *Gastrophilus* spp., *Geomyza tripunctata*, *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit*, *Pegomyia hyoscyami*, *Phorbia* spp., *Rhagoletis* spp., *Rivelia quadrifasciata*, *Scatella* spp., *Sciara* spp., *Stomoxys* spp., *Tabanus* spp., *Tannia* spp. and *Tipula* spp.;

from the order Hemiptera, for example,

*Acanthocoris scabrator*, *Acrosternum* spp., *Adelphocoris lineolatus*, *Amblypelta nitida*, *Bathycoelia thalassina*, *Blissus* spp., *Cimex* spp., *Clavigralla tomentosicollis*, *Creontiades* spp., *Distantiella theobroma*, *Dichelops furcatus*, *Dysdercus* spp., *Edessa* spp., *Euchistus* spp., *Eurydema pulchrum*, *Eurygaster* spp., *Halyomorpha halys*, *Horcias nobilellus*, *Leptocorisa* spp., *Lygus* spp., *Margarodes* spp., *Murgantia histrionic*, *Neomegalotomus* spp., *Nesidiocoris tenuis*, *Nezara* spp., *Nysius simulans*, *Oebalus insularis*, *Piesma* spp., *Piezodorus* spp., *Rhodnius* spp., *Sahlbergella singularis*, *Scaptocoris castanea*, *Scotinophara* spp., *Thyanta* spp., *Triatoma* spp., *Vatiga illudens*;

*Acyrthosium pisum, Adalges* spp, *Agalliana ensigera, Agonoscena targionii, Aleurodicus* spp, *Aleurocanthus* spp, *Aleurolobus barodensis, Aleurothrixus floccosus, Aleyrodes brassicae, Amarasca biguttula, Amritodus atkinsoni, Aonidiella* spp., *Aphididae, Aphis* spp., *Aspidiotus* spp., *Aulacorthum solani, Bactericera cockerelli, Bemisia* spp, *Brachycaudus* spp, *Brevicoryne brassicae, Cacopsylla* spp, *Cavariella aegopodii* Scop., *Ceroplaster* spp., *Chrysomphalus aonidium, Chrysomphalus dictyospermi, Cicadella* spp, *Cofana spectra, Cryptomyzus* spp, *Cicadulina* spp, *Coccus hesperidum, Dalbulus maidis, Dialeurodes* spp, *Diaphorina citri, Diuraphis noxia, Dysaphis* spp, *Empoasca* spp., *Eriosoma larigerum, Erythroneura* spp., *Gascardia* spp., *Glycaspis brimblecombei, Hyadaphis pseudobrassicae, Hyalopterus* spp, *Hyperomyzus pallidus, Idioscopus clypealis, Jacobiasca lybica, Laodelphax* spp., *Lecanium corni, Lepidosaphes* spp., *Lopaphis erysimi, Lyogenys maidis, Macrosiphum* spp., *Mahanarva* spp, *Metcalfa pruinosa, Metopolophium dirhodum, Myndus crudus, Myzus* spp., *Neotoxoptera* sp, *Nephotettix* spp., *Nilaparvata* spp., *Nippolachnus piri* Mats, *Odonaspis ruthae, Oregma lanigera* Zehnter, *Parabemisia myricae, Paratrioza cockerelli, Parlatoria* spp., *Pemphigus* spp., *Peregrinus maidis, Perkinsiella* spp, *Phorodon humuli, Phylloxera* spp, *Planococcus* spp., *Pseudaulacaspis* spp., *Pseudococcus* spp., *Pseudatomoscelis seriatus, Psylla* spp., *Pulvinaria aethiopica, Quadraspidiotus* spp., *Quesada gigas, Recilia dorsalis, Rhopalosiphum* spp., *Saissetia* spp., *Scaphoideus* spp., *Schizaphis* spp., *Sitobion* spp., *Sogatella furcifera, Spissistilus festinus, Tarophagus Proserpina, Toxoptera* spp, *Trialeurodes* spp, *Tridiscus sporoboli, Trionymus* spp, *Trioza erytreae, Unaspis citri, Zygina flammigera, Zyginidia scutellaris;* from the order Hymenoptera, for example,

*Acromyrmex, Arge* spp, *Atta* spp., *Cephus* spp., *Diprion* spp., *Diprionidae, Gilpinia polytoma, Hoplo-campa* spp., *Lasius* spp., *Monomorium pharaonis, Neodiprion* spp., *Pogonomyrmex* spp, *Slenopsis invicta, Solenopsis* spp. and *Vespa* spp.;

from the order Isoptera, for example,

*Coptotermes* spp, *Corniternes cumulans, Incisitermes* spp, *Macrotermes* spp, *Mastotermes* spp, *Microtermes* spp, *Reticulitermes* spp.; *Solenopsis geminate* from the order Lepidoptera, for example,

*Acleris* spp., *Adoxophyes* spp., *Aegeria* spp., *Agrotis* spp., *Alabama argillaceae, Amylois* spp., *Anticarsia gemmatalis, Archips* spp., *Argyresthia* spp, *Argyrotaenia* spp., *Autographa* spp., *Bucculatrix thurberiella, Busseola fusca, Cadra cautella, Carposina nipponensis, Chilo* spp., *Choristoneura* spp., *Chrysoteuchia topiaria, Clysia ambiguella, Cnaphalocrocis* spp., *Cnephasia* spp., *Cochylis* spp., *Coleophora* spp., *Colias lesbia, Cosmophila flava, Crambus* spp, *Crocidolomia binotalis, Cryptophlebia leucotreta, Cydalima perspectalis, Cydia* spp., *Diaphania perspectalis, Diatraea* spp., *Diparopsis castanea, Earias* spp., *Eldana saccharina, Ephestia* spp., *Epinotia* spp, *Estigmene acrea, Etiella zinckinella, Eucosma* spp., *Eupoecilia ambiguella, Euproctis* spp., *Euxoa* spp., *Feltia jaculiferia, Gra-pholita* spp., *Hedya nubiferana, Heliothis* spp., *Hellula undalis, Herpetogramma* spp, *Hyphantria cunea, Keiferia lycopersicella, Lasmopalpus lignosellus, Leucoptera scitella, Lithocollethis* spp., *Lobesia botrana, Loxostege bifidalis, Lymantria* spp., *Lyonetia* spp., *Malacosoma* spp., *Mamestra brassicae, Manduca sexta, Mythimna* spp, *Noctua* spp, *Operophtera* spp., *Orniodes indica, Ostrinia nubilalis, Pammene* spp., *Pandemis* spp., *Panolis flammea, Papaipema nebris, Pectinophora gossypi-ela, Perileucoptera coffeella, Pseudaletia unipuncta, Phthorimaea operculella, Pieris rapae, Pieris* spp., *Plutella xylostella, Prays* spp., *Pseudoplusia* spp, *Rachiplusia nu, Richia albicosta, Scirpophaga* spp., *Sesamia* spp., *Sparganothis* spp., *Spodoptera* spp., *Sylepta derogate, Synanthedon* spp., *Thaumetopoea* spp., *Tortrix* spp., *Trichoplusia ni, Tuta absoluta,* and *Yponomeuta* spp.;

from the order Mallophaga, for example,

*Damalinea* spp. and *Trichodectes* spp.;

from the order Orthoptera, for example,

*Blatta* spp., *Blattella* spp., *Gryllotalpa* spp., *Leucophaea maderae, Locusta* spp., *Neocurtilla hexadactyla, Periplaneta* spp., *Scapteriscus* spp, and *Schistocerca* spp.;

from the order Psocoptera, for example,

*Liposcelis* spp.;

from the order Siphonaptera, for example,

*Ceratophyllus* spp., *Ctenocephalides* spp. and *Xenopsylla cheopis;* from the order Thysanoptera, for example,

*Calliothrips phaseoli, Frankliniella* spp., *Heliothrips* spp, *Hercinothrips* spp., *Parthenothrips* spp, *Scirtothrips aurantii, Sericothrips variabilis, Taeniothrips* spp., *Thrips* spp;

from the order Thysanura, for example, *Lepisma saccharina.*

The active ingredients according to the invention can be used for controlling, i. e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, *asparagus*, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family and latex plants.

The compositions and/or methods of the present invention may be also used on any ornamental and/or vegetable crops, including flowers, shrubs, broad-leaved trees and evergreens.

For example the invention may be used on any of the following ornamental species: *Ageratum* spp., *Alonsoa* spp., *Anemone* spp., *Anisodontea capsenisis, Anthemis* spp., *Antirrhinum* spp., *Aster* spp., *Begonia* spp. (e.g. *B. elatior, B. semperflorens, B. tubéreux*), *Bougainvillea* spp., *Brachycome* spp., *Brassica* spp. (ornamental), *Calceolaria* spp., *Capsicum annuum, Catharanthus roseus, Canna* spp., *Centaurea* spp., *Chrysanthemum* spp., *Cineraria* spp. (*C. maritime*), *Coreopsis* spp., *Crassula coccinea, Cuphea ignea, Dahlia* spp., *Delphinium* spp., *Dicentra spectabilis, Dorotheantus* spp., *Eustoma grandiflorum, Forsythia* spp., *Fuchsia* spp., *Geranium gnaphalium, Gerbera* spp., *Gomphrena globosa, Heliotropium* spp., *Helianthus* spp., *Hibiscus* spp., *Hortensia* spp., *Hydrangea* spp., *Hypoestes phyllostachya, Impatiens* spp. (*I. Walleriana*), *Iresines* spp., *Kalanchoe* spp., *Lantana camara, Lavatera trimestris, Leonotis leonurus, Lilium* spp., *Mesembryanthemum* spp., *Mimulus* spp.,

*Monarda* spp., *Nemesia* spp., *Tagetes* spp., *Dianthus* spp. (carnation), *Canna* spp., *Oxalis* spp., *Bellis* spp., *Pelargonium* spp. (*P. peltatum, P. Zonale*), *Viola* spp. (pansy), *Petunia* spp., *Phlox* spp., *Plecthranthus* spp., *Poinsettia* spp., *Parthenocissus* spp. (*P. quinquefolia, P. tricuspidata*), *Primula* spp., *Ranunculus* spp., *Rhododendron* spp., *Rosa* spp. (rose), *Rudbeckia* spp., *Saintpaulia* spp., *Salvia* spp., *Scaevola aemola, Schizanthus wisetonensis, Sedum* spp., *Solanum* spp., *Surfinia* spp., *Tagetes* spp., *Nicotinia* spp., *Verbena* spp., *Zinnia* spp. and other bedding plants.

For example the invention may be used on any of the following vegetable species: *Allium* spp. (*A. sativum, A. cepa, A. oschaninii, A. Porrum, A. ascalonicum, A. fistulosum*), *Anthriscus cerefolium, Apium graveolus, Asparagus officinalis, Beta vulgarus, Brassica* spp. (*B. Oleracea, B. Pekinensis, B. rapa*), *Capsicum annuum, Cicer arietinum, Cichorium endivia, Cichorum* spp. (*C. intybus, C. endivia*), *Citrillus lanatus, Cucumis* spp. (*C. sativus, C. melo*), *Cucurbita* spp. (*C. pepo, C. maxima*), *Cyanara* spp. (*C. scolymus, C. cardunculus*), *Daucus carota, Foeniculum vulgare, Hypericum* spp., *Lactuca sativa, Lycopersicon* spp. (*L. esculentum, L. lycopersicum*), *Mentha* spp., *Ocimum basilicum, Petroselinum crispum, Phaseolus* spp. (*P. vulgaris, P. coccineus*), *Pisum sativum, Raphanus sativus, Rheum rhaponticum, Rosemarinus* spp., *Salvia* spp., *Scorzonera hispanica, Solanum melongena, Spinacea oleracea, Valerianella* spp. (*V. locusta, V. eriocarpa*) and *Vicia faba*.

Preferred ornamental species include African violet, Begonia, Dahlia, Gerbera, Hydrangea, Verbena, Rosa, Kalanchoe, Poinsettia, Aster, Centaurea, Coreopsis, Delphinium, Monarda, Phlox, Rudbeckia, Sedum, Petunia, Viola, Impatiens, Geranium, Chrysanthemum, Ranunculus, Fuchsia, Salvia, Hortensia, rosemary, sage, St. Johnswort, mint, sweet pepper, tomato and cucumber.

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatoes) and *Chilo supressalis* (preferably in rice).

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatoes) and *Chilo supressalis* (preferably in rice).

In a further aspect, the invention may also relate to a method of controlling damage to plant and parts thereof by plant parasitic nematodes (Endoparasitic-, Semiendoparasitic- and Ectoparasitic nematodes), especially plant parasitic nematodes such as root knot nematodes, *Meloidogyne hapla, Meloidogyne incognita, Meloidogyne javanica, Meloidogyne arenaria* and other *Meloidogyne* species; cyst-forming nematodes, *Globodera rostochiensis* and other *Globodera* species; *Heterodera avenae, Heterodera glycines, Heterodera schachtii, Heterodera trifolii*, and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Pratylenchus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus, Rotylenchus reniformis* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species, such as *Subanguina* spp., *Hypsoperine* spp., *Macroposthonia* spp., *Melinius* spp., *Punctodera* spp., and *Quinisulcius* spp.

The compounds of the invention may also have activity against the molluscs. Examples of which include, for example, Ampullariidae; *Arion* (*A. ater, A. circumscriptus, A. hortensis, A. rufus*); Bradybaenidae (*Bradybaena fruticum*); *Cepaea* (*C. hortensis, C. Nemoralis*); ochlodina; *Deroceras* (*D. agrestis, D. empiricorum, D. laeve, D. reticulatum*); *Discus* (*D. rotundatus*); *Euomphalia; Galba* (*G. trunculata*); *Helicelia* (*H. itala, H. obvia*); Helicidae *Helicigona arbustorum*); *Helicodiscus; Helix* (*H. aperta*); *Limax* (*L. cinereoniger, L. flavus, L. marginatus, L. maximus, L. tenellus*); Lymnaea; *Milax* (*M. gagates, M. marginatus, M. sowerbyi*); *Opeas; Pomacea* (*P. canaticulata*); *Vallonia* and *Zanitoides*.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins, for example insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810). Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. CryI-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and moths (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

Transgenic crops of insect-resistant plants are also described in BATS (Zentrum für Biosicherheit und Nachhaltigkeit, Zentrum BATS, Clarastrasse 13, 4058 Basel, Switzerland) Report 2003, (http://bats.ch).

The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818 and EP-A-0 353 191. The methods of producing such transgenic plants are generally known to the person skilled in the art and are described, for example, in the publications mentioned above.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

Further areas of use of the compositions according to the invention are the protection of stored goods and store rooms and the protection of raw materials, such as wood, textiles, floor coverings or buildings, and also in the hygiene sector, especially the protection of humans, domestic animals and productive livestock against pests of the mentioned type.

The present invention also provides a method for controlling pests (such as mosquitoes and other disease vectors; see also http://www.who.int/malaria/vector_control/irs/en/). In one embodiment, the method for controlling pests comprises applying the compositions of the invention to the target pests, to their locus or to a surface or substrate by brushing, rolling, spraying, spreading or dipping. By way of example, an IRS (indoor residual spraying) application of a surface such as a wall, ceiling or floor surface is contemplated by the method of the invention. In another embodiment, it is contemplated to apply such compositions to a substrate such as non-woven or a fabric material in the form of (or which can be used in the manufacture of) netting, clothing, bedding, curtains and tents.

In one embodiment, the method for controlling such pests comprises applying a pesticidally effective amount of the compositions of the invention to the target pests, to their locus, or to a surface or substrate so as to provide effective residual pesticidal activity on the surface or substrate. Such application may be made by brushing, rolling, spraying, spreading or dipping the pesticidal composition of the invention. By way of example, an IRS application of a surface such as a wall, ceiling or floor surface is contemplated by the method of the invention so as to provide effective residual pesticidal activity on the surface. In another embodiment, it is contemplated to apply such compositions for residual control of pests on a substrate such as a fabric material in the form of (or which can be used in the manufacture of) netting, clothing, bedding, curtains and tents.

Substrates including non-woven, fabrics or netting to be treated may be made of natural fibres such as cotton, raffia, jute, flax, sisal, hessian, or wool, or synthetic fibres such as polyamide, polyester, polypropylene, polyacrylonitrile or the like. The polyesters are particularly suitable. The methods of textile treatment are known, e.g. WO 2008/151984, WO 2003/034823, U.S. Pat. No. 5,631,072, WO 2005/64072, WO2006/128870, EP 1724392, WO2005113886 or WO 2007/090739.

Further areas of use of the compositions according to the invention are the field of tree injection/trunk treatment for all ornamental trees as well all sort of fruit and nut trees.

In the field of tree injection/trunk treatment, the compounds according to the present invention are especially suitable against wood-boring insects from the order Lepidoptera as mentioned above and from the order Coleoptera, especially against woodborers listed in the following tables A and B:

TABLE A

Examples of exotic woodborers of economic importance.

| Family | Species | Host or Crop Infested |
|---|---|---|
| Buprestidae | *Agrilus planipennis* | Ash |
| Cerambycidae | *Anoplura glabripennis* | Hardwoods |
| Scolytidae | *Xylosandrus crassiusculus* | Hardwoods |
| | *X. mutilatus* | Hardwoods |
| | *Tomicus piniperda* | Conifers |

TABLE B

Examples of native woodborers of economic importance.

| Family | Species | Host or Crop Infested |
|---|---|---|
| Buprestidae | *Agrilus anxius* | Birch |
| | *Agrilus politus* | Willow, Maple |
| | *Agrilus sayi* | Bayberry, Sweetfern |
| | *Agrilus vittaticolllis* | Apple, Pear, Cranberry, Serviceberry, Hawthorn |
| | *Chrysobothris femorata* | Apple, Apricot, Beech, Boxelder, Cherry, Chestnut, Currant, Elm, Hawthorn, Hackberry, Hickory, Horsechestnut, Linden, Maple, Mountain-ash, Oak, Pecan, Pear, Peach, Persimmon, Plum, Poplar, Quince, Redbud, Serviceberry, Sycamore, Walnut, Willow |
| | *Texania campestris* | Basswood, Beech, Maple, Oak, Sycamore, Willow, Yellow-poplar |
| Cerambycidae | *Goes pulverulentus* | Beech, Elm, Nuttall, Willow, Black oak, Cherrybark oak, Water oak, Sycamore |
| | *Goes tigrinus* | Oak |
| | *Neoclytus acuminatus* | Ash, Hickory, Oak, Walnut, Birch, Beech, Maple, Eastern hophornbeam, Dogwood, Persimmon, Redbud, Holly, Hackberry, Black locust, Honeylocust, Yellow-poplar, Chestnut, Osage-orange, *Sassafras*, Lilac, Mountain-mahogany, Pear, Cherry, Plum, Peach, Apple, Elm, Basswood, Sweetgum |
| | *Neoptychodes trilineatus* | Fig, Alder, Mulberry, Willow, Netleaf hackberry |
| | *Oberea ocellata* | Sumac, Apple, Peach, Plum, Pear, Currant, Blackberry |
| | *Oberea tripunctata* | Dogwood, Viburnum, Elm, Sourwood, Blueberry, |

TABLE B-continued

Examples of native woodborers of economic importance.

| Family | Species | Host or Crop Infested |
|---|---|---|
| | Oncideres cingulata | Rhododendron, Azalea, Laurel, Poplar, Willow, Mulberry Hickory, Pecan, Persimmon, Elm, Sourwood, Basswood, Honeylocust, Dogwood, Eucalyptus, Oak, Hackberry, Maple, Fruit trees |
| | Saperda calcarata | Poplar |
| | Strophiona nitens | Chestnut, Oak, Hickory, Walnut, Beech, Maple |
| Scolytidae | Corthylus columbianus | Maple, Oak, Yellow-poplar, Beech, Boxelder, Sycamore, Birch, Basswood, Chestnut, Elm |
| | Dendroctonus frontalis | Pine |
| | Dryocoetes betulae | Birch, Sweetgum, Wild cherry, Beech, Pear |
| | Monarthrum fasciatum | Oak, Maple, Birch, Chestnut, Sweetgum, Blackgum, Poplar, Hickory, Mimosa, Apple, Peach, Pine |
| | Phloeotribus liminaris | Peach, Cherry, Plum, Black cherry, Elm, Mulberry, Mountain-ash |
| | Pseudopityophthorus pruinosus | Oak, American beech, Black cherry, Chickasaw plum, Chestnut, Maple, Hickory, Hornbeam, Hophornbeam |
| Sesiidae | Paranthrene simulans | Oak, American chestnut |
| | Sannina uroceriformis | Persimmon |
| | Synanthedon exitiosa | Peach, Plum, Nectarine, Cherry, Apricot, Almond, Black cherry |
| | Synanthedon pictipes | Peach, Plum, Cherry, Beach, Black Cherry |
| | Synanthedon rubrofascia | Tupelo |
| | Synanthedon scitula | Dogwood, Pecan, Hickory, Oak, Chestnut, Beech, Birch, Black cherry, Elm, Mountain-ash, Viburnum, Willow, Apple, Loquat, Ninebark, Bayberry |
| | Vitacea polistiformis | Grape |

The present invention may be also used to control any insect pests that may be present in turfgrass, including for example beetles, caterpillars, fire ants, ground pearls, millipedes, sow bugs, mites, mole crickets, scales, mealybugs ticks, spittlebugs, southern chinch bugs and white grubs. The present invention may be used to control insect pests at various stages of their life cycle, including eggs, larvae, nymphs and adults.

In particular, the present invention may be used to control insect pests that feed on the roots of turfgrass including white grubs (such as *Cyclocephala* spp. (e.g. masked chafer, *C. lurida*), *Rhizotrogus* spp. (e.g. European chafer, *R. majalis*), *Cotinus* spp. (e.g. Green June beetle, *C. nitida*), *Popillia* spp. (e.g. Japanese beetle, *P. japonica*), *Phyllophaga* spp. (e.g. May/June beetle), *Ataenius* spp. (e.g. Black turfgrass ataenius, *A. spretulus*), *Maladera* spp. (e.g. Asiatic garden beetle, *M. castanea*) and *Tomarus* spp.), ground pearls (*Margarodes* spp.), mole crickets (tawny, southern, and short-winged; *Scapteriscus* spp., *Gryllotalpa africana*) and leatherjackets (European crane fly, *Tipula* spp.).

The present invention may also be used to control insect pests of turfgrass that are thatch dwelling, including armyworms (such as fall armyworm *Spodoptera frugiperda*, and common armyworm *Pseudaletia unipuncta*), cutworms, billbugs (*Sphenophorus* spp., such as *S. venatus verstitus* and *S. parvulus*), and sod webworms (such as *Crambus* spp. and the tropical sod webworm, *Herpetogramma phaeopteralis*).

The present invention may also be used to control insect pests of turfgrass that live above the ground and feed on the turfgrass leaves, including chinch bugs (such as southern chinch bugs, *Blissus insularis*), Bermudagrass mite (*Eriophyes cynodoniensis*), rhodesgrass mealybug (*Antonina graminis*), two-lined spittlebug (*Propsapia bicincta*), leafhoppers, cutworms (Noctuidae family), and greenbugs. The present invention may also be used to control other pests of turfgrass such as red imported fire ants (*Solenopsis invicta*) that create ant mounds in turf.

In the hygiene sector, the compositions according to the invention are active against ectoparasites such as hard ticks, soft ticks, mange mites, harvest mites, flies (biting and licking), parasitic fly larvae, lice, hair lice, bird lice and fleas.

Examples of such parasites are:

Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp.

Of the order Blattarida, for example *Blatta orientalis*, *Periplaneta americana*, *Blattelagermanica* and *Supella* spp.

Of the subclass Acaria (Acarida) and the orders Meta- and Meso-stigmata, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergatesspp.*, *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus*, *Chlorophorus pilosis*, *Anobium punctatum*, *Xestobium rufovillosum*, *Ptilinuspecticornis*, *Dendrobium pertinex*, *Ernobius mollis*, *Priobium carpini*, *Lyctus brunneus*, *Lyctus africanus*, *Lyctus planicollis*, *Lyctus linearis*, *Lyctus pubescens*, *Trogoxylon aequale*, *Minthesrugicollis*, *Xyleborus* spec., *Tryptodendron* spec., *Apate monachus*, *Bostrychus capucins*, *Heterobostrychus brunneus*, *Sinoxylon* spec. and *Dinoderus minutus*, and also hymenopterans such as *Sirex juvencus*, *Urocerus gigas*, *Urocerus gigas taignus* and *Urocerus augur*, and termites such as *Kalotermes flavicollis*, *Cryptotermes brevis*, *Heterotermes indicola*, *Reticulitermes flavipes*, *Reticulitermes santonensis*, *Reticulitermes lucifugus*, *Mastotermes darwiniensis*, *Zootermopsis nevadensis* and *Coptotermes formosanus*, and bristletails such as *Lepisma saccharina*.

The compounds according to the invention can be used as pesticidal agents in unmodified form, but they are generally formulated into compositions in various ways using formulation adjuvants, such as carriers, solvents and surface-active substances. The formulations can be in various physical forms, e.g. in the form of dusting powders, gels, wettable powders, water-dispersible granules, water-dispersible tablets, effervescent pellets, emulsifiable concentrates, micro-emulsifiable concentrates, oil-in-water emulsions, oil-flowables, aqueous dispersions, oily dispersions, suspoemulsions, capsule suspensions, emulsifiable granules, soluble liquids, water-soluble concentrates (with water or a water-miscible organic solvent as carrier), impregnated polymer films or in other forms known e.g. from the Manual on Development and Use of FAO and WHO Specifications for Pesticides, United Nations, First Edition, Second Revision (2010). Such formulations can either be used directly or diluted prior to use. The dilutions can be made, for example, with water, liquid fertilisers, micronutrients, biological organisms, oil or solvents.

The formulations can be prepared e.g. by mixing the active ingredient with the formulation adjuvants in order to obtain compositions in the form of finely divided solids, granules, solutions, dispersions or emulsions. The active ingredients can also be formulated with other adjuvants, such as finely divided solids, mineral oils, oils of vegetable or animal origin, modified oils of vegetable or animal origin, organic solvents, water, surface-active substances or combinations thereof.

The active ingredients can also be contained in very fine microcapsules. Microcapsules contain the active ingredients in a porous carrier. This enables the active ingredients to be released into the environment in controlled amounts (e.g. slow-release). Microcapsules usually have a diameter of from 0.1 to 500 microns. They contain active ingredients in an amount of about from 25 to 95% by weight of the capsule weight. The active ingredients can be in the form of a monolithic solid, in the form of fine particles in solid or liquid dispersion or in the form of a suitable solution. The encapsulating membranes can comprise, for example, natural or synthetic rubbers, cellulose, styrene/butadiene copolymers, polyacrylonitrile, polyacrylate, polyesters, polyamides, polyureas, polyurethane or chemically modified polymers and starch xanthates or other polymers that are known to the person skilled in the art. Alternatively, very fine microcapsules can be formed in which the active ingredient is contained in the form of finely divided particles in a solid matrix of base substance, but the microcapsules are not themselves encapsulated.

The formulation adjuvants that are suitable for the preparation of the compositions according to the invention are known per se. As liquid carriers there may be used: water, toluene, xylene, petroleum ether, vegetable oils, acetone, methyl ethyl ketone, cyclohexanone, acid anhydrides, acetonitrile, acetophenone, amyl acetate, 2-butanone, butylene carbonate, chlorobenzene, cyclohexane, cyclohexanol, alkyl esters of acetic acid, diacetone alcohol, 1,2-dichloropropane, diethanolamine, p-diethylbenzene, diethylene glycol, diethylene glycol abietate, diethylene glycol butyl ether, diethylene glycol ethyl ether, diethylene glycol methyl ether, N,N-dimethylformamide, dimethyl sulfoxide, 1,4-dioxane, dipropylene glycol, dipropylene glycol methyl ether, dipropylene glycol dibenzoate, diproxitol, alkylpyrrolidone, ethyl acetate, 2-ethylhexanol, ethylene carbonate, 1,1,1-trichloroethane, 2-heptanone, alpha-pinene, d-limonene, ethyl lactate, ethylene glycol, ethylene glycol butyl ether, ethylene glycol methyl ether, gamma-butyrolactone, glycerol, glycerol acetate, glycerol diacetate, glycerol triacetate, hexadecane, hexylene glycol, isoamyl acetate, isobornyl acetate, isooctane, isophorone, isopropylbenzene, isopropyl myristate, lactic acid, laurylamine, mesityl oxide, methoxypropanol, methyl isoamyl ketone, methyl isobutyl ketone, methyl laurate, methyl octanoate, methyl oleate, methylene chloride, m-xylene, n-hexane, n-octylamine, octadecanoic acid, octylamine acetate, oleic acid, oleylamine, o-xylene, phenol, polyethylene glycol, propionic acid, propyl lactate, propylene carbonate, propylene glycol, propylene glycol methyl ether, p-xylene, toluene, triethyl phosphate, triethylene glycol, xylenesulfonic acid, paraffin, mineral oil, trichloroethylene, perchloroethylene, ethyl acetate, amyl acetate, butyl acetate, propylene glycol methyl ether, diethylene glycol methyl ether, methanol, ethanol, isopropanol, and alcohols of higher molecular weight, such as amyl alcohol, tetrahydrofurfuryl alcohol, hexanol, octanol, ethylene glycol, propylene glycol, glycerol, N-methyl-2-pyrrolidone and the like.

Suitable solid carriers are, for example, talc, titanium dioxide, pyrophyllite clay, silica, attapulgite clay, kieselguhr, limestone, calcium carbonate, bentonite, calcium montmorillonite, cottonseed husks, wheat flour, soybean flour, pumice, wood flour, ground walnut shells, lignin and similar substances.

A large number of surface-active substances can advantageously be used in both solid and liquid formulations, especially in those formulations which can be diluted with a carrier prior to use. Surface-active substances may be anionic, cationic, non-ionic or polymeric and they can be used as emulsifiers, wetting agents or suspending agents or for other purposes. Typical surface-active substances include, for example, salts of alkyl sulfates, such as diethanolammonium lauryl sulfate; salts of alkylarylsulfonates, such as calcium dodecylbenzenesulfonate; alkylphenol/alkylene oxide addition products, such as nonylphenol ethoxylate; alcohol/alkylene oxide addition products, such as tridecylalcohol ethoxylate; soaps, such as sodium stearate; salts of alkylnaphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryltrimethylammonium chloride, polyethylene glycol esters of fatty acids, such as polyethylene glycol stearate; block copolymers of ethylene oxide and propylene oxide; and salts of mono- and di-alkylphosphate esters; and also further substances described e.g. in McCutcheon's Detergents and Emulsifiers Annual, MC Publishing Corp., Ridgewood N.J. (1981).

Further adjuvants that can be used in pesticidal formulations include crystallisation inhibitors, viscosity modifiers, suspending agents, dyes, anti-oxidants, foaming agents, light absorbers, mixing auxiliaries, antifoams, complexing agents, neutralising or pH-modifying substances and buffers, corrosion inhibitors, fragrances, wetting agents, take-up enhancers, micronutrients, plasticisers, glidants, lubricants, dispersants, thickeners, antifreezes, microbicides, and liquid and solid fertilisers.

The compositions according to the invention can include an additive comprising an oil of vegetable or animal origin, a mineral oil, alkyl esters of such oils or mixtures of such oils and oil derivatives. The amount of oil additive in the composition according to the invention is generally from 0.01 to 10%, based on the mixture to be applied. For example, the oil additive can be added to a spray tank in the desired concentration after a spray mixture has been prepared. Preferred oil additives comprise mineral oils or an oil of vegetable origin, for example rapeseed oil, olive oil or sunflower oil, emulsified vegetable oil, alkyl esters of oils of vegetable origin, for example the methyl derivatives, or an oil of animal origin, such as fish oil or beef tallow. Preferred oil additives comprise alkyl esters of $C_8$-$C_{22}$ fatty acids, especially the methyl derivatives of $C_{12}$-$C_{18}$ fatty acids, for example the methyl esters of lauric acid, palmitic acid and oleic acid (methyl laurate, methyl palmitate and methyl oleate, respectively). Many oil derivatives are known from the Compendium of Herbicide Adjuvants, 10$^{th}$ Edition, Southern Illinois University, 2010.

The inventive compositions generally comprise from 0.1 to 99% by weight, especially from 0.1 to 95% by weight, of compounds of the present invention and from 1 to 99.9% by weight of a formulation adjuvant which preferably includes from 0 to 25% by weight of a surface-active substance. Whereas commercial products may preferably be formulated as concentrates, the end user will normally employ dilute formulations.

The rates of application vary within wide limits and depend on the nature of the soil, the method of application, the crop plant, the pest to be controlled, the prevailing climatic conditions, and other factors governed by the method of application, the time of application and the target crop. As a general guideline compounds may be applied at a rate of from 1 to 2000 l/ha, especially from 10 to 1000 l/ha.

Preferred formulations can have the following compositions (weight %):

Emulsifiable Concentrates:
active ingredient: 1 to 95%, preferably 60 to 90%
surface-active agent: 1 to 30%, preferably 5 to 20%
liquid carrier: 1 to 80%, preferably 1 to 35%
Dusts:
active ingredient: 0.1 to 10%, preferably 0.1 to 5%
solid carrier: 99.9 to 90%, preferably 99.9 to 99%
Suspension Concentrates:
active ingredient: 5 to 75%, preferably 10 to 50%
water: 94 to 24%, preferably 88 to 30%
surface-active agent: 1 to 40%, preferably 2 to 30%
Wettable Powders:
active ingredient: 0.5 to 90%, preferably 1 to 80%
surface-active agent: 0.5 to 20%, preferably 1 to 15%
solid carrier: 5 to 95%, preferably 15 to 90%
Granules:
active ingredient: 0.1 to 30%, preferably 0.1 to 15%
solid carrier: 99.5 to 70%, preferably 97 to 85%

The following Examples further illustrate, but do not limit, the invention.

| Wettable powders | a) | b) | c) |
| --- | --- | --- | --- |
| active ingredients | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The combination is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
| --- | --- | --- | --- |
| active ingredients | 25% | 50% | 75% |
| light mineral oil | 5% | 5% | 5% |
| highly dispersed silicic acid | 5% | 5% | — |
| Kaolin | 65% | 40% | — |
| Talcum | — | — | 20% |

The combination is thoroughly mixed with the adjuvants and the mixture is thoroughly ground in a suitable mill, affording powders that can be used directly for seed treatment.

| Emulsifiable concentrate | |
| --- | --- |
| active ingredients | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredients | 5% | 6% | 4% |
| Talcum | 95% | — | — |
| Kaolin | — | 94% | — |
| mineral filler | — | — | 96% |

Ready-for-use dusts are obtained by mixing the combination with the carrier and grinding the mixture in a suitable mill. Such powders can also be used for dry dressings for seed.

| Extruder qranules | |
|---|---|
| Active ingredients | 15% |
| sodium lignosulfonate | 2% |
| carboxymethylcellulose | 1% |
| Kaolin | 82% |

The combination is mixed and ground with the adjuvants, and the mixture is moistened with water. The mixture is extruded and then dried in a stream of air.

| Coated qranules | |
|---|---|
| Active ingredients | 8% |
| polyethylene glycol (mol. wt. 200) | 3% |
| Kaolin | 89% |

The finely ground combination is uniformly applied, in a mixer, to the kaolin moistened with polyethylene glycol. Non-dusty coated granules are obtained in this manner.

Suspension Concentrate

| | |
|---|---|
| active ingredients | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Flowable Concentrate for Seed Treatment

| | |
|---|---|
| active ingredients | 40% |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of the combination are mixed with 2 parts of an aromatic solvent and 7 parts of toluene diisocyanate/polymethylene-polyphenylisocyanate-mixture (8:1). This mixture is emulsified in a mixture of 1.2 parts of polyvinylalcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed. The obtained capsule suspension is stabilized by adding 0.25 parts of a thickener and 3 parts of a dispersing agent. The capsule suspension formulation contains 28% of the active ingredients. The medium capsule diameter is 8-15 microns. The resulting formulation is applied to seeds as an aqueous suspension in an apparatus suitable for that purpose.

Formulation types include an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP), a soluble granule (SG) or any technically feasible formulation in combination with agriculturally acceptable adjuvants.

PREPARATORY EXAMPLES

"Mp" means melting point in ° C. Free radicals represent methyl groups. $^1$H NMR measurements were recorded on a Brucker 400 MHz spectrometer, chemical shifts are given in ppm relevant to a TMS standard. Spectra measured in deuterated solvents as indicated. Common abbreviations: aq=aqueous, min=minute, h=hour, sat=saturated, Rt= retention time, mCPBA=meta-chloroperoxybenzoic acid, MeOH=methanol, EtOH=ethanol, EA=ethyl acetate, THF= tetrahydrofuran, NaHCO$_3$=sodium hydrogen carbonate, Na$_2$CO$_3$=sodium carbonate, HCl=hydrogen chloride, DCM or CH$_2$Cl$_2$=dichloromethane, DCE=1,2-dichloroethane, Et$_3$N=triethylamine, DMF=N,N-dimethyl-formamide, TFA= trifluoroacetic acid, HATU=1-[bis(dimethylamino)methylene]-1H-1,2,3-triazolo[4,5-b]pyridinium 3-oxid hexafluorophosphate, MW=microwave. Either one of the LCMS methods below was used to characterize the compounds. The characteristic LCMS values obtained for each compound were the retention time ("Rt", recorded in minutes) and the measured molecular ion (M+H)$^+$.

LCMS Methods:

Method A:

Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 μm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH: gradient: gradient: 0 min 0% B, 100% A; 1.2-1.5 min 100% B; Flow (ml/min) 0.85.

Method B:

Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 µm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH: gradient: gradient: 0 min 0% B, 100% A; 2.7-3.0 min 100% B; Flow (ml/min) 0.85.

Method C:

Spectra were recorded on a Mass Spectrometer from Agilent Technologies (6410 Triple Quadruple Mass Spectrometer) equipped with an electrospray source (Polarity: Positive and Negative Polarity Switch, Capillary: 4.00 kV, Fragmentor: 100.00 V, Gas Temperature: 350° C., Gas Flow: 11 L/min, Nebulizer Gas: 45 psi, Mass range: 110-1000 Da, DAD Wavelength range: 210-400 nm). Column: KINETEX EVO C18, length 50 mm, diameter 4.6 mm, particle size 2.6 µm. Column oven temperature 40° C. Solvent gradient: A=Water with 0.1% formic acid:Acetonitrile (95:5 v/v). B=Acetonitrile with 0.1% formic acid. Gradient=0 min 90% A, 10% B; 0.9-1.8 min 0% A, 100% B, 2.2-2.5 min 90% A, 10% B. Flow rate 1.8 mL/min.

Method D:

Spectra were recorded on a Mass Spectrometer from Waters (Acquity SDS Mass Spectrometer) equipped with an electrospray source (Polarity: Positive and Negative Polarity Switch, Capillary: 3.00 kV, Cone Voltage: 41.00 V, Source temperature: 150° C., Desolvation Gas Flow: 1000 L/Hr, Desolvation temperature: 500° C., Gas Flow @Cone: 50 L/hr, Mass range: 110-800 Da, PDA wavelength range: 210-400 nm. Column: Acquity UPLC HSS T3 C18, length 30 mm, diameter 2.1 mm, particle size 1.8 µm. Column oven temperature 40° C. Solvent gradient: A=Water with 0.1% formic acid:Acetonitrile (95:5 v/v). B=Acetonitrile with 0.05% formic acid. Gradient=0 min 90% A, 10% B; 0.2 min 50% A, 50% B; 0.7-1.3 min 0% A, 100% B; 1.4-1.6 min 90% A, 10% B. Flow rate 0.8 mL/min.

a) Synthesis of Intermediates:

Example I1: Preparation of ethyl N-methyl-4-(trifluoromethyl)pyridine-2-carboximidothioate (Intermediate I1)

(I1)

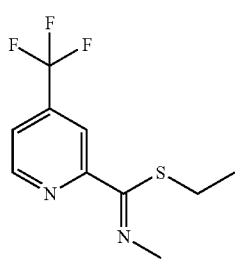

Step I1.1: Preparation of N-methyl-4-(trifluoromethyl)pyridine-2-carboxamide

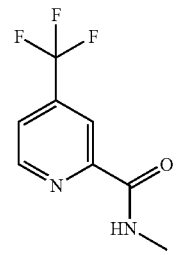

To a solution of 4-(trifluoromethyl)pyridine-2-carboxylic acid (97%, 10.0 g, 50.76 mmol) in dichloromethane (200 ml) was added dropwise N,N-dimethylformamide (0.1 ml) and oxalyl chloride (5.66 ml, 66.00 mmol). The reaction mixture was stirred at ambient temperature overnight, then concentrated to dryness in vacuo to afford 4-(trifluoromethyl)pyridine-2-carbonyl chloride (10.5 g) as a solid.

To methylamine (2M in tetrahydrofuran) (62.6 ml, 125.2 mmol) in tetrahydrofuran (40 ml) at 0-5° C. was added triethylamine (10.4 ml, 75.03 mmol), followed by a solution of 4-(trifluoromethyl)pyridine-2-carbonyl chloride (10.5 g, 50.11 mmol, preparation above) in tetrahydrofuran (60 ml) dropwise. The mixture was allowed to warm to ambient temperature, and stirred for 2 hours. The resulting suspension was filtered, the solid residue washed with t-butyl methyl ether (3×) and the filtrate evaporated under reduced pressure. The residue was dissolved in t-butyl methyl ether, the organic phase washed with water (3×) and brine, dried over sodium sulfate and concentrated in vacuo. The crude material was diluted with t-butyl methyl ether, treated with activated charcoal, the mixture stirred for 15 minutes and filtered. Evaporation of the filtrate in vacuo afforded N-methyl-4-(trifluoromethyl) pyridine-2-carboxamide as a solid (9.2 g), mp 60-62° C. This material was used without further purification. LCMS (method B): 205 (M+H)$^+$; retention time: 0.86 min. $^1$H-NMR (CDCl$_3$, ppm) 3.07 (d, 3H), 7.66 (d, 1H), 8.01 (br s, 1H), 8.45 (s, 1H), 8.74 (d, 1H).

Step I1.2: Preparation of N-methyl-4-(trifluoromethyl)pyridine-2-carbothioamide

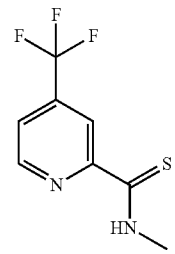

To a solution of N-methyl-4-(trifluoromethyl)pyridine-2-carboxamide (32.5 g, 159.2 mmol) in pyridine (870 ml) was added phosphorus pentasulfide (42.5 g, 95.6 mmol) and the mixture was stirred at reflux temperature for 5 hours. After cooling, the solvent was removed in vacuo, the residue diluted with water and the aqueous phase extracted with diethyl ether (3×). The combined organic layers were washed with a water/brine (1:1) solution (4×), dried over sodium sulfate and concentrated under reduced pressure to afford N-methyl-4-(trifluoromethyl)pyridine-2-carbothioamide as a solid (30.9 g), mp 69-70° C. This material was used without further purification. LCMS (method B): 221 (M+H)$^+$; retention time: 1.42 min. $^1$H-NMR (CDCl$_3$, ppm) 3.43 (d, 3H), 7.66 (d, 1H), 8.68 (d, 1H), 8.96 (s, 1H), 10.14 (br s, 1H).

Step I1.3: Preparation of ethyl N-methyl-4-(trifluoromethyl)pyridine-2-carboximidothioate (I1)

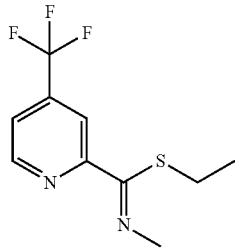

(I1)

To a solution of N-methyl-4-(trifluoromethyl)pyridine-2-carbothioamide (10.2 g, 46.32 mmol) in ethanol (200 ml) was added sodium ethoxide (21 wt % in EtOH) (15.2 g, 46.3 mmol, 17.3 ml) and the mixture was stirred at room temperature for 40 minutes. Iodoethane (14.5 g, 92.68 mmol, 7.49 ml) was added and stirring continued at room temperature overnight. The reaction mixture was concentrated in vacuo, diluted with t-butyl methyl ether, the organic phase washed successively with water (3×), a sat. aqueous sodium carbonate solution and brine, dried over sodium sulfate and evaporated under reduced pressure to afford ethyl N-methyl-4-(trifluoromethyl)pyridine-2-carboximidothioate, as a liquid (10.4 g). This material was used without further purification LCMS (method B): 249 (M+H)$^+$; retention time: 1.20 min. $^1$H-NMR (CDCl$_3$, ppm, major isomer) 1.15 (t, 3H), 2.87 (q, 2H), 3.53 (s, 3H), 7.55 (d, 1H), 7.91 (s, 1H), 8.84 (d, 1H).

Example I2: Preparation of 6-ethylsulfanyl-1-methyl-2-(trifluoromethyl)benzimidazole-5-carbohydrazide (Intermediate I2)

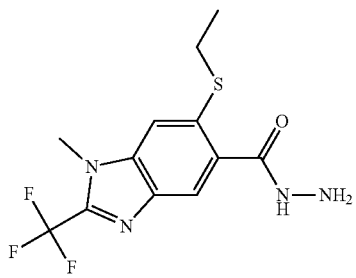

(I2)

Step I2.1: Synthesis of 4-chloro-2-ethylsulfanyl-5-nitro-benzoic Acid

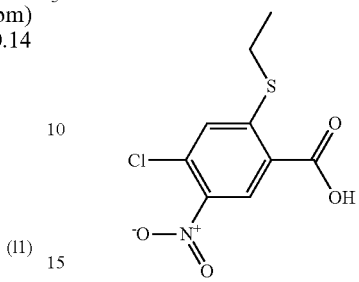

To a solution of 4-chloro-2-fluoro-5-nitro-benzoic acid (20 g, 91.095 mmol, commercially available) in 1-methyl-2-pyrrolidone (250 mL) at 90° C. was added sodium t-butoxide (9.6302 g, 100.20 mmol). After 10 min ethylsulfanylsodium (9.366 g, 100.20 mmol) was added. The reaction was stirred at 90° C. for two hours. The conversion is complete, two products were formed. The reaction mixture was poured into one liter of water and pH was acidified by addition of hydrochloride acid conc. (37%) and precipitate was formed. Filtration of the solid gave the mixture of two products. Filtrate was allowed to stand. The solid was suspended in ethyl ether and filtered. The solid (pure) was identified as the bis-ethylsulfanyl product. The filtrate was concentration under vacuum to give 4-chloro-2-ethylsulfanyl-5-nitro-benzoic acid (8.9 g, 34 mmol). LC-MS (method A): Rt=1.00 min, (260, MH$^-$) (262, MH$^+$). $^1$H NMR (300 MHz, CDCl$_3$) ppm 13.84 (s, 1H) 8.52 (s, 1H); 7.6 (s, 1H); 3.09 (q, 2H); 1.3 (t, 3H).

Step I2.2: Synthesis of 2-ethylsulfanyl-4-(methylamino)-5-nitro-benzoic Acid

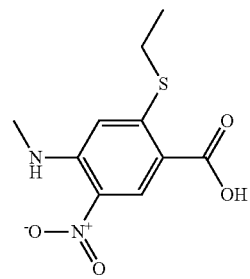

To a solution of 4-chloro-2-ethylsulfanyl-5-nitro-benzoic acid (8.9 g, 34 mmol) in tetrahydrofuran (20 mL, 244 mmol) was added gently methylamine (2 mol/L) in tetrahydrofuran (100 mL, 200 mmol). The mixture was stirred overnight at ambient temperature. Only a few conversions were observed. The suspension was transferred in an autoclave, 30 mL of methylamine 2N was added, and the reaction was stirred at 80° C. for five hours. The reaction is not complete and 20 mL more of 2N methylamine was added then the reaction was stirred in an autoclave over week end. Reaction is finished, and reaction mixture was concentrated under vacuum. Solids were taken up in water and basified with sodium hydroxide 1N, then extracted with ethyl acetate. The water phase was acidified with hydrochloride acid conc. 37% and extracted with ethyl acetate. All organic layers are combined and were dried on magnesium sulfate, and concentrated on vacuum. The residue was then purified by flash chromatography to give 2-ethylsulfanyl-4-(methylamino)-5-nitro-benzoic acid (3.95 g, 15.4 mmol) as a yellow-brownish solid. LC-MS (method A): Rt=1.04 min, (257, MH$^+$). $^1$H NMR (300 MHz, CDCl$_3$) ppm 12.87 (s, 1H) 8.68 (s, 1H); 6.55 (s, 1H); 3.05 (s, 3H); 3.00 (q, 2H) 1.33 (t, 3H).

Step I2.3: Synthesis of 6-ethylsulfanyl-1-methyl-2-(trifluoromethyl)benzimidazole-5-carboxylic Acid

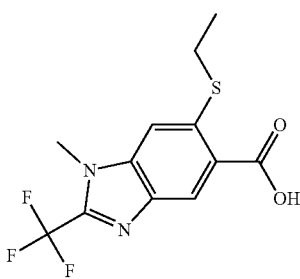 [SMILES: CCSc1cc2c(cc1C(=O)O)nc(C(F)(F)F)n2C]

To a solution of 2-ethylsulfanyl-4-(methylamino)-5-nitro-benzoic acid (0.300 g, 1.17 mmol) in 2,2,2-trifluoroacetic acid (10 mL, 129 mmol) at 0° C., zinc (0.260 g, 3.98 mmol) was added and cooling bath was removed. After 30 min, reduction is complete according to LC/MS; a few cyclized product was observed. The brown solution was then heated at 70° C. to cyclize the di-amino product. After one hour LC/MS showed completion of the cyclisation. Reaction mixture was concentrated to the half, poured into water and extracted with ethyl acetate. Organic phase was washed with water and brine, dried over magnesium sulfate and concentrated under vacuum. The residue was purified by flash chromatography to give 6-ethylsulfanyl-1-methyl-2-(trifluoromethyl)benzimidazole-5-carboxylic acid (0.14 g, 0.46 mmol). LC-MS (method A): Rt=1.06 min, (303, MH$^-$) (305, MH$^+$). $^1$H NMR (300 MHz, CDCl$_3$) ppm 13.03 (s, 1H) 8.30 (s, 1H); 7.64 (s, 1H); 4.00 (s, 3H); 3.06 (q, 2H) 1.32 (t, 3H).

Step I2.4: Synthesis of 6-ethylsulfanyl-1-methyl-2-(trifluoromethyl)benzimidazole-5-carbohydrazide (I2)

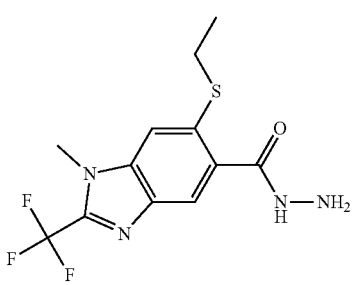

To a solution of 6-ethylsulfanyl-1-methyl-2-(trifluoromethyl)benzimidazole-5-carboxylic acid (659 mg, 2.07 mmol) in methanol (20 ml) was added hydrazine monohydrate (1.64 ml, 33.13 mmol) and the mixture stirred at reflux for 3 hours. 3 mL of hydrazine were added and after 3 hours at 80° C., 20-30% of conversion was observed. 3 mL more of hydrazine were added and finally 5 mL more followed by stirring at 80° C. over night were needed to complete the reaction After cooling, the reaction mixture was concentrated under reduced pressure, the residue triturated with water, filtered and the solid was washed with water then, dried under vacuum to afford 6-ethylsulfanyl-1-methyl-2-(trifluoromethyl) benzimidazole-5-carbohydrazide (732 mg) as a solid. LCMS (method A): 317 (M–H)$^-$/319 (M+H)$^+$, retention time 0.69 min. This material was used without further purification.

Example I3: Synthesis of 3-ethylsulfonylquinoline-2-carbohydrazide (Intermediate I3)

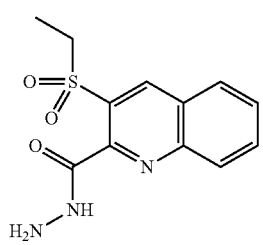

Step I3.1: Synthesis of ethyl 3-ethylsulfanylquinoline-2-carboxylate

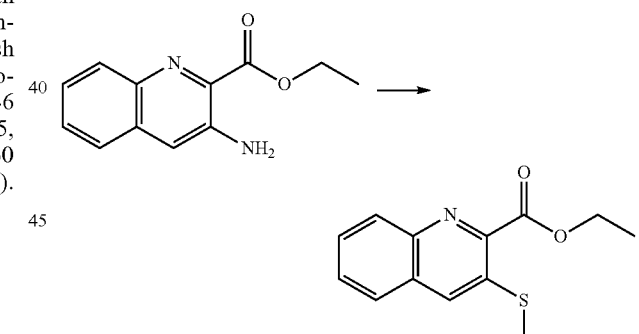

To stirred solution of compound ethyl 3-aminoquinoline-2-carboxylate (3.6 g, 16.66 mmol, commercially available) in DCE (30 ml) was added diethyldisulfide (4.51 ml, 36.6 mmol), t-butyl nitrite was then added dropwise at ambient temperature. The reaction mixture was heated to 40° C. for 2 hours. Reaction was monitored by TLC. After completion of the starting material, reaction mixture was diluted with CH$_2$Cl$_2$ and washed with water (2×10 mL). Organic layer was dried over sodium sulfate. Filtered, concentrated and purified by column chromatography using hexane-ethyl acetate (100-200 silica gel) to give the desired compound as a yellow liquid (amount: 1.0 g). $^1$H NMR (400 MHz, CDCl$_3$): δ (ppm) 8.14 (d, 1H), 8.06 (s, 1H), 7.75 (d, 1H), 7.68 (m, 1H), 7.58 (m, 1H), 4.54 (q, 2H), 3.03 (q, 2H), 1.48 (t, 3H), 1.40 (t, 3H).

Step I3.2: Synthesis of ethyl 3-ethylsulfonylquinoline-2-carboxylate

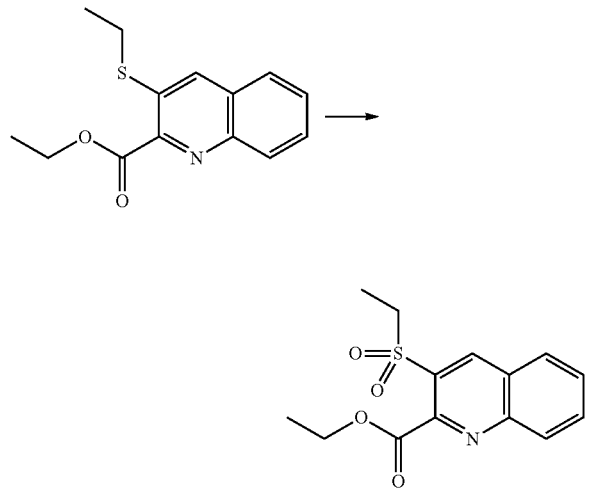

The ethyl 3-ethylsulfonylquinoline-2-carboxylate was prepared with mCPBA in dichloromethane using a protocol identical to the one used in Example P2 below. LC-MS (method A): Rt=0.86 min; (M+H) 294; mp: 76-78° C.

Step I3.3: Synthesis of 3-ethylsulfonylquinoline-2-carbohydrazide (I3)

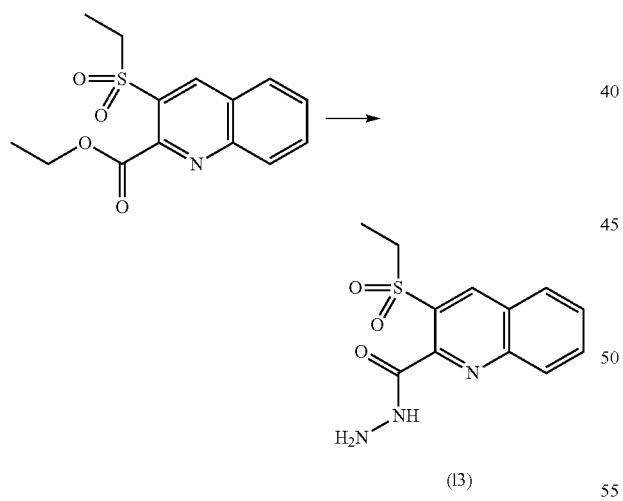

To stirred solution of ethyl 3-ethylsulfonylquinoline-2-carboxylate (prepared in step I3.2, 0.5 g) in methanol (4 ml) was added slowly hydrazine monohydrate (0.166 mL). The reaction mixture was purged with argon, then heated in the microwave for 60 min at 120° C. The solvent was evaporated under vacuum and the residue gum was solved in ethylacetate (50 ml), washed 4 times with 20 ml water, dried over sodium sulfate, filtered and reduced under vacuum to dryness to give the desired compound (0.409 g). LC-MS (method A): Rt=0.55 min; (M+H) 280.

Example I4: Synthesis of ethyl N-methyl-6-(trifluoromethyl)pyrimidine-4-carboximidothioate (Intermediate I4)

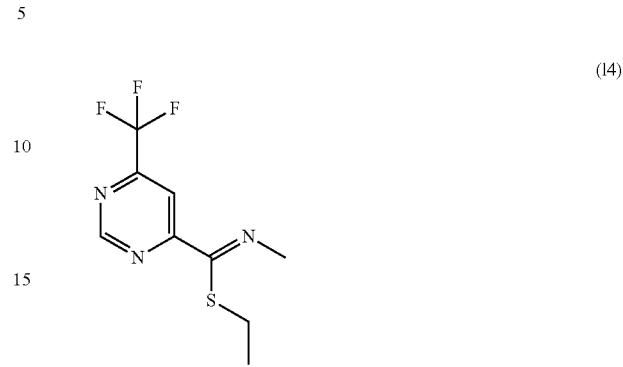

Intermediate I4 was prepared using steps I1.1, I1.2 and I1.3 of example I1 above, starting from 6-(trifluoromethyl)pyrimidine-4-carboxylic acid (commercially available). $^{1}$H NMR (400 MHz, CDCl$_3$) δ ppm 1.18 (t, 3H), 2.96 (q, 2H), 3.56 (s, 3H), 8.04 (s, 1H), 9.42 (s, 1H).

Example I5: Synthesis of 5-chloro-2-ethylsulfonyl-4-nitro-benzohydrazide Hydrochloride Salt (Intermediate I5)

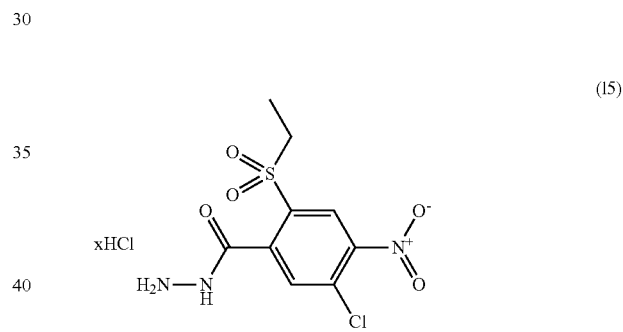

Step I5.1: Synthesis of methyl 5-chloro-2-ethylsulfonyl-benzoate

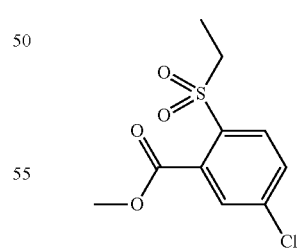

To a solution of methyl 5-chloro-2-ethylsulfanyl-benzoate (prepared according to Synthesis 2011 (21), 3429-3434) (3.00 g, 13.0 mmol) in dichloromethane (100 ml) cooled at 0° C., was added 3-chlorobenzenecarboperoxoic acid (5.97 g, 26.7 mmol) portionwise to maintain the temperature below 5° C. The reaction mixture was stirred for 10 min at 0° C. and then for 3 hours at room temperature. The reaction mixture was cooled at 0° C., quenched with water (20 ml), and the aqueous layer was extracted three times with dichloromethane (3×15 ml). The combined organic layers were washed with a saturated sodium hydrogenocarbonate solution (2×15 ml), dried over sodium sulfate, filtered and concentrated. The crude material was purified by column chromatography over silica gel, eluting with ethyl acetate in cyclohexane. The selected fractions were evaporated to yield the title compound as a white solid. LCMS (method C): 263/265 (M+H)+; retention time: 1.42 min.

Step I5.2: Synthesis of
5-chloro-2-ethylsulfonyl-benzoic Acid

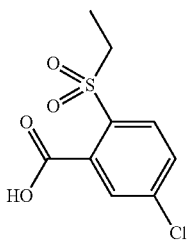

To a solution of methyl 5-chloro-2-ethylsulfonyl-benzoate (4.00 g, 15.2 mmol) in tetrahydrofuran (100 ml), was added a solution of lithium hydroxide hydrate (774 mg, 18.3 mmol) in water (10 ml). The reaction mixture was stirred for 3 hours at room temperature and evaporated to dryness directly. The resulting crude material was taken up in concentrated HCl, the resulting white solid that precipitated was filtered off, dissolved again in ethyl acetate and the solution was dried over sodium sulfate, filtered and concentrated. The crude compound was triturated in n-pentane to afford the desired product as a white solid. LCMS (method C): 272/274 (M+Na)+; retention time: 1.03 min.

Step I5.3: Synthesis of
5-chloro-2-ethylsulfonyl-4-nitro-benzoic Acid

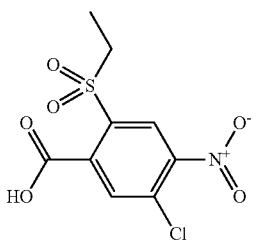 [SMILES: CCS(=O)(=O)c1cc([N+](=O)[O-])c(Cl)cc1C(=O)O]

To a solution of 5-chloro-2-ethylsulfonyl-benzoic acid (3.50 g, 14.0 mmol) in concentrated sulfuric acid (15 ml) was added fuming nitric acid (3.6 ml, 84.0 mmol). The reaction mixture was heated at 100° C. for 1.5 hours. After cooling down to room temperature, the orange reaction mixture was slowly poured into iced water. The white precipitate was filtered, washed with cold water and cyclohexane, and dissolved again in ethyl acetate. The resulting solution was dried over sodium sulfate, filtered and concentrated to afford the title compound. LCMS (method C): 292/294 (M−H)−; retention time: 0.96 min.

Step I5.4: Synthesis of tert-butyl N-[(5-chloro-2-ethylsulfonyl-4-nitro-benzoyl)amino]carbamate

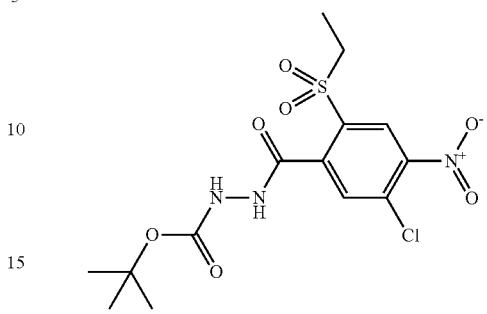

To a solution of 5-chloro-2-ethylsulfonyl-4-nitro-benzoic acid (400 mg, 1.36 mmol) in N,N-dimethyl-formamide (10 ml) were added HATU (673 mg, 1.77 mmol) and triethylamine (0.574 ml, 4.09 mmol). After stirring for 5 min, tert-butyl N-aminocarbamate (234 mg, 1.77 mmol) was added, and the reaction mixture was stirred for 12 hours at room temperature. The reaction was quenched with water, the aqueous phase was extracted with ethyl acetate, the combined organic phases were dried over sodium sulfate, filtered and concentrated. The crude material was purified by column chromatography over silica gel, eluting with ethyl acetate in cyclohexane. The selected fractions were evaporated to yield the title compound as a white solid. 1H NMR (400 MHz, CDCl3) δ 9.52 (s, 1H), 9.00 (br s, 1H), 8.42 (s, 1H), 7.43 (s, 1H), 7.29 (s, 1H), 7.19-7.11 (m, 1H), 7.17-7.02 (m, 1H), 7.14 (br s, 1H), 3.57 (q, J=7.3 Hz, 2H), 1.74 (s, 4H), 1.58-1.58 (m, 1H), 1.48-1.39 (m, 21H), 1.31-1.24 (m, 4H).

Step I5.5: Synthesis of
5-chloro-2-ethylsulfonyl-4-nitro-benzohydrazide
Hydrochloride Salt (I5)

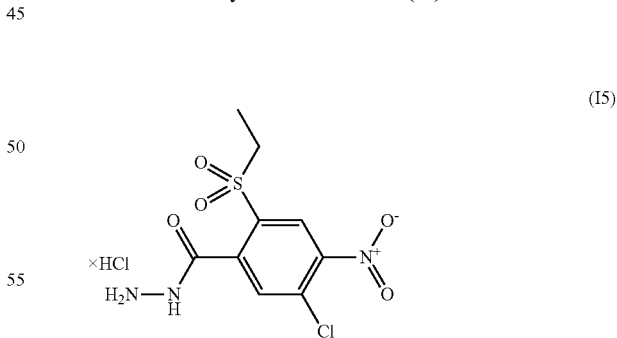

A solution of tert-butyl N-[(5-chloro-2-ethylsulfonyl-4-nitro-benzoyl)amino]carbamate (2.90 g, 7.1 mmol) in HCl (4M in dioxane) (70 ml, 280 mmol) was stirred at room temperature for 2 hours. The reaction mixture was evaporated to dryness, and the resulting white solid was triturated in diethyl ether to afford the desired compound. LCMS (method C; free base): 308/310 (M+H)+; retention time: 1.13 min.

Example I6: Synthesis of 4-chloro-2-ethylsulfanyl-5-nitro-benzohydrazide Hydrochloride Salt (Intermediate I6)

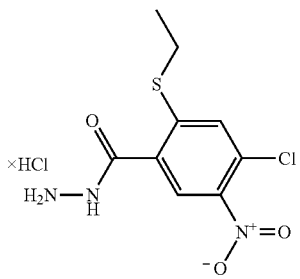
(I6)

Step I6.1: Synthesis of tert-butyl N-[(4-chloro-2-ethylsulfanyl-5-nitro-benzoyl)amino]carbamate

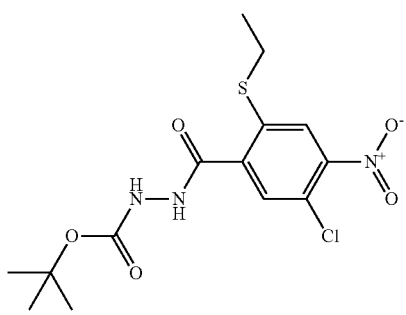 [SMILES: CCSc1cc([N+](=O)[O-])c(Cl)cc1C(=O)NNC(=O)OC(C)(C)C]

To a solution of 4-chloro-2-ethylsulfanyl-5-nitro-benzoic acid (preparation EXAMPLE I2, Step I2.1) (5.00 g, 19.1 mmol) in N,N-dimethylformamide (80 ml) were added triethylamine (8.05 ml, 57.3 mmol), HATU (8.72 g, 22.9 mmol) and tert-butyl N-aminocarbamate (3.03 g, 22.9 mmol). The reaction mixture was stirred for 12 hours at room temperature, quenched with water, and the aqueous phase was extracted with ethyl acetate. The combined organic phases were dried over sodium sulfate, filtered and concentrated. The crude material was purified by column chromatography over silica gel, eluting with ethyl acetate in cyclohexane. The selected fractions were evaporated to yield the title compound as a white solid. LCMS (method D): 374/376 (M−H)⁻; retention time: 0.95 min.

Step I6.2: Synthesis of 4-chloro-2-ethylsulfanyl-5-nitro-benzohydrazide Hydrochloride Salt (Intermediate I6)

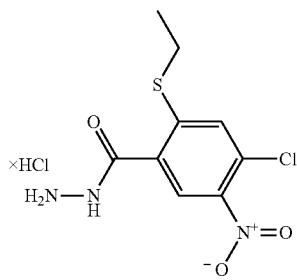
(I6)

A solution of tert-butyl N-[(4-chloro-2-ethylsulfanyl-5-nitro-benzoyl)amino]carbamate (200 mg, 0.53 mmol) in HCl (4M in dioxane) (2 ml, 8.00 mmol, 15 equiv.) was stirred at room temperature for 30 min. The reaction mixture was evaporated to dryness, and the resulting white solid was triturated in diethyl ether to afford the desired compound. LCMS (method D): 276/278 (M+H)⁺; retention time: 0.58 min.

Example I7: Synthesis of 6-ethylsulfonyl-2,2-dimethyl-3H-furo[3,2-b]pyridine-5-carbohydrazide (Intermediate I7)

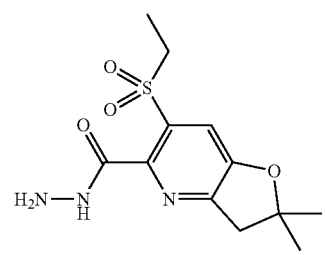
(I7)

Step I7.1: Synthesis of 5-bromo-3-fluoro-pyridine-2-carboxylic Acid

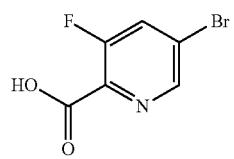 [SMILES: O=C(O)c1ncc(Br)cc1F]

A mixture of 5-bromo-3-fluoro-pyridine-2-carbonitrile (21.0 g, 100 mmol) in concentrated HCl (200 ml) was refluxed at 140° C. for 4 hours. After cooling to room temperature, the reaction mixture was poured into ice-water. The precipitated solid was filtered under vacuum and dried to give the desired compound (18.3 g). $^1$H NMR (d$_6$-DMSO, 400 MHz): 13.76 (s, 1H), 8.64 (s, 1H), 8.33-8.36 (dd, 1H). $^{19}$F NMR (d$_6$-DMSO, 300 MHz): −113.70 (d, 1F).

Step I7.2: Synthesis of methyl 5-bromo-3-fluoro-pyridine-2-carboxylate

To a solution of 5-bromo-3-fluoro-pyridine-2-carboxylic acid (11 g, 50.0 mmol) in methanol (100 ml), was added SOCl$_2$ (50 ml, 685 mmol) dropwise at room temperature. The reaction mixture was stirred at room temperature for 3 hours. The mixture was poured into water and extracted with ethyl acetate three times. The combined organic layers were dried over sodium sulfate, filtered and concentrated under vacuum to give methyl 5-bromo-3-fluoro-pyridine-2-carboxylate. ¹H NMR (CDCl₃, 400 MHz): 8.58 (s, 1H), 7.76 (dd, 1H), 3.98 (s, 3H). ¹⁹F NMR (CDCl₃, 300 MHz): −112.36 (d, 1F).

Step I7.3: Synthesis of methyl 3-fluoro-5-hydroxy-pyridine-2-carboxylate

A mixture of methyl 5-bromo-3-fluoro-pyridine-2-carboxylate (4.68 g, 20 mmol), bis(pinacolato)diboron (7.62 g, 30 mmol), potassium acetate (2.94 g, 30 mmol), tris(dibenzylideneacetone)dipalladium (732 mg, 0.80 mmol), tricyclohexylphosphine (448 mg, 1.6 mmol) in 1,4-dioxane (100 ml) was stirred at 90° C. under nitrogen atmosphere for 16 hours. After cooling to room temperature, the reaction mixture was poured into water and extracted with ethyl acetate three times. The combined organic layers were dried over sodium sulfate, filtered and concentrated under vacuum. The crude product was used without purification directly.

To a solution of the crude material obtained above in THF (100 ml) was added a 30% aqueous H₂O₂ (30 ml) solution. After stirring at room temperature for 24 hours, the mixture was poured into water and extracted with ethyl acetate three times. The combined organic layers were dried over sodium sulfate, filtered and concentrated under vacuum. The crude product was purified by recrystallization from a mixture of petroleum ether and ethyl acetate to give methyl 3-fluoro-5-hydroxy-pyridine-2-carboxylate (1.75 g). ¹H NMR (d₆-DMSO, 400 MHz): 11.38 (s, 1H), 8.09 (s, 1H), 7.16 (d 1H), 3.82 (s, 3H). ¹⁹F NMR (d⁶-DMSO, 300 MHz): −116.50 (d, 1F).

Step I7.4: Synthesis of methyl 3-fluoro-5-(2-methylallyloxy)pyridine-2-carboxylate

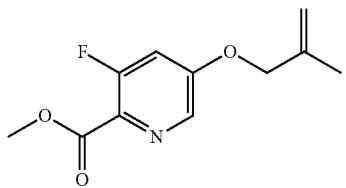 [SMILES: C=C(C)COc1cnc(C(=O)OC)c(F)c1]

To a stirred solution of methyl 3-fluoro-5-hydroxy-pyridine-2-carboxylate (4.3 g, 25 mmol) and 3-chloro-2-methyl-prop-1-ene (4.5 g, 4.9 ml, 50 mmol) in acetone (40 ml) and DMF (10 ml) were added potassium carbonate (6.9 g, 50 mmol) and a catalytic amount of potassium iodide (72 mg, 0.43 mmol). The reaction mixture was refluxed at 90° C. for 24 hours. After cooling to room temperature, the solids were filtered and the solution was concentrated under vacuum. The crude product was purified over silica by flash column chromatography (petroleum ether/ethyl acetate 4:1 mixture) to give methyl 3-fluoro-5-(2-methylallyloxy)pyridine-2-carboxylate (3.54 g). ¹H NMR (CDCl₃, 400 MHz): 8.24 (d, 1H), 7.00 (d, 1H), 5.07 (d, 2H), 4.51 (s, 2H), 3.95 (s, 3H), 1.80 (s, 3H). ¹⁹F NMR (CDCl₃, 300 MHz): −116.53 (d, 1F).

Step I7.5: Synthesis of methyl 6-fluoro-2,2-dimethyl-3H-furo[3,2-b]pyridine-5-carboxylate

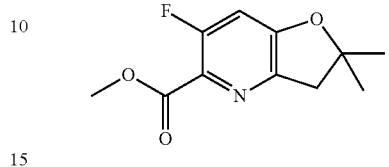

A solution of methyl 3-fluoro-5-(2-methylallyloxy)pyridine-2-carboxylate (900 mg, 4.0 mmol) in N-methyl-2-pyrrolidone NMP (15 ml) was refluxed at 200° C. for 24 hours under nitrogen atmosphere. After cooling to room temperature, the reaction mixture was diluted with ethyl acetate and water. The organic layer was washed with brine, dried over sodium sulfate, filtered and concentrated. The crude product was used without further purification directly.

A solution of the crude product obtained above in formic acid (40 ml) was refluxed at 120° C. for 24 hours. The reaction mixture was evaporated to dryness and the residue was purified over silica by flash column chromatography (petroleum ether/ethyl acetate 4:1) to afford methyl 6-fluoro-2,2-dimethyl-3H-furo[3,2-b]pyridine-5-carboxylate (180 mg, 0.80 mmol). ¹H NMR (CDCl₃, 400 MHz): 6.76 (d, 1H), 3.97 (s, 3H), 3.15 (s, 2H), 1.55 (s, 6H). ¹⁹F NMR (CDCl₃, 300 MHz): −118.58 (d, 1F).

Step I7.6: Synthesis of methyl 6-ethylsulfanyl-2,2-dimethyl-3H-furo[3,2-b]pyridine-5-carboxylate

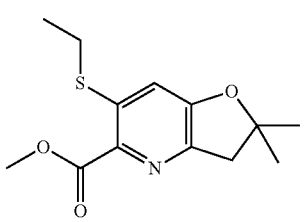

To a solution of methyl 6-fluoro-2,2-dimethyl-3H-furo[3,2-b]pyridine-5-carboxylate (6.0 g, 20 mmol) in DMF (120 ml) was added sodium ethanethiolate (2.2 g, 26 mmol) portionwise at 0° C. After complete addition, the reaction mixture was stirred at room temperature for 30 min. The mixture was diluted with water and ethyl acetate, the phases were separated and the aqueous phase was extracted with ethyl acetate three times. The combined organic layers were then washed with water three times, dried over sodium sulfate, filtered and evaporated to dryness. The residue was purified over silica by flash column chromatography to obtain methyl 6-ethylsulfanyl-2,2-dimethyl-3H-furo[3,2-b]pyridine-5-carboxylate. ¹H NMR (CDCl₃, 400 MHz): 6.94 (s, 1H), 3.97 (s, 3H), 3.15 (s, 2H), 2.90 (q, 2H), 1.54 (s, 6H), 1.41 (t, 3H).

Step I7.7: Synthesis of methyl 6-ethylsulfonyl-2,2-dimethyl-3H-furo[3,2-b]pyridine-5-carboxylate

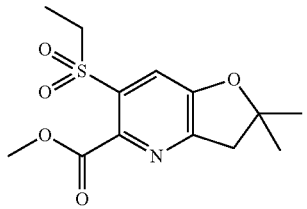

A solution of methyl 6-ethylsulfanyl-2,2-dimethyl-3H-furo[3,2-b]pyridine-5-carboxylate (212 mg, 0.5 mmol) and mCPBA (344 mg, 2.0 mmol) in DCM (20 ml) was stirred at room temperature for 4 hours. The mixture was poured into a saturated solution of sodium hydrogenocarbonate and sodium sulfite in water, and extracted with DCM three times. The combined organic layers were dried over sodium sulfate, filtered and concentrated under vacuum. The crude product was purified over silica by flash column chromatography to obtain methyl 6-ethylsulfonyl-2,2-dimethyl-3H-furo[3,2-b]pyridine-5-carboxylate. $^1$H NMR (CDCl$_3$, 400 MHz): 7.57 (s, 1H), 4.01 (s, 3H), 3.24 (s, 2H), 3.58 (q, 2H), 1.58 (s, 6H), 1.41 (t, 3H).

Step I7.8: Synthesis of 6-ethylsulfonyl-2,2-dimethyl-3H-furo[3,2-b]pyridine-5-carboxylic Acid

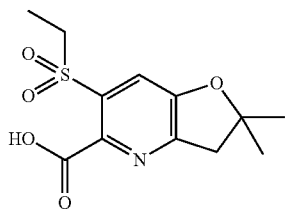 [SMILES: CCS(=O)(=O)c1cc2c(nc1C(=O)O)CC(C)(C)O2]

To a stirred solution of methyl 6-ethylsulfonyl-2,2-dimethyl-3H-furo[3,2-b]pyridine-5-carboxylate (5.98 g, 18 mmol) in THF (30 ml) was added NaOH (4 g, 100 mmol) and water (120 ml). The reaction mixture was stirred at room temperature for 2 hours, then poured into diluted aqueous hydrochloric acid and concentrated under vacuum. The pH value was adjusted to 2 with aqueous HCl and the mixture extracted with ethyl acetate three times. The combined organic layers were dried over anhydrous sodium sulfate, filtered and concentrated in vacuo to provide 6-ethylsulfonyl-2,2-dimethyl-3H-furo[3,2-b]pyridine-5-carboxylic acid as a solid. $^1$H NMR (d$_6$-DMSO, 400 MHz): 13.72 (s, 1H), 7.49 (s, 1H), 3.53 (q, 2H), 3.26 (s, 2H), 1.52 (s, 6H), 1.20 (t, 3H).

Step I7.9: Synthesis of 6-ethylsulfonyl-2,2-dimethyl-3H-furo[3,2-b]pyridine-5-carbohydrazide (I7)

(I7)

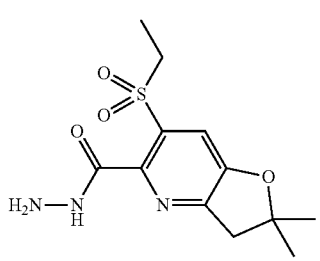

To a solution of methyl 6-ethylsulfonyl-2,2-dimethyl-3H-furo[3,2-b]pyridine-5-carboxylate (490 mg, 1.64 mmol) in methanol (10 ml) under argon was added hydrazine monohydrate (0.812 ml, 16.4 mmol) and the reaction was heated to reflux for 2 hours. After addition of more hydrazine monohydrate (8.2 mmol), the reaction mixture was heated in the microwave at 75° C. for 145 min. The solvent was evaporated under vacuum and the residue was purified by CombiFlash (silica gel, 0-1% methanol in dichloromethane) to afford 6-ethylsulfonyl-2,2-dimethyl-3H-furo[3,2-b]pyridine-5-carbohydrazide (I7) as a solid. LCMS (method A): retention time 0.63 min; 300 (M+H)$^+$.

b) Synthesis of Examples of Compounds of Formula (I):

Example P1: Preparation of 6-ethylsulfanyl-1-methyl-5-[4-methyl-5-[4-(trifluoromethyl)-2-pyridyl]-1,2,4-triazol-3-yl]-2-(trifluoromethyl)benzimidazole (Compound A1)

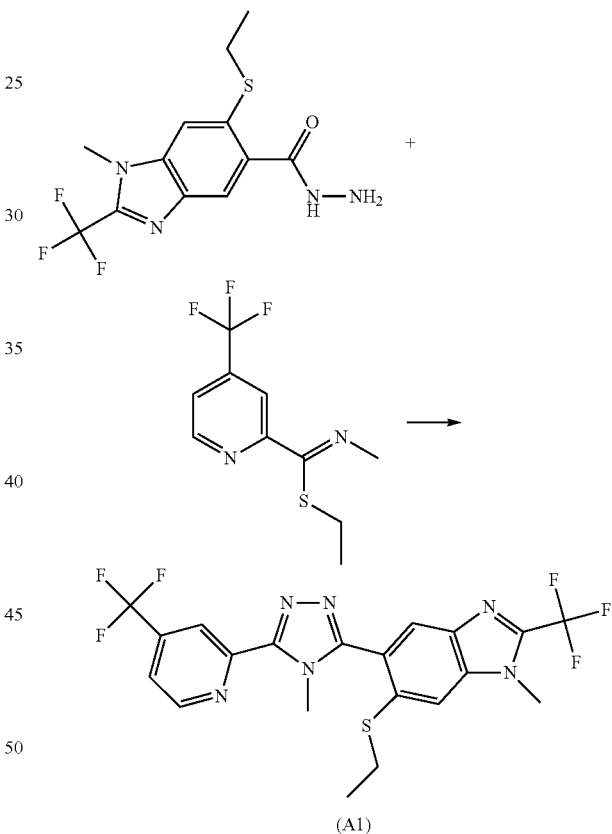

(A1)

A solution of ethyl N-methyl-4-(trifluoromethyl)pyridine-2-carboximidothioate (intermediate I1, 0.377 g, 1.52 mmol) and 6-ethylsulfanyl-1-methyl-2-(trifluoromethyl)benzimidazole-5-carbohydrazide (intermediate I2, 0.483 g, 1.52 mmol) in pyridine (10 ml) was heated for 6 hour at 150° C. under MW. After cooling, the reaction mixture was concentrated under reduced pressure and the residue was purified over silica by flash column chromatography (cyclohexane/ethyl acetate) to afford 6-ethylsulfanyl-1-methyl-5-[4-methyl-5-[4-(trifluoromethyl)-2-pyridyl]-1,2,4-triazol-3-yl]-2-(trifluoromethyl) benzimidazole (compound A1) as a solid (358 mg). $^1$H NMR (400 MHz, CDCl$_3$) δ ppm 1.24 (t, 3H), 2.88 (q, 2H), 3.88 (s, 3H), 4.02 (s, 3H), 7.57 (dd, 1H), 7.61 (s, 1H), 7.98 (s, 1H), 8.74 (s, 1H), 8.86 (d, 1H).

Example P2: Preparation of 6-ethylsulfonyl-1-methyl-5-[4-methyl-5-[4-(trifluoromethyl)-2-pyridyl]-1,2,4-triazol-3-yl]-2-(trifluoromethyl)benzimidazole (Compound A2)

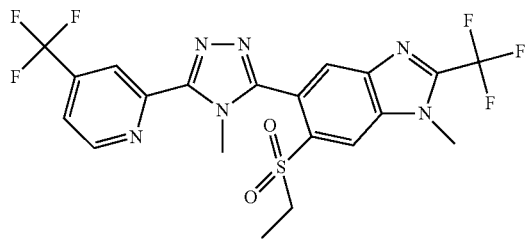

To a solution of 6-ethylsulfanyl-1-methyl-5-[4-methyl-5-[4-(trifluoromethyl)-2-pyridyl]-1,2,4-triazol-3-yl]-2-(trifluoromethyl)benzimidazole (compound A1) (346 mg, 0.7113 mmol) in dichloromethane (15 ml) at 10° C. was added mCPBA (75 wt % in water) (360 mg, 01.56 mmol, 75%) in one portion and the mixture was stirred at room temperature for 2 hours. The reaction mixture was quenched with a sat. sodium thiosulfate solution and extracted with dichloromethane. The organic phase was washed with aqueous sodium hydroxide, dried over sodium sulfate and concentrated under reduced pressure to afford 6-ethyl-sulfonyl-1-methyl-5-[4-methyl-5-[4-(trifluoromethyl)-2-pyridyl]-1,2,4-triazol-3-yl]-2-(trifluoromethyl) benzimidazole (compound A2) (365 mg). $^1$H-NMR (CDCl$_3$, ppm) δ ppm 1.27-1.32 (m, 3H), 3.54 (m, 2H), 3.87 (s, 3H), 4.15 (s, 3H), 7.59 (dd, 1H), 8.05 (s, 1H), 8.43 (s, 1H), 8.70 (s, 1H), 8.86 (d, 1H).

Example P3: Preparation of 5-ethylsulfonyl-6-[4-methyl-5-[4-(trifluoromethyl)-2-pyridyl]-1,2,4-triazol-3-yl]-2-(trifluoromethyl)-1,3-benzothiazole (Compound A6)

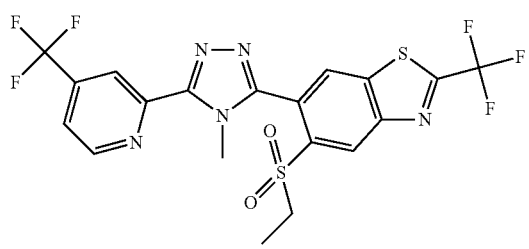

Step P3.1: Synthesis of 2-[5-(5-chloro-2-ethylsulfonyl-4-nitro-phenyl)-4-methyl-1,2,4-triazol-3-yl]-4-(trifluoromethyl)pyridine

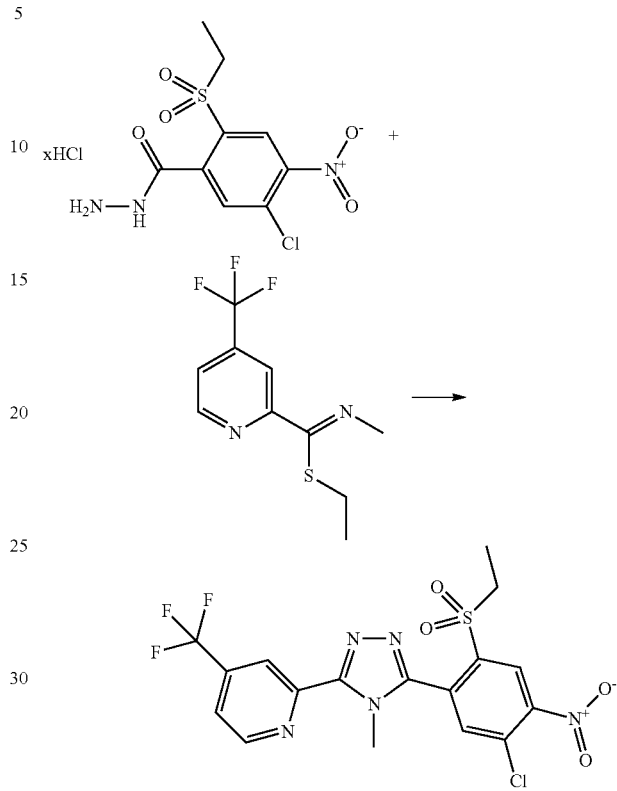

To a solution of 5-chloro-2-ethylsulfonyl-4-nitro-benzohydrazide hydrochloride salt (I5) (700 mg, 2.03 mmol) in acetic acid (20 ml) was added ethyl N-methyl-4-(trifluoromethyl)pyridine-2-carboximidothioate (I1) (1.01 g, 4.06 mmol). The reaction mixture was stirred for 2 hours at room temperature, and directly concentrated. Ice was added to the residue, the pH was neutralized by addition of a saturated potassium carbonate solution, and the aqueous phase was extracted with ethyl acetate. The combined organic phases were washed with brine, dried over sodium sulfate and concentrated. The crude material was purified by column chromatography over silica gel, eluting with ethyl acetate in cyclohexane. The selected fractions were evaporated to yield the title compound. LCMS (method C): 476/478 (M+H)$^+$; retention time: 1.57 min.

Step P3.2: Synthesis of 2-[5-(5-tert-butylsulfanyl-2-ethylsulfonyl-4-nitro-phenyl)-4-methyl-1,2,4-triazol-3-yl]-4-(trifluoromethyl)pyridine

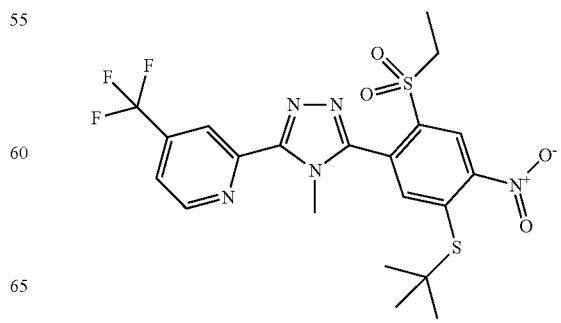

To a solution of 2-[5-(5-chloro-2-ethylsulfonyl-4-nitrophenyl)-4-methyl-1,2,4-triazol-3-yl]-4-(trifluoromethyl)pyridine (900 mg, 1.89 mmol) in N,N-dimethylformamide (50 ml) were added potassium carbonate (392 mg, 2.84 mmol) and 2-methylpropane-2-thiol (0.3 ml, 2.84 mmol). The reaction mixture was stirred for 3 hours at room temperature, quenched with water, and the aqueous phase was extracted with ethyl acetate. The combined organic phases were dried over sodium sulfate, filtered and concentrated. The crude material was purified by column chromatography over silica gel, eluting with ethyl acetate in cyclohexane. The selected fractions were evaporated to yield the title compound, pure enough to be used in the next step. LCMS (method D): 530 (M+H)$^+$; retention time: 1.11 min.

Step P3.3: Synthesis of 2-tert-butylsulfanyl-5-ethylsulfonyl-4-[4-methyl-5-[4-(trifluoromethyl)-2-pyridyl]-1,2,4-triazol-3-yl]aniline TFA Salt

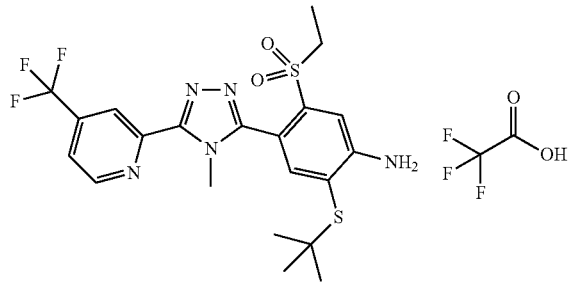 [SMILES: CCS(=O)(=O)c1cc(N)c(SC(C)(C)C)cc1-c1nnc(-c2cc(C(F)(F)F)ccn2)n1C ; O=C(O)C(F)(F)F]

To a solution of 2-[5-(5-tert-butylsulfanyl-2-ethylsulfonyl-4-nitro-phenyl)-4-methyl-1,2,4-triazol-3-yl]-4-(trifluoromethyl)pyridine (230 mg, 0.43 mmol) in trifluoroacetic acid (15 ml) was added zinc powder (230 mg, 3.51 mmol). The reaction mixture was refluxed at 90° C. for 1 hour. After cooling down to room temperature, the reaction was filtered over Celite, the solvent was removed, and the crude material was used directly without further purification. LCMS (method D; free base): 500 (M+H)$^+$; retention time: 1.02 min.

Step P3.4: Synthesis of N-[2-tert-butylsulfanyl-5-ethylsulfonyl-4-[4-methyl-5-[4-(trifluoromethyl)-2-pyridyl]-1,2,4-triazol-3-yl]phenyl]-2,2,2-trifluoroacetamide

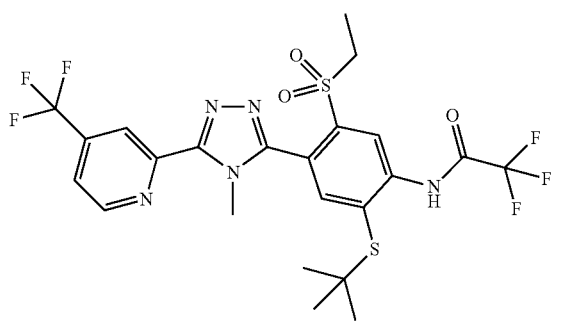 [SMILES: CCS(=O)(=O)c1cc(NC(=O)C(F)(F)F)c(SC(C)(C)C)cc1-c1nnc(-c2cc(C(F)(F)F)ccn2)n1C]

A solution of 2-tert-butylsulfanyl-5-ethylsulfonyl-4-[4-methyl-5-[4-(trifluoromethyl)-2-pyridyl]-1,2,4-triazol-3-yl]aniline TFA salt (230 mg, 0.38 mmol) in trifluoroacetic anhydride (15 ml) was stirred at room temperature for 30 min. The reaction mixture was concentrated and the crude residue used in the next step directly. LCMS (method D): 594 (M–H)$^-$; retention time: 1.17 min.

Step P3.5: Synthesis of 5-ethylsulfonyl-6-[4-methyl-5-[4-(trifluoromethyl)-2-pyridyl]-1,2,4-triazol-3-yl]-2-(trifluoromethyl)-1,3-benzothiazole (A6)

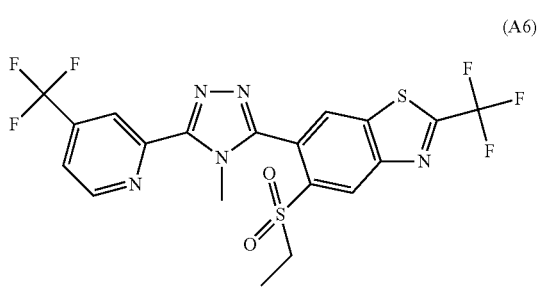 [SMILES: CCS(=O)(=O)c1cc2nc(C(F)(F)F)sc2cc1-c1nnc(-c2cc(C(F)(F)F)ccn2)n1C]

A solution of N-[2-tert-butylsulfanyl-5-ethylsulfonyl-4-[4-methyl-5-[4-(trifluoromethyl)-2-pyridyl]-1,2,4-triazol-3-yl]phenyl]-2,2,2-trifluoro-acetamide (230 mg, 0.39 mmol) in trifluoroacetic anhydride (20 ml) was stirred at 110° C. overnight. After cooling down to room temperature, the reaction mixture was concentrated, the crude residue was taken up in water and the aqueous phase was extracted with ethyl acetate. The combined organic phases were washed with a saturated sodium hydrogenocarbonate solution, dried over sodium sulfate, filtered and concentrated. The crude material was purified by column chromatography over silica gel, eluting with ethyl acetate in cyclohexane. The selected fractions were evaporated to yield the title compound. LCMS (method D): 522 (M+H)$^+$; retention time: 1.04 min.

Example P4: Preparation of 6-ethylsulfonyl-5-[4-methyl-5-[4-(trifluoromethyl)-2-pyridyl]-1,2,4-triazol-3-yl]-2-(trifluoromethyl)-1,3-benzothiazole (Compound A8)

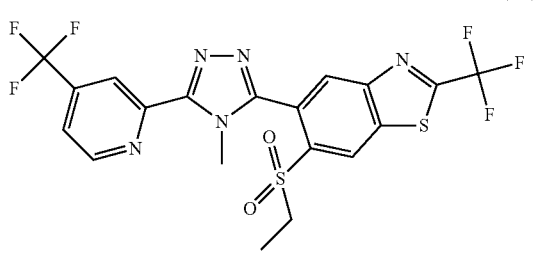

Step P4.1: Synthesis of 2-[5-(4-chloro-2-ethylsulfanyl-5-nitro-phenyl)-4-methyl-1,2,4-triazol-3-yl]-4-(trifluoromethyl)pyridine

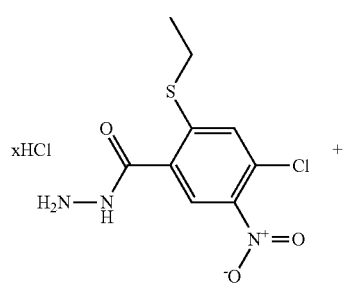

+

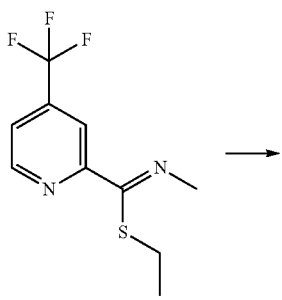

→

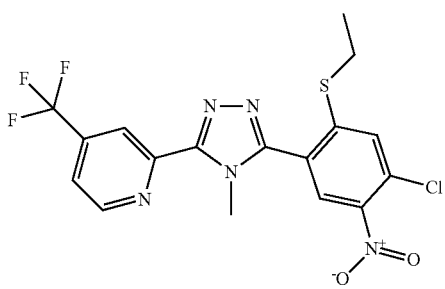

To a solution of 4-chloro-2-ethylsulfanyl-5-nitro-benzohydrazide hydrochloride salt (I6) (3.5 g, 13 mmol) in acetic acid (100 ml) was added ethyl N-methyl-4-(trifluoromethyl)pyridine-2-carboximidothioate (I1) (4.7 g, 19 mmol). The reaction mixture was heated at 110° C. for 2 hours. A solid precipitated upon cooling down to room temperature, which was filtered and discarded. The mother liquor was evaporated to dryness. The residue was triturated in ethyl acetate and the resulting solid was filtered off to give the title compound. LCMS (method C): 444/446 (M+H)$^+$; retention time: 1.61 min.

Step P4.2: Synthesis of 2-[5-(4-tert-butylsulfanyl-2-ethylsulfanyl-5-nitro-phenyl)-4-methyl-1,2,4-triazol-3-yl]-4-(trifluoromethyl)pyridine

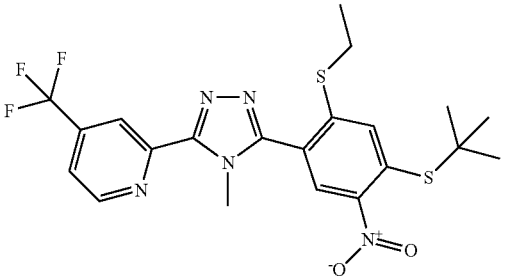

To a solution of 2-[5-(4-chloro-2-ethylsulfanyl-5-nitro-phenyl)-4-methyl-1,2,4-triazol-3-yl]-4-(trifluoro-methyl)pyridine (600 mg, 1.35 mmol) in N,N-dimethylformamide (10 ml) were added 2-methylpropane-2-thiol (235 mg, 2.70 mmol) and potassium carbonate (280 mg, 2.03 mmol). The reaction mixture was heated at 55° C. for 2 hours. After cooling down to room temperature and degassing with nitrogen for 2 hours, the reaction mixture was poured over crushed ice. The aqueous phase was extracted with ethyl acetate, the combined organic phases were washed with brine, dried over sodium sulfate, filtered and concentrated. The crude material was purified by column chromatography over silica gel, eluting with ethyl acetate in cyclohexane. The selected fractions were evaporated to give the title compound. LCMS (method D): 498 (M+H)$^+$; retention time: 1.18 min.

Step P4.3: Synthesis of 2-tert-butylsulfanyl-4-ethylsulfanyl-5-[4-methyl-5-[4-(trifluoromethyl)-2-pyridyl]-1,2,4-triazol-3-yl]aniline TFA Salt

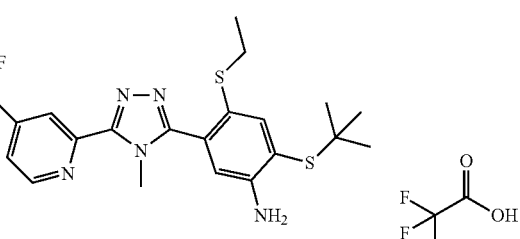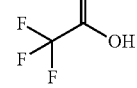

To a solution of 2-[5-(4-tert-butylsulfanyl-2-ethylsulfanyl-5-nitro-phenyl)-4-methyl-1,2,4-triazol-3-yl]-4-(trifluoromethyl)pyridine (210 mg, 0.42 mmol) in trifluoroacetic acid (10 ml) was added zinc powder (220 mg, 3.38 mmol). The reaction mixture was refluxed at 80° C. for 1 hour. After cooling down to room temperature, the reaction mixture was filtered over Celite, the solvent was removed, and the crude material was used directly without further purification. LCMS (method C, free base): 468 (M+H)$^+$; retention time: 1.20 min.

Step P4.4: Synthesis of N-[2-tert-butylsulfanyl-4-ethylsulfanyl-5-[4-methyl-5-[4-(trifluoromethyl)-2-pyridyl]-1,2,4-triazol-3-yl]phenyl]-2,2,2-trifluoro-acetamide

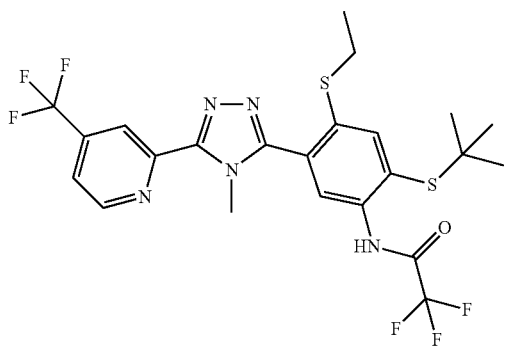 [SMILES: CCSc1cc(SC(C)(C)C)c(NC(=O)C(F)(F)F)cc1-c1nnc(-c2cc(C(F)(F)F)ccn2)n1C]

A solution of 2-tert-butylsulfanyl-4-ethylsulfanyl-5-[4-methyl-5-[4-(trifluoromethyl)-2-pyridyl]-1,2,4-triazol-3-yl] aniline TFA salt (190 mg, 0.31 mmol) in trifluoroacetic anhydride (10 ml) was stirred at room temperature for 1 hour. The reaction mixture was evaporated to dryness and the crude material used directly in the next step without purification. LCMS (method C): 562 (M−H)⁻; retention time: 1.31 min.

Step P4.5: Synthesis of 6-ethylsulfanyl-5-[4-methyl-5-[4-(trifluoromethyl)-2-pyridyl]-1,2,4-triazol-3-yl]-2-(trifluoromethyl)-1,3-benzothiazole (Compound A7)

(A7)

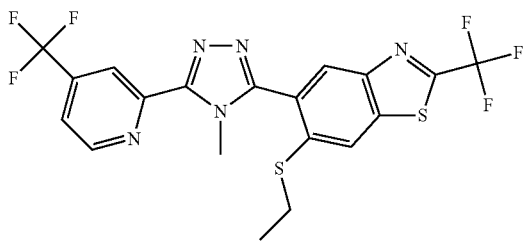

A solution of N-[2-tert-butylsulfanyl-4-ethylsulfanyl-5-[4-methyl-5-[4-(trifluoromethyl)-2-pyridyl]-1,2,4-triazol-3-yl]phenyl]-2,2,2-trifluoro-acetamide (210 mg, 0.37 mmol) in 2,2,2-trifluoroacetic acid (10 ml) was stirred at 100° C. for 12 hours. After cooling to room temperature, the reaction mixture was evaporated under reduced pressure, the crude residue carefully treated with an aqueous saturated solution of potassium carbonate and the aqueous phase extracted with ethyl acetate (2×25 ml). The combined organic phases were washed with brine, dried over sodium sulfate, filtered and concentrated. The crude material was purified by column chromatography over silica gel, eluting with ethyl acetate in cyclohexane. The selected fractions were evaporated to yield the title compound a solid, mp 180-182° C. LCMS (method C): 490 (M+H)⁺; retention time: 1.69 min. ¹H NMR (400 MHz, CDCl₃) δ ppm 1.32 (t, J=7.34 Hz, 3H), 2.98 (q, J=7.34 Hz, 2H), 3.95 (s, 3H), 7.60 (d, J=5.1 Hz, 1H), 8.05 (s, 1H), 8.27 (s, 1H), 8.76 (s, 1H), 8.88 (d, J=5.1 Hz, 1H).

Step P4.6: Synthesis of 6-ethylsulfonyl-5-[4-methyl-5-[4-(trifluoromethyl)-2-pyridyl]-1,2,4-triazol-3-yl]-2-(trifluoromethyl)-1,3-benzothiazole (Compound A8)

(A8)

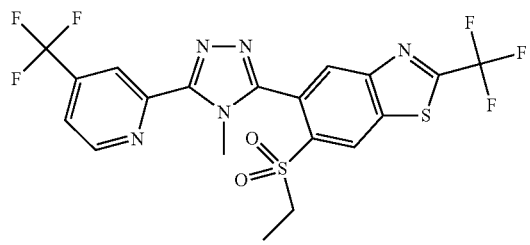

To a solution of 6-ethylsulfanyl-5-[4-methyl-5-[4-(trifluoromethyl)-2-pyridyl]-1,2,4-triazol-3-yl]-2-(trifluoromethyl)-1,3-benzothiazole (compound A7) (90 mg, 0.18 mmol) in dichloromethane (10 ml) cooled at 0° C., was added 3-chlorobenzenecarboperoxoic acid (87 mg, 0.39 mmol) in portion to maintain the temperature below 5° C. The reaction mixture was stirred for 10 min at 0° C. and then for 3 hours at room temperature. After completion of the reaction, the mixture was cooled at 0° C. and quenched with water. The aqueous phase was extracted with dichloromethane (3×15 ml), the combined organic phases were washed with a saturated sodium hydrogenocarbonate solution (2×15 ml), dried over sodium sulfate, filtered and concentrated. Purification by column chromatography over silica gel, eluting with ethyl acetate in cyclohexane and evaporation of the selected fractions afforded the title compound. LCMS (method C): 522 (M+H)⁺; retention time: 1.42 min.

Example P5: Preparation of 1-ethyl-6-ethylsulfonyl-5-[4-methyl-5-[4-(trifluoromethyl)-2-pyridyl]-1,2,4-triazol-3-yl]triazolo[4,5-b]pyridine (Compound A13)

(A13)

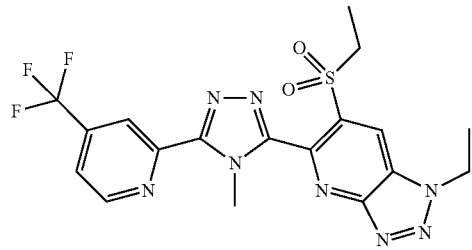

Step P5.1: Synthesis of tert-butyl N-[5-ethylsulfonyl-6-[4-methyl-5-[4-(trifluoromethyl)-2-pyridyl]-1,2,4-triazol-3-yl]-3-pyridyl]carbamate

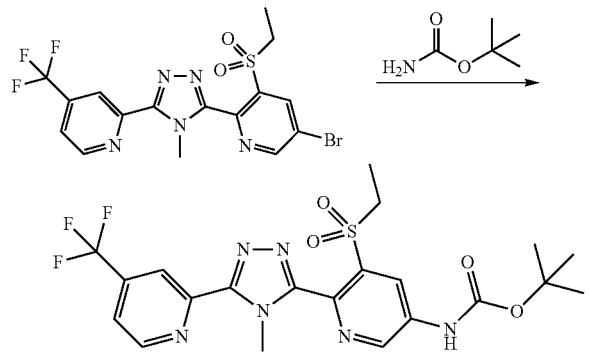

To a solution of 5-bromo-3-ethylsulfonyl-2-[4-methyl-5-[4-(trifluoromethyl)-2-pyridyl]-1,2,4-triazol-3-yl]pyridine (WO2017/016910) (0.1 g, 0.210 mmol) in anhydrous 1,4-dioxane (1 mL) under nitrogen was added cesium carbonate (0.096 g, 0.294 mmol), followed by the addition of palladium(II) acetate (0.0014 g, 0.0063 mmol) and tert-butyl carbamate (0.0295 g, 0.252 mmol). The reaction mixture was degassed with nitrogen for 15 minutes. 2-Dicyclohexylphosphino-2',4',6'-triisopropylbiphenyl XPhos (0.0092 g, 0.019 mmol) was added and the reaction mixture heated at 110° C. in a preheated oil bath for 14 hours. The mixture was filtered through a celite bed and the bed washed with EtOAc (20 ml). The organic layer was evaporated and directly subjected to column chromatography (gradient cyclohexane+0-60% EtOAc) to give tert-butyl N-[5-ethylsulfonyl-6-[4-methyl-5-[4-(trifluoromethyl)-2-pyridyl]-1,2,4-triazol-3-yl]-3-pyridyl]carbamate (0.078 g). $^1$H NMR (400 MHz, CDCl$_3$) δ ppm 1.37 (t, 3H), 1.57 (s, 9H), 3.78 (q, 2H), 4.02 (s, 3H), 7.14 (s, 1H), 7.58 (d, 1H), 8.59 (d, 1H), 8.69 (s, 1H), 8.86 (d, 1H), 9.04 (d, 1H).

Step P5.2: Synthesis of tert-butyl N-ethyl-N-[5-ethylsulfonyl-6-[4-methyl-5-[4-(trifluoromethyl)-2-pyridyl]-1,2,4-triazol-3-yl]-3-pyridyl]carbamate

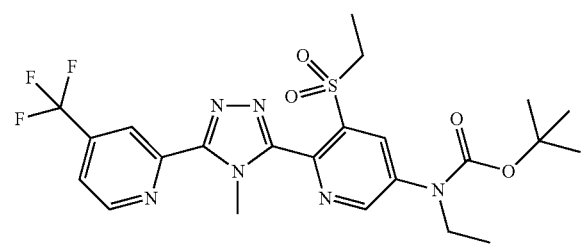 [SMILES: CCN(C(=O)OC(C)(C)C)c1cnc(-c2nnc(-c3cc(C(F)(F)F)ccn3)n2C)c(S(=O)(=O)CC)c1]

To a suspension of sodium hydride (0.936 g, 23.41 mmol, 60% dispersion in mineral oil) in tetrahydrofuran (10 ml) at 0° C. was added a solution of tert-butyl N-[5-ethylsulfonyl-6-[4-methyl-5-[4-(trifluoro-methyl)-2-pyridyl]-1,2,4-triazol-3-yl]-3-pyridyl]carbamate (2.0 g, 3.902 mmol) in tetrahydrofuran (50 ml) dropwise. The mixture was stirred for 30 minutes, then iodoethane (3.65 g, 23.41 mmol) was added dropwise. The reaction mixture was warmed to room temperature for 3 hours and quenched using a saturated aqueous ammonium chloride solution. The aqueous layer was extracted with ethyl acetate (3×30 ml), the combined organic layer dried over sodium sulfate and concentrated under reduced pressure. The residue was purified by CombiFlash (silica gel, 20% EtOAc-cyclohexane) to afford tert-butyl N-ethyl-N-[5-ethylsulfonyl-6-[4-methyl-5-[4-(trifluoromethyl)-2-pyridyl]-1,2,4-triazol-3-yl]-3-pyridyl]carbamate (1.6 g). LCMS (method D): retention time 1.14 min; 541 (M+H)$^+$.

Step P5.3: Synthesis of N-ethyl-5-ethylsulfonyl-6-[4-methyl-5-[4-(trifluoromethyl)-2-pyridyl]-1,2,4-triazol-3-yl]pyridin-3-amine

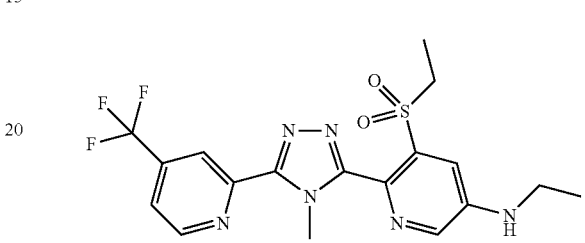

To a solution of tert-butyl N-ethyl-N-[5-ethylsulfonyl-6-[4-methyl-5-[4-(trifluoromethyl)-2-pyridyl]-1,2,4-triazol-3-yl]-3-pyridyl]carbamate (1.60 g, 2.960 mmol) in 1,4-dioxane (10 ml) was added a 4N hydrogen chloride solution in 1,4-dioxane (50 ml) and the mixture stirred at room temperature for 3 hours, then evaporated to dryness. Water (10 ml) was added to the residue and the mixture neutralised with an aqueous saturated potassium carbonate solution. The aqueous phase was extracted with ethyl acetate (3×20 ml), the combined organic layers washed with brine (20 ml), dried over sodium sulfate and concentrated under reduced pressure. The crude product was purified by CombiFlash (silica gel, 40% EtOAc-cyclohexane) to afford N-ethyl-5-ethylsulfonyl-6-[4-methyl-5-[4-(trifluoromethyl)-2-pyridyl]-1,2,4-triazol-3-yl]pyridin-3-amine (0.9 g). LCMS (method D): retention time 0.92 min; 441 (M+H)$^+$. $^1$H NMR (400 MHz, CDCl$_3$) δ ppm 1.3-1.43 (m, 6H), 3.35 (q, J=7.21 Hz, 2H), 3.73 (q, J=7.38 Hz, 2H), 4.00 (s, 3H), 7.52-7.59 (m, 2H), 8.29 (d, J=2.81 Hz, 1H), 8.69 (s, 1H), 8.85 (d, J=5.01 Hz, 1H).

Step P5.4: Synthesis of 2-bromo-N-ethyl-5-ethylsulfonyl-6-[4-methyl-5-[4-(trifluoromethyl)-2-pyridyl]-1,2,4-triazol-3-yl]pyridin-3-amine

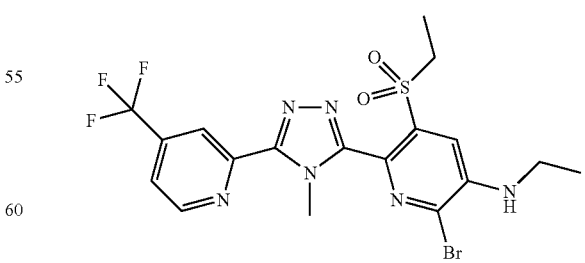

To a solution of N-ethyl-5-ethylsulfonyl-6-[4-methyl-5-[4-(trifluoromethyl)-2-pyridyl]-1,2,4-triazol-3-yl]pyridin-3-amine (850 mg, 1.93 mmol) in N,N-dimethylformamide (20 ml) was added N-bromosuccinimide (515 mg, 2.90 mmol).

The reaction mixture was stirred at room temperature for 3 hours. The mixture was poured on cold water, the aqueous phase was extracted with ethyl acetate. The combined organic layers were dried over sodium sulfate, filtered and concentrated. The crude was purified by column chromatography over silica gel, eluting with ethyl acetate in cyclohexane and evaporation of the selected fractions afforded the title compound. LCMS (method D): 519/521 (M+H)$^+$; retention time: 1.01 min.

Step P5.5: Synthesis of 2-azido-N-ethyl-5-ethylsulfonyl-6-[4-methyl-5-[4-(trifluoromethyl)-2-pyridyl]-1,2,4-triazol-3-yl]pyridin-3-amine

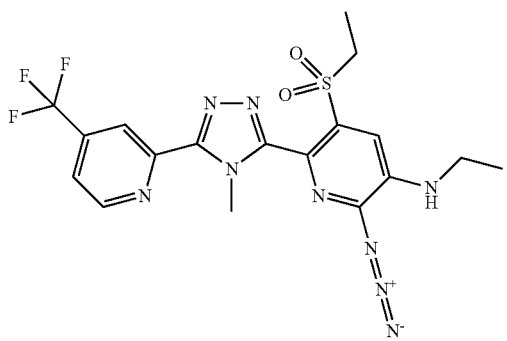 [SMILES: CCNc1cc(S(=O)(=O)CC)c(-c2nnc(-c3cc(C(F)(F)F)ccn3)n2C)nc1N=[N+]=[N-]]

To a solution of 2-bromo-N-ethyl-5-ethylsulfonyl-6-[4-methyl-5-[4-(trifluoromethyl)-2-pyridyl]-1,2,4-triazol-3-yl]pyridin-3-amine (900 mg, 1.73 mmol) in N,N-dimethylformamide (30 ml) under argon was added sodium azide (203 mg, 3.12 mmol). The reaction mixture was heated at 100° C. for 3 hours under vigorous stirring. After cooling down to room temperature, the mixture was poured on cold water, the aqueous phase was extracted with ethyl acetate. The combined organic layers were washed with brine, dried over sodium sulfate, filtered and concentrated. Purification by column chromatography over silica gel eluting with ethyl acetate in cyclohexane and evaporation of the selected fractions afforded the desired compound. LCMS (method D): 482 (M+H)$^+$; retention time: 0.95 min.

Step P5.6: Synthesis of N3-ethyl-5-ethylsulfonyl-6-[4-methyl-5-[4-(trifluoromethyl)-2-pyridyl]-1,2,4-triazol-3-yl]pyridine-2,3-diamine

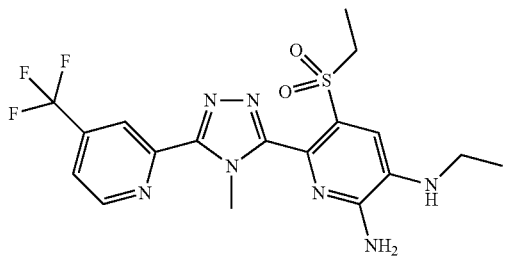 [SMILES: CCNc1cc(S(=O)(=O)CC)c(-c2nnc(-c3cc(C(F)(F)F)ccn3)n2C)nc1N]

To a solution of 2-azido-N-ethyl-5-ethylsulfonyl-6-[4-methyl-5-[4-(trifluoromethyl)-2-pyridyl]-1,2,4-triazol-3-yl]pyridin-3-amine (750 mg, 1.56 mmol) in tetrahydrofuran (30 ml) and water (3 ml) was added triphenylphosphine (1.24 g, 4.67 mmol). The reaction mixture was heated at 60° C. for 2 hours, cooled down to room temperature and the solvent was evaporated under reduced pressure. The crude residue was diluted with HCl (25 ml) and the mixture was heated again at 60° C. for 14 hours. After cooling down to room temperature, the reaction mixture was carefully poured into a saturated potassium carbonate solution. The precipitated solid was filtered off, washed with diethyl ether, and dried under vacuum to afford the desired product. LCMS (method D): 456 (M+H)$^+$; retention time: 0.80 min.

Step P5.7: Synthesis of 1-ethyl-6-ethylsulfonyl-5-[4-methyl-5-[4-(trifluoromethyl)-2-pyridyl]-1,2,4-triazol-3-yl]triazolo[4,5-b]pyridine (A13)

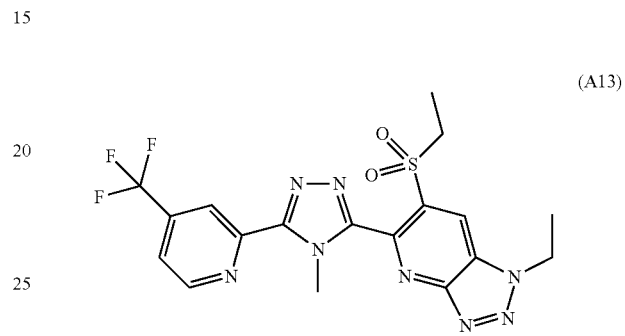

To a solution of N3-ethyl-5-ethylsulfonyl-6-[4-methyl-5-[4-(trifluoromethyl)-2-pyridyl]-1,2,4-triazol-3-yl]pyridine-2,3-diamine (660 mg, 1.32 mmol) in acetic acid (15 ml) was added a solution of sodium nitrite (454 mg, 6.59 mmol) in water (5 ml). The reaction mixture was stirred at room temperature for 2 hours. After completion of the reaction, the mixture was evaporated to dryness. The residue was diluted in water, and the aqueous phase was extracted twice with ethyl acetate, the combined organic phases were dried over sodium sulfate, filtered and concentrated. Purification by column chromatography over silica gel eluting with ethyl acetate in cyclohexane and evaporation of the selected fractions afforded the desired compound. LCMS (method D): 467 (M+H)$^+$; retention time: 0.95 min.

Example P6: Preparation of 6-ethylsulfonyl-1-methyl-5-[4-methyl-5-[4-(trifluoromethyl)-2-pyridyl]-1,2,4-triazol-3-yl]triazolo[4,5-b]pyridine (Compound A9), 6-ethylsulfonyl-3-methyl-5-[4-methyl-5-[4-(trifluoro-methyl)-2-pyridyl]-1,2,4-triazol-3-yl]triazolo[4,5-b]pyridine (Compound A10) and 6-ethylsulfonyl-2-methyl-5-[4-methyl-5-[4-(trifluoromethyl)-2-pyridyl]-1,2,4-triazol-3-yl]triazolo[4,5-b]pyridine (Compound A18)

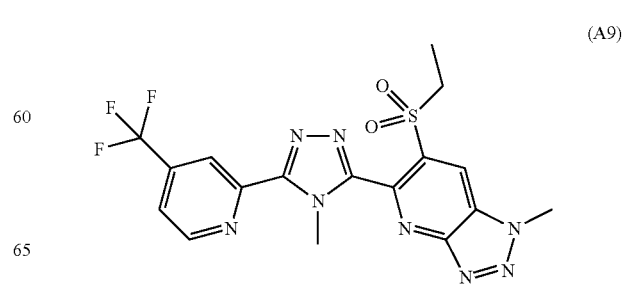

(A10)

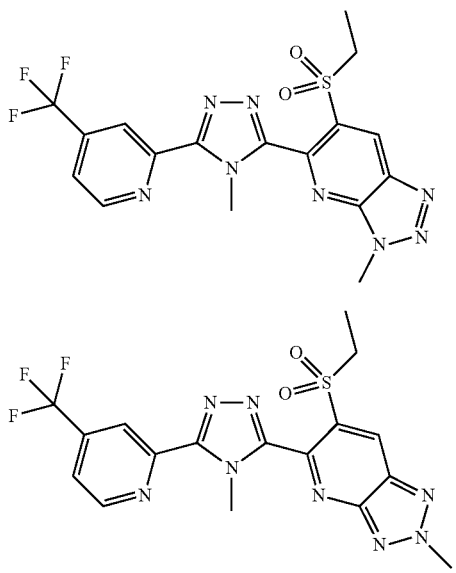

(A18)

Step P6.1: Synthesis of 5-ethylsulfonyl-6-[4-methyl-5-[4-(trifluoromethyl)-2-pyridyl]-1,2,4-triazol-3-yl]pyridin-3-amine

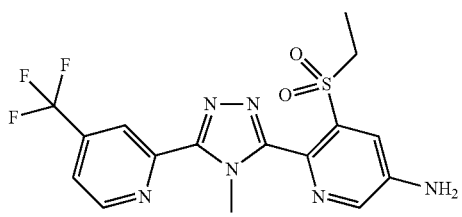 [SMILES: CCS(=O)(=O)c1cc(N)cnc1-c1nnc(-c2cc(C(F)(F)F)ccn2)n1C]

Crude tert-butyl N-[5-ethylsulfonyl-6-[4-methyl-5-[4-(trifluoromethyl)-2-pyridyl]-1,2,4-triazol-3-yl]-3-pyridyl]carbamate was obtained from 5-bromo-3-ethylsulfonyl-2-[4-methyl-5-[4-(trifluoromethyl)-2-pyridyl]-1,2,4-triazol-3-yl]pyridine (WO2017/016910) (25.0 g, 52.5 mmol), cesium carbonate (24.0 g, 73.5 mmol), palladium(II) acetate (0.71 g, 3.15 mmol), tert-butyl carbamate (7.38 g, 63.0 mmol) and 2-dicyclohexylphosphino-2',4',6'-triisopropylbiphenyl XPhos (4.59 g, 9.45 mmol) in anhydrous 1,4-dioxane (250 mL) according to procedure EXAMPLE P5, step P5.1. The reaction mixture was heated at 100° C. for 14 hours, filtered through a celite bed and concentrated under reduced pressure.

The residue was added in portions to a 4N hydrogen chloride solution in 1,4-dioxane (360 mL) and the mixture stirred at 24° C. for 16 hours. The resulting suspension was filtered, the solid residue dissolved in water and neutralized (pH 8) by slow addition of solid sodium bicarbonate. The aqueous layer was extracted with $CH_2Cl_2$ (3×100 mL), the combined organic layers dried over sodium sulfate and evaporated under reduced pressure to provide 5-ethylsulfonyl-6-[4-methyl-5-[4-(trifluoromethyl)-2-pyridyl]-1,2,4-triazol-3-yl]pyridin-3-amine (13.6 g). $^1$H NMR (400 MHz, DMSO-$d_6$) ppm 1.17 (t, 3H), 3.64 (d, 2H), 3.81 (s, 3H), 6.51 (s, 2H), 7.58 (d, 1H), 7.94 (d, 1H), 8.31 (d, 1H), 8.47 (s, 1H), 9.03 (d, 1H). This material was used without further purification.

Step P6.2: Synthesis of 2-bromo-5-ethylsulfonyl-6-[4-methyl-5-[4-(trifluoromethyl)-2-pyridyl]-1,2,4-triazol-3-yl]pyridin-3-amine

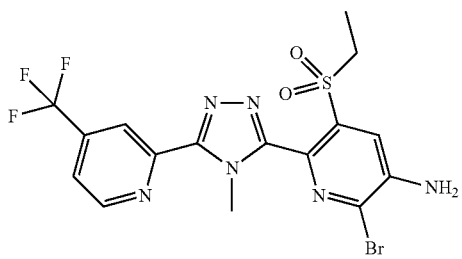 [SMILES: CCS(=O)(=O)c1cc(N)c(Br)nc1-c1nnc(-c2cc(C(F)(F)F)ccn2)n1C]

To a solution of 5-ethylsulfonyl-6-[4-methyl-5-[4-(trifluoromethyl)-2-pyridyl]-1,2,4-triazol-3-yl]pyridin-3-amine (4.00 g, 8.90 mmol) in N,N-dimethylformamide (40 ml) was added N-bromosuccinimide (2.59 g, 14.6 mmol). The reaction mixture was stirred at room temperature for 3 hours, and then poured into cold water. The aqueous phase was extracted with ethyl acetate, the combined organic layers were dried over sodium sulfate, filtered and concentrated. Purification by column chromatography over silica gel eluting with ethyl acetate in cyclohexane and evaporation of the selected fractions afforded the desired compound as a solid, mp 251-253° C. LCMS (method C): 491/493 (M+H)+; retention time: 1.54 min.

Step P6.3: Synthesis of 2-azido-5-ethylsulfonyl-6-[4-methyl-5-[4-(trifluoromethyl)-2-pyridyl]-1,2,4-triazol-3-yl]pyridin-3-amine

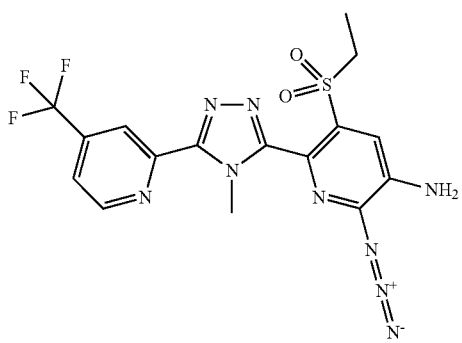 [SMILES: CCS(=O)(=O)c1cc(N)c(N=[N+]=[N-])nc1-c1nnc(-c2cc(C(F)(F)F)ccn2)n1C]

To a solution of 2-bromo-5-ethylsulfonyl-6-[4-methyl-5-[4-(trifluoromethyl)-2-pyridyl]-1,2,4-triazol-3-yl]pyridin-3-amine (330 mg, 0.67 mmol) in N,N-dimethylformamide (10 ml) under argon, was added sodium azide (79 mg, 1.21 mmol). The reaction mixture was heated at 100° C. under vigorous stirring for 3 hours. After cooling down to room temperature, the mixture was poured into cold water, and the aqueous phase was extracted with ethyl acetate. The combined organic phases were washed with brine, dried over sodium sulfate, filtered and concentrated. The crude material was purified by column chromatography over silica gel eluting with ethyl acetate in cyclohexane and evaporation of the selected fractions afforded the desired compound. LCMS (method D): 454 (M+H)$^+$; retention time: 0.85 min.

Step P6.4: Synthesis of 5-ethylsulfonyl-6-[4-methyl-5-[4-(trifluoromethyl)-2-pyridyl]-1,2,4-triazol-3-yl]pyridine-2,3-diamine

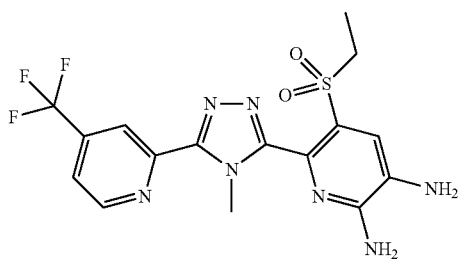 [SMILES: CCS(=O)(=O)c1cc(N)c(N)nc1-c1nnc(-c2cc(C(F)(F)F)ccn2)n1C]

To a solution of 2-azido-5-ethylsulfonyl-6-[4-methyl-5-[4-(trifluoromethyl)-2-pyridyl]-1,2,4-triazol-3-yl]pyridin-3-amine (1.00 g, 2.21 mmol) in tetrahydrofuran (40 ml) and water (4.0 ml) was added triphenylphosphine (1.75 g, 6.62 mmol). The reaction mixture was heated at 60° C. for 2 hours. Heating was stopped while adding carefully concentrated HCl portionwise to the mixture (10 ml, 10 ml and 5 ml). The resulting mixture was then further heated at 60° C. for 14 hours. After cooling down to room temperature, the mixture was carefully poured into a saturated potassium carbonate solution. The aqueous layer was extracted three times with ethyl acetate, the combined organic layers were washed three times with water, dried over sodium sulfate, filtered and concentrated. The crude oil was purified by column chromatography over silica gel eluting with methanol in dichloromethane and the selected fractions were evaporated to afford the desired compound. LCMS (method D): 428 (M+H)$^+$; retention time: 0.64 min.

Step P6.5: Synthesis of 6-ethylsulfonyl-5-[4-methyl-5-[4-(trifluoromethyl)-2-pyridyl]-1,2,4-triazol-3-yl]-1H-triazolo[4,5-b]pyridine (A12)

(A12)

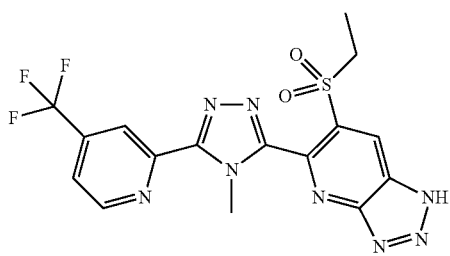

To a solution of 5-ethylsulfonyl-6-[4-methyl-5-[4-(trifluoromethyl)-2-pyridyl]-1,2,4-triazol-3-yl]pyridine-2,3-diamine (450 mg, 1.05 mmol) in acetic acid (9.0 ml) was added a solution of sodium nitrite (363 mg, 5.26 mmol) in water (3.0 ml). The reaction mixture was stirred at room temperature for 2 hours. After completion of the reaction, the mixture was concentrated to dryness, the residue was diluted with water (10 ml), and the aqueous phase was extracted with ethyl acetate (2×10 ml). The combined organic phases were washed with brine (10 ml), dried over sodium sulfate and concentrated. The crude material was purified by column chromatography over silica gel eluting with methanol in dichloromethane and the selected fractions were evaporated to afford the desired compound. LCMS (method C): 439 (M+H)$^+$; retention time: 1.42 min.

Step P6.6: Synthesis of 6-ethylsulfonyl-1-methyl-5-[4-methyl-5-[4-(trifluoromethyl)-2-pyridyl]-1,2,4-triazol-3-yl]triazolo[4,5-b]pyridine (A9), 6-ethylsulfonyl-3-methyl-5-[4-methyl-5-[4-(trifluoro-methyl)-2-pyridyl]-1,2,4-triazol-3-yl]triazolo[4,5-b]pyridine (A10) and 6-ethylsulfonyl-2-methyl-5-[4-methyl-5-[4-(trifluoromethyl)-2-pyridyl]-1,2,4-triazol-3-yl]triazolo[4,5-b]pyridine (A18)

(A9)

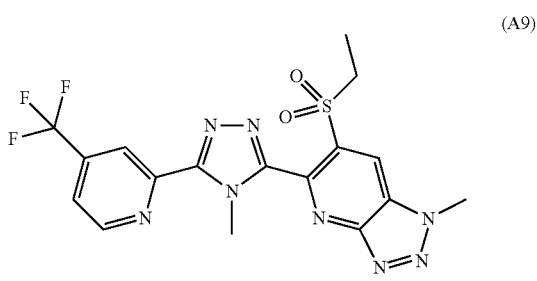

(A10)

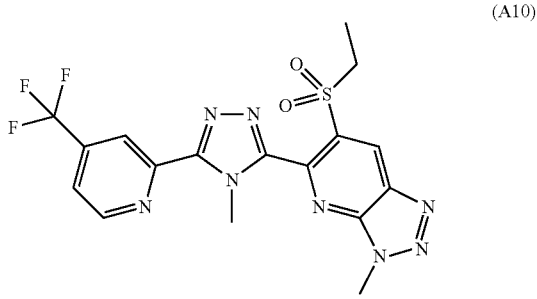

(A18)

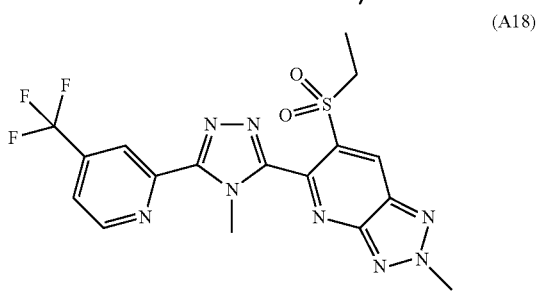

To a solution of 6-ethylsulfonyl-5-[4-methyl-5-[4-(trifluoromethyl)-2-pyridyl]-1,2,4-triazol-3-yl]-1H-triazolo[4,5-b]pyridine (300 mg, 0.68 mmol) in N,N-dimethylformamide (8.0 ml) were added cesium carbonate (446 mg, 1.37 mmol) followed by methyl iodide (0.085 ml, 194 mg, 1.37 mmol). The reaction mixture was stirred at room temperature for 3 hours. After completion of the reaction, the mixture was poured into cold water, and the aqueous phase was extracted three times with ethyl acetate. The combined organic layers were washed with brine, dried over sodium sulfate and concentrated. Purification of the crude material by two sequential column chromatographies over silica gel eluting with ethyl acetate in cyclohexane (40% and then 30%) and evaporation of the selected fractions afforded the three desired regioisomers.

(A9) LCMS (method C): 453 (M+H)$^+$; retention time: 1.48 min.

(A10) LCMS (method D): 453 (M+H)$^+$; retention time: 0.94 min.
(A18) LCMS (method D): 453 (M+H)$^+$; retention time: 0.92 min.

Example P7: Preparation of 6-ethylsulfonyl-2,2-dimethyl-5-[4-methyl-5-[6-(trifluoromethyl)pyrimidin-4-yl]-1,2,4-triazol-3-yl]-3H-furo[3,2-b]pyridine (Compound A20)

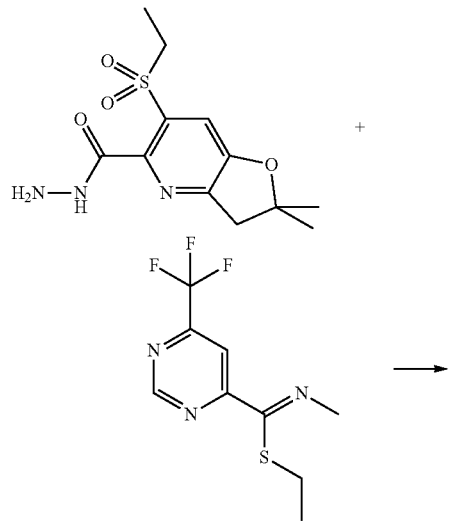

(A20)

+

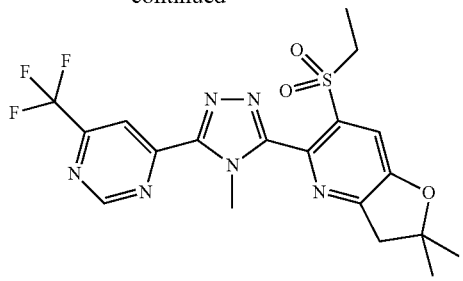

A solution of 6-ethylsulfonyl-2,2-dimethyl-3H-furo[3,2-b]pyridine-5-carbohydrazide (I7) (85 mg, 0.284 mmol) and ethyl N-methyl-6-(trifluoromethyl)pyrimidine-4-carboximidothioate (I4) (99.9 mg, 85%, 0.341 mmol) in acetic acid (1.5 ml) under argon was heated in the microwave at 120° C. for 15 minutes. The solvent was evaporated under vacuum and the residue purified by CombiFlash (silica gel, 0-30% ethyl acetate in cyclohexane) to afford of 6-ethylsulfonyl-2,2-dimethyl-5-[4-methyl-5-[6-(trifluoromethyl)pyrimidin-4-yl]-1,2,4-triazol-3-yl]-3H-furo[3,2-b]pyridine (A20) as a solid, mp 189-191° C. LCMS (method A): retention time 0.98 min; 469 (M+H)$^+$. $^1$H NMR (400 MHz, CDCl$_3$) δ ppm 1.34 (t, J=7.5 Hz, 3H), 1.63 (s, 6H), 3.28 (s, 2H), 3.60 (q, J=7.5 Hz, 2H), 4.05 (s, 3H), 7.68 (s, 1H), 8.77 (d, J=1.4 Hz, 1H), 9.44 (d, J=1.4 Hz, 1H). $^{19}$F NMR (CDCl$_3$, 400 MHz): -70.09 (s, 3F).

TABLE 2

Examples of compounds of formula (I)

| No. | Structures | Analytic | IUPAC name |
|---|---|---|---|
| A1 | 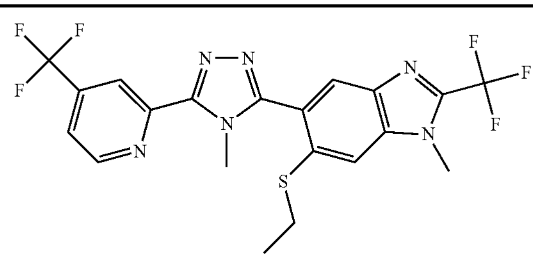 | See experimental part | 6-ethylsulfanyl-1-methyl-5-[4-methyl-5-[4-(trifluoromethyl)-2-pyridyl]-1,2,4-triazol-3-yl]-2-(trifluoromethyl)benzimidazole |
| A2 | 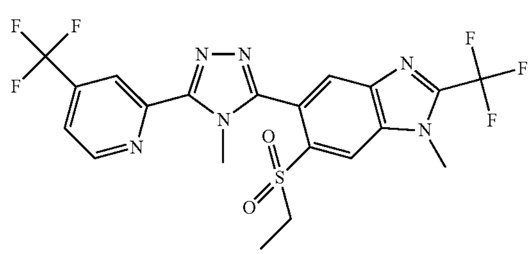 [SMILES: CCS(=O)(=O)c1cc2c(cc1-c1nnc(-c3cc(C(F)(F)F)ccn3)n1C)nc(C(F)(F)F)n2C] | See experimental part | 6-ethylsulfonyl-1-methyl-5-[4-methyl-5-[4-(trifluoromethyl)-2-pyridyl]-1,2,4-triazol-3-yl]-2-(trifluoromethyl)benzimidazole |

TABLE 2-continued

Examples of compounds of formula (I)

| No. | Structures | Analytic | IUPAC name |
|---|---|---|---|
| A3 | 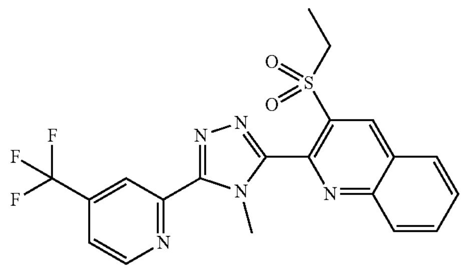 | LC-MS (method A) Rt = 0.98 min, 448 (M + H)$^+$ - prepared by the same method used in Example P1 for the compound A1 using Intermediate I1 and Intermediate I3. | 3-ethylsulfonyl-2-[4-methyl-5-[4-(trifluoromethyl)-2-pyridyl]-1,2,4-triazol-3-yl]quinoline |
| A4 | 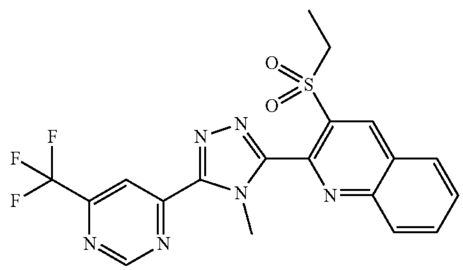 [SMILES: CCS(=O)(=O)c1cc2ccccc2nc1-c1nnc(-c2cc(C(F)(F)F)ncn2)n1C] | LC-MS (method A) Rt = 0.97 min, 449 (M + H)$^+$ - prepared by the same method used in Example P1 for the compound A1 using Intermediate I4 and Intermediate I3. | 3-ethylsulfonyl-2-[4-methyl-5-[6-(trifluoromethyl)pyrimidin-4-yl]-1,2,4-triazol-3-yl]quinoline |

TABLE 3

Examples of compounds of formula (I) (continued)

| No. | Structures | LCMS R$_t$ (min) | LCMS [M + H]$^+$ (measured) | Method | Mp (° C.) | IUPAC name |
|---|---|---|---|---|---|---|
| A5 | | 0.74 | 519 | D | 218-220 | 6-ethylsulfonyl-1-methyl-5-[4-methyl-5-[6-(trifluoromethyl)-3-pyridyl]-1,2,4-triazol-3-yl]-2-(trifluoromethyl)benzimidazole |
| A6 | | 1.04 | 522 | D | 245-247 | 5-ethylsulfonyl-6-[4-methyl-5-[4-(trifluoromethyl)-2-pyridyl]-1,2,4-triazol-3-yl]-2-(trifluoromethyl)-1,3-benzothiazole |

TABLE 3-continued

Examples of compounds of formula (I) (continued)

| No. | Structures | LCMS R$_t$ (min) | [M + H]$^+$ (measured) | Method | Mp (° C.) | IUPAC name |
|---|---|---|---|---|---|---|
| A7 | 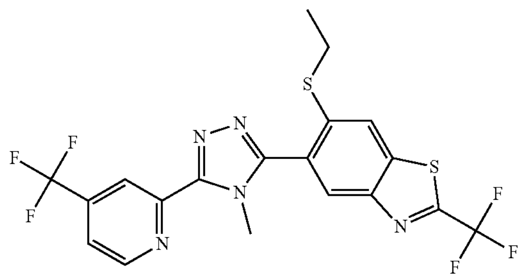 [SMILES: CCSc1cc2sc(C(F)(F)F)nc2cc1-c1nnc(-c2cc(C(F)(F)F)ccn2)n1C] | 1.69 | 490 | C | 180-182 | 6-ethylsulfanyl-5-[4-methyl-5-[4-(trifluoromethyl)-2-pyridyl]-1,2,4-triazol-3-yl]-2-(trifluoromethyl)-1,3-benzothiazole |
| A8 | 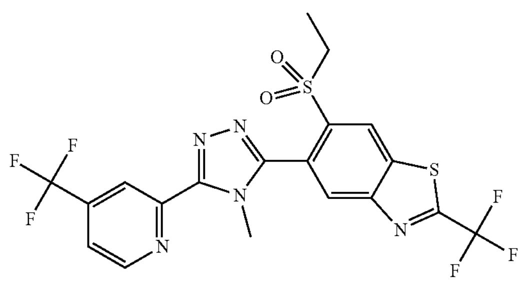 [SMILES: CCS(=O)(=O)c1cc2sc(C(F)(F)F)nc2cc1-c1nnc(-c2cc(C(F)(F)F)ccn2)n1C] | 1.42 | 522 | C | | 6-ethylsulfonyl-5-[4-methyl-5-[4-(trifluoromethyl)-2-pyridyl]-1,2,4-triazol-3-yl]-2-(trifluoromethyl)-1,3-benzothiazole |
| A9 | 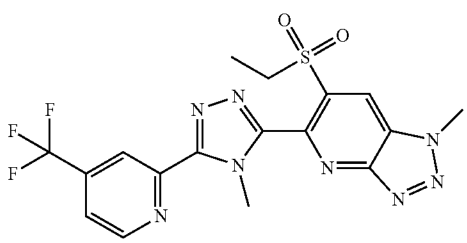 [SMILES: CCS(=O)(=O)c1cc2c(nnn2C)nc1-c1nnc(-c2cc(C(F)(F)F)ccn2)n1C] | 1.48 | 453 | C | 176-178 | 6-ethylsulfonyl-1-methyl-5-[4-methyl-5-[4-(trifluoromethyl)-2-pyridyl]-1,2,4-triazol-3-yl]triazolo[4,5-b]pyridine |
| A10 | 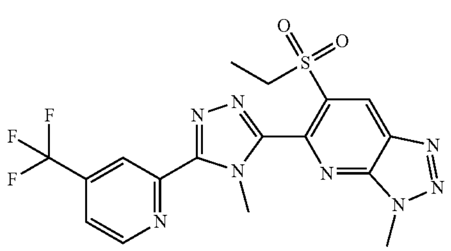 [SMILES: CCS(=O)(=O)c1cc2nnn(C)c2nc1-c1nnc(-c2cc(C(F)(F)F)ccn2)n1C] | 0.94 | 453 | D | 201-203 | 6-ethylsulfonyl-3-methyl-5-[4-methyl-5-[4-(trifluoromethyl)-2-pyridyl]-1,2,4-triazol-3-yl]triazolo[4,5-b]pyridine |
| A11 | 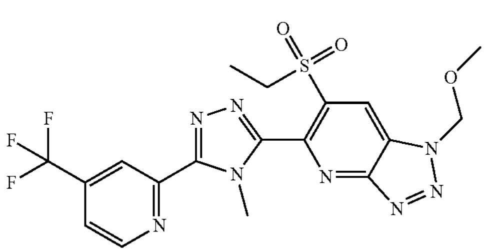 [SMILES: CCS(=O)(=O)c1cc2c(nnn2COC)nc1-c1nnc(-c2cc(C(F)(F)F)ccn2)n1C] | 0.90 | 483 | D | 176-178 | 6-ethylsulfonyl-1-(methoxymethyl)-5-[4-methyl-5-[4-(trifluoromethyl)-2-pyridyl]-1,2,4-triazol-3-yl]triazolo[4,5-b]pyridine |

TABLE 3-continued

Examples of compounds of formula (I) (continued)

| No. | Structures | LCMS $R_t$ (min) | [M + H]+ (measured) | Method | Mp (° C.) | IUPAC name |
|---|---|---|---|---|---|---|
| A12 | 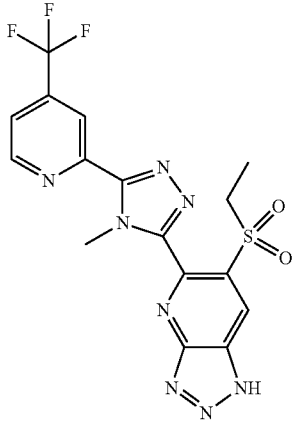 [SMILES: CCS(=O)(=O)c1cc2[nH]nnc2nc1-c1nnc(-c2cc(C(F)(F)F)ccn2)n1C] | 1.42 | 439 | C | 303-305 | 6-ethylsulfonyl-5-[4-methyl-5-[4-(trifluoromethyl)-2-pyridyl]-1,2,4-triazol-3-yl]-1H-triazolo[4,5-b]pyridine |
| A13 | 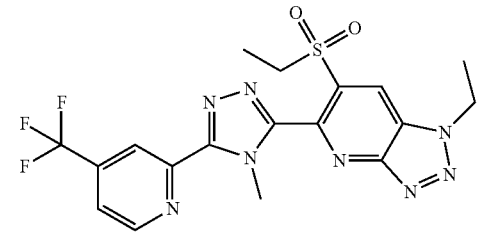 [SMILES: CCn1nnc2nc(-c3nnc(-c4cc(C(F)(F)F)ccn4)n3C)c(S(=O)(=O)CC)cc21] | 0.95 | 467 | D | 238-240 | 1-ethyl-6-ethylsulfonyl-5-[4-methyl-5-[4-(trifluoromethyl)-2-pyridyl]-1,2,4-triazol-3-yl]triazolo[4,5-b]pyridine |
| A14 | 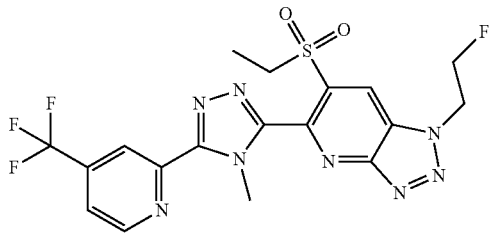 [SMILES: CCS(=O)(=O)c1cc2c(nnn2CCF)nc1-c1nnc(-c2cc(C(F)(F)F)ccn2)n1C] | 0.90 | 485 | D | 194-196 | 6-ethylsulfonyl-1-(2-fluoroethyl)-5-[4-methyl-5-[4-(trifluoromethyl)-2-pyridyl]-1,2,4-triazol-3-yl]triazolo[4,5-b]pyridine |
| A15 | 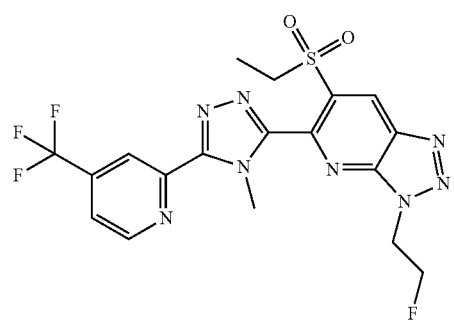 [SMILES: CCS(=O)(=O)c1cc2nnn(CCF)c2nc1-c1nnc(-c2cc(C(F)(F)F)ccn2)n1C] | 0.91 | 485 | D | 172-174 | 6-ethylsulfonyl-3-(2-fluoroethyl)-5-[4-methyl-5-[4-(trifluoromethyl)-2-pyridyl]-1,2,4-triazol-3-yl]triazolo[4,5-b]pyridine |

TABLE 3-continued

Examples of compounds of formula (I) (continued)

| No. | Structures | LCMS R<sub>t</sub> (min) | [M + H]<sup>+</sup> (measured) | Method | Mp (° C.) | IUPAC name |
|---|---|---|---|---|---|---|
| A16 | 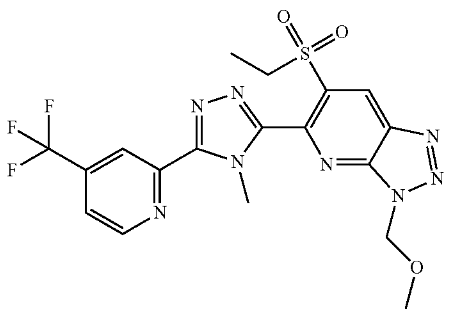 [SMILES: CCS(=O)(=O)c1cc2nnn(COC)c2nc1-c1nnc(-c2cc(C(F)(F)F)ccn2)n1C] | 0.95 | 483 | D | 198-200 | 6-ethylsulfonyl-3-(methoxymethyl)-5-[4-methyl-5-[4-(trifluoromethyl)-2-pyridyl]-1,2,4-triazol-3-yl]triazolo[4,5-b]pyridine |
| A17 | 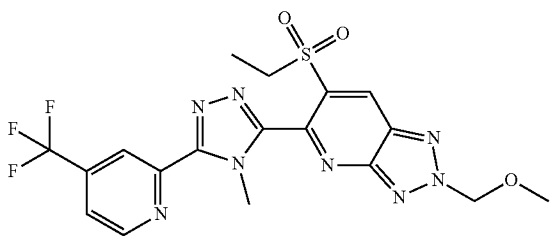 [SMILES: CCS(=O)(=O)c1cc2nn(COC)nc2nc1-c1nnc(-c2cc(C(F)(F)F)ccn2)n1C] | 0.96 | 483 | D | 197-199 | 6-ethylsulfonyl-2-(methoxymethyl)-5-[4-methyl-5-[4-(trifluoromethyl)-2-pyridyl]-1,2,4-triazol-3-yl]triazolo[4,5-b]pyridine |
| A18 | 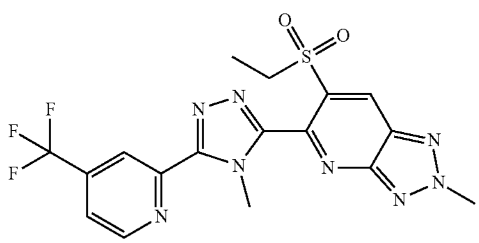 [SMILES: CCS(=O)(=O)c1cc2nn(C)nc2nc1-c1nnc(-c2cc(C(F)(F)F)ccn2)n1C] | 0.92 | 453 | D | 269-271 | 6-ethylsulfonyl-2-methyl-5-[4-methyl-5-[4-(trifluoromethyl)-2-pyridyl]-1,2,4-triazol-3-yl]triazolo[4,5-b]pyridine |
| A19 | 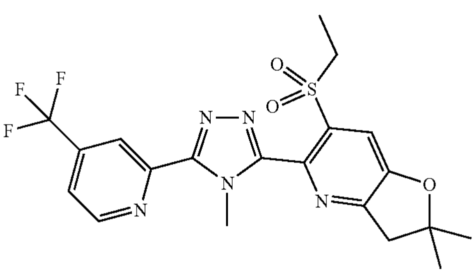 [SMILES: CCS(=O)(=O)c1cc2c(nc1-c1nnc(-c3cc(C(F)(F)F)ccn3)n1C)CC(C)(C)O2] | 1.00 | 468 | A | 254-255 | 6-ethylsulfonyl-2,2-dimethyl-5-[4-methyl-5-[4-(trifluoromethyl)-2-pyridyl]-1,2,4-triazol-3-yl]-3H-furo[3,2-b]pyridine |
| A20 | 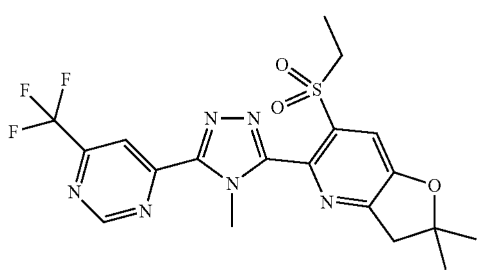 [SMILES: CCS(=O)(=O)c1cc2c(nc1-c1nnc(-c3cc(C(F)(F)F)ncn3)n1C)CC(C)(C)O2] | 0.98 | 469 | A | 189-191 | 6-ethylsulfonyl-2,2-dimethyl-5-[4-methyl-5-[6-(trifluoromethyl)pyrimidin-4-yl]-1,2,4-triazol-3-yl]-3H-furo[3,2-b]pyridine |

The activity of the compositions according to the invention can be broadened considerably, and adapted to prevailing circumstances, by adding other insecticidally, acaricidally and/or fungicidally active ingredients. The mixtures of the compounds of formula I with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use. Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and *Bacillus thuringiensis* preparations.

The following mixtures of the compounds of formula I with active ingredients are preferred (the abbreviation "TX" means "one compound selected from the group consisting of the compounds described in Tables 1, 2 and 3 of the present invention"):

an adjuvant selected from the group of substances consisting of petroleum oils (628)+TX, an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulfide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel [CCN]+TX, coumaphos (174)+TX, crotamiton [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulfon (1039)+TX, diafenthiuron (226)+TX, dialifos (1042)+TX, diazinon (227)+TX, dichlofluanid (230)+TX, dichlorvos (236)+TX, dicliphos+TX, dicofol (242)+TX, dicrotophos (243)+TX, dienochlor (1071)+TX, dimefox (1081)+TX, dimethoate (262)+TX, dinactin (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfiram [CCN]+TX, disulfoton (278)+TX, DNOC (282)+TX, dofenapyn (1113)+TX, doramectin [CCN]+TX, endosulfan (294)+TX, endothion (1121)+TX, EPN (297)+TX, eprinomectin [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad+TX, fenpyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (473)+TX, isopropyl O-(methoxyaminothiophosphoryl)salicylate (IUPAC name) (473)+TX, ivermectin [CCN]+TX, jasmolin I (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime [CCN]+TX, mipafox (1293)+TX, monocrotophos (561)+TX, morphothion (1300)+TX, moxidectin [CCN]+TX, naled (567)+TX, NC-184 (compound code)+TX, NC-512 (compound code)+TX, nifluridide (1309)+TX, nikkomycins [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin I (696)+TX, pyrethrin II (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos+TX, selamectin [CCN]+TX, SI-0009 (compound code)+TX, sophamide (1402)+TX, spirodiclofen (738)+TX, spiromesifen (739)+TX, SSI-121 (development code) (1404)+TX, sulfiram [CCN]+TX, sulfluramid (750)+TX, sulfotep (753)+TX, sulfur (754)+TX, SZI-121 (development code) (757)+TX, tau-fluvalinate (398)+TX, tebufenpyrad (763)+TX, TEPP (1417)+TX, terbam+TX, tetrachlorvinphos (777)+TX, tetradifon (786)+TX, tetranactin (653)+TX, tetrasul (1425)+TX, thiafenox+TX, thiocarboxime (1431)+TX, thiofanox (800)+TX, thiometon (801)+TX, thioquinox (1436)+TX, thuringiensin [CCN]+TX, triamiphos (1441)+TX, triarathene (1443)+TX, triazophos (820)+TX, triazuron+TX, trichlorfon (824)+TX, trifenofos (1455)+TX, trinactin (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin [CCN]+TX, emamectin (291)+TX, emamectin benzoate (291)+TX, eprinomectin [CCN]+TX, ivermectin [CCN]+TX, milbemycin oxime [CCN]+TX, moxidectin [CCN]+TX, piperazine [CCN]+TX, selamectin [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal [CCN]+TX, a biological agent selected from the group of substances consisting of *Adoxophyes orana* GV (12)+TX, *Agrobacterium radiobacter* (13)+TX, *Amblyseius* spp. (19)+TX, *Anagrapha falcifera* NPV (28)+TX, *Anagrus atomus* (29)+TX, *Aphelinus abdominalis* (33)+TX, *Aphidius colemani* (34)+TX, *Aphidoletes aphidimyza* (35)+TX, *Autographa californica* NPV (38)+TX, *Bacillus firmus* (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (53)+TX, *Beauveria brongniartii* (54)+TX, *Chrysoperla carnea* (151)+TX, *Cryptolaemus montrouzieri* (178)+TX, *Cydia pomonella* GV (191)+TX, *Dacnusa sibirica* (212)+TX, *Diglyphus isaea* (254)+TX, *Encarsia formosa* (scientific name) (293)+TX, *Eretmocerus eremicus* (300)+TX, *Helicoverpa zea* NPV (431)+TX, *Heterorhabditis bacteriophora* and *H. megidis* (433)+TX, *Hippodamia convergens* (442)+TX, *Leptomastix dactylopii* (488)+TX, *Macrolophus caliginosus* (491)+TX, *Mamestra brassicae* NPV (494)+TX, *Metaphycus helvolus* (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (575)+TX, *Orius* spp. (596)+TX, *Paecilomyces fumosoroseus* (613)+TX, *Phytoseiulus persimilis* (644)+TX, *Spodoptera exigua* multicapsid nuclear polyhedrosis virus (scientific name) (741)+TX, *Steinernema bibionis* (742)+TX, *Steinernema carpocapsae* (742)+TX, *Steinernema feltiae* (742)+TX, *Steinernema glaseri* (742)+TX, *Steinernema riobrave* (742)+TX, *Steinernema riobravis* (742)+TX, *Steinernema scapterisci* (742)+TX, *Steinernema* spp. (742)+TX, *Trichogramma* spp. (826)+TX, *Typhlodromus occidentalis* (844) and *Verticillium lecanii* (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir [CCN]+TX, busulfan [CCN]+TX, diflubenzuron (250)+TX, dimatif [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron [CCN]+TX, tepa [CCN]+TX, thiohempa [CCN]+TX, thiotepa [CCN]+TX, tretamine [CCN] and uredepa [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin [CCN]+TX, brevicomin [CCN]+TX, codlelure [CCN]+TX, codlemone (167)+TX, cuelure (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure [CCN]+TX, ethyl 4-methyloctanoate (IUPAC name) (317)+TX, eugenol [CCN]+TX, frontalin [CCN]+TX, gossyplure (420)+TX, grandlure (421)+TX, grandlure I (421)+TX, grandlure II (421)+TX, grandlure III (421)+TX, grandlure IV (421)+TX, hexalure [CCN]+TX, ipsdienol [CCN]+TX, ipsenol [CCN]+TX, japonilure (481)+TX, lineatin [CCN]+TX, litlure [CCN]+TX, looplure [CCN]+TX, medlure [CCN]+TX, megatomoic acid [CCN]+TX, methyl eugenol (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure [CCN]+TX, oryctalure (317)+TX, ostramone [CCN]+TX, siglure [CCN]+TX, sordidin (736)+TX, sulcatol [CCN]+TX, tetradec-11-en-1-yl acetate (IUPAC name) (785)+TX, trimedlure (839)+TX, trimedlure A (839)+TX, trimedlure B1 (839)+TX, trimedlure B2 (839)+TX, trimedlure C (839) and trunc-call [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulfinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy)ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin [CCN]+TX, allyxycarb (866)+TX, alpha-cypermethrin (202)+TX, alpha-ecdysone [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (41)+TX, azamethiphos (42)+TX, azinphos-ethyl (44)+TX, azinphos-methyl (45)+TX, azothoate (889)+TX, Bacillus thuringiensis delta endotoxins (52)+TX, barium hexafluorosilicate [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (79)+TX, bioethanomethrin [CCN]+TX, biopermethrin (908)+TX, bioresmethrin (80)+TX, bis(2-chloroethyl) ether (IUPAC name) (909)+TX, bistrifluron (83)+TX, borax (86)+TX, brofenvalerate+TX, bromfenvinfos (914)+TX, bromocyclen (918)+TX, bromo-DDT [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin 1 (696)+TX, cinerin II (696)+TX, cinerins (696)+TX, cis-resmethrin+TX, cismethrin (80)+TX, clocythrin+TX, cloethocarb (999)+TX, closantel [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton [CCN]+TX, crotoxyphos (1010)+TX, crufomate (1011)+TX, cryolite (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate [CCN]+TX, d-limonene [CCN]+TX, d-tetramethrin (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos+TX, dicresyl [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin [CCN]+TX, DSP (1115)+TX, ecdysterone [CCN]+TX, EI 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin [CCN]+TX, esfenvalerate (302)+TX, etaphos [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+

TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (473)+TX, isodrin (1235)+TX, isofenphos (1236)+TX, isolane (1237)+TX, isoprocarb (472)+TX, isopropyl O-(methoxyaminothiophosphoryl)salicylate (IUPAC name) (473)+TX, isoprothiolane (474)+TX, isothioate (1244)+TX, isoxathion (480)+TX, ivermectin [CCN]+TX, jasmolin I (696)+TX, jasmolin II (696)+TX, jodfenphos (1248)+TX, juvenile hormone I [CCN]+TX, juvenile hormone II [CCN]+TX, juvenile hormone III [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (519)+TX, metam-sodium (519)+TX, methacrifos (1266)+TX, methamidophos (527)+TX, methanesulfonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquinbutyl (1276)+TX, methothrin (533)+TX, methoxychlor (534)+TX, methoxyfenozide (535)+TX, methyl bromide (537)+TX, methyl isothiocyanate (543)+TX, methylchloroform [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime [CCN]+TX, mipafox (1293)+TX, mirex (1294)+TX, monocrotophos (561)+TX, morphothion (1300)+TX, moxidectin [CCN]+TX, naftalofos [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, niflurdide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, omethoate (594)+TX, oxamyl (602)+TX, oxydemetonmethyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron [CCN]+TX, pentachlorophenol (623)+TX, pentachlorophenyl laurate (IUPAC name) (623)+TX, permethrin (626)+TX, petroleum oils (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I [CCN]+TX, precocene II [CCN]+TX, precocene III [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin I (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia [CCN]+TX, quinalphos (711)+TX, quinalphos-methyl (1376)+TX, quinothion (1380)+TX, quintiofos (1381)+TX, R-1492 (development code) (1382)+TX, rafoxanide [CCN]+TX, resmethrin (719)+TX, rotenone (722)+TX, RU 15525 (development code) (723)+TX, RU 25475 (development code) (1386)+TX, ryania (1387)+TX, ryanodine (traditional name) (1387)+TX, sabadilla (725)+TX, schradan (1389)+TX, sebufos+TX, selamectin [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulfuryl fluoride (756)+TX, sulprofos (1408)+TX, tar oils (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron+TX, trichlorfon (824)+TX, trichlormetaphos-3 [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (725)+TX, veratrine (725)+TX, XMC (853)+TX, xylylcarb (854)+TX, YI-5302 (compound code)+TX, zeta-cypermethrin (205)+TX, zetamethrin+TX, zinc phosphide (640)+TX, zolaprofos (1469) and ZXI 8901 (development code) (858)+TX, cyantraniliprole [736994-63-19+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX, triflumezopyrim (disclosed in WO 2012/092115)+TX, fluxametamide (WO 2007/026965)+TX, epsilon-metofluthrin [240494-71-7]+TX, epsilon-momfluorothrin [1065124-65-3]+TX, fluazaindolizine [1254304-22-7]+TX, chloropralethrin [399572-87-3]+TX, fluxametamide [928783-29-3]+TX, cyhalodiamide [1262605-53-7]+TX, tioxazafen [330459-31-9]+TX, broflanilide [1207727-04-5]+TX, flufiprole [704886-18-0]+TX, cyclaniliprole [1031756-98-5]+TX, tetraniliprole [1229654-66-3]+TX, guadipyr (described in WO2010/060231)+TX, cycloxaprid (described in WO2005/077934)+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (210)+TX, dazomet (216)+TX, DBCP (1045)+TX, DCIP (218)+TX, diamidafos (1044)+TX, dichlofenthion (1051)+TX, dicliphos+TX, dimethoate (262)+TX, doramectin [CCN]+TX, emamectin (291)+TX, emamectin benzoate (291)+TX, eprinomectin [CCN]+TX, ethoprophos (312)+TX, ethylene dibromide (316)+TX, fenamiphos (326)+TX, fenpyrad+TX, fensulfothion (1158)+TX, fosthiazate (408)+TX, fosthietan (1196)+TX, furfural [CCN]+TX, GY-81 (development code) (423)+TX, heterophos [CCN]+TX, iodomethane (IUPAC name) (542)+TX, isamidofos (1230)+TX, isazofos (1231)+TX, ivermectin [CCN]+TX, kinetin (210)+TX, mecarphon (1258)+TX, metam (519)+TX, metam-potassium (519)+TX, metam-sodium (519)+TX, methyl bromide (537)+TX, methyl isothiocyanate (543)+TX, milbemycin oxime [CCN]+TX, moxidectin [CCN]+TX, *Myrothecium verrucaria* composition (565)+TX, NC-184 (compound code)+TX, oxamyl (602)+TX, phorate (636)+TX, phosphamidon (639)+TX, phosphocarb [CCN]+TX, sebufos+TX, selamectin [CCN]+TX, spinosad (737)+TX, terbam+TX, terbufos (773)+TX, tetrachlorothiophene (IUPAC/Chemical Abstracts name) (1422)+TX, thiafenox+TX, thionazin (1434)+TX, triazophos (820)+TX, triazuron+TX, xylenols [CCN]+TX, YI-5302 (compound code) and zeatin (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin [CCN] and ribavirin [CCN]+TX, a wound protectant selected from the group of substances consisting of mercuric oxide (512)+TX, octhilinone (590) and thiophanate-methyl (802)+TX, and biologically active compounds selected from the group consisting of azaconazole (60207-31-0]+TX, bitertanol [70585-36-3]+TX, bromuconazole [116255-48-2]+TX, cyproconazole [94361-06-5]+TX, difenoconazole [119446-68-3]+TX, diniconazole [83657-24-3]+TX, epoxiconazole [106325-08-0]+TX, fenbuconazole [114369-43-6]+TX, fluquinconazole [136426-54-5]+TX, flusilazole [85509-19-9]+TX, flutriafol [76674-21-0]+TX, hexaconazole [79983-71-4]+TX, imazalil [35554-44-0]+TX, imibenconazole [86598-92-7]+TX, ipconazole [125225-28-7]+TX, metconazole [125116-23-6]+TX, myclobutanil [88671-89-0]+TX, pefurazoate [101903-30-4]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebuconazole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidine [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, benalaxyl [71626-11-4]+TX, furalaxyl [57646-30-7]+TX, metalaxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3] [112-65-2] (free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoxim-methyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxine-copper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzolar-S-methyl [135158-54-2]+TX, anilazine [101-05-3]+TX, benthiavalicarb [413615-35-7]+TX, blasticidin-S [2079-00-7]+TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimethomorph [110488-70-5]+TX, SYP-LI90 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfocarb [66952-49-6]+TX, metrafenone [220899-03-6]+TX, pencycuron [66063-05-6]+TX, phthalide [27355-22-2]+TX, polyoxins [11113-80-7]+TX, probenazole [27605-76-1]+TX, propamocarb [25606-41-1]+TX, proquinazid [189278-12-4]+TX, pyroquilon [57369-32-1]+TX, quinoxyfen [124495-18-7]+TX, quintozene [82-68-8]+TX, sulfur [7704-34-9]+TX, tiadinil [223580-51-6]+TX, triazoxide [72459-58-6]+TX, tricyclazole [41814-78-2]+TX, triforine [26644-46-2]+TX, validamycin [37248-47-8]+TX, zoxamide (RH7281) [156052-68-5]+TX, mandipropamid [374726-62-2]+TX, isopyrazam [881685-58-1]+TX, sedaxane [874967-67-6]+TX, 3-difluoromethyl-1-methyl-1H-pyrazole-4-carboxylic acid (9-dichloromethylene-1,2,3,4-tetrahydro-1,4-methano-naphthalen-5-yl)-amide (disclosed in WO 2007/048556)+TX, 3-difluoromethyl-1-methyl-1H-pyrazole-4-carboxylic acid (3',4',5'-trifluoro-biphenyl-2-yl)-amide (disclosed in WO 2006/087343)+TX, [(3S,4R,4aR,6S,6aS,12R,12aS,12bS)-3-[(cyclopropylcarbonyl)oxy]-1,3,4,4a,5,6,6a,12,12a,12b-decahydro-6,12-dihydroxy-4,6a,12b-trimethyl-1-oxo-9-(3-pyridinyl)-2H,11Hnaphtho[2,1-b]pyrano[3,4-e]pyran-4-yl] methyl-cyclopropanecarboxylate [915972-17-7]+TX and 1,3,5-trimethyl-N-(2-methyl-1-oxopropyl)-N-[3-(2-methylpropyl)-4-[2,2,2-trifluoro-1-methoxy-1-(trifluoromethyl) ethyl]phenyl]-1H-pyrazole-4-carboxamide [926914-55-8]+TX; quinofumelin [861647-84-9]+TX; mefentrifluconazole [1417782-03-6]+TX; fluindapyr [1383809-87-7]+TX; bromadiolone [28772-56-7] and its isomers, in particular a mixture of ≥80% (1RS,3SR)-isomer and ≤20% (1RS, 3RS)-isomer+TX; and microbials including: *Acinetobacter lwoffii*+TX, *Acremonium alternatum*+TX+TX, *Acremonium cephalosporium*+TX+TX, *Acremonium diospyri*+TX, *Acremonium obclavatum*+TX, *Adoxophyes orana granulovirus* (AdoxGV) (Capex®)+TX, *Agrobacterium radiobacter* strain K84 (Galltrol-A®)+TX, *Alternaria alternate*+TX, *Alternaria cassia*+TX, *Alternaria destruens* (Smolder®)+TX, *Ampelomyces quisqualis* (AQ10®)+TX, *Aspergillus flavus* AF36 (AF36®)+TX, *Aspergillus flavus* NRRL 21882

(Aflaguard®)+TX, *Aspergillus* spp.+TX, *Aureobasidium pullulans*+TX, *Azospirillum*+TX, (MicroAZ®+TX, TAZO B®)+TX, *Azotobacter*+TX, *Azotobacter chroocuccum* (Azotomeal®)+TX, *Azotobacter* cysts (Bionatural Blooming Blossoms®)+TX, *Bacillus amyloliquefaciens*+TX, *Bacillus cereus*+TX, *Bacillus chitinosporus* strain CM-1+TX, *Bacillus chitinosporus* strain AQ746+TX, *Bacillus licheniformis* strain HB-2 (Biostart™ Rhizoboost®)+TX, *Bacillus licheniformis* strain 3086 (EcoGuard®+TX, Green Releaf®)+TX, *Bacillus circulans*+TX, *Bacillus firmus* (BioSafe®+TX, BioNem-WP®+TX, VOTiVO®)+TX, *Bacillus firmus* strain 1-1582+TX, *Bacillus macerans*+TX, *Bacillus marismortui*+TX, *Bacillus megaterium*+TX, *Bacillus mycoides* strain AQ726+TX, *Bacillus papillae* (Milky Spore Powder®)+TX, *Bacillus pumilus* spp.+TX, *Bacillus pumilus* strain GB34 (Yield Shield®)+TX, *Bacillus pumilus* strain AQ717+TX, *Bacillus pumilus* strain QST 2808 (Sonata®+TX, Ballad Plus®)+TX, *Bacillus spahericus* (VectoLex®)+TX, *Bacillus* spp.+TX, *Bacillus* spp. strain AQ175+TX, *Bacillus* spp. strain AQ177+TX, *Bacillus* spp. strain AQ178+TX, *Bacillus subtilis* strain QST 713 (CEASE®+TX, Serenade®+TX, Rhapsody®)+TX, *Bacillus subtilis* strain QST 714 (JAZZ®)+TX, *Bacillus subtilis* strain AQ153+TX, *Bacillus subtilis* strain AQ743+TX, *Bacillus subtilis* strain QST3002+TX, *Bacillus subtilis* strain QST3004+TX, *Bacillus subtilis* var. *amyloliquefaciens* strain FZB24 (Taegro®+TX, Rhizopro®)+TX, *Bacillus thuringiensis* Cry 2Ae+TX, *Bacillus thuringiensis* Cry1Ab+TX, *Bacillus thuringiensis aizawai* GC 91 (Agree®)+TX, *Bacillus thuringiensis israelensis* (BMP123®+TX, Aquabac®+TX, VectoBac®)+TX, *Bacillus thuringiensis kurstaki* (Javelin®+TX, Deliver®+TX, CryMax®+TX, Bonide®+TX, Scutella WP®+TX, Turilav WP®+TX, Astuto®+TX, Dipel WP®+TX, Biobit®+TX, Foray®)+TX, *Bacillus thuringiensis kurstaki* BMP 123 (Baritone®)+TX, *Bacillus thuringiensis kurstaki* HD-1 (Bioprotec-CAF/3P®)+TX, *Bacillus thuringiensis* strain BD#32+TX, *Bacillus thuringiensis* strain AQ52+TX, *Bacillus thuringiensis* var. *aizawai* (XenTari®+TX, DiPel®)+TX, bacteria spp. (GROWMEND®+TX, GROWSWEET®+TX, Shootup®)+TX, bacteriophage of *Clavipacter michiganensis* (AgriPhage®)+TX, Bakflor®+TX, *Beauveria bassiana* (Beaugenic®+TX, Brocaril WP®)+TX, *Beauveria bassiana* GHA (Mycotrol ES®+TX, Mycotrol O®+TX, BotaniGuard®)+TX, *Beauveria brongniartii* (Engerlingspilz®+TX, Schweizer Beauveria®+TX, Melocont®)+TX, *Beauveria* spp.+TX, *Botrytis cineria*+TX, *Bradyrhizobium japonicum* (TerraMax®)+TX, *Brevibacillus brevis*+TX, *Bacillus thuringiensis tenebrionis* (Novodor®)+TX, BtBooster+TX, *Burkholderia cepacia* (Deny®+TX, Intercept®+TX, Blue Circle®)+TX, *Burkholderia gladii*+TX, *Burkholderia gladioli*+TX, *Burkholderia* spp.+TX, Canadian thistle fungus (CBH Canadian Bioherbicide®)+TX, *Candida butyri*+TX, *Candida famata*+TX, *Candida fructus*+TX, *Candida glabrata*+TX, *Candida guilliermondii*+TX, *Candida melibiosica*+TX, *Candida oleophila* strain O+TX, *Candida parapsilosis*+TX, *Candida pelliculosa*+TX, *Candida pulcherrima*+TX, *Candida reukaufii*+TX, *Candida saitoana* (Bio-Coat®+TX, Biocure®)+TX, *Candida sake*+TX, *Candida* spp.+TX, *Candida tenius*+TX, *Cedecea dravisae*+TX, *Cellulomonas flavigena*+TX, *Chaetomium cochliodes* (Nova-Cide®)+TX, *Chaetomium globosum* (Nova-Cide®)+TX, *Chromobacterium subtsugae* strain PRAA4-1T (Grandevo®)+TX, *Cladosporium cladosporioides*+TX, *Cladosporium oxysporum*+TX, *Cladosporium chlorocephalum*+TX, *Cladosporium* spp.+TX, *Cladosporium tenuissimum*+TX, *Clonostachys rosea* (EndoFine®)+TX, *Colletotrichum acutatum*+TX, *Coniothyrium minitans* (Cotans WG®)+TX, *Coniothyrium* spp.+TX, *Cryptococcus albidus* (YIELDPLUS®)+TX, *Cryptococcus humicola*+TX, *Cryptococcus infirmo-miniatus*+TX, *Cryptococcus laurentii*+TX, *Cryptophlebia leucotreta granulovirus* (Cryptex®)+TX, *Cupriavidus campinensis*+TX, *Cydia pomonella granulovirus* (CYD-X®)+TX, *Cydia pomonella granulovirus* (Madex®+TX, Madex Plus®+TX, Madex Max/Carpovirusine®)+TX, *Cylindrobasidium laeve* (Stumpout®)+TX, *Cylindrocladium*+TX, *Debaryomyces hansenii*+TX, *Drechslera hawaiinensis*+TX, *Enterobacter cloacae*+TX, Enterobacteriaceae+TX, *Entomophtora virulenta* (Vektor®)+TX, *Epicoccum nigrum*+TX, *Epicoccum purpurascens*+TX, *Epicoccum* spp.+TX, *Filobasidium floriforme*+TX, *Fusarium acuminatum*+TX, *Fusarium chlamydosporum*+TX, *Fusarium oxysporum* (Fusaclean®/Biofox C®)+TX, *Fusarium proliferatum*+TX, *Fusarium* spp.+TX, *Galactomyces geotrichum*+TX, *Gliocladium catenulatum* (Primastop®+TX, Prestop®)+TX, *Gliocladium roseum*+TX, *Gliocladium* spp. (SoilGard®)+TX, *Gliocladium virens* (Soilgard®)+TX, *Granulovirus* (Granupom®)+TX, *Halobacillus halophilus*+TX, *Halobacillus litoralis*+TX, *Halobacillus trueperi*+TX, *Halomonas* spp.+TX, *Halomonas subglaciescola*+TX, *Halovibrio variabilis*+TX, *Hanseniaspora uvarum*+TX, *Helicoverpa armigera* nucleopolyhedrovirus (Helicovex®)+TX, *Helicoverpa zea* nuclear polyhedrosis virus (Gemstar®)+TX, Isoflavone—formononetin (Myconate®)+TX, *Kloeckera apiculata*+TX, *Kloeckera* spp.+TX, *Lagenidium giganteum* (Laginex®)+TX, *Lecanicillium longisporum* (Vertiblast®)+TX, *Lecanicillium muscarium* (Vertikil®)+TX, *Lymantria Dispar* nucleopolyhedrosis virus (Disparvirus®)+TX, *Marinococcus halophilus*+TX, *Meira geulakonigii*+TX, *Metarhizium anisopliae* (Met52®)+TX, *Metarhizium anisopliae* (Destruxin WP®)+TX, *Metschnikowia fruticola* (Shemer®)+TX, *Metschnikowia pulcherrima*+TX, *Microdochium dimerum* (Antibot®)+TX, *Micromonospora coerulea*+TX, *Microsphaeropsis ochracea*+TX, *Muscodor albus* 620 (Muscudor®)+TX, *Muscodor roseus* strain A3-5+TX, *Mycorrhizae* spp. (AMykor®+TX, Root Maximizer®)+TX, *Myrothecium verrucaria* strain AARC-0255 (DiTera®)+TX, BROS PLUS®+TX, *Ophiostoma piliferum* strain D97 (Sylvanex®)+TX, *Paecilomyces farinosus*+TX, *Paecilomyces fumosoroseus* (PFR-97®+TX, PreFeRal®)+TX, *Paecilomyces linacinus* (Biostat WP®)+TX, *Paecilomyces lilacinus* strain 251 (MeloCon WG®)+TX, *Paenibacillus polymyxa*+TX, *Pantoea agglomerans* (BlightBan C9-1®)+TX, *Pantoea* spp.+TX, *Pasteuria* spp. (Econem®)+TX, *Pasteuria nishizawae*+TX, *Penicillium aurantiogriseum*+TX, *Penicillium billai* (Jumpstart®+TX, TagTeam®)+TX, *Penicillium brevicompactum*+TX, *Penicillium frequentans*+TX, *Penicillium griseofulvum*+TX, *Penicillium purpurogenum*+TX, *Penicillium* spp.+TX, *Penicillium viridicatum*+TX, *Phlebiopsis gigantean* (Rotstop®)+TX, phosphate solubilizing bacteria (Phosphomeal®)+TX, *Phytophthora cryptogea*+TX, *Phytophthora palmivora* (Devine®)+TX, *Pichia anomala*+TX, *Pichia guilermondii*+TX, *Pichia membranaefaciens*+TX, *Pichia onychis*+TX, *Pichia stipites*+TX, *Pseudomonas aeruginosa*+TX, *Pseudomonas aureofasciens* (Spot-Less Biofungicide®)+TX, *Pseudomonas cepacia*+TX, *Pseudomonas chloraphis* (AtEze®)+TX, *Pseudomonas corrugate*+TX, *Pseudomonas fluorescens* strain A506 (BlightBan A506®)+TX, *Pseudomonas putida*+TX, *Pseudomonas reactans*+TX, *Pseudomonas* spp.+TX, *Pseudomonas syringae* (Bio-Save®)+TX, *Pseudomonas viridiflava*+TX, *Pseudomons fluorescens* (Zequanox®)+TX, *Pseudozyma flocculosa* strain PF-A22 UL (Sporodex L®)+TX, *Puccinia canaliculata*+TX, *Puccinia thlaspeos* (Wood Warrior®)+TX, *Pythium paroecandrum*+TX, *Pythium oligandrum* (Polygandron®+TX, Polyversum®)+TX, *Pythium periplocum*+TX, *Rhanella aquatilis*+TX, *Rhanella* spp.+TX, *Rhizobia* (Dormal®+TX, Vault®)+TX, *Rhizoctonia*+TX, *Rhodococcus globerulus* strain AQ719+TX, *Rhodosporidium diobovatum*+TX, *Rhodosporidium toruloides*+TX, *Rhodotorula* spp.+TX, *Rhodotorula glutinis*+TX, *Rhodotorula graminis*+TX, *Rhodotorula mucilagnosa*+TX, *Rhodotorula rubra*+TX, *Saccharomyces cerevisiae*+TX, *Salinococcus roseus*+TX, *Sclerotinia minor*+TX, *Sclerotinia minor* (SARRITOR®)+TX, *Scytalidium* spp.+TX, *Scytalidium uredinicola*+TX, *Spodoptera exigua* nuclear polyhedrosis virus (Spod-X®+TX, Spexit®)+TX, *Serratia marcescens*+TX, *Serratia plymuthica*+TX, *Serratia* spp.+TX, *Sordaria fimicola*+TX, *Spodoptera littoralis* nucleolyhedrovirus (Littovir®)+TX, *Sporobolomyces roseus*+TX, *Stenotrophomonas maltophilia*+TX, *Streptomyces ahygroscopicus*+TX, *Streptomyces albaduncus*+TX, *Streptomyces exfoliates*+TX, *Streptomyces galbus*+TX, *Streptomyces griseoplanus*+TX, *Streptomyces griseoviridis* (Mycostop®)+TX, *Streptomyces lydicus* (Actinovate®)+TX, *Streptomyces lydicus* WYEC-108 (ActinoGrow®)+TX, *Streptomyces violaceus*+TX, *Tilletiopsis minor*+TX, *Tilletiopsis* spp.+TX, *Trichoderma asperellum* (T34 Biocontrol®)+TX, *Trichoderma gamsii* (Tenet®)+TX, *Trichoderma atroviride* (Plantmate®)+TX, *Trichoderma hamatum* TH 382+TX, *Trichoderma harzianum rifai* (Mycostar®)+TX, *Trichoderma harzianum* T-22 (Trianum-P®+TX, PlantShield HC®+TX, RootShield®+TX, Trianum-G®)+TX, *Trichoderma harzianum* T-39 (Trichodex®)+TX, *Trichoderma inhamatum*+TX, *Trichoderma koningii*+TX, *Trichoderma* spp. LC 52 (Sentinel®)+TX, *Trichoderma lignorum*+TX, *Trichoderma longibrachiatum*+TX, *Trichoderma polysporum* (Binab T®)+TX, *Trichoderma taxi*+TX, *Trichoderma virens*+TX, *Trichoderma virens* (formerly *Gliocladium virens* GL-21) (SoilGuard®)+TX, *Trichoderma viride*+TX, *Trichoderma viride* strain ICC 080 (Remedier®)+TX, *Trichosporon pullulans*+TX, *Trichosporon* spp.+TX, *Trichothecium* spp.+TX, *Trichothecium roseum*+TX, *Typhula phacorrhiza* strain 94670+TX, *Typhula phacorrhiza* strain 94671+TX, *Ulocladium atrum*+TX, *Ulocladium oudemansii* (Botry-Zen®)+TX, *Ustilago maydis*+TX, various bacteria and supplementary micronutrients (Natural II®)+TX, various fungi (Millennium Microbes®)+TX, *Verticillium chlamydosporium*+TX, *Verticillium lecanii* (Mycotal®+TX, Vertalec®)+TX, Vip3Aa20 (VIPtera®)+TX, *Virgibacillus marismortui*+TX, *Xanthomonas campestris* pv. *Poae* (Camperico®)+TX, *Xenorhabdus bovienii*+TX, *Xenorhabdus nematophilus*; and Plant extracts including: pine oil (Retenol®)+TX, azadirachtin (Plasma Neem Oil®+TX, AzaGuard®+TX, MeemAzal®+TX, Molt-X®+TX, Botanical IGR (Neemazad®+TX, Neemix®)+TX, canola oil (Lilly Miller Vegol®)+TX, *Chenopodium ambrosioides* near *ambrosioides* (Requiem®)+TX, *Chrysanthemum* extract (Crisant®)+TX, extract of neem oil (Trilogy®)+TX, essentials oils of Labiatae (Botania®)+TX, extracts of clove rosemary peppermint and thyme oil (Garden insect Killer®)+TX, Glycinebetaine (Greenstim®)+TX, garlic+TX, lemongrass oil (GreenMatch®)+TX, neem oil+TX, *Nepeta cataria* (Catnip oil)+TX, *Nepeta catarina*+TX, nicotine+TX, oregano oil (MossBuster®)+TX, Pedaliaceae oil (Nematon®)+TX, pyrethrum+TX, *Quillaja saponaria* (NemaQ®)+TX, *Reynoutria sachalinensis* (Regalia®+TX, Sakalia®)+TX, rotenone (Eco Roten®)+TX, Rutaceae plant extract (Soleo®)+TX, soybean oil (Ortho Ecosense®)+TX, tea tree oil (Timorex Gold®)+TX, thymus oil+TX, AGNIQUE® MMF+TX, BugOil®+TX, mixture of rosemary sesame peppermint thyme and cinnamon extracts (EF 300®)+TX, mixture of clove rosemary and peppermint extract (EF 400®)+TX, mixture of clove peppermint garlic oil and mint (Soil Shot®)+TX, kaolin (Screen®)+TX, storage glucam of brown algae (Laminarin®); and pheromones including: blackheaded fireworm pheromone (3M Sprayable Blackheaded Fireworm Pheromone®)+TX, Codling Moth Pheromone (Paramount dispenser-(CM)/Isomate C-Plus®)+TX, Grape Berry Moth Pheromone (3M MEC-GBM Sprayable Pheromone®)+TX, Leafroller pheromone (3M MEC—LR Sprayable Pheromone®)+TX, Muscamone (Snip7 Fly Bait®+TX, Starbar Premium Fly Bait®)+TX, Oriental Fruit Moth Pheromone (3M oriental fruit moth sprayable Pheromone®)+TX, Peachtree Borer Pheromone (Isomate-P®)+TX, Tomato Pinworm Pheromone (3M Sprayable Pheromone®)+TX, Entostat powder (extract from palm tree) (Exosex CM®)+TX, (E+TX,Z+TX, Z)-3+TX,8+TX,11 Tetradecatrienyl acetate+TX, (Z+TX,Z+TX,E)-7+TX,11+TX,13-Hexadecatrienal+TX, (E+TX,Z)-7+TX,9-Dodecadien-1-yl acetate+TX, 2-Methyl-1-butanol+TX, Calcium acetate+TX, Scenturion®+TX, Biolure®+TX, Check-Mate®+TX, Lavandulyl senecioate; and Macrobials including: *Aphelinus abdominalis*+TX, *Aphidius ervi* (*Aphelinus*-System®)+TX, *Acerophagus papaya*+TX, *Adalia bipunctata* (*Adalia*-System®)+TX, *Adalia bipunctata* (Adaline®)+TX, *Adalia bipunctata* (Aphidalia®)+TX, *Ageniaspis citricola*+TX, *Ageniaspis fuscicollis*+TX, *Amblyseius andersoni* (Anderline®+TX, Andersoni-System®)+TX, *Amblyseius californicus* (Amblyline®+TX, Spical®)+TX, *Amblyseius cucumeris* (Thripex®+TX, Bugline Cucumeris®)+TX, *Amblyseius fallacis* (Fallacis®)+TX, *Amblyseius swirskii* (Bugline Swirskii®+TX, Swirskii-Mite®)+TX, *Amblyseius womersleyi* (WomerMite®)+TX, *Amitus hesperidum*+TX, *Anagrus atomus*+TX, *Anagyrus fusciventris*+TX, *Anagyrus kamali*+TX, *Anagyrus loecki*+TX, *Anagyrus pseudococci* (Citripar®)+TX, *Anicetus benefices*+TX, *Anisopteromalus calandrae*+TX, *Anthocoris nemoralis* (*Anthocoris*-System®)+TX, *Aphelinus abdominalis* (Apheline®+TX, Aphiline®)+TX, *Aphelinus asychis*+TX, *Aphidius colemani* (Aphipar®)+TX, *Aphidius ervi* (Ervipar®)+TX, *Aphidius gifuensis*+TX, *Aphidius matricariae* (Aphipar-M®)+TX, *Aphidoletes aphidimyza* (Aphidend®)+TX, *Aphidoletes aphidimyza* (Aphidoline®)+TX, *Aphytis lingnanensis*+TX, *Aphytis melinus*+TX, *Aprostocetus hagenowii*+TX, *Atheta coriaria* (Staphyline®)+TX, *Bombus* spp.+TX, *Bombus terrestris* (Natupol Beehive®)+TX, *Bombus terrestris* (Beeline®+TX, Tripol®)+TX, *Cephalonomia stephanoderis*+TX, *Chilocorus nigritus*+TX, *Chrysoperla carnea* (Chrysoline®)+TX, *Chrysoperla carnea* (Chrysopa®)+TX, *Chrysoperla rufilabris*+TX, *Cirrospilus ingenuus*+TX, *Cirrospilus quadristriatus*+TX, *Citrostichus phyllocnistoides*+TX, *Closterocerus chamaeleon*+TX, *Closterocerus* spp.+TX, *Coccidoxenoides perminutus* (Planopar®)+TX, *Coccophagus cowperi*+TX, *Coccophagus lycimnia*+TX, *Cotesia flavipes*+TX, *Cotesia plutellae*+TX, *Cryptolaemus montrouzieri* (Cryptobug®+TX, Cryptoline®)+TX, *Cybocephalus nipponicus*+TX, *Dacnusa sibirica*+TX, *Dacnusa sibirica* (Minusa®)+TX, *Diglyphus isaea* (Diminex®)+TX, *Delphastus catalinae* (*Delphastus*®)+TX, *Delphastus pusillus*+TX, *Diachasmimorpha krausii*+TX, *Diachasmimorpha longicaudata*+TX, *Diaparsis jucunda*+TX, *Diaphorencyrtus aligarhensis*+TX, *Diglyphus isaea*+TX, *Diglyphus isaea* (Miglyphus®+TX, Digline®)+TX, *Dacnusa sibirica* (DacDigline®+TX, Minex®)+TX, *Diversinervus* spp.+TX, *Encarsia citrina*+TX, *Encarsia formosa* (*Encarsia* Max®+

TX, Encarline®+TX, En-Strip®)+TX, *Eretmocerus eremicus* (Enermix®)+TX, *Encarsia guadeloupae*+TX, *Encarsia haitiensis*+TX, *Episyrphus balteatus* (Syrphidend®)+TX, *Eretmoceris siphonini*+TX, *Eretmocerus californicus*+TX, *Eretmocerus eremicus* (Ercal®+TX, Eretline e®)+TX, *Eretmocerus eremicus* (Bemimix®)+TX, *Eretmocerus hayati*+TX, *Eretmocerus mundus* (Bemipar®+TX, Eretline m®)+TX, *Eretmocerus siphonini*+TX, *Exochomus quadripustulatus*+TX, *Feltiella acarisuga* (Spidend®)+TX, *Feltiella acarisuga* (Feltiline®)+TX, *Fopius arisanus*+TX, *Fopius ceratitivorus*+TX, Formononetin (Wirless Beehome®)+TX, *Franklinothrips vespiformis* (Vespop®)+TX, *Galendromus occidentalis*+TX, *Goniozus legneri*+TX, *Habrobracon hebetor*+TX, *Harmonia axyridis* (HarmoBeetle®)+TX, *Heterorhabditis* spp. (Lawn Patrol®)+TX, *Heterorhabditis bacteriophora* (NemaShield HB®+TX, Nemaseek®+TX, Terranem-Nam®+TX, Terranem®+TX, Larvanem®+TX, B-Green®+TX, NemAttack®+TX, Nematop®)+TX, *Heterorhabditis megidis* (Nemasys H®+TX, BioNem H®+TX, Exhibitline hm®+TX, Larvanem-M®)+TX, *Hippodamia convergens*+TX, *Hypoaspis aculeifer* (Aculeifer-System®+TX, Entomite-A®)+TX, *Hypoaspis miles* (Hypoline m®+TX, Entomite-M®)+TX, *Lbalia leucospoides*+TX, *Lecanoideus floccissimus*+TX, *Lemophagus errabundus*+TX, *Leptomastidea abnormis*+TX, *Leptomastix dactylopii* (Leptopar®)+TX, *Leptomastix epona*+TX, *Lindorus lophanthae*+TX, *Lipolexis oregmae*+TX, *Lucilia caesar* (Natufly®)+TX, *Lysiphlebus testaceipes*+TX, *Macrolophus caliginosus* (Mirical-N®+TX, Macroline c®+TX, Mirical®)+TX, *Mesoseiulus longipes*+TX, *Metaphycus flavus*+TX, *Metaphycus lounsburyi*+TX, *Micromus angulatus* (Milacewing®)+TX, *Microterys flavus*+TX, *Muscidifurax raptorellus* and *Spalangia cameroni* (Biopar®)+TX, *Neodryinus typhlocybae*+TX, *Neoseiulus californicus*+TX, *Neoseiulus cucumeris* (THRYPEX®)+TX, *Neoseiulus fallacis*+TX, *Nesideocoris tenuis* (NesidioBug®+TX, Nesibug®)+TX, *Ophyra aenescens* (Biofly®)+TX, *Orius insidiosus* (Thripor-I®+TX, Oriline i®)+TX, *Orius laevigatus* (Thripor-L®+TX, Oriline I®)+TX, *Orius majusculus* (Oriline m®)+TX, *Orius strigicollis* (Thripor-S®)+TX, *Pauesia juniperorum*+TX, *Pediobius foveolatus*+TX, *Phasmarhabdita hermaphrodita* (Nemaslug®)+TX, *Phymastichus coffea*+TX, *Phytoseiulus macropilus*+TX, *Phytoseiulus persimilis* (Spidex®+TX, Phytoline p®)+TX, *Podisus maculiventris* (*Podisus®*)+TX, *Pseudacteon curvatus*+TX, *Pseudacteon obtusus*+TX, *Pseudacteon tricuspis*+TX, *Pseudaphycus maculipennis*+TX, *Pseudleptomastix mexicana*+TX, *Psyllaephagus pilosus*+TX, *Psyttalia concolor* (complex)+TX, *Quadrastichus* spp.+TX, *Rhyzobius lophanthae*+TX, *Rodolia cardinalis*+TX, *Rumina decollate*+TX, *Semielacher petiolatus*+TX, *Sitobion avenae* (Ervibank®)+TX, *Steinernema carpocapsae* (Nematac C®+TX, Millenium®+TX, BioNem C®+TX, NemAttack®+TX, Nemastar®+TX, Capsanem®)+TX, *Steinernema feltiae* (NemaShield®+TX, Nemasys F®+TX, BioNem F®+TX, Steinernema-System®+TX, NemAttack®+TX, Nemaplus®+TX, Exhibitline sf®+TX, Sciarid®+TX, Entonem®)+TX, *Steinernema kraussei* (Nemasys L®+TX, BioNem L®+TX, Exhibitline srb®)+TX, *Steinernema riobrave* (BioVector®+TX, BioVektor®)+TX, *Steinernema scapterisci* (Nematac S®)+TX, *Steinernema* spp.+TX, *Steinernematid* spp. (Guardian Nematodes®)+TX, *Stethorus punctillum* (*Stethorus®*)+TX, *Tamarixia radiate*+TX, *Tetrastichus setifer*+TX, *Thripobius semiluteus*+TX, *Torymus sinensis*+TX, *Trichogramma brassicae* (Tricholine b®)+TX, *Trichogramma brassicae* (TrichoStrip®)+TX, *Trichogramma evanescens*+TX, *Trichogramma minutum*+TX, *Trichogramma ostriniae*+TX, *Trichogramma platneri*+TX, *Trichogramma pretiosum*+TX, *Xanthopimpla stemmator*; and other biologicals including: abscisic acid+TX, bioSea®+TX, *Chondrostereum purpureum* (Chontrol Paste®)+TX, *Colletotrichum gloeosporioides* (Collego®)+TX, Copper Octanoate (Cueva®)+TX, Delta traps (Trapline d®)+TX, *Erwinia amylovora* (Harpin) (ProAct®+TX, Ni-HIBIT Gold CST®)+TX, Ferri-phosphate (Ferramol®)+TX, Funnel traps (Trapline y@)+TX, Gallex®+TX, Grower's Secret®+TX, Homo-brassonolide+TX, Iron Phosphate (Lilly Miller Worry Free Ferramol Slug & Snail Bait®)+TX, MCP hail trap (Trapline f®)+TX, *Microctonus hyperodae*+TX, *Mycoleptodiscus terrestris* (Des-X®)+TX, BioGain®+TX, Aminomite®+TX, Zenox®+TX, Pheromone trap (Thripline ams®)+TX, potassium bicarbonate (MilStop®)+TX, potassium salts of fatty acids (Sanova®)+TX, potassium silicate solution (Sil-Matrix®)+TX, potassium iodide+potassiumthiocyanate (Enzicur®)+TX, SuffOil-X®+TX, Spider venom+TX, *Nosema locustae* (Semaspore Organic Grasshopper Control®)+TX, Sticky traps (Trapline YF®+TX, Rebell Amarillo®)+TX and Traps (Takitrapline y+b®)+TX.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright© 1995-2004]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed. "CAS Reg. No" means the Chemical Abstracts Registry Number.

The active ingredient mixture of the compounds of formula I selected from Tables 1, 2 and 3 with active ingredients described above comprises a compound selected from Tables 1, 2 and 3 and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of formula I selected from Tables 1, 2 and 3 and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from Tables 1, 2 and 3 and the active ingredients as described above is not essential for working the present invention.

The compositions according to the invention can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compounds of the invention and compositions thereof are also be suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

The present invention also comprises seeds coated or treated with or containing a compound of formula I. The term "coated or treated with and/or containing" generally signifies that the active ingredient is for the most part on the surface of the seed at the time of application, although a greater or lesser part of the ingredient may penetrate into the seed material, depending on the method of application. When the said seed product is (re)planted, it may absorb the active ingredient. In an embodiment, the present invention makes available a plant propagation material adhered thereto with a compound of formula (I). Further, it is hereby made available, a composition comprising a plant propagation material treated with a compound of formula (I).

Seed treatment comprises all suitable seed treatment techniques known in the art, such as seed dressing, seed coating, seed dusting, seed soaking and seed pelleting. The seed treatment application of the compound formula (I) can be carried out by any known methods, such as spraying or by dusting the seeds before sowing or during the sowing/planting of the seeds.

BIOLOGICAL EXAMPLES

Example B1: Activity Against *Bemisia tabaci* (Cotton White Fly): Feeding/Contact Activity Cotton leaf discs were placed on agar in 24-well microtiter plates and sprayed with aqueous test solutions prepared from 10'000 ppm DMSO stock solutions. After drying the leaf discs were infested with adult white flies. The samples were checked for mortality 6 days after incubation.

The following compound resulted in at least 80% mortality at an application rate of 200 ppm: A2, A6, A8, A9 and A10.

Example B2: Activity Against *Diabrotica balteata* (Corn Root Worm)

Maize sprouts placed onto an agar layer in 24-well microtiter plates were treated with aqueous test solutions prepared from 10'000 ppm DMSO stock solutions by spraying. After drying, the plates were infested with L2 larvae (6 to 10 per well). The samples were assessed for mortality and growth inhibition in comparison to untreated samples 4 days after infestation.

The following compounds gave an effect of at least 80% in at least one of the two categories (mortality or growth inhibition) at an application rate of 200 ppm: A2, A3, A4, A6, A7, A8, A9, A10 and A20.

Example B3: Activity Against *Myzus persicae* (Green Peach Aphid): Feeding/Contact Activity Sunflower leaf discs were placed onto agar in a 24-well microtiter plate and sprayed with aqueous test solutions prepared from 10'000 ppm DMSO stock solutions. After drying, the leaf discs were infested with an aphid population of mixed ages. The samples were assessed for mortality 6 days after infestation.

The following compounds resulted in at least 80% mortality at an application rate of 200 ppm: A2, A3, A4, A5, A8, A9, A10, A13, A14 and A18.

Example B4: Activity Against *Myzus persicae* (Green Peach Aphid): Systemic Activity Roots of pea seedlings infested with an aphid population of mixed ages were placed directly into aqueous test solutions prepared from 10'000 DMSO stock solutions. The samples were assessed for mortality 6 days after placing seedlings into test solutions.

The following compounds resulted in at least 80% mortality at a test rate of 24 ppm: A2, A3, A5, A10, A13, A14, A15, A17, A18 and A20.

Example B5: Activity Against *Plutella xylostella* (Diamond Back Moth)

24-well microtiter plates with artificial diet were treated with aqueous test solutions prepared from 10'000 ppm DMSO stock solutions by pipetting. After drying, the plates were infested with L2 larvae (10 to 15 per well). The samples were assessed for mortality and growth inhibition in comparison to untreated samples 5 days after infestation.

The following compounds gave an effect of at least 80% in at least one of the two categories (mortality or growth inhibition) at an application rate of 200 ppm: A2, A3, A4, A6, A8, A9, A10, A13, A14 and A19.

Example B6: Activity Against *Spodoptera littoralis* (Egyptian Cotton Leaf Worm)

Test compounds were applied by pipette from 10'000 ppm DMSO stock solutions into 24-well plates and mixed with agar. Lettuce seeds were placed onto the agar and the multi well plate was closed by another plate which contained also agar. After 7 days the compound was absorbed by the roots and the lettuce grew into the lid plate. The lettuce leaves were then cut off into the lid plate. *Spodoptera* eggs were pipetted through a plastic stencil onto a humid gel blotting paper and the lid plate was closed with it. The samples were assessed for mortality, anti-feedant effect and growth inhibition in comparison to untreated samples 6 days after infestation.

The following compound gave an effect of at least 80% in at least one of the three categories (mortality, anti-feeding, or growth inhibition) at a test rate of 12.5 ppm: A2, A8.

Example B7: Activity Against *Aedes aegypti* (Yellow Fever Mosquito)

Test solutions, at an application rate of 200 ppm in ethanol, were applied to 12 well tissue culture plates. Once the deposits were dry, five, two to five day old adult female *Aedes aegypti* were added to each well, and sustained with a 10% sucrose solution in a cotton wool plug. Assessment of knockdown was made one hour after introduction, and mortality was assessed at 24 and 48 hours after introduction.

For example, the following compounds gave at least 80% control of *Aedes aegypti* after 48 h and/or 24 h: A1 and A2.

Example B8: Activity Against *Spodoptera littoralis* (Egyptian Cotton Leaf Worm)

Cotton leaf discs were placed onto agar in 24-well microtiter plates and sprayed with aqueous test solutions prepared from 10'000 ppm DMSO stock solutions. After drying the leaf discs were infested with five L1 larvae. The samples were assessed for mortality, anti-feeding effect, and growth inhibition in comparison to untreated samples 3 days after infestation. Control of *Spodoptera littoralis* by a test sample is given when at least one of the categories mortality, anti-feedant effect, and growth inhibition is higher than the untreated sample.

The following compounds resulted in at least 80% control at an application rate of 200 ppm: A2, A3, A5, A6, A7, A8, A9, A10, A19 and A20.

Example B9: Activity Against *Euschistus heros* (Neotropical Brown Stink Bug)

Soybean leaves on agar in 24-well microtiter plates were sprayed with aqueous test solutions prepared from 10'000 ppm DMSO stock solutions. After drying the leaves were infested with N2 nymphs. The samples were assessed for mortality and growth inhibition in comparison to untreated samples 5 days after infestation.

The following compounds gave an effect of at least 80% in at least one of the two categories (mortality or growth inhibition) at an application rate of 200 ppm: A5, A8, A9, A13, A14, A18 and A20.

Example B10: Activity Against *Anopheles stephensi* (Indian Malaria Mosquito)

Test solutions, at an application rate of 200 ppm in ethanol, were applied to 12 well tissue culture plates. Once the deposits were dry, five, two to five day old adult female *Anopheles stephensi* were added to each well, and sustained with a 10% sucrose solution in a cotton wool plug. Assessment of knockdown was made one hour after introduction, and mortality was assessed at 24 and 48 hours after introduction.

For example, the following compound gave at least 80% control of *Anopheles stephensi* after 48 h and/or 24 h: A2.

The invention claimed is:
1. A compound of formula I

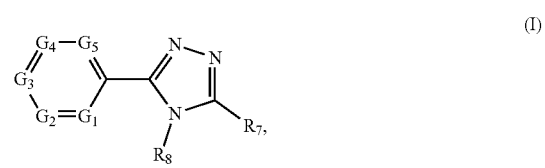

wherein
$G_1$ is nitrogen or $CR_2$;
$G_2$ is nitrogen or $CR_3$;
$G_3$ is nitrogen or $CR_4$;
$G_4$ is nitrogen or $CR_5$;

$G_5$ is nitrogen or $CR_6$, with the proviso that not more than 2 nitrogens as G may follow consecutively;

$R_2$, $R_3$, $R_4$, $R_5$ and $R_6$ are, independently from each other, hydrogen, halogen, $C_1$-$C_4$haloalkyl or $C_1$-$C_4$haloalkyl substituted by one or two cyano or methoxy; or $R_2$, $R_3$, $R_4$, $R_5$ and $R_6$ are, independently from each other, $C_1$-$C_4$haloalkylsulfanyl, $C_1$-$C_4$haloalkylsulfinyl, $C_1$-$C_4$haloalkylsulfonyl, $C_1$-$C_4$haloalkoxy, $SF_5$, phenylcarbonylthio, cyano, mercapto, $C_1$-$C_4$alkoxycarbonyl, $C_1$-$C_4$alkylcarbonyl or —$C(O)C_1$-$C_4$haloalkyl; or $R_2$, $R_3$, $R_4$, $R_5$ and $R_6$ are, independently from each other, $C_3$-$C_6$cycloalkyl which can be mono- or polysubstituted by substituents selected from the group consisting of halogen, cyano, $C_1$-$C_4$ haloalkyl and $C_1$-$C_4$alkyl;

$R_8$ is hydrogen or $C_1$-$C_4$alkyl which can be mono- or polysubstituted by substituents selected from the group consisting of halogen, $C_1$-$C_4$haloalkylsulfanyl, $C_1$-$C_4$haloalkylsulfinyl and $C_1$-$C_4$haloalkylsulfonyl;

$R_7$ is the following group:

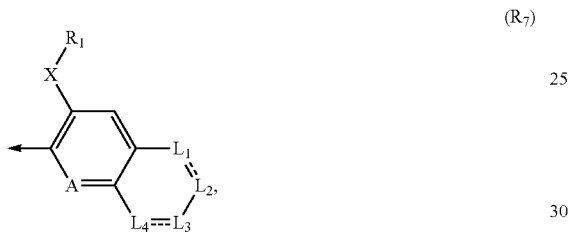

(R_7)

wherein the arrow denotes the point of attachment to the triazole ring which contains the group $R_8$;

and wherein

X is S, S(O) or $SO_2$;

$R_1$ is $C_1$-$C_4$alkyl or is $C_3$-$C_6$cycloalkyl$C_1$-$C_4$alkyl which can be mono- or polysubstituted by substituents selected from the group consisting of halogen, cyano, $C_1$-$C_4$ haloalkyl and $C_1$-$C_4$alkyl; or $R_1$ is $C_3$-$C_6$cycloalkyl which can be mono- or polysubstituted by substituents selected from the group consisting of halogen, cyano, $C_1$-$C_4$ haloalkyl and $C_1$-$C_4$alkyl;

$L_1$, $L_2$, $L_3$ and $L_4$ form together with the two carbon atoms to which $L_1$ and $L_4$ are attached, an aromatic, partially saturated carbocyclic or heterocyclic ring system; wherein $L_1$ is nitrogen, $S(O)_n$, oxygen, N—$R_{10a}$ or $C(R_{10a})_m$;
$L_2$ is nitrogen, $S(O)_n$, oxygen, N—$R_{10b}$ or $C(R_{10b})_m$;
$L_3$ is nitrogen, $S(O)_n$, oxygen, N—$R_{10c}$ or $C(R_{10c})_m$;
$L_4$ is nitrogen, $S(O)_n$, oxygen, a direct bond, N—$R_{10d}$ or $C(R_{10d})_m$; with the provisos that no more than 2 substituents selected from $L_1$, $L_2$, $L_3$ and $L_4$ can be oxygen or sulfur; and if two L groups are oxygen, they are not adjacent to each other; and no more than three L groups can be nitrogen;

A is CH or N;
n is 0, 1 or 2;
m is 1 or 2; and $R_{10a}$, $R_{10b}$, $R_{10c}$ and $R_{10d}$ are, independently from each other, hydrogen, halogen, nitro, cyano, amino, hydroxyl, $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, $C_1$-$C_6$alkoxy, $C_1$-$C_4$alkoxy$C_1$-$C_4$alkyl, $C_1$-$C_6$haloalkoxy, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl, $C_2$-$C_6$alkylcarbonyl, $C_2$-$C_6$ alkoxycarbonyl, $C_2$-$C_6$ haloalkylcarbonyl, $C_2$-$C_6$halo- alkoxycarbonyl, ($C_1$-$C_6$alkyl)NH, ($C_1$-$C_6$alkyl)$_2$N, ($C_1$-$C_6$cycloalkyl)NH, ($C_1$-$C_6$cycloalkyl)$_2$N, $C_1$-$C_6$alkyl-carbonylamino, $C_1$-$C_6$cycloalkylcarbonylamino or —$SF_5$; additionally one of $R_{10a}$, $R_{10b}$, $R_{10c}$ and $R_{10d}$ can be oxo; or $R_{10a}$, $R_{10b}$, $R_{10c}$ and $R_{10d}$ are, independently from each other, $C_3$-$C_6$cycloalkyl mono- or polysubstituted by substituents selected from the group consisting of halogen, $C_1$-$C_4$ haloalkyl, $C_1$-$C_4$alkyl and cyano; and agrochemically acceptable salts, stereoisomers, enantiomers, tautomers and N-oxides of those compounds.

2. A compound of formula I according to claim 1, wherein $R_7$ is selected from the group consisting of $J_1$ to $J_{16}$, where the arrow represents the point of attachment of the group J to the triazole ring which contains the group $R_8$, and wherein A, X and $R_1$ are as defined according to claim 1;

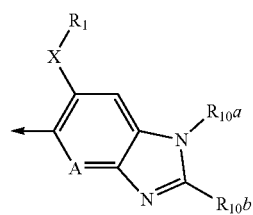

J_1

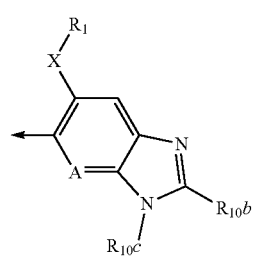

J_2

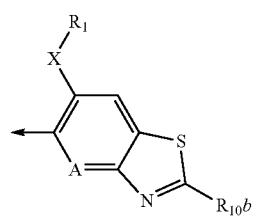

J_3

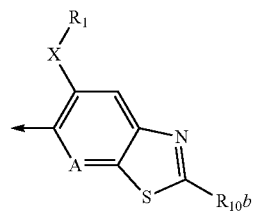

J_4

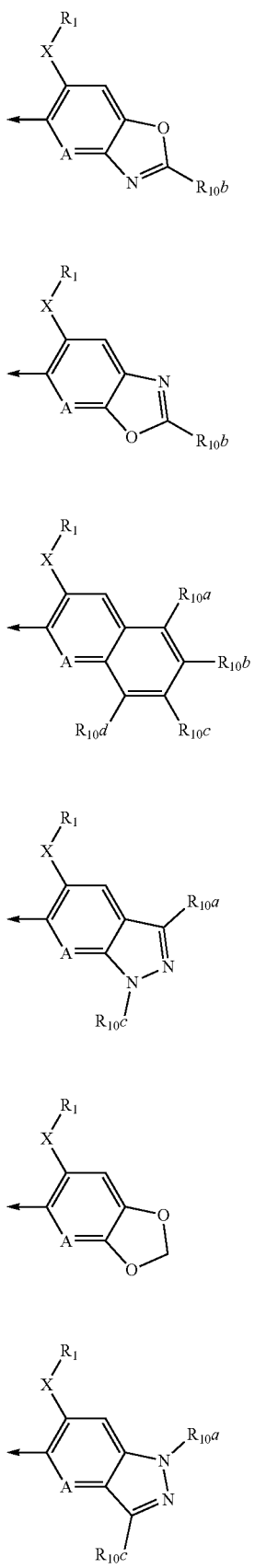
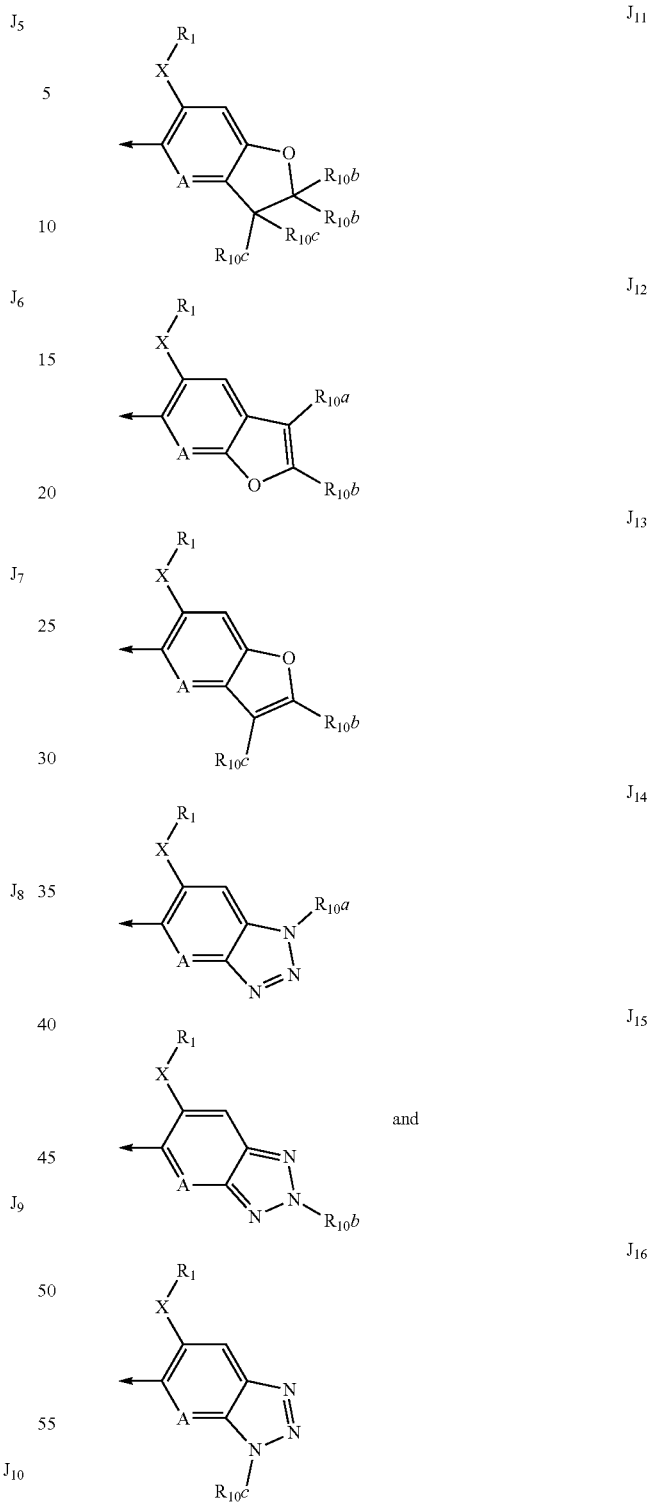

wherein each group $J_1$ to $J_{16}$ is mono- or disubstituted with $R_{10a}$, $R_{10b}$, $R_{10c}$ and $R_{10d}$, wherein $R_{10a}$, $R_{10b}$, $R_{10c}$ and $R_{10d}$ are independently selected from hydrogen, halogen, cyano, amino, $C_3$-$C_6$cycloalkyl, $C_1$-$C_6$haloalkyl, $C_1$-$C_6$alkoxy, $C_1$-$C_4$alkoxy$C_1$-$C_4$alkyl, $C_1$-$C_6$haloalkoxy, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl or $C_1$-$C_6$haloalkylsulfonyl.

3. A compound of formula I according to claim 1, represented by the compounds of formula I-1a

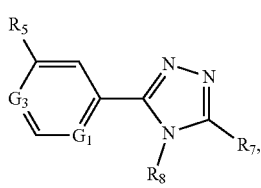

(I-1a)

wherein $R_7$ is

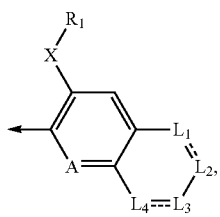

($R_7$)

and X, A, $R_1$, $R_5$, $R_8$, $G_1$, $G_3$, $L_1$, $L_2$, $L_3$ and $L_4$ are as defined under formula I in claim 1, and wherein the arrow denotes the point of attachment to the triazole ring which contains the group $R_8$.

4. A compound of formula I-1a according to claim 3, wherein

A is C—H or N;
$G_1$ is nitrogen or $CR_2$;
$G_3$ is nitrogen or $CR_4$;
X is S, S(O) or $SO_2$;
$R_1$ is $C_1$-$C_4$alkyl, $C_3$-$C_6$cycloalkyl-$C_1$-$C_4$alkyl or $C_3$-$C_6$cycloalkyl;
$R_8$ is $C_1$-$C_4$alkyl which can be mono- or polysubstituted by substituents selected from halogen, $C_1$-$C_4$ haloalkylsulfanyl, $C_1$-$C_4$haloalkylsulfinyl and $C_1$-$C_4$halo- alkylsulfonyl;
$R_2$, $R_4$ and $R_5$ are, independently from each other, hydrogen, halogen, $C_1$-$C_4$haloalkyl, $C_1$-$C_4$haloalkyl substituted by one or two cyano or methoxy; or
$R_2$, $R_4$ and $R_5$ are, independently from each other, $C_1$-$C_4$haloalkylsulfanyl, $C_1$-$C_4$haloalkylsulfinyl, $C_1$-$C_4$ haloalkylsulfonyl, $C_1$-$C_4$haloalkoxy, $SF_5$, phenylcarbonylthio, cyano, mercapto, $C_1$-$C_4$alkoxycarbonyl, $C_1$-$C_4$alkylcarbonyl or —C(O)$C_1$-$C_4$haloalkyl; or
$R_2$, $R_4$ and $R_5$ are, independently from each other, $C_3$-$C_6$cycloalkyl which can be mono- or polysubstituted by substituents selected from the group consisting of halogen, cyano, $C_1$-$C_4$ haloalkyl and $C_1$-$C_4$alkyl;
$L_1$, $L_2$, $L_3$ and $L_4$ are as defined under formula I in claim 1; and
$R_{10a}$, $R_{10b}$, $R_{10c}$ and $R_{10d}$, independently from each other, are hydrogen, halogen, nitro, cyano, hydroxyl, $C_1$-$C_6$alkyl, $C_2$-$C_6$alkenyl, $C_2$-$C_6$alkynyl, $C_3$-$C_6$ cycloalkyl, $C_3$-$C_6$cycloalkyl-$C_1$-$C_4$ cycloalkyl, $C_1$-$C_6$ haloalkyl, $C_2$-$C_6$haloalkenyl, $C_2$-$C_6$haloalkynyl, $C_3$-$C_6$ halocycloalkyl, $C_3$-$C_6$cyclohaloalkyl-$C_1$-$C_4$ cycloalkyl, $C_1$-$C_6$alkoxy, $C_1$-$C_4$alkoxy$C_1$-$C_4$alkyl, $C_1$-$C_6$ haloalkoxy, $C_1$-$C_4$alkylthio, $C_1$-$C_4$haloalkylthio, $C_1$-$C_4$ haloalkylsulfonyl, $C_1$-$C_4$ haloalkylsulfinyl, $C_1$-$C_4$haloalkylsulfonyl, $C_2$-$C_4$alkylcarbonyl, $C_2$-$C_6$alkoxycarbonyl or —$SF_5$; additionally one of $R_{10a}$, $R_{10b}$, $R_{10c}$ and $R_{10d}$ can be oxo.

5. A compound of formula I-1a according to claim 3, wherein $R_7$ is selected from the group consisting of $J_1$ to $J_{16}$ (where the arrow represents the point of attachment of the group J to the triazole ring which contains the group $R_8$),

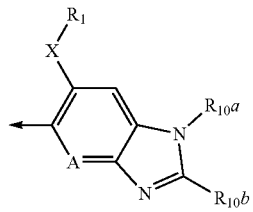

$J_1$

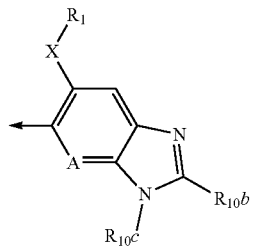

$J_2$

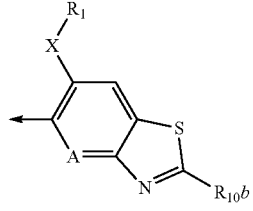

$J_3$

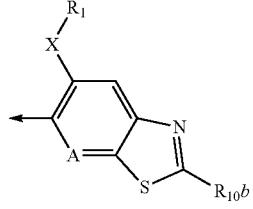

$J_4$

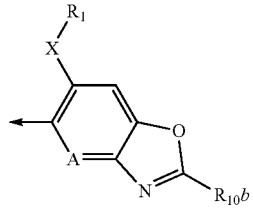

$J_5$

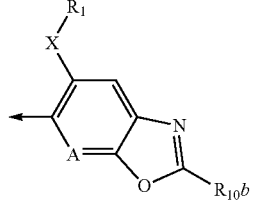

$J_6$

167
-continued

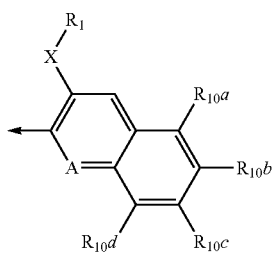 J7

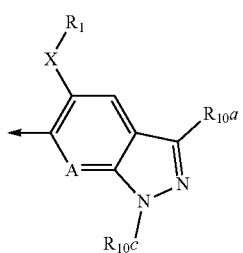 J8

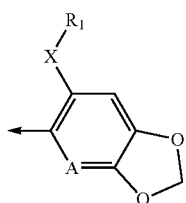 J9

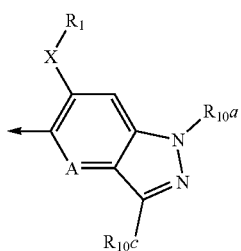 J10

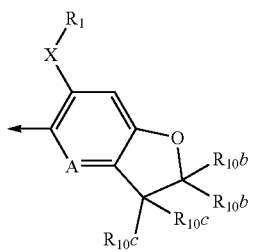 J11

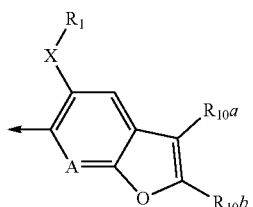 J12

168
-continued

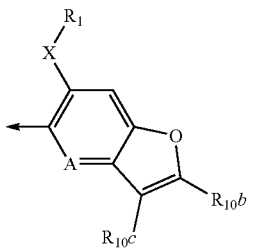 J13

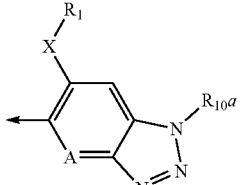 J14

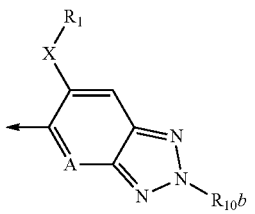 J15 and

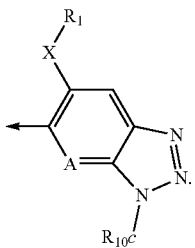 J16

6. A compound of formula I-1a according to claim 5, wherein

A is C—H or N;

$G_1$ is nitrogen or $CR_2$;

$G_3$ is nitrogen or $CR_4$;

X is S, S(O) or $SO_2$;

$R_1$ is $C_1$-$C_4$alkyl;

$R_8$ is $C_1$-$C_4$alkyl;

$R_2$, $R_4$ and $R_5$ are, independently from each other, hydrogen, halogen or $C_1$-$C_4$haloalkyl; or $R_2$, $R_4$ and $R_5$ are, independently from each other, $C_1$-$C_4$haloalkylsulfanyl, $C_1$-$C_4$haloalkylsulfinyl, $C_1$-$C_4$ haloalkylsulfonyl, $C_1$-$C_4$haloalkoxy or cyano; and $R_{10a}$, $R_{10b}$, $R_{10c}$ and $R_{10d}$, independently from each other, are hydrogen, halogen, nitro, cyano, hydroxyl, $C_1$-$C_6$ alkyl, $C_2$-$C_6$alkenyl, $C_2$-$C_6$alkynyl, $C_3$-$C_6$cycloalkyl, $C_3$-$C_6$cycloalkyl-$C_1$-$C_4$ cycloalkyl, $C_1$-$C_6$haloalkyl, $C_2$-$C_6$haloalkenyl, $C_2$-$C_6$haloalkynyl, $C_3$-$C_6$halocycloalkyl, $C_3$-$C_6$cyclohaloalkyl-$C_1$-$C_4$ cycloalkyl, $C_1$-$C_6$ alkoxy, $C_1$-$C_4$alkoxy$C_1$-$C_4$alkyl, $C_1$-$C_6$haloalkoxy, $C_1$-$C_4$alkylthio, $C_1$-$C_4$alkylsulfinyl, $C_1$-$C_4$ alkylsulfonyl, $C_1$-$C_4$haloalkylthio, $C_1$-$C_4$haloalkylsulfinyl, $C_1$-$C_4$ haloalkylsulfonyl, $C_2$-$C_4$alkylcarbonyl or $C_2$-$C_4$ alkoxycarbonyl, or $C_2$-$C_6$alkoxycarbonyl.

7. A compound of formula I according to claim 1 represented by the compounds of formula I-1c

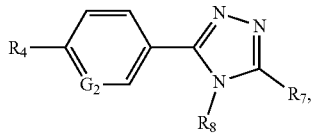
(I-1c)

wherein $R_7$ is

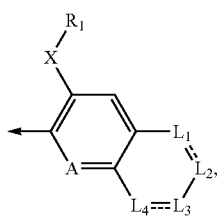
($R_7$)

and X, A, $R_1$, $R_4$, $R_8$, $G_2$, $L_1$, $L_2$, $L_3$ and $L_4$ are as defined under formula I in claim 1, and wherein the arrow denotes the point of attachment to the triazole ring which contains the group $R_8$.

8. A compound of formula I-1c according to claim 7, wherein
A is C—H or N;
$G_2$ is nitrogen or $CR_3$;
X is S, S(O) or $SO_2$;
$R_1$ is $C_1$-$C_4$alkyl, $C_3$-$C_6$cycloalkyl-$C_1$-$C_4$alkyl or $C_3$-$C_6$cycloalkyl;
$R_8$ is $C_1$-$C_4$alkyl which can be mono- or polysubstituted by substituents selected from halogen, $C_1$-$C_4$ haloalkylsulfanyl, $C_1$-$C_4$haloalkylsulfinyl and $C_1$-$C_4$halo-alkylsulfonyl;
$R_3$ and $R_4$ are, independently from each other, hydrogen, halogen, $C_1$-$C_4$haloalkyl, $C_1$-$C_4$haloalkyl substituted by one or two cyano or methoxy; or
$R_3$ and $R_4$ are, independently from each other, $C_1$-$C_4$haloalkylsulfanyl, $C_1$-$C_4$haloalkylsulfinyl, $C_1$-$C_4$ haloalkylsulfonyl, $C_1$-$C_4$haloalkoxy, $SF_5$, phenylcarbonylthio, cyano, mercapto, $C_1$-$C_4$alkoxycarbonyl, $C_1$-$C_4$ alkylcarbonyl or —C(O)$C_1$-$C_4$haloalkyl; or
$R_3$ and $R_4$ are, independently from each other, $C_3$-$C_6$cycloalkyl which can be mono- or polysubstituted by substituents selected from the group consisting of halogen, cyano, $C_1$-$C_4$ haloalkyl and $C_1$-$C_4$alkyl;
$L_1$, $L_2$, $L_3$ and $L_4$ are as defined under formula I in claim 1; and
$R_{10a}$, $R_{10b}$, $R_{10c}$ and $R_{10d}$, independently from each other, are hydrogen, halogen, nitro, cyano, hydroxyl, $C_1$-$C_6$alkyl, $C_2$-$C_6$alkenyl, $C_2$-$C_6$alkynyl, $C_3$-$C_6$ cycloalkyl, $C_3$-$C_6$cycloalkyl-$C_1$-$C_4$ cycloalkyl, $C_1$-$C_6$ haloalkyl, $C_2$-$C_6$haloalkenyl, $C_2$-$C_6$haloalkynyl, $C_3$-$C_6$ halocycloalkyl, $C_3$-$C_6$cyclohaloalkyl-$C_1$-$C_4$ cycloalkyl, $C_1$-$C_6$alkoxy, $C_1$-$C_4$alkoxy$C_1$-$C_4$alkyl, $C_1$-$C_6$haloalkoxy, $C_1$-$C_4$alkylthio, $C_1$-$C_4$alkylsulfinyl, $C_1$-$C_4$ alkylsulfonyl, $C_1$-$C_4$haloalkylthio, $C_1$-$C_4$halo-alkylsulfinyl, $C_1$-$C_4$haloalkylsulfonyl, $C_2$-$C_4$alkylcarbonyl, $C_2$-$C_6$alkoxycarbonyl or —$SF_5$; additionally one of $R_{10a}$, $R_{10b}$, $R_{10c}$ and $R_{10d}$ can be oxo.

9. A compound of formula I-1c according to claim 7, wherein $R_7$ is selected from the group consisting of $J_1$ to $J_{16}$, where the arrow represents the point of attachment of the group J to the triazole ring which contains the group $R_8$

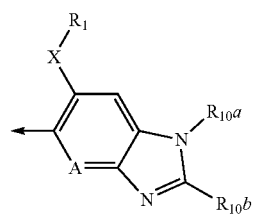
$J_1$

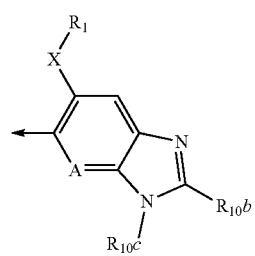
$J_2$

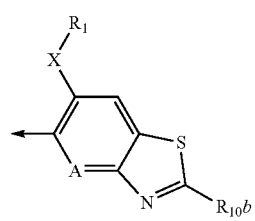
$J_3$

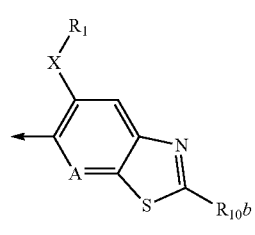
$J_4$

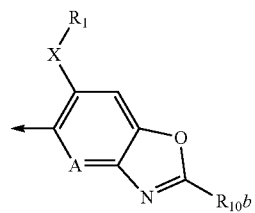
$J_5$

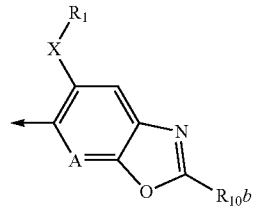
$J_6$

-continued

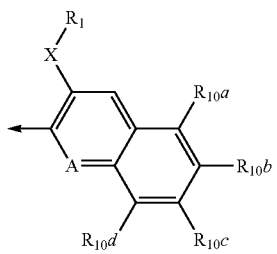 J₇

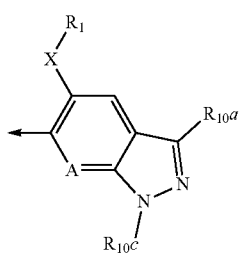 J₈

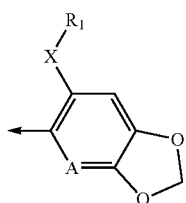 J₉

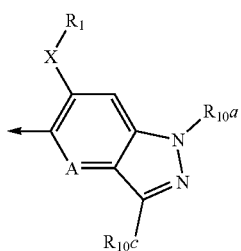 J₁₀

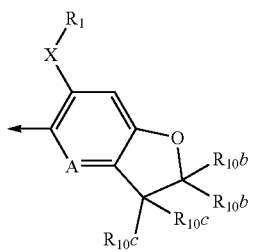 J₁₁

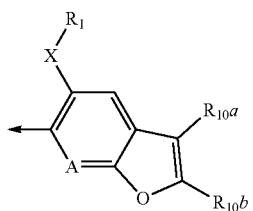 J₁₂

-continued

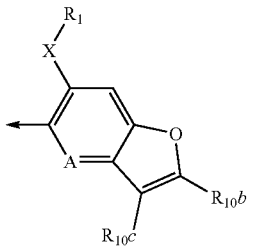 J₁₃

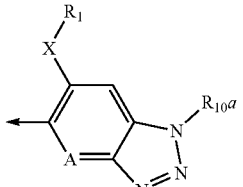 J₁₄

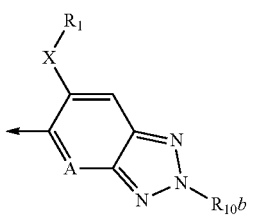 J₁₅ and

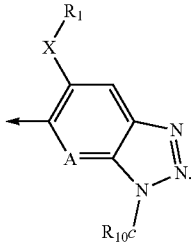 J₁₆

10. A compound of formula I-1c according to claim 9, wherein

A is C—H or N;

$G_2$ is nitrogen or $CR_3$;

X is S, S(O) or $SO_2$;

$R_1$ is $C_1$-$C_4$alkyl;

$R_8$ is $C_1$-$C_4$alkyl;

$R_3$ and $R_4$ are, independently from each other, hydrogen, halogen or $C_1$-$C_4$haloalkyl; or $R_3$ and $R_4$ are, independently from each other, $C_1$-$C_4$haloalkylsulfanyl, $C_1$-$C_4$haloalkylsulfinyl, $C_1$-$C_4$ haloalkylsulfonyl, $C_1$-$C_4$haloalkoxy or cyano; and $R_{10a}$, $R_{10b}$, $R_{10c}$ and $R_{10d}$, independently from each other, are hydrogen, halogen, nitro, cyano, hydroxyl, $C_1$-$C_6$ alkyl, $C_2$-$C_6$alkenyl, $C_2$-$C_6$alkynyl, $C_3$-$C_6$cycloalkyl, $C_3$-$C_6$cycloalkyl-$C_1$-$C_4$ cycloalkyl, $C_1$-$C_6$haloalkyl, $C_2$-$C_6$haloalkenyl, $C_2$-$C_6$haloalkynyl, $C_3$-$C_6$halocycloalkyl, $C_3$-$C_6$cyclohaloalkyl-$C_1$-$C_4$ cycloalkyl, $C_1$-$C_6$ alkoxy, $C_1$-$C_4$alkoxy$C_1$-$C_4$alkyl, $C_1$-$C_6$haloalkoxy, $C_1$-$C_4$alkylthio, $C_1$-$C_4$alkylsulfinyl, $C_1$-$C_4$alkylsulfonyl, $C_1$-$C_4$haloalkylthio, $C_1$-$C_4$haloalkylsulfinyl, $C_1$-$C_4$haloalkylsulfonyl, $C_2$-$C_4$alkylcarbonyl or $C_2$-$C_6$-alkoxycarbonyl.

11. A compound of formula I according to claim 1, wherein the ring, which is formed by the groups $G_1$ to $G_5$, represents pyridyl or pyrimidyl, which both can be substituted by $C_1$-$C_4$haloalkyl;

$R_8$ is methyl; and $R_7$ is selected from the group consisting of $J_1$, $J_3$, $J_4$, $J_7$, $J_{11}$ and $J_{14}$ to $J_{16}$, where the arrow represents the point of attachment of the group J to the triazole ring which contains the group $R_8$

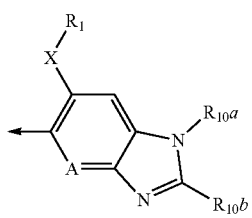
$J_1$

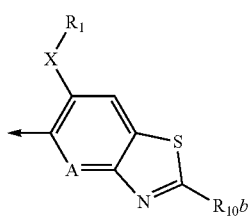
$J_3$

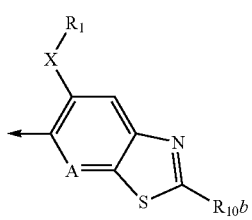
$J_4$

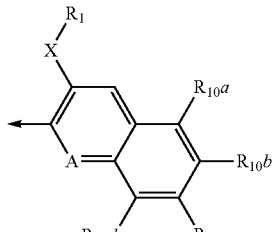
$J_7$

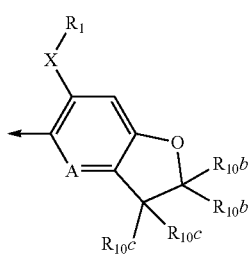
$J_{11}$

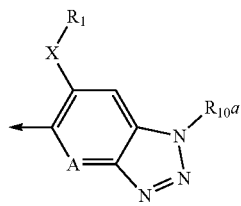
$J_{14}$

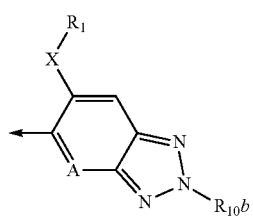
$J_{15}$ and

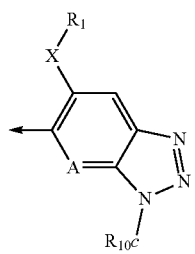
$J_{16}$ wherein each radical X—$R_1$ is ethylsufanyl or ethylsulfonyl; and $R_{10a}$, $R_{10b}$, $R_{10c}$ and $R_{10d}$, independently from each other, are hydrogen, $C_1$-$C_6$alkyl, $C_1$-$C_6$haloalkyl or $C_1$-$C_4$alkoxy$C_1$-$C_4$alkyl.

12. A pesticidal composition, which comprises at least one compound of formula I according to claim 1 or, where appropriate, a tautomer thereof, in each case in free form or in agrochemically utilizable salt form, as active ingredient and at least one auxiliary.

13. A method for controlling pests, which comprises applying a composition according to claim 12 to the pests or their environment with the exception of a method for treatment of the human or animal body by surgery or therapy and diagnostic methods practised on the human or animal body.

14. A method for the protection of seeds from the attack by pests, which comprises treating the seeds or the site, where the seeds are planted, with a composition according to claim 12.

15. A compound of formula VIb-I7-1d

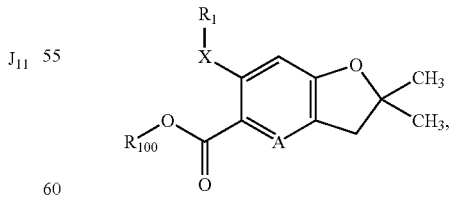
VIb-I7-1d wherein

X, $R_1$ and A are as defined under formula I in claim 1; and $R_{100}$ is hydrogen or $C_1$-$C_4$alkyl.

* * * * *